United States Patent
Skolnick et al.

(10) Patent No.: US 9,205,074 B2
(45) Date of Patent: Dec. 8, 2015

(54) 1-ARYL-3-AZABICYCLO[3.1.0]HEXANES: PREPARATION AND USE TO TREAT NEUROPSYCHIATRIC DISORDERS

(71) Applicant: NEUROVANCE, INC., Cambridge, MA (US)

(72) Inventors: Phil Skolnick, Edgewater, NJ (US); Anthony Basile, Hoboken, NJ (US); Zhengming Chen, Belle Meade, NJ (US); Joseph W. Epstein, Monroe, NY (US)

(73) Assignee: Neurovance, Inc., Cambridge, MA (US)

( * ) Notice: Subject to any disclaimer, the term of this patent is extended or adjusted under 35 U.S.C. 154(b) by 0 days.

(21) Appl. No.: 14/494,512

(22) Filed: Sep. 23, 2014

(65) Prior Publication Data

US 2015/0148399 A1 May 28, 2015

Related U.S. Application Data

(63) Continuation of application No. 13/887,367, filed on May 5, 2013, now Pat. No. 8,877,798, which is a continuation of application No. 13/366,219, filed on Feb. 3, 2012, now Pat. No. 8,461,196, which is a continuation of application No. 13/207,199, filed on Aug. 10, 2011, now abandoned, which is a continuation of application No. 12/334,432, filed on Dec. 12, 2008, now abandoned, which is a continuation of application No. 11/493,431, filed on Jul. 25, 2006, now abandoned.

(60) Provisional application No. 60/703,364, filed on Jul. 27, 2005.

(51) Int. Cl.
*A61K 31/403* (2006.01)
*C07D 209/52* (2006.01)

(52) U.S. Cl.
CPC ............ *A61K 31/403* (2013.01); *C07D 209/52* (2013.01)

(58) Field of Classification Search
CPC .................................................. A61K 31/403
See application file for complete search history.

(56) References Cited

U.S. PATENT DOCUMENTS

| | | |
|---|---|---|
| 3,892,722 A | 7/1975 | Babitsky et al. |
| 4,022,652 A | 5/1977 | Hirano et al. |
| 4,088,652 A | 5/1978 | Fanshawe et al. |
| 4,118,393 A | 10/1978 | Fanshawe et al. |
| 4,118,417 A | 10/1978 | Epstein |
| 4,122,193 A | 10/1978 | Scherm et al. |
| 4,131,611 A | 12/1978 | Fanshawe et al. |
| 4,196,120 A | 4/1980 | Fanshawe et al. |
| 4,231,935 A | 11/1980 | Fanshawe et al. |
| 4,336,268 A | 6/1982 | Bruderer et al. |
| 4,431,661 A | 2/1984 | McKenzie et al. |
| 4,435,419 A | 3/1984 | Epstein et al. |
| 4,467,102 A | 8/1984 | Toda et al. |
| 4,504,657 A | 3/1985 | Bouzard et al. |
| 4,521,431 A | 6/1985 | Crookes |
| 4,591,598 A | 5/1986 | Urbach et al. |
| 5,039,680 A | 8/1991 | Imperato et al. |
| 5,075,341 A | 12/1991 | Mendelson et al. |
| 5,130,430 A | 7/1992 | Shaw |
| 5,198,459 A | 3/1993 | Imperato et al. |
| 5,204,366 A | 4/1993 | Lavanish et al. |
| 5,232,934 A | 8/1993 | Downs |
| 5,488,056 A | 1/1996 | Bodick et al. |
| 5,556,837 A | 9/1996 | Nestler et al. |
| 5,556,838 A | 9/1996 | Mayer et al. |
| 5,574,052 A | 11/1996 | Rose et al. |
| 5,672,360 A | 9/1997 | Sackler et al. |
| 5,762,925 A | 6/1998 | Sagen |
| 5,905,154 A | 5/1999 | Kremer et al. |
| 5,911,992 A | 6/1999 | Braswell et al. |
| 5,916,920 A | 6/1999 | Fernandez et al. |
| 5,969,156 A | 10/1999 | Briggs et al. |
| 5,985,864 A | 11/1999 | Imai et al. |
| 6,109,269 A | 8/2000 | Rise et al. |
| 6,121,261 A | 9/2000 | Glatt et al. |
| 6,132,724 A | 10/2000 | Blum |
| 6,194,000 B1 | 2/2001 | Smith et al. |
| 6,204,284 B1 | 3/2001 | Beer et al. |
| 6,245,357 B1 | 6/2001 | Edgren et al. |
| 6,245,911 B1 | 6/2001 | Imai et al. |
| 6,268,507 B1 | 7/2001 | Massey et al. |
| 6,372,919 B1 | 4/2002 | Lippa et al. |
| 6,569,887 B2 | 5/2003 | Lippa et al. |
| 6,716,868 B2 | 4/2004 | Lippa et al. |

(Continued)

FOREIGN PATENT DOCUMENTS

AU 519620 B2 12/1981
BE 858683 A1 3/1978

(Continued)

OTHER PUBLICATIONS

U.S. Appl. No. 60/661,662, filed Mar. 8, 2005, Skolnick et al.
U.S. Appl. No. 60/701,562, filed Jul. 22, 2005, Skolnick et al.
U.S. Appl. No. 60/702,880, filed Jul. 26, 2005, Lippa et al.
Armarego, W. et al., "Quinazolines. Part XVIII. A Second Stereospecific *cis*-Addition of the Elements of Nitromethane across a Tetrasubstituted Ethylenic Double Bond. A Concerted Mechanism for the Reaction of Nitroacetic Acid with Enamines," Journal of the Chemical Society (C), 1971, 19, 3222-3229.
Baldessarini, R., "Drugs and the Treatment of Psychiatric Disorders" in Goodman and Gilman's The Pharmacological Basis of Therapeutics, Ninth Edition, J.G. Hardman et al., Eds., McGraw-Hill, New York, 1996, p. 399 and Chapter 18, pp. 431-459.
Bayes, M. et al., "Gateways to Clinical Trials," Methods and Findings in Experimental and Clinical Pharmacology, 2003, 25 (3), 225-248.
Beer, B. et al., "DOV 216,303, A 'Triple' Reuptake Inhibitor: Safety, Tolerability, and Pharmacokinetic Profile," The Journal of Clinical Pharmacology, 2004, 44 (12), 1360-1367.

(Continued)

*Primary Examiner* — Samantha Shterengarts
(74) *Attorney, Agent, or Firm* — Hoxie & Associates LLC

(57) ABSTRACT

The invention provides novel, multiply-substituted 1-aryl-3-azabicyclo[3.1.0]hexanes, and related processes and intermediates for preparing these compounds, as well as compositions and methods employing these compounds for the treatment and/or prevention of central nervous system (CNS) disorders, including depression and anxiety.

24 Claims, No Drawings

(56) References Cited

U.S. PATENT DOCUMENTS

| | | | |
|---|---|---|---|
| 7,041,835 | B2 | 5/2006 | Lippa et al. |
| 7,081,471 | B2 | 7/2006 | Lippa et al. |
| 7,094,799 | B2 | 8/2006 | Russell et al. |
| 7,098,229 | B2 | 8/2006 | Lippa et al. |
| 7,098,230 | B2 | 8/2006 | Lippa et al. |
| 7,378,419 | B2 | 5/2008 | Monneret et al. |
| 2003/0045567 | A1 | 3/2003 | Lippa et al. |
| 2004/0122017 | A1 | 6/2004 | Clader et al. |
| 2004/0127541 | A1 | 7/2004 | Codd et al. |
| 2006/0223875 | A1 | 10/2006 | Skolnick et al. |
| 2007/0082939 | A1 | 4/2007 | Lippa et al. |
| 2008/0058535 | A1 | 3/2008 | Chen et al. |
| 2008/0269348 | A1 | 10/2008 | Skolnick et al. |
| 2008/0293822 | A1 | 11/2008 | Skolnick et al. |
| 2014/0206740 | A1 | 7/2014 | McKinney et al. |

FOREIGN PATENT DOCUMENTS

| | | | |
|---|---|---|---|
| BE | 893707 | A1 | 12/1982 |
| EP | 0100426 | A1 | 2/1984 |
| FR | 2 859 208 | A1 | 3/2005 |
| JP | S53-37656 | A | 4/1978 |
| JP | S58-13568 | A | 1/1983 |
| JP | 2007-523208 | A | 8/2007 |
| JP | 2009-502798 | A | 1/2009 |
| PL | 120 095 | B2 | 2/1982 |
| WO | WO 03/047568 | A1 | 6/2003 |
| WO | WO 2005/080382 | A1 | 9/2005 |
| WO | WO 2006/023659 | A2 | 3/2006 |
| WO | WO 2006/096810 | A2 | 9/2006 |
| WO | WO 2006/108701 | A1 | 10/2006 |
| WO | WO 2006/136223 | A1 | 12/2006 |
| WO | WO 2007/013936 | A2 | 2/2007 |
| WO | WO 2007/014264 | A2 | 2/2007 |
| WO | WO 2007/016155 | A2 | 2/2007 |
| WO | WO 2007/022933 | A1 | 3/2007 |
| WO | WO 2007/022934 | A2 | 3/2007 |
| WO | WO 2007/022935 | A1 | 3/2007 |
| WO | WO 2007/022980 | A1 | 3/2007 |
| WO | WO 2008/013856 | A2 | 1/2008 |
| WO | WO 2013/019271 | A1 | 2/2013 |

OTHER PUBLICATIONS

Blum, K. et al., "Dopamine D2 Receptor Gene Variants: Association and Linkage Studies in Impulsive-Addictive-Compulsive Behaviour," Pharmacogenetics, 1995, 5 (3), 121-141.

Bray, G., "A Concise Review on the Therapeutics of Obesity," Nutrition, 2000, 16 (10), 953-960.

Byrn, S. et al., Hydrates and Solvates in Solid-State Chemistry of Drugs, Second Edition, 1999, Chapter 11, pp. 233-247.

Caira, M., "Crystalline Polymorphism of Organic Compounds," Topics in Current Chemistry, 1998, 198, 163-208.

Casadio, S. et al., "Acide Phenyl-1-Hydroxymethyl-2-Cyclopropane Carboxylique Et Derives," Bollettino Chimico Farmaceutico, 1978, 117, 331-342.

Crown, W., "Economic Outcomes Associated with Tricyclic Antidepressant and Selective Serotonin Reuptake Inhibitor Treatments for Depression," Acta Psychiatrica Scandinavica Supplementum, 2000, 403, 62-66.

Czobor, P., "A Double-Blind, Placebo Controlled Randomized Study of DOV 220,075 (Bicifadine) SR and Codeine 60 mg in the Treatment of Post-Operative Dental Pain," American Pain Society 2003, Abstract (915).

Czobor, P., "A Two Center Double-Blind Placebo-Controlled Randomized Study of DOV 220,075 (Bicifadine) SR and Tramadol 100 mg in the Treatment of Post-Operative Dental Pain," American Pain Society, 2004, Abstract (801).

D'Aquila, P.S. et al., "The Role of Dopamine in the Mechanism of Action of Antidepressant Drugs," European Journal of Pharmacology, 2000, 405 (1-3), 365-373.

Davis, P. et al., "Inhibitors of Protein Kinase C. 1. 2,3-Bisarylmaleimides," Journal of Medicinal Chemistry, 1992, 35 (1), 177-184.

Epstein, J. et al., "1-Aryl-3-azabicyclo[3.1.0]hexanes, A New Series of Nonnarcotic Analgesic Agents," Journal of Medicinal Chemistry, 1981, 24 (5), 481-490.

Epstein, J. et al., "Bicifadine: Non-Narcotic Analgesic Activity of 1-Aryl-3-Azabicycl[3.1.0]Hexanes," NIDA Research Monograph, 1982, 41, 93-98.

Ettmayer, P. et al., "Lessons Learned from Marketed and Investigational Prodrugs," Journal of Medicinal Chemistry, 2004, 47 (10), 2393-2404.

Fauci, A. et al., Eds., Harrison's Principles of Internal Medicine, Fourteenth Edition, 1998, pp. 2485-2503.

Frazer, A., "Norepinephrine Involvement in Antidepressant Action," Journal of Clinical Psychiatry, 2000, 61 (Suppl. 10), 25-30.

Fredman, S. et al., "Partial Response, Nonresponse, and Relapse with Selective Serotonin Reuptake Inhibitors in Major Depression: A Survey of Current 'Next-Step' Practices," Journal of Clinical Psychiatry, 2000, 61 (6), 403-408.

Grant, J., Ed., Hackh's Chemical Dictionary, Fourth Edition, McGraw-Hill Book Company, New York, 1969, pp. 474-475.

Hitri, A. et al., "Molecular, Functional and Biochemical Characteristics of the Dopamine Transporter: Regional Differences and Clinical Relevance," Clinical Neuropharmacology, 1994, 17 (1), 1-22.

Hoffman, B. et al., "Localization and Dynamic Regulation of Biogenic Amine Transporters in the Mammalian Central Nervous System," Frontiers in Neuroendocrinology, 1998, 19 (3), 187-231.

International Preliminary Report on Patentability for International Application No. PCT/US2006/029006, Date of issuance of the report Jan. 29, 2008, 5 pages.

International Search Report mailed Sep. 24, 2007, for International Application No. PCT/US2006/029006, 2 pages.

Janowsky, A. et al., "Characterization of Sodium-Dependent [$^3$H]GBR-12935 Binding in Brain: A Radioligand for Selective Labelling of the Dopamine Transport Complex," Journal of Neurochemistry, 1986, 46 (4), 1272-1276.

Kiyatkin, E., "Dopamine Mechanisms of Cocaine Addiction," The International Journal of Neuroscience, 1994, 78 (1-2), 75-101.

Kozma, D. et al., "Optical Resolution in Two Immiscible Solvents in the Presence of an Intermediate Solvent. Optical Resolution of N-methyl-amphetamine by O,O'-Dibenzoyl-R,R-tartartic Acid in Dichloroethane-Water-Methanol Solvent System," Synthetic Communications, 1999, 29 (24), 4315-4319.

Kreek, M., "Cocaine, Dopamine and the Endogenous Opiod System," Journal of Addictive Diseases, 1996, 15(14), 73-96.

Leonhardt, M. et al., "New Approaches in the Pharmacological Treatment of Obesity," European Journal of Nutrition, 1999, 38 (1), 1-13.

Lima, L. et al., "Bioisosterism: A Useful Strategy for Molecular Modification and Drug Design," Current Medicinal Chemistry, 2005, 12 (1), 23-49.

Marrazzo, A. et al., "1-Phenyl-3-azabicyclo[3.1.0]hexane Derivatives as New Ligands for Sigma Receptors," Arkivoc, 2004, 5, 156-169.

McArdle, P. et al., "A Method for the Prediction of the Crystal Structure of Ionic Organic Compounds—The Crystal Structures of O-Toluidinium Chlorid and Bromide and Polymorphism of Bicifadine Hydrochloride," CrystEngComm, 2004, 6 (53), 303-309.

McBriar, M. et al., "Discovery of Bicycloalkyl Urea Melanin Concentrating Hormone Receptor Antagonists: Orally Efficacious Antiobesity Therapeutics," Journal of Medicinal Chemistry, 2005, 48 (7), 2274-2277.

McBriar, M. et al., "Discovery of Orally Efficacious Melanin-Concentrating Hormone Receptor01 Antagonists as Antiobesity Agents. Synthesis, SAR, and Biological Evaluation of Bicyclo[3.1.0]hexyl Ureas," Journal of Medicinal Chemistry, 2006, 49 (7), 2294-2310.

McMillen, B. et al., "Effect of DOV 102,677 on the Volitional Consumption of Ethanol by Myers' High Ethanol-Preferring Rat," Alcoholism, Clinical and Experimental Research, 2007, 31 (11), 1866-1871.

Meyerson, L. et al., "Allosteric Interaction Between the Site Labeled by [$^3$H]Imipramine and the Serotonin Transporter in Human Platelets," Journal of Neurochemistry, 2006, 48 (2), 560-565.

Micheli, F. et al., "1-(Aryl)-6-[alkoxyalkyl]-3-azabicyclo[3.1.0]hexanes and 6-(Aryl)-6-[alkoxyalky]-3-azabicyclo[3.1.

(56) References Cited

OTHER PUBLICATIONS

0]hexanes: A New Series of Potent and Selective Triple Reuptake Inhibitors," Journal of Medicinal Chemistry, 2010, 53 (6), 2534-2551.
Mouzin, G. et al., "A Convenient Synthesis of Bifunctional Vicinal Cyclopropanes," Synthesis, 1978, 4, 304-305.
Nagatsu, T. et al., "Changes in Cytokines and Neurotrophins in Parkinson's Disease," Journal of Neural Transmission. Supplementa, 2000, 60, 277-290.
Noble, E., "Polymorphisms of the D2 Dopamine Receptor Gene and Alcoholism and Other Substance Use Disorders," Alcohol and Alcoholism—Supplements, 1994, 2, 35-43.
"Pain Therapeutics Takes Different Path, Improving Long-term Pain Relief by Reducing Dependency and Tolerance," Genetic Engineering and Biotechnology News, 2006, 26 (12), 2 pages.
Perovic, S. et al., "Pharmacological Profile of Hypericum Extract, Effect of Serotonin Uptake by Postsynaptic Receptors," Arzneimittel Forschung / Drug Research, 1995, 45 (II), 11, 1145-1148.
Porter, E., "Single Dose Comparison of Bicifadine, Codeine, and Placebo in Postoperative Pain," Current Therapeutic Research, 1981, 30 (3), 156-160.
Rondestvedt, C. et al., "Arylation of Unsaturated Systems by Free Radicals. VII. The Meerwein Reaction. V. Further Arylations of Maleimides. Ultraviolet Spectra of Arylmaleimides, Arylmaleic Anhydrides and Arylmaleo- and Fumaronitriles," Journal of the American Chemical Society, 1956, 78, 6115-6120.
Rouhi, A., "The Right Stuff, From Research and Development to the Clinic, Getting Drug Crystals Right is Full of Pitfalls," Chemical and Engineering News, 2003, 81 (8), 32-35.
Scates, A. et al., "Reboxetine: A Selective Neorepinephrine Reuptake Inhibitor for the Treatment of Depression," The Annals of Pharmacotherapy, 2000, 34 (11), 1302-1312.
Shuto, S. et al., "Synthesis of (+)- and (−)-Milnaciprans and Their Conformationally Restricted Analogs," Tetrahedron Letters, 1996, 37 (5), 641-644.
Simon, G. et al., "TCAs or SSRIs as Initial Therapy for Depression," Journal of Family Practice, 1999, 48, 845-846.
Skolnick, P., "Beyond Monoamine-Based Therapies: Clues to New Approaches," Journal of Clinical Psychiatry, 2002, 63 (Suppl. 2), 19-23.
Skolnick, P. et al., "Antidepressant-like Actions of DOV 21,947, A 'Triple' Uptake Inhibitor," European Journal of Pharmacology, 2003, 461, 99-104.
Skolnick, P. et al., "'Broad Spectrum' Antidepressants: Is More Better for the Treatment of Depression," Life Sciences, 2003, 73 (25), 3175-3179.
Stacy, M. et al., "Treatment Options for Early Parkinson's Disease," American Family Physician, 1996, 53 (4), 1281-1287.
Stella, V., "Prodrugs as Therapeutics," Expert Opinion on Therapeutic Patents, 2004, 14 (3), 277-280.
Sullivan, A. et al., "Mechanisms of Appetite Modulation by Drugs," Federation Proceedings, 1985, 44 (1 Pt. 1), 139-144.
Taylor, A. et al., "Scales for the Identification of Adults with Attention Deficit Hyperactivity Disorder (ADHD): A Systematic Review," Research in Developmental Disabilities, 2011, 32 (3), 924-938.
Testa, B., "Prodrug Research: Futile or Fertile," Biochemical Pharmacology, 2004, 68 (11), 2097-2106.
Theeuwes, F., "Drug Delivery Fuels Specialty Pharma, Rich Source of Innovation Now Significant Platform to Launch New Companies," Genetic Engineering and Biotechnology News, 2007, 27 (10), 2 pages.
Tominaga, Y. et al., "Synthesis of Methylthiomaleimides for the Preparation of Pyridazines and Related Compounds," Journal of Heterocyclic Chemistry, 2002, 39 (3), 571-591.
Vilsmaier, E. et al., "Functionalized Chloroenamines in Aminocyclopropane Synthesis III. Synthesis and Assignment of Configuration of Two Isomeric Morpholinobicyclo[3.1.0]hexane Derivatives," Tetrahedron, 1989, 45 (12), 3683-3694.
Vippagunta, S. et al., "Crystalline Solids," Advanced Drug Delivery Reviews, 2001, 48 (1), 3-26.
Wang, R. et al., "The Oral Analgesic Efficacy of Bicifadine Hydrochloride in Postopeartive Pain," The Journal of Clinical Pharmacology, 1982, 22 (4), 160-164.
Wong, E. et al., "Reboxetine: A Pharmacologically Potent, Selective, and Specific Norepinephrine Reuptake Inhibitor," Biological Psychiatry, 2000, 47 (9), 818-829.
Xu, F. et al., "Stereocontrolled Synthesis of Trisubstituted Cyclopropanes: Expedient, Atom-Economical, Asymmetric Syntheses of (+)-Bicifadine and DOV21947," Organic Letters, 2006, 8 (17), 3885-3888.
Xu, F. et al., Supporting Information for "Stereocontrolled Synthesis of Trisubstituted Cyclopropanes: Expedient, Atom-Economical, Asymmetric Syntheses of (+)-Bicifadine and DOV21947," Organic Letters, 2006, S1-S14, available at: http://pubs.acs.org/doi/suppl/10.1021/o1061650w.
Xu, F. et al., "Chlorination/Cyclodehydration of Amino Alcohols with $SOCl_2$: An Old Reaction Revisited," Journal of Organic Chemistry, 2008, 73, 312-315.
Xu, F. et al., Supporting Information for "Chlorination/Cyclodehydration of Amino Alcohols with $SOCl_2$: An Old Reaction Revisited," Journal of Organic Chemistry, 2008, S1-S32, available at: http://pubs.acs.org/doi/suppl/10.1021/jo701877h.
Yuki, H. et al., "Studies on Antiviral Agents. II. Synthesis and Biological Activity of Maleimide Derivatives," Chemical and Pharmaceutical Bulletin, 1967, 15 (8), 1101-1106.
Zhang, M. et al., "Studies on the Structure-Activity Relationship of Bicifadine Analogs as Monoamine Transporter Inhibitors," Bioorganic and Chemistry Letters, 2008, 18 (13), 3682-3686.
Morissette, S. et al., "High-Throughput Crystallization: Polymorphs, Salts, Co-Crystals and Solvates of Pharmaceutical Solids," Advanced Drug Delivery Reviews, 2004, 56 (3), 275-300.
Wolff, M., Ed., Burger's Medicinal Chemistry and Drug Discovery, Fifth Edition, vol. 1, 1995, pp. 975-977.
Requirement for Restriction/Election issued May 12, 2014, in U.S. Appl. No. 13/907,921, 9 pages.
Response to Restriction Requirement filed Sep. 12, 2014, in U.S. Appl. No. 13/907,921, 7 pages.
Non-Final Office Action issued Dec. 1, 2014, in U.S. Appl. No. 13/907,921, 8 pages.
Reply to Office Action filed Jun. 1, 2015, in U.S. Appl. No. 13/907,921, 11 pages.

1-ARYL-3-AZABICYCLO[3.1.0]HEXANES: PREPARATION AND USE TO TREAT NEUROPSYCHIATRIC DISORDERS

REFERENCE TO RELATED APPLICATION

This application claims priority as a continuation of prior application United States latent application Ser. No. 13/887,367 filed May 5, 2013 which is a continuation of United States patent application Ser. No. 13/366,219 filed Feb. 3, 2012 now issued as U.S. Pat. No. 8,461,196, which is a continuation of United States patent application Ser. No. 13/207,199 filed Aug. 10, 2011 which is a continuation of U.S. patent application Ser. No. 12/334,432, filed Dec. 12, 2008, which is a continuation of U.S. patent application Ser. No. 11/493,431, filed Jul. 25, 2006, which claims the benefit of U.S. Provisional Application 60/703,364 filed on Jul. 27, 2005, the disclosures of each of which are incorporated herein by reference in their entireties.

TECHNICAL FIELD

The present invention relates to novel 1-aryl-3-azabicyclo[3.1.0]hexanes, intermediates and methods for the production thereof, and their use for treating disorders of the central nervous system (CNS), including neuropsychiatric disorders.

BACKGROUND OF THE INVENTION 1-(3,4-dichlorophenyl)-3-azabicyclo[3.1.0]hexane has been reported to inhibit reuptake of norepinephrine, serotonin and dopamine—three biogenic amines that have been implicated in a wide variety of neuropsychiatric disorders ranging from anxiety and depression to eating disorders and drug addiction. One potential use of 1-(3,4-dichlorophenyl)-3-azabicyclo[3.1.0]hexane is as an antidepressant. The ability of this compound to inhibit reuptake of three biogenic amines closely linked to depression suggests a possible use of the compound as a "broad spectrum antidepressant." In this context, compounds having such activity may yield a more rapid onset and/or higher efficacy of antidepressant activity than currently available antidepressants, including agents that inhibit single or dual reuptake of serotonin and/or norepinephrine [Skolnick, P. et al., Eur. J. Pharmacol. 461: 99 (2003); Skolnick, P. et al., Life Sci. 73: 3175-3179, (2003)].

In view of the limited availability and understanding of currently-known "broad spectrum antidepressants," there remains a compelling need in the art to identify additional drugs having multiple reuptake inhibitory potential for inhibiting reuptake of multiple biogenic amines linked to disorders of the central nervous system (CNS), including neuropsychiatric disorders, such as depression and anxiety.

SUMMARY OF EXEMPLARY EMBODIMENTS OF THE INVENTION

It is therefore an object of the present invention to provide novel compounds having activity to inhibit reuptake of multiple biogenic amines linked to CNS disorders, and to provide related compositions, and methods for treating and managing CNS disorders, including depression and anxiety.

It is a further object of the present invention to produce and select novel 1-aryl-3-azabicyclo[3.1.0]hexanes as therapeutic agents.

It is another object of the invention to provide new synthetic methods and compositions useful for producing 1-aryl-3-azabicyclo[3.1.0]hexanes and related compounds.

It is an additional object of the invention to provide novel 1-aryl-3-azabicyclo[3.1.0]hexane compositions and methods useful to treat or manage CNS disorders by modulating transport of one or more biogenic amines, for example to simultaneously inhibit or block reuptake of norepinephrine and/or serotonin and/or dopamine.

The invention achieves these objects and satisfies additional objects and advantages by providing novel 1-aryl-3-azabicyclo[3.1.0]hexanes that possess unexpected activities for modulating biogenic amine transport.

In certain embodiments of the invention, novel 1-aryl-3-azabicyclo[3.1.0]hexanes are provided that have at least two substituents on the aryl ring.

In other embodiments of the invention, novel 1-aryl-3-azabicyclo[3.1.0]hexanes are provided that are substituted with a napthyl group on the nitrogen at the '3' position.

In exemplary embodiments, novel 1-aryl-3-azabicyclo[3.1.0]hexanes of the invention are provided having the following formula I:

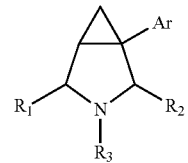

Formula 1 and enantiomers and pharmaceutically acceptable salts thereof, wherein:

Ar is a phenyl group substituted with two substituents independently selected from halogen, $C_{1-3}$ alkyl, $C_{2-4}$ alkenyl, $C_{2-4}$ alkynyl, halo($C_{1-3}$)alkyl, cyano, hydroxy, $C_{3-5}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxy, nitro, amino, $C_{1-3}$ alkylamino, and di($C_{1-3}$)alkylamino;

$R_1$ and $R_2$ are independently selected from hydrogen, unsubstituted $C_{1-10}$ alkyl, $C_{3-10}$ alkenyl and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy; and $R_3$ is selected from hydrogen, $C_{1-6}$ alkyl, $C_{1-6}$ alkoxycarbonyl, $C_{2-6}$ alkanoyl, $C_{3-8}$ cycloalkyl, $C_{4-9}$ cycloalkanoyl, aryl, heteroaryl, saturated heterocyclic, $C_{2-10}$ alkenyl, $C_{2-10}$ alkynyl, and substituted $C_{1-6}$ alkyl, $C_{2-10}$ alkenyl and $C_{2-10}$ alkynyl wherein the substituent is one or more of cyano, halogen, hydroxy, $C_{1-6}$ alkoxy, $C_{1-6}$ alkoxycarbonyl, $C_{2-6}$ alkyloxycarbonyloxy, $C_{1-6}$ alkanoyl, $C_{1-6}$ alkanoyloxy, $C_{3-8}$ cycloalkyl, $C_{3-8}$ cycloalkyloxy, $C_{4-9}$ cycloalkanoyl, aryl, aryloxy, heteroaryl and saturated heterocyclic; with the proviso that when Ar is 3,4-dichlorophenyl, $R_3$ cannot be hydrogen.

In further embodiments, the invention provides compounds of the following formula II:

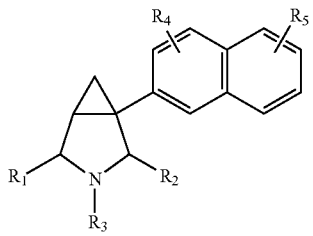

Formula II and enantiomers and pharmaceutically acceptable salts thereof, wherein: $R_1$ and $R_2$ are independently selected from hydrogen, unsubstituted $C_{1-10}$ alkyl, $C_{3-10}$ alkenyl and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy;

$R_3$ is selected from hydrogen, $C_{1-6}$ alkyl, $C_{1-6}$ alkoxycarbonyl, $C_{2-6}$ alkanoyl, $C_{3-8}$ cycloalkyl, $C_{4-9}$ cycloalkanoyl, aryl, heteroaryl, saturated heterocyclic, $C_{2-10}$ alkenyl, $C_{2-10}$ alkynyl, and substituted $C_{1-6}$ alkyl, $C_{2-10}$ alkenyl and $C_{2-10}$ alkynyl wherein the substituent is one or more of cyano, halogen, hydroxy, $C_{1-6}$ alkoxy, $C_{1-6}$ alkoxycarbonyl, $C_{2-6}$ alkyloxycarbonyloxy, $C_{1-6}$ alkanoyl, $C_{1-6}$ alkanoyloxy, $C_{3-8}$ cycloalkyl, $C_{3-8}$ cycloalkyloxy, $C_{4-9}$ cycloalkanoyl, aryl, aryloxy, heteroaryl and saturated heterocyclic; and $R_4$ and $R_5$ are independently hydrogen or 1-4 substituents independently selected from halogen, $C_{1-3}$ alkyl, $C_{2-4}$ alkenyl, $C_{2-4}$ alkynyl, halo($C_{1-3}$)alkyl, cyano, hydroxy, $C_{3-5}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxy, nitro, amino, $C_{1-3}$ alkylamino, and di($C_{1-3}$)alkylamino.

In additional embodiments, the invention provides compounds of the following formula III:

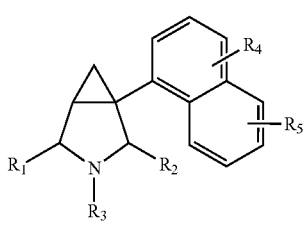

Formula III and enantiomers and pharmaceutically acceptable salts thereof, wherein:

$R_1$ and $R_2$ are independently selected from hydrogen, unsubstituted $C_{1-10}$ alkyl, $C_{3-10}$ alkenyl and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy;

$R_3$ is selected from hydrogen, $C_{1-6}$ alkyl, $C_{1-6}$ alkoxycarbonyl, $C_{2-6}$ alkanoyl, $C_{3-8}$ cycloalkyl, $C_{4-9}$ cycloalkanoyl, aryl, heteroaryl, saturated heterocyclic, $C_{2-10}$ alkenyl, to alkynyl, and substituted $C_{1-6}$ alkyl, $C_{2-10}$ alkenyl and $C_{2-10}$ alkynyl wherein the substituent is one or more of cyano, halogen, hydroxy, $C_{1-6}$ alkoxy, $C_{1-6}$ alkoxycarbonyl, $C_{2-6}$ alkyloxycarbonyloxy, $C_{1-6}$ alkanoyl, $C_{1-6}$ alkanoyloxy, $C_{3-8}$ cycloalkyl, $C_{3-8}$ cycloalkyloxy, $C_{4-9}$ cycloalkanoyl, aryl, aryloxy, heteroaryl and saturated heterocyclic; and $R_4$ and $R_5$ are independently hydrogen or 1-4 substituents independently selected from halogen, $C_{1-3}$ alkyl, $C_{2-4}$ alkenyl, $C_{2-4}$ alkynyl, halo($C_{1-3}$)alkyl, cyano, hydroxy, $C_{3-5}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxy, nitro, amino, $C_{1-3}$ alkylamino, and di($C_{1-3}$)alkylamino.

Useful 1-aryl-3-azabicyclo[3.1.0]hexanes of the invention include the substituted 1-aryl-3-azabicyclo[3.1.0]hexanes compounds described herein, as well as their active, pharmaceutically acceptable salts, polymorphs, solvates, hydrates and or prodrugs, or combinations thereof.

The invention also provides novel methods of making 1-aryl-3-azabicyclo[3.1.0]hexanes, including synthetic methods that form novel intermediate compounds of the invention for producing 1-aryl-3-azabicyclo[3.1.0]hexanes. In related embodiments, the invention provides novel processes for preparing 1-aryl-3-azabicyclo[3.1.0]hexanes, to yield novel compounds useful in biologically active and/or therapeutic compositions.

In yet additional embodiments, the invention provides pharmaceutical compositions and methods for treating disorders of the central nervous system (CNS), including a wide array of serious neurological or psychiatric conditions, in mammals that are amenable to treatment using agents that inhibit or otherwise modulate biogenic amine transport.

The foregoing objects and additional objects, features, aspects and advantages of the present invention are further exemplified and described in the following detailed description.

DETAILED DESCRIPTION OF EXEMPLARY EMBODIMENTS OF THE INVENTION

The present invention fulfills these needs and satisfies additional objects and advantages by providing novel 1-aryl-3-azabicyclo[3.1.0]hexanes as therapeutic agents to treat and manage a wide variety of disorders of the central nervous system (CNS), including neuropsychiatric disorders. CNS disorders for treatment using the compositions and methods of the invention are amenable to treatment, prophylaxis, and/or alleviation of the disorder and/or associated symptom(s) by inhibiting reuptake of multiple biogenic amines causally linked to the targeted CNS disorder, wherein the biogenic amines targeted for reuptake inhibition are selected from norepinephrine, and/or serotonin, and/or dopamine. In exemplary embodiments, the novel compounds of the invention are employed in effective compositions and methods for treating a neuropsychiatric disorder, such as depression or anxiety.

In one embodiment, the invention provides compounds of the following formula I:

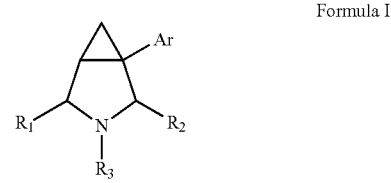

Formula I and enantiomers and pharmaceutically acceptable salts thereof, wherein:

Ar is a phenyl group substituted with two substituents independently selected from halogen, $C_{1-3}$ alkyl, $C_{2-4}$ alkenyl, $C_{2-4}$ alkynyl, halo($C_{1-3}$)alkyl, cyano, hydroxy, $C_{3-5}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxy, nitro, amino, $C_{1-3}$ alkylamino, and di($C_{1-3}$)alkylamino;

$R_1$ and $R_2$ are independently selected from hydrogen, unsubstituted $C_{1-10}$ alkyl, $C_{3-10}$ alkenyl and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy; and $R_3$ is selected from hydrogen, $C_{1-6}$ alkyl, $C_{1-6}$ alkoxycarbonyl, $C_{2-6}$ alkanoyl, $C_{3-8}$ cycloalkyl, $C_{4-9}$ cycloalkanoyl, aryl, heteroaryl, saturated heterocyclic, $C_{2-10}$ alkenyl, $C_{2-10}$ alkynyl, and substituted $C_{1-6}$ alkyl, $C_{2-10}$ alkenyl and $C_{2-10}$ alkynyl wherein the substituent is one or more of cyano, halogen, hydroxy, $C_{1-6}$ alkoxy, $C_{1-6}$ alkoxycarbonyl, $C_{2-6}$ alkyloxycarbonyloxy, $C_{1-6}$ alkanoyl, $C_{1-6}$ alkanoyloxy, $C_{3-8}$ cycloalkyl, $C_{3-8}$ cycloalkyloxy, $C_{4-9}$ cycloalkanoyl, aryl, aryloxy, heteroaryl and saturated heterocyclic; with the proviso that when Ar is 3,4-dichlorophenyl, $R_3$ cannot be hydrogen.

In certain embodiments, Ar is a phenyl group substituted with two substituents independently selected from methyl, ethyl, fluoro, chloro, trifluoromethyl, cyano, nitro, and trifluoromethoxy. In additional embodiments, $R_1$ and $R_2$ are hydrogen or methyl and $R_3$ is hydrogen, methyl, ethyl, propyl, isopropyl, butyl, isobutyl, tert-butyl or cyclopropyl.

In another embodiment, the invention provides compounds of the following formula II:

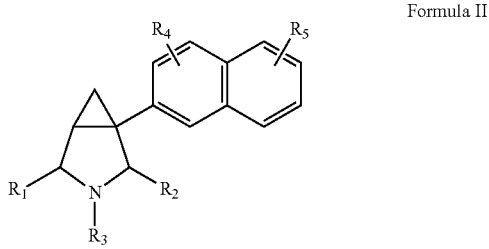

Formula II and enantiomers and pharmaceutically acceptable salts thereof, wherein:

$R_1$ and $R_2$ are independently selected from hydrogen, unsubstituted $C_{1-10}$ alkyl, $C_{3-10}$ alkenyl and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy;

$R_3$ is selected from hydrogen, $C_{1-6}$ alkyl, $C_{1-6}$ alkoxycarbonyl, $C_{2-6}$ alkanoyl, $C_{3-8}$ cycloalkyl, $C_{4-9}$ cycloalkanoyl, aryl, heteroaryl, saturated heterocyclic, $C_{2-10}$ alkenyl, $C_{2-10}$ alkynyl, and substituted $C_{1-6}$ alkyl, $C_{2-10}$ alkenyl and $C_{2-10}$ alkynyl wherein the substituent is one or more of cyano, halogen, hydroxy, $C_{1-6}$ alkoxy, $C_{1-5}$ alkoxycarbonyl, $C_{2-6}$ alkyloxycarbonyloxy, $C_{1-6}$ alkanoyl, $C_{1-6}$ alkanoyloxy, $C_{3-8}$ cycloalkyl, $C_{3-8}$ cycloalkyloxy, $C_{4-9}$ cycloalkanoyl, aryl, aryloxy, heteroaryl and saturated heterocyclic; and $R_4$ and $R_5$ are independently hydrogen or 1-4 substituents independently selected from halogen, $C_{1-3}$ alkyl, $C_{2-4}$ alkenyl, $C_{2-4}$ alkynyl, halo($C_{1-3}$)alkyl, cyano, hydroxy, $C_{3-5}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxy, nitro, amino, $C_{1-3}$ alkylamino, and di($C_{1-3}$)alkylamino.

In certain embodiments, $R_4$ and $R_5$ are independently hydrogen or 1-4 substituents independently selected from methyl, ethyl, fluoro, chloro, trifluoromethyl, cyano, nitro, methoxy, ethoxy and trifluoromethoxy. In additional embodiments, $R_1$ and $R_2$ are hydrogen, $R_3$ is hydrogen, methyl, ethyl or isopropyl and $R_4$ and $R_5$ are independently selected from hydrogen, methyl, chloro, fluoro, propyl, methoxy and ethoxy.

In a further embodiment, the invention provides compounds of the following formula III:

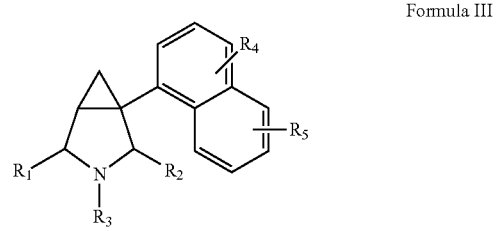

Formula III and enantiomers and pharmaceutically acceptable salts thereof, wherein: $R_1$ and $R_2$ are independently selected from hydrogen, unsubstituted $C_{1-10}$ alkyl, $C_{3-10}$ alkenyl and $C_{3-10}$ alkynyl, and substituted $C_{1-10}$ alkyl, $C_{3-10}$ alkenyl and $C_{3-10}$ alkynyl wherein the substituent is one or more of hydroxy, cyano, halogen, $C_{1-6}$ alkoxy, aryl substituted $C_{1-6}$ alkoxy, aryloxy, aryloxy substituted with one or more halogens, $C_{1-6}$ alkyl, $C_{1-6}$ alkyl independently substituted with one or more of cyano and halogen, $C_{1-4}$ alkoxy, and $C_{1-4}$ haloalkoxy;

$R_3$ is selected from hydrogen, $C_{1-6}$ alkyl, $C_{1-6}$ alkoxycarbonyl, $C_{2-6}$ alkanoyl, $C_{3-8}$ cycloalkyl, $C_{4-9}$ cycloalkanoyl, aryl, heteroaryl, saturated heterocyclic, $C_{2-10}$ alkenyl, $C_{2-10}$ alkynyl, and substituted $C_{1-6}$ alkyl, $C_{2-10}$ alkenyl and $C_{2-10}$ alkynyl wherein the substituent is one or more of cyano, halogen, hydroxy, $C_{1-6}$ alkoxy, $C_{1-6}$ alkoxycarbonyl, $C_{2-6}$ alkyloxycarbonyloxy, $C_{1-6}$ alkanoyl, $C_{1-6}$ alkanoyloxy, $C_{3-8}$ cycloalkyl, $C_{3-8}$ cycloalkyloxy, $C_{4-9}$ cycloalkanoyl, aryl, aryloxy, heteroaryl and saturated heterocyclic; and $R_4$ and $R_5$ are independently hydrogen or 1-4 substituents independently selected from halogen, $C_{1-3}$ alkyl, $C_{2-4}$ alkenyl, $C_{2-4}$ alkynyl, halo($C_{1-3}$)alkyl, cyano, hydroxy, $C_{3-5}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxy, nitro, amino, $C_{1-3}$ alkylamino, and di($C_{1-3}$)alkylamino.

In certain embodiments, $R_4$ and $R_5$ are independently hydrogen or 1-4 substituents independently selected from methyl, ethyl, fluoro, chloro, trifluoromethyl, cyano, nitro, methoxy, ethoxy and trifluoromethoxy. In additional embodiments, $R_1$ and $R_2$ are hydrogen, $R_3$ is hydrogen, methyl, ethyl or isopropyl and $R_4$ and $R_5$ are independently selected from hydrogen, methyl, chloro, fluoro, propyl, methoxy and ethoxy.

Within exemplary embodiments, the invention provides an assemblage of novel 1-aryl-3-azabicyclo[3.1.0]hexanes having multiple substitutions on the aryl ring. Novel, multiply aryl-substituted, 1-aryl-3-azabicyclo[3.1.0]hexanes of the invention include the following, exemplary compounds, which have been made and characterized as illustrative embodiments of the invention (Table 1).

TABLE 1

Exemplary 1-aryl-3-azabicyclo[3.1.0]hexanes having multiple substitutions on the aryl ring

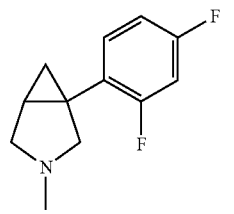

1-(2,4-difluorophenyl)-3-methyl-3-aza-bicyclo[3.1.0]hexane

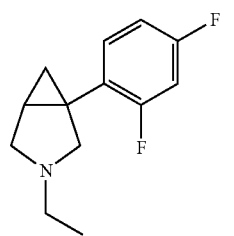 [SMILES: CCN1CC2CC2(c2ccc(F)cc2F)C1]

3-ethyl-1-(2,4-difluorophenyl)-3-aza-bicyclo[3.1.0]hexane

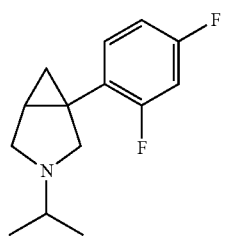 [SMILES: CC(C)N1CC2CC2(c2ccc(F)cc2F)C1]

1-(2,4-difluorophenyl)-3-isopropyl-3-aza-bicyclo[3.1.0]hexane

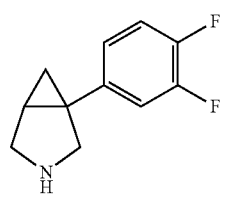 [SMILES: Fc1ccc(C23CNCC2C3)cc1F]

1-(3,4-difluorophenyl)-3-aza-bicyclo[3.1.0]hexane

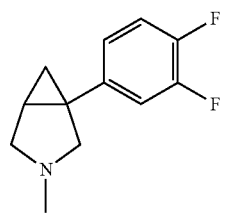

1-(3,4-difluorophenyl)-3-methyl-3-aza-bicyclo[3.1.0]hexane

TABLE 1-continued

Exemplary 1-aryl-3-azabicyclo[3.1.0]hexanes having multiple substitutions on the aryl ring

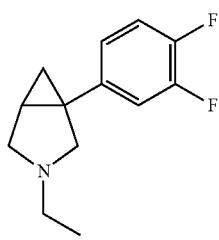

1-(3,4-difluorophenyl)-3-ethyl-3-aza-bicyclo[3.1.0]hexane

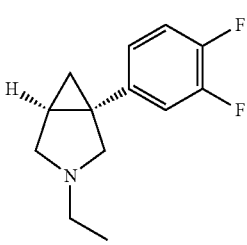 [SMILES: CCN1C[C@H]2C[C@@]2(c2ccc(F)c(F)c2)C1]

(1R,5S)-3-ethyl-1-(3,4-difluorophenyl)-3-aza-bicyclo[3.1.0]hexane

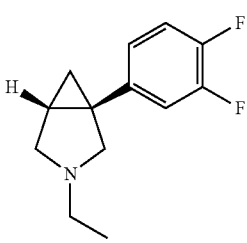 [SMILES: CCN1C[C@@H]2C[C@]2(c2ccc(F)c(F)c2)C1]

(1S,5R)-3-ethyl-1-(3,4-difluorophenyl)-3-aza-bicyclo[3.1.0]hexane

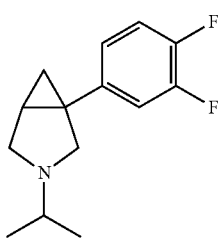 [SMILES: CC(C)N1CC2CC2(c2ccc(F)c(F)c2)C1]

1-(3,4-difluorophenyl)-3-isopropyl-3-aza-bicyclo[3.1.0]hexane

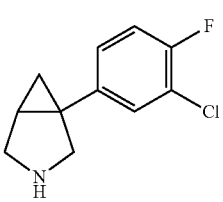 [SMILES: Fc1ccc(C23CNCC2C3)cc1Cl]

1-(3-chloro-4-fluorophenyl)-3-aza-bicyclo[3.1.0]hexane

TABLE 1-continued

Exemplary 1-aryl-3-azabicyclo[3.1.0]hexanes having multiple substitutions on the aryl ring

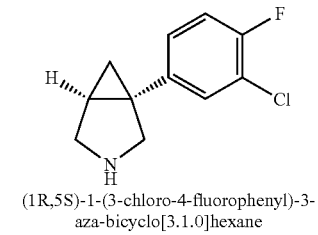

(1R,5S)-1-(3-chloro-4-fluorophenyl)-3-
aza-bicyclo[3.1.0]hexane

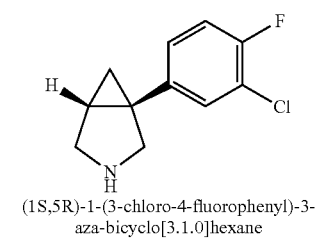

(1S,5R)-1-(3-chloro-4-fluorophenyl)-3-
aza-bicyclo[3.1.0]hexane

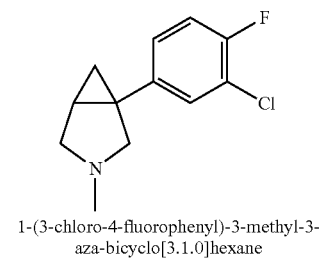

1-(3-chloro-4-fluorophenyl)-3-methyl-3-
aza-bicyclo[3.1.0]hexane

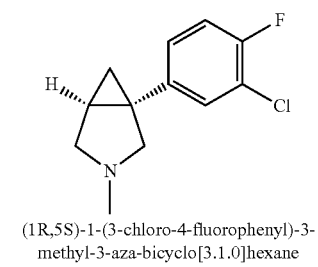

(1R,5S)-1-(3-chloro-4-fluorophenyl)-3-
methyl-3-aza-bicyclo[3.1.0]hexane

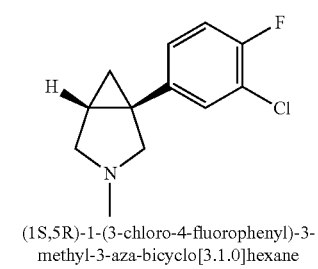

(1S,5R)-1-(3-chloro-4-fluorophenyl)-3-
methyl-3-aza-bicyclo[3.1.0]hexane

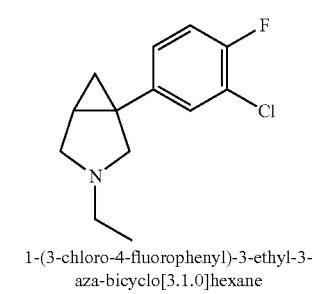

1-(3-chloro-4-fluorophenyl)-3-ethyl-3-
aza-bicyclo[3.1.0]hexane

TABLE 1-continued

Exemplary 1-aryl-3-azabicyclo[3.1.0]hexanes having multiple substitutions on the aryl ring

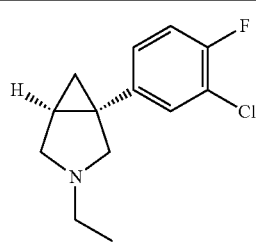

(1R,5S)-1-(3-chloro-4-fluorophenyl)-3-
ethyl-3-aza-bicyclo[3.1.0]hexane

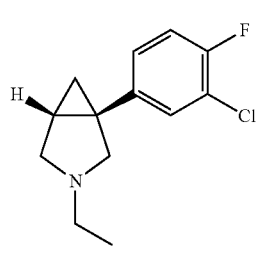 [SMILES: CCN1C[C@@H]2C[C@]2(c2ccc(F)c(Cl)c2)C1]

(1S,5R)-1-(3-chloro-4-fluorophenyl)-3-
ethyl-3-aza-bicyclo[3.1.0]hexane

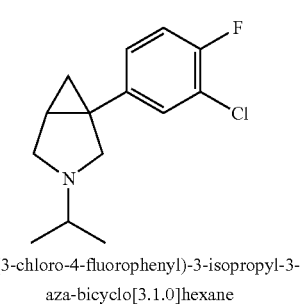

1-(3-chloro-4-fluorophenyl)-3-isopropyl-3-
aza-bicyclo[3.1.0]hexane

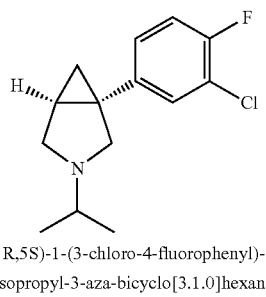

(1R,5S)-1-(3-chloro-4-fluorophenyl)-3-
isopropyl-3-aza-bicyclo[3.1.0]hexane

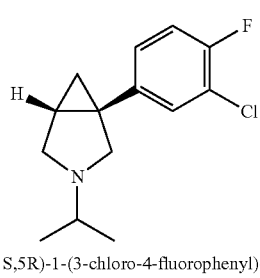

(1S,5R)-1-(3-chloro-4-fluorophenyl)-3-
isopropyl-3-aza-bicyclo[3.1.0]hexane

TABLE 1-continued

Exemplary 1-aryl-3-azabicyclo[3.1.0]hexanes having multiple substitutions on the aryl ring

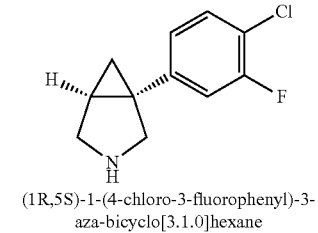

(1R,5S)-1-(4-chloro-3-fluorophenyl)-3-aza-bicyclo[3.1.0]hexane

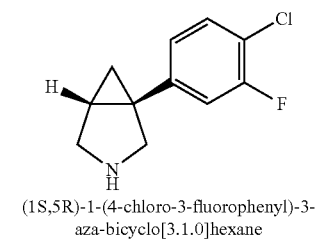

(1S,5R)-1-(4-chloro-3-fluorophenyl)-3-aza-bicyclo[3.1.0]hexane

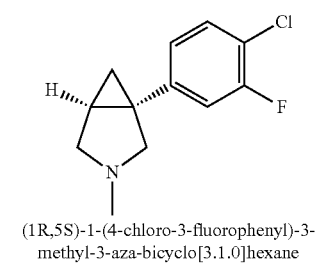

(1R,5S)-1-(4-chloro-3-fluorophenyl)-3-methyl-3-aza-bicyclo[3.1.0]hexane

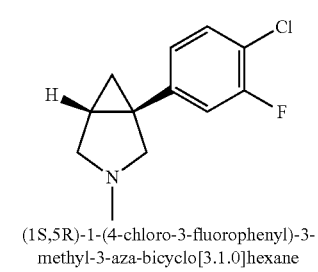

(1S,5R)-1-(4-chloro-3-fluorophenyl)-3-methyl-3-aza-bicyclo[3.1.0]hexane

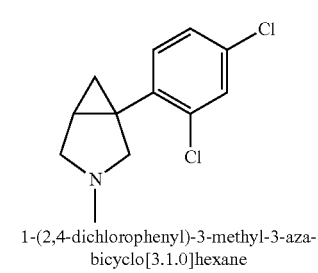

1-(2,4-dichlorophenyl)-3-methyl-3-aza-bicyclo[3.1.0]hexane

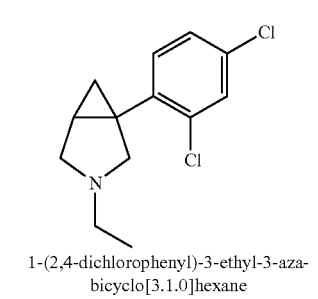

1-(2,4-dichlorophenyl)-3-ethyl-3-aza-bicyclo[3.1.0]hexane

TABLE 1-continued

Exemplary 1-aryl-3-azabicyclo[3.1.0]hexanes having multiple substitutions on the aryl ring

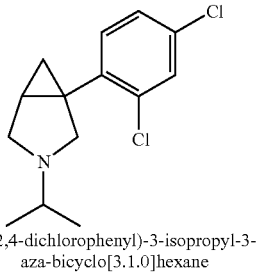

1-(2,4-dichlorophenyl)-3-isopropyl-3-aza-bicyclo[3.1.0]hexane

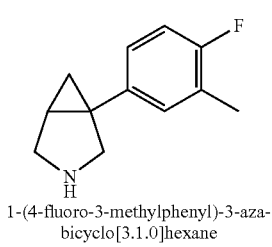

1-(4-fluoro-3-methylphenyl)-3-aza-bicyclo[3.1.0]hexane

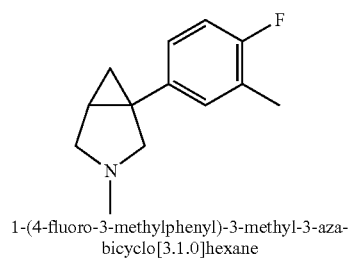

1-(4-fluoro-3-methylphenyl)-3-methyl-3-aza-bicyclo[3.1.0]hexane

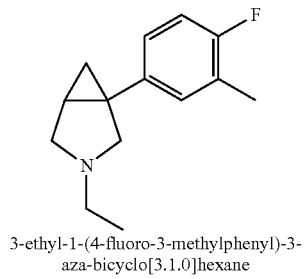

3-ethyl-1-(4-fluoro-3-methylphenyl)-3-aza-bicyclo[3.1.0]hexane

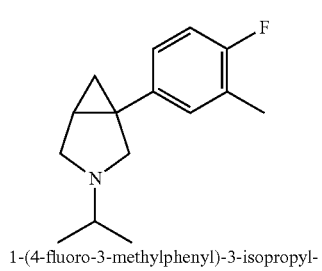

1-(4-fluoro-3-methylphenyl)-3-isopropyl-3-aza-bicyclo[3.1.0]hexane

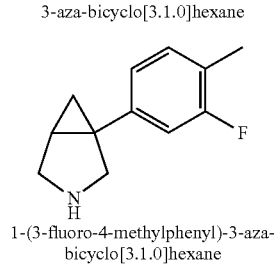

1-(3-fluoro-4-methylphenyl)-3-aza-bicyclo[3.1.0]hexane

TABLE 1-continued

Exemplary 1-aryl-3-azabicyclo[3.1.0]hexanes having multiple substitutions on the aryl ring

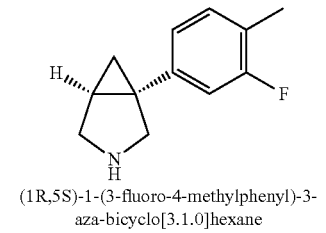

(1R,5S)-1-(3-fluoro-4-methylphenyl)-3-aza-bicyclo[3.1.0]hexane

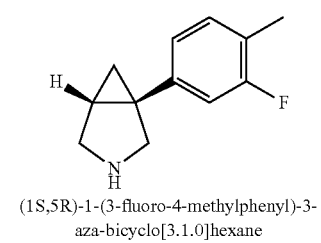

(1S,5R)-1-(3-fluoro-4-methylphenyl)-3-aza-bicyclo[3.1.0]hexane

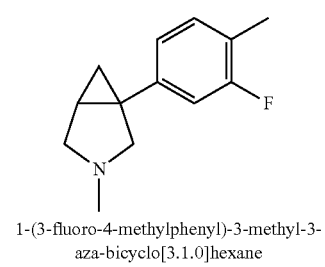

1-(3-fluoro-4-methylphenyl)-3-methyl-3-aza-bicyclo[3.1.0]hexane

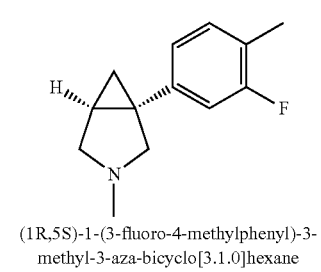

(1R,5S)-1-(3-fluoro-4-methylphenyl)-3-methyl-3-aza-bicyclo[3.1.0]hexane

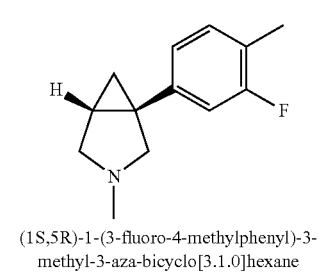

(1S,5R)-1-(3-fluoro-4-methylphenyl)-3-methyl-3-aza-bicyclo[3.1.0]hexane

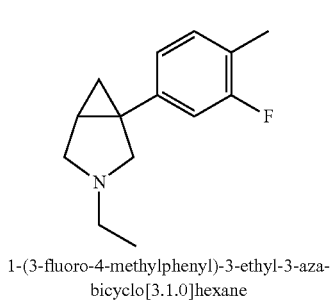

1-(3-fluoro-4-methylphenyl)-3-ethyl-3-aza-bicyclo[3.1.0]hexane

TABLE 1-continued

Exemplary 1-aryl-3-azabicyclo[3.1.0]hexanes having multiple substitutions on the aryl ring

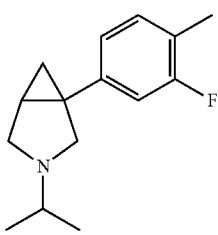 [SMILES: Cc1ccc(C23CC2CN(C(C)C)C3)cc1F]

1-(3-fluoro-4-methylphenyl)-3-isopropyl-3-aza-bicyclo[3.1.0]hexane

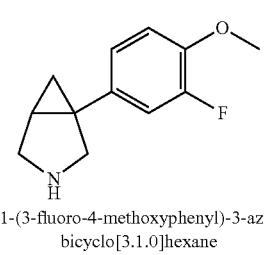

1-(3-fluoro-4-methoxyphenyl)-3-aza-bicyclo[3.1.0]hexane

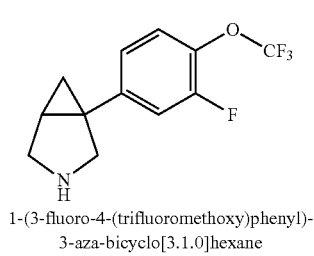

1-(3-fluoro-4-(trifluoromethoxy)phenyl)-3-aza-bicyclo[3.1.0]hexane

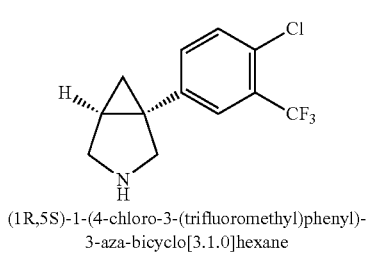

(1R,5S)-1-(4-chloro-3-(trifluoromethyl)phenyl)-3-aza-bicyclo[3.1.0]hexane

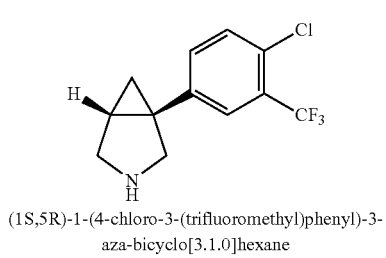

(1S,5R)-1-(4-chloro-3-(trifluoromethyl)phenyl)-3-aza-bicyclo[3.1.0]hexane

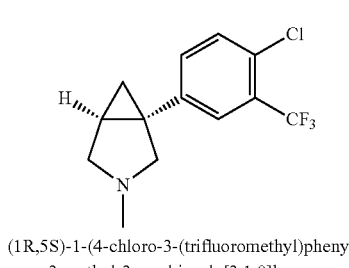

(1R,5S)-1-(4-chloro-3-(trifluoromethyl)phenyl)-3-methyl-3-aza-bicyclo[3.1.0]hexane TABLE 1-continued Exemplary 1-aryl-3-azabicyclo[3.1.0]hexanes having multiple substitutions on the aryl ring

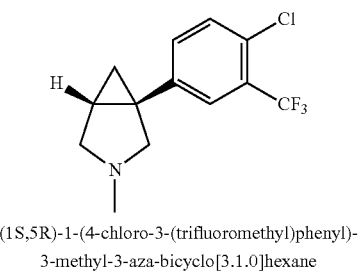

(1S,5R)-1-(4-chloro-3-(trifluoromethyl)phenyl)-
3-methyl-3-aza-bicyclo[3.1.0]hexane

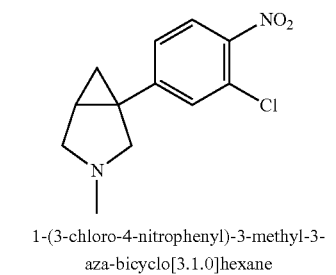

1-(3-chloro-4-nitrophenyl)-3-methyl-3-
aza-bicyclo[3.1.0]hexane

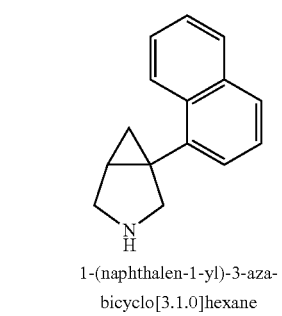

1-(naphthalen-1-yl)-3-aza-
bicyclo[3.1.0]hexane

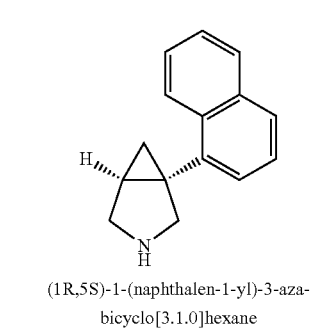

(1R,5S)-1-(naphthalen-1-yl)-3-aza-
bicyclo[3.1.0]hexane

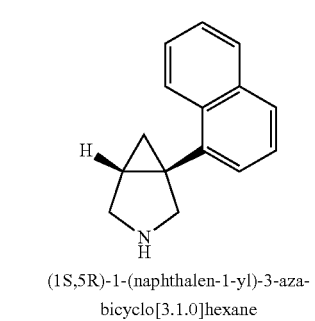

(1S,5R)-1-(naphthalen-1-yl)-3-aza-
bicyclo[3.1.0]hexane

TABLE 1-continued

Exemplary 1-aryl-3-azabicyclo[3.1.0]hexanes having multiple substitutions on the aryl ring

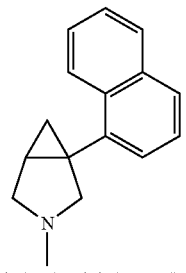

3-methyl-1-(naphthalen-1-yl)-3-aza-
bicyclo[3.1.0]hexane

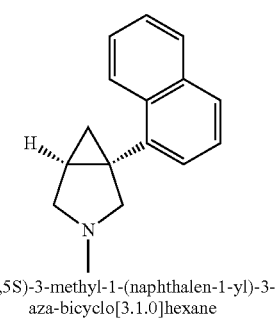

(1R,5S)-3-methyl-1-(naphthalen-1-yl)-3-
aza-bicyclo[3.1.0]hexane

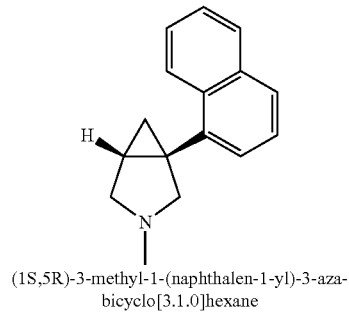

(1S,5R)-3-methyl-1-(naphthalen-1-yl)-3-aza-
bicyclo[3.1.0]hexane

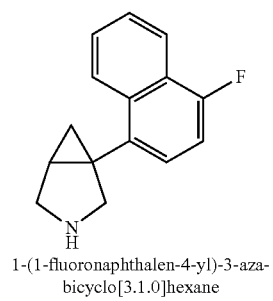

1-(1-fluoronaphthalen-4-yl)-3-aza-
bicyclo[3.1.0]hexane

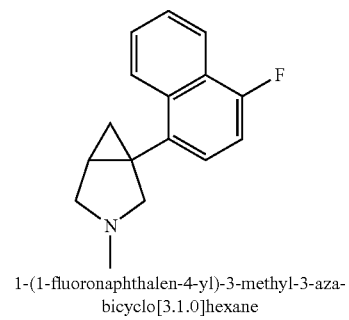

1-(1-fluoronaphthalen-4-yl)-3-methyl-3-aza-
bicyclo[3.1.0]hexane

TABLE 1-continued

Exemplary 1-aryl-3-azabicyclo[3.1.0]hexanes having multiple substitutions on the aryl ring

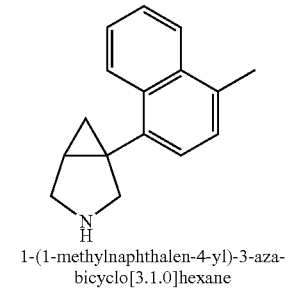
1-(1-methylnaphthalen-4-yl)-3-aza-
bicyclo[3.1.0]hexane

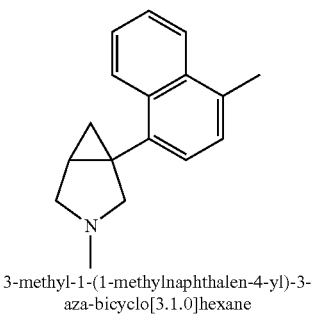
3-methyl-1-(1-methylnaphthalen-4-yl)-3-
aza-bicyclo[3.1.0]hexane

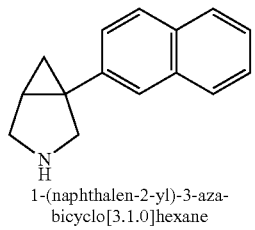
1-(naphthalen-2-yl)-3-aza-
bicyclo[3.1.0]hexane

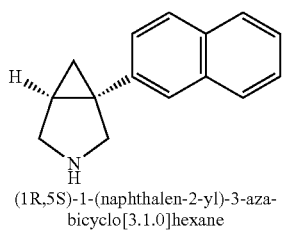
(1R,5S)-1-(naphthalen-2-yl)-3-aza-
bicyclo[3.1.0]hexane

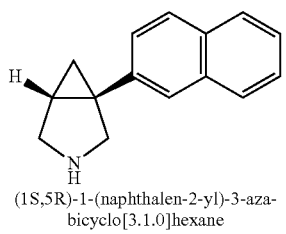
(1S,5R)-1-(naphthalen-2-yl)-3-aza-
bicyclo[3.1.0]hexane

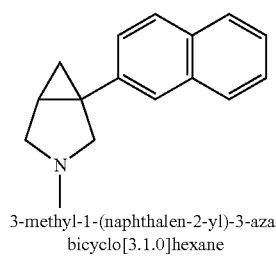
3-methyl-1-(naphthalen-2-yl)-3-aza-
bicyclo[3.1.0]hexane

TABLE 1-continued

Exemplary 1-aryl-3-azabicyclo[3.1.0]hexanes having multiple substitutions on the aryl ring

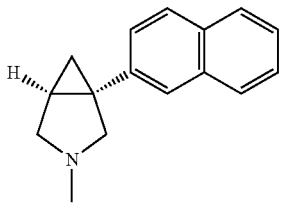 [SMILES: CN1C[C@H]2C[C@@]2(c2ccc3ccccc3c2)C1]
(1R,5S)-3-methyl-1-(naphthalen-2-yl)-3-
aza-bicyclo[3.1.0]hexane

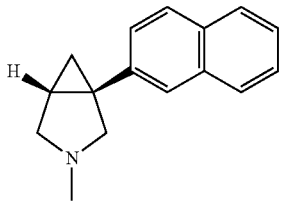 [SMILES: CN1C[C@@H]2C[C@]2(c2ccc3ccccc3c2)C1]
(1S,5R)-3-methyl-1-(naphthalen-2-yl)-3-aza-
bicyclo[3.1.0]hexane

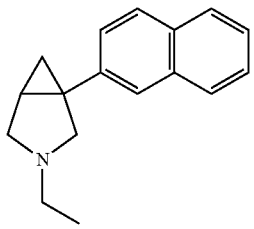 [SMILES: CCN1CC2CC2(c2ccc3ccccc3c2)C1]
3-ethyl-1-(naphthalen-2-yl)-3-aza-
bicyclo[3.1.0]hexane

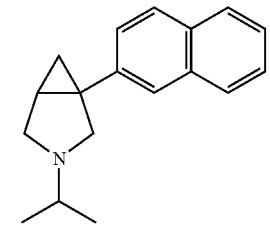 [SMILES: CC(C)N1CC2CC2(c2ccc3ccccc3c2)C1]
3-isopropyl-1-(naphthalen-2-yl)-3-aza-
bicyclo[3.1.0]hexane

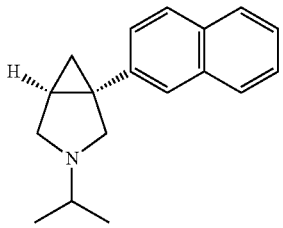 [SMILES: CC(C)N1C[C@H]2C[C@@]2(c2ccc3ccccc3c2)C1]
(1R,5S)-3-isopropyl-1-(naphthalen-2-yl)-3-aza-
bicyclo[3.1.0]hexane

TABLE 1-continued

Exemplary 1-aryl-3-azabicyclo[3.1.0]hexanes having multiple substitutions on the aryl ring

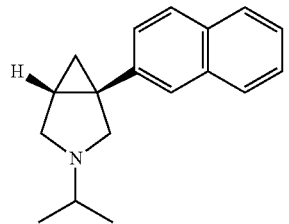 [SMILES: CC(C)N1C[C@@H]2C[C@]2(c2ccc3ccccc3c2)C1]

(1S,5R)-3-isopropyl-1-(naphthalen-2-yl)-3-aza-bicyclo[3.1.0]hexane

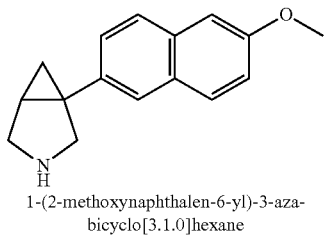

1-(2-methoxynaphthalen-6-yl)-3-aza-bicyclo[3.1.0]hexane

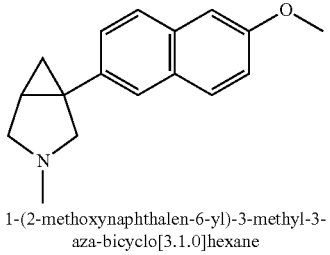

1-(2-methoxynaphthalen-6-yl)-3-methyl-3-aza-bicyclo[3.1.0]hexane

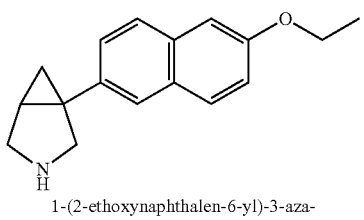

1-(2-ethoxynaphthalen-6-yl)-3-aza-bicyclo[3.1.0]hexane

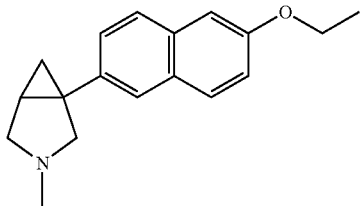 [SMILES: CCOc1ccc2cc(C34CC3CN(C)C4)ccc2c1]

1-(2-ethoxynaphthalen-6-yl)-3-methyl-3-aza-bicyclo[3.1.0]hexane

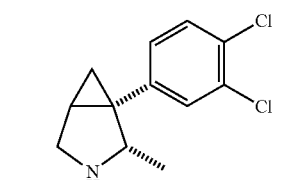

Cis-1-(3,4-dichlorophenyl)-2-methyl-3-aza-bicyclo[3.1.0]hexane

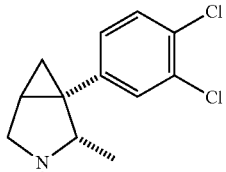

Cis-1-(3,4-dichlorophenyl)-2,3-dimethyl-3-aza-bicyclo[3.1.0]hexane

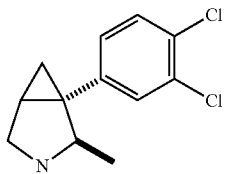

Trans-1-(3,4-dichlorophenyl)-2-methyl-3-aza-bicyclo[3.1.0]hexane

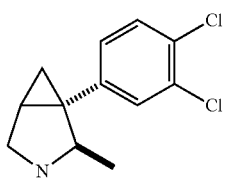

Trans-1-(3,4-dichlorophenyl)-2,3-dimethyl-3-aza-bicyclo[3.1.0]hexane

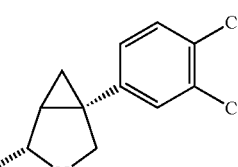

Cis-1-(3,4-dichlorophenyl)-4-methyl-3-aza-bicyclo[3.1.0]hexane

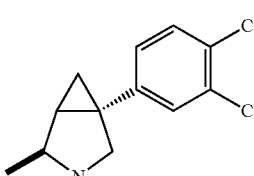

Trans-1-(3,4-dichlorophenyl)-4-methyl-3-aza-bicyclo[3.1.0]hexane

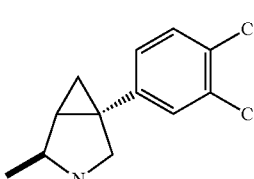

Trans-1-(3,4-dichlorophenyl)-3,4-dimethyl-3-aza-bicyclo[3.1.0]hexane

It will be understood that the exemplary, multiply aryl-substituted compounds identified in Table 1 are illustrative, and that the subject modifications comprising multiple aryl substitutions can be varied to comprise other substituents, can include yet additional substituents (e.g., three or more substitutions on the aryl ring), combined with one another, or additionally combined with one or more substitutions on the azabicyclo[3.1.0]hexane ring, to yield yet additional compounds within the invention for treating CNS disorders (including a range of neuropsychiatric disorders, such as depression and anxiety). For example, the invention provides an illustrative assemblage of novel 1-(3,4-dichlorophenyl)-3-azabicyclo[3.1.0]hexanes having multiple substitutions, (e.g., as illustrated by multiple chloro substitutions) on the aryl ring, combined with a substitution on the nitrogen (alternatively, an "aza substitution") at the '3' position. Novel 1-(3,4-dichlorophenyl)-3-azabicyclo[3.1.0]hexanes of the invention having a substitution on the nitrogen at the '3' position of the invention include the following, exemplary compounds, which have been made and characterized as illustrative embodiments of the invention (Table 2). The subject compounds are depicted as hydrochloride salts, whereas it will be understood that the invention encompasses all forms of the compounds as described herein, including free base forms, and all pharmaceutically acceptable salts, polymorphs, solvates, hydrates, and prodrugs thereof:

TABLE 2

Exemplary 1-aryl-3-azabicyclo[3.1.0]hexanes having multiple substitutions on the aryl ring combined with an aza substitution

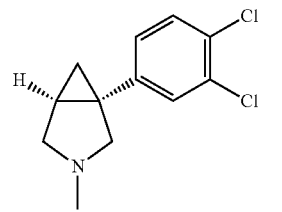

(1R,5S)-1-(3,4-dichlorophenyl)-3-methyl-
3-aza-bicyclo[3.1.0]hexane

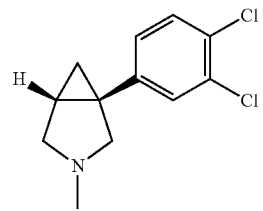

(1S,5R)-1-(3,4-dichlorophenyl)-3-methyl-
3-aza-bicyclo[3.1.0]hexane

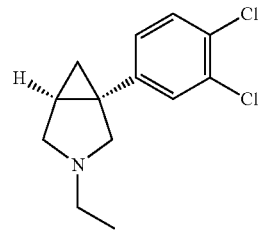 [SMILES: CCN1C[C@H]2C[C@@]2(c2ccc(Cl)c(Cl)c2)C1]

(1R,5S)-1-(3,4-dichlorophenyl)-3-ethyl-3-
aza-bicyclo[3.1.0]hexane

TABLE 2-continued

Exemplary 1-aryl-3-azabicyclo[3.1.0]hexanes having multiple substitutions on the aryl ring combined with an aza substitution

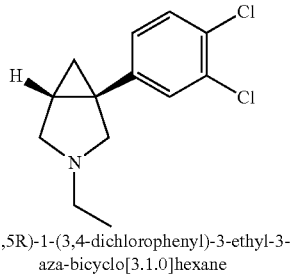

(1S,5R)-1-(3,4-dichlorophenyl)-3-ethyl-3-
aza-bicyclo[3.1.0]hexane

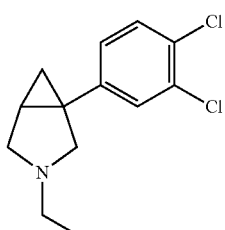

1-(3,4-dichlorophenyl)-3-propyl-3-
aza-bicyclo[3.1.0]hexane

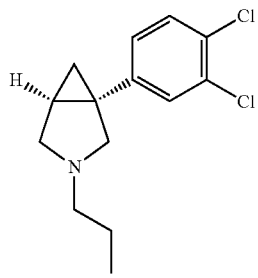 [SMILES: CCCN1C[C@H]2C[C@@]2(c2ccc(Cl)c(Cl)c2)C1]

(1R,5S)-1-(3,4-dichlorophenyl)-3-propyl-
3-aza-bicyclo[3.1.0]hexane

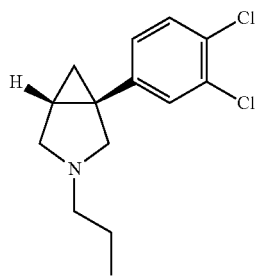 [SMILES: CCCN1C[C@@H]2C[C@]2(c2ccc(Cl)c(Cl)c2)C1]

(1S,5R)-1-(3,4-dichlorophenyl)-3-propyl-
3-aza-bicyclo[3.1.0]hexane

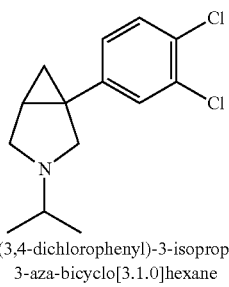

1-(3,4-dichlorophenyl)-3-isopropyl-
3-aza-bicyclo[3.1.0]hexane

TABLE 2-continued

Exemplary 1-aryl-3-azabicyclo[3.1.0]hexanes having
multiple substitutions on the aryl ring combined with an aza substitution

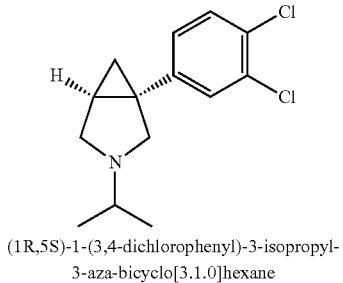

(1R,5S)-1-(3,4-dichlorophenyl)-3-isopropyl-
3-aza-bicyclo[3.1.0]hexane

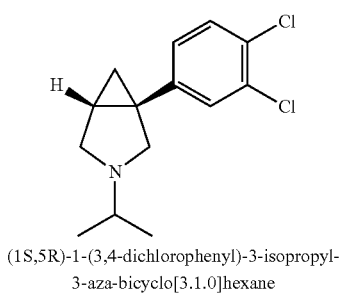

(1S,5R)-1-(3,4-dichlorophenyl)-3-isopropyl-
3-aza-bicyclo[3.1.0]hexane

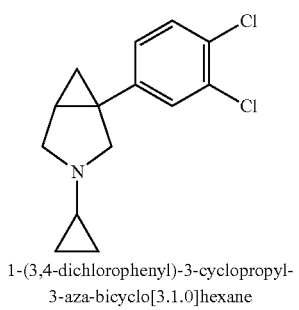

1-(3,4-dichlorophenyl)-3-cyclopropyl-
3-aza-bicyclo[3.1.0]hexane

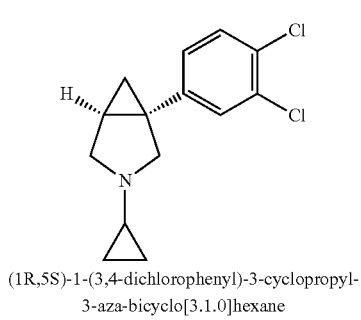

(1R,5S)-1-(3,4-dichlorophenyl)-3-cyclopropyl-
3-aza-bicyclo[3.1.0]hexane

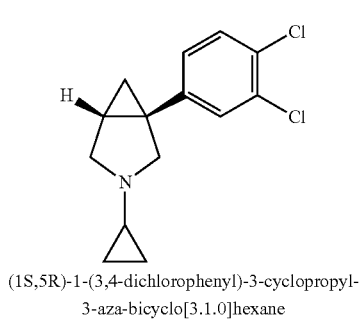

(1S,5R)-1-(3,4-dichlorophenyl)-3-cyclopropyl-
3-aza-bicyclo[3.1.0]hexane

TABLE 2-continued

Exemplary 1-aryl-3-azabicyclo[3.1.0]hexanes having
multiple substitutions on the aryl ring combined with an aza substitution

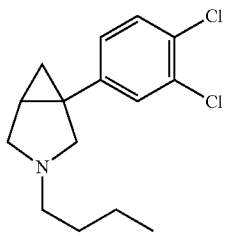 [SMILES: CCCCN1CC2CC2(c2ccc(Cl)c(Cl)c2)C1]

3-butyl-1-(3,4-dichlorophenyl)-
3-aza-bicyclo[3.1.0]hexane

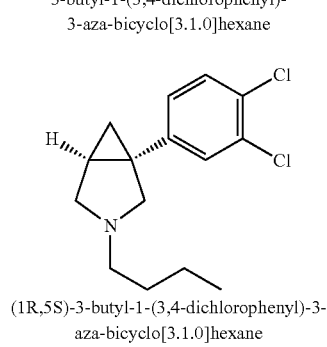

(1R,5S)-3-butyl-1-(3,4-dichlorophenyl)-3-
aza-bicyclo[3.1.0]hexane

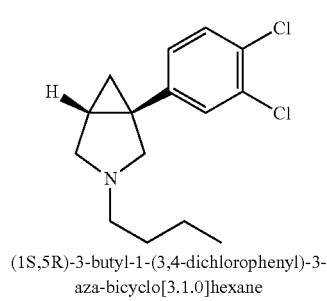

(1S,5R)-3-butyl-1-(3,4-dichlorophenyl)-3-
aza-bicyclo[3.1.0]hexane

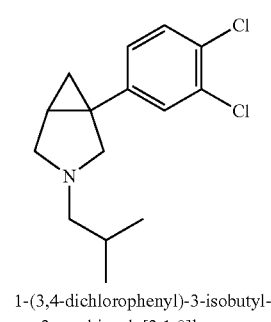

1-(3,4-dichlorophenyl)-3-isobutyl-
3-aza-bicyclo[3.1.0]hexane

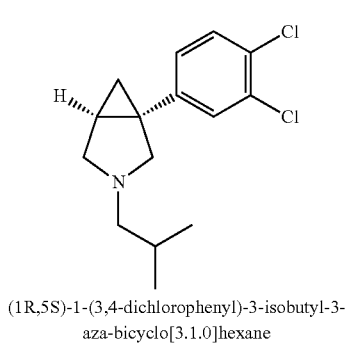

(1R,5S)-1-(3,4-dichlorophenyl)-3-isobutyl-3-
aza-bicyclo[3.1.0]hexane

TABLE 2-continued

Exemplary 1-aryl-3-azabicyclo[3.1.0]hexanes having
multiple substitutions on the aryl ring combined with an aza substitution

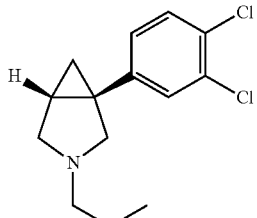

(1S,5R)-1-(3,4-dichlorophenyl)-3-isobutyl-3-
aza-bicyclo[3.1.0]hexane

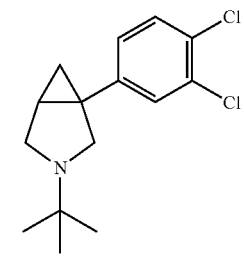 [SMILES: CC(C)(C)N1CC2CC2(c2ccc(Cl)c(Cl)c2)C1]

3-tert-butyl-1-(3,4-dichlorophenyl)-
3-aza-bicyclo[3.1.0]hexane

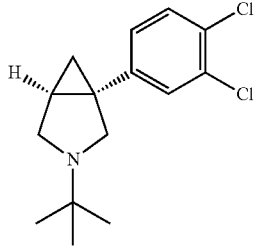 [SMILES: CC(C)(C)N1C[C@H]2C[C@@]2(c2ccc(Cl)c(Cl)c2)C1]

(1R,5S)-3-tert-butyl-1-(3,4-dichlorophenyl)-
3-aza-bicyclo[3.1.0]hexane

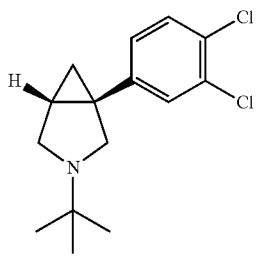 [SMILES: CC(C)(C)N1C[C@@H]2C[C@]2(c2ccc(Cl)c(Cl)c2)C1]

(1S,5R)-3-tert-butyl-1-(3,4-dichlorophenyl)-3-
aza-bicyclo[3.1.0]hexane

Within related aspects of the invention, enantiomeric forms of the novel compounds described herein, having chiral symmetric structure, are provided, which provide yet additional drug candidates for treating CNS disorders. In certain embodiments, the invention provides enantiomers, diastereomers, and other stereoisomeric forms of the disclosed compounds, including racemic and resolved forms and mixtures thereof. The individual enantiomers may be separated according to methods that are well known to those of ordinary skill in the art. In certain embodiments, the enantiomers, diastereomers and other stereoisomeric forms of the disclosed compounds are substantially free of the corresponding enantiomers, diastereomers and stereoisomers. In other embodiments, the enantiomers, diastereomers and other stereoisomeric forms of the disclosed compounds contain no more than about 10%, about 5%, about 2% or about 1% of the corresponding enantiomers, diastereomers and stereoisomers. When the compounds described herein contain olefinic double bonds or other centers of geometric asymmetry, and unless specified otherwise, it is intended to include both E and Z geometric isomers. All tautomers are intended to be encompassed by the present invention as well.

As noted above, the compounds of the present invention can be prepared as both acid addition salts formed from an acid and the basic nitrogen group of 1-aryl-3-azabicyclo [3.1.0]hexanes and base salts. As further noted below, the methods of the present invention can be used to prepare compounds as both acid addition salts formed from an acid and the basic nitrogen group of 1-aryl-3-azabicyclo[3.1.0] hexanes and base salts. Suitable acid addition salts are formed from acids which form non-toxic salts and include, for example, hydrochloride, hydrobromide, hydroiodide, sulphate, hydrogen sulphate, nitrate, phosphate, and hydrogen phosphate salts. Other examples of pharmaceutically acceptable addition salts include inorganic and organic acid addition salts. Additional pharmaceutically acceptable salts include, but are not limited to, metal salts such as sodium salt, potassium salt, cesium salt and the like; alkaline earth metals such as calcium salt, magnesium salt and the like; organic amine salts such as triethylamine salt, pyridine salt, picoline salt, ethanolamine salt, triethanolamine salt, dicyclohexylamine salt, N,N'-dibenzylethylenediamine salt and the like; organic acid salts such as acetate, citrate, lactate, succinate, tartrate, maleate, fumarate, mandelate, acetate, dichloroacetate, trifluoroacetate, oxalate, formate and the like; sulfonates such as methanesulfonate, benzenesulfonate, p-toluenesulfonate and the like; and amino acid salts such as arginate, asparginate, glutamate, tartrate, gluconate and the like. Suitable base salts are formed from bases which form non-toxic salts and include, for example, aluminum, calcium, lithium, magnesium, potassium, sodium, zinc and diethanolamine salts.

In other detailed embodiments, the invention provides prodrugs of the disclosed compounds. Prodrugs are considered to be any covalently bonded carriers which release the active parent drug in vivo. Examples of prodrugs include esters or amides of a compound of the present invention with hydroxyalkyl or aminoalkyl as a substituent. These may be prepared by reacting such compounds with anhydrides such as succinic anhydride.

The invention disclosed herein will also be understood to encompass in vivo metabolic products of the disclosed compounds. Such products may result for example from the oxidation, reduction, hydrolysis, amidation, esterification and the like of the administered compound, primarily due to enzymatic processes. Accordingly, the invention includes compounds produced by a process comprising contacting a compound of this invention with a mammal for a period of time sufficient to yield a metabolic product thereof. Such products typically are identified by preparing a radiolabelled compound of the invention, administering it parenterally in a detectable dose to an animal such as rat, mouse, guinea pig, monkey, or to man, allowing sufficient time for metabolism to occur and isolating its conversion products from the urine, blood or other biological samples.

The invention disclosed herein will also be understood to encompass the disclosed compounds isotopically-labelled by having one or more atoms replaced by an atom having a different atomic mass or mass number. Examples of isotopes that can be incorporated into the disclosed compounds include isotopes of hydrogen, carbon, nitrogen, oxygen, phosphorous, fluorine and chlorine, such as $^2$H, $^3$H, $^{14}$H, $^{14}$C, $^{15}$N, $^{18}$O, $^{17}$O, $^{31}$P, $^{32}$P, $^{35}$S, $^{18}$F, and $^{36}$Cl, respectively.

The compounds of the instant invention may be prepared using methods known to those skilled in the art, and in other embodiments by employing novel synthetic schemes as provided herein, which, along with the exemplified intermediate compounds, also fall within the scope of the invention. Accordingly, the present invention also provides novel methods and compositions for producing the compounds of the present invention as well as other 1-aryl-3-azabicyclo[3.1.0] hexanes.

In certain embodiments, the present invention provides methods for making a 1-aryl-3-azabicyclo[3.1.0]hexane of the following formula IV,

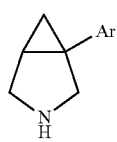

Formula IV wherein Ar is a phenyl group substituted with two substituents independently selected from halogen, $C_{1-3}$ alkyl, $C_{2-4}$ alkenyl, $C_{2-4}$ alkynyl, halo($C_{1-3}$)alkyl, cyano, hydroxy, $C_{3-5}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxy, nitro, amino, $C_{1-3}$ alkylamino, and di($C_{1-3}$)alkylamino, an unsubstituted napthyl group or a napthyl group having 1-4 substituents independently selected from halogen, $C_{1-3}$ alkyl, $C_{2-4}$ alkenyl, $C_{2-4}$ alkynyl, halo($C_{1-3}$)alkyl, cyano, hydroxy, $C_{3-5}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxy, nitro, amino, $C_{1-3}$ alkylamino, and di($C_{1-3}$)alkylamino, and enantiomers and diastereomers thereof, comprising the steps of:

(a) reacting a compound of the following formula (i),

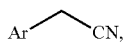

wherein Ar is defined as above, with epichlohydrin or an enantiomer thereof, to produce a compound of the following formula (ii),

or an enantiomer or diastereomer thereof;

(b) reducing the compound of formula (ii) to produce a compound of the following formula (iii),

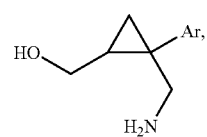

or an enantiomer or diastereomer thereof;

(c) causing cyclization of the compound of formula (iii) to produce the 1-aryl-3-azabicyclo[3.1.0]hexane, or an enantiomer or diastereomer thereof In other embodiments, the present invention provides methods for making a 1-aryl-3-azabicyclo[3.1.0]hexane of the following formula IV,

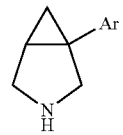

Formula IV wherein Ar is a phenyl group substituted with two substituents independently selected from halogen, $C_{1-3}$ alkyl, $C_{2-4}$ alkenyl, $C_{2-4}$ alkynyl, halo($C_{1-3}$)alkyl, cyano, hydroxy, $C_{3-5}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxy, nitro, amino, $C_{1-3}$ alkylamino, and di($C_{1-3}$)alkylamino, an unsubstituted napthyl group or a napthyl group having 1-4 substituents independently selected from halogen, $C_{1-3}$ alkyl, $C_{2-4}$ alkenyl, $C_{2-4}$ alkynyl, halo($C_{1-3}$)alkyl, cyano, hydroxy, $C_{3-5}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxy, nitro, amino, $C_{1-3}$ alkylamino, and di($C_{1-3}$)alkylamino, and enantiomers and diastereomers thereof, comprising the steps of:

(a) reacting a compound of the following formula (i),

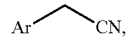

wherein Ar is defined as above, with epichlohydrin to produce a compound of the following formula (ii),

(b) reducing the compound of formula (ii) to produce a compound of the following formula (iii),

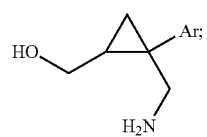

(c) reacting the compound of formula (iii) with (Boc)$_2$O to produce a compound of the following formula (iv),

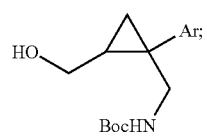

(d) causing cyclization of the compound of formula (iv) to produce a compound of the following formula (v),

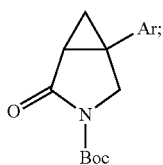

(e) deprotecting the compound of formula (v) to produce a compound of the following formula (vi), and

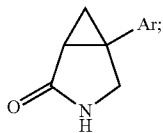

(f) reducing the compound of formula (vi) to produce the 1-aryl-3-azabicyclo[3.1.0]hexane.

In additional embodiments, the present invention provides methods of making a 1-aryl-3-azabicyclo[3.1.0]hexane of the following formula V, Formula V

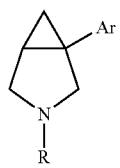

wherein Ar is a phenyl group substituted with two substituents independently selected from halogen, $C_{1-3}$ alkyl, $C_{2-4}$ alkenyl, $C_{2-4}$ alkynyl, halo($C_{1-3}$)alkyl, cyano, hydroxy, $C_{3-5}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxy, nitro, amino, $C_{1-3}$ alkylamino, and di($C_{1-3}$)alkylamino, an unsubstituted napthyl group or a napthyl group having 1-4 substituents independently selected from halogen, $C_{1-3}$ alkyl, $C_{2-4}$ alkenyl, $C_{2-4}$ alkynyl, halo($C_{1-3}$)alkyl, cyano, hydroxy, $C_{3-5}$ cycloalkyl, $C_{1-3}$ alkoxy, $C_{1-3}$ alkoxy($C_{1-3}$)alkyl, carboxy ($C_{1-3}$)alkyl, $C_{1-3}$ alkanoyl, halo($C_{1-3}$)alkoxy, nitro, amino, $C_{1-3}$ alkylamino, and di($C_{1-3}$)alkylamino, and R is hydrogen, methyl, ethyl, isopropyl or a nitrogen protecting group, and enantiomers and diastereomers thereof, comprising the steps of:

(a) reacting a compound of the following formula (vii),

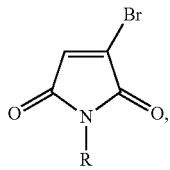

wherein R is as defined above, with

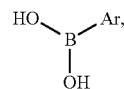

wherein Ar is as defined above, to produce a compound of the following formula (viii),

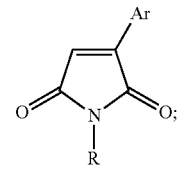

(b) causing cyclopropanation of the compound of formula (viii) to produce a compound of the following formula (ix), and

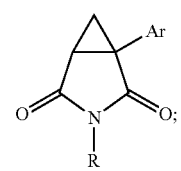

(c) reducing the compound of formula (ix) to produce the 1-aryl-3-azabicyclo[3.1.0]hexane.

In practicing the methods of the present for methods for making 1-aryl-3-azabicyclo[3.1.0]hexanes, various reagents may be utilized for the different reaction steps. In general, suitable reagents for the various reaction steps may be selected by one of ordinary skill in the art based on the present disclosure.

Suitable reducing agents and methodologies include, for example, lithium aluminum hydride (LAH), sodium aluminum hydride (SAH), $NaBH_4$ with $ZnCl_2$ and catalytic hydrogenation.

Suitable nitrogen protecting groups include, for example, benzyl, allyl, tert-butyl and 3,4-dimethoxy-benzyl groups. In general, nitrogen protecting groups are well known to those skilled in the art, see for example, "Nitrogen Protecting Groups in Organic Synthesis", John Wiley and Sons, New York, N.Y., 1981, Chapter 7; "Nitrogen Protecting Groups in Organic Chemistry", Plenum Press, New York, N.Y., 1973, Chapter 2; T. W. Green and P. G. M. Wuts in "Protective Groups in Organic Chemistry", 3rd edition, John Wiley & Sons, New York, N.Y., 1999.

When the nitrogen protecting group is no longer needed, it may be removed by methods well known in the art. For example, benzyl or 3,4-dimethoxy-benzyl groups may be removed by catalytic hydrogenation. In general, methods of removing nitrogen protecting groups are well known to those skilled in the art, see for example, "Nitrogen Protecting Groups in Organic Synthesis", John Wiley and Sons, New York, N.Y., 1981, Chapter 7; "Nitrogen Protecting Groups in Organic Chemistry", Plenum Press, New York, N.Y., 1973, Chapter 2; T. W. Green and P. G. M. Wuts in "Protective Groups in Organic Chemistry", 3rd edition, John Wiley & Sons, inc. New York, N.Y., 1999.

Suitable reagents for causing cyclization include, for example, SOCl$_2$, POCl$_3$, oxalyl chloride, phosphorous tribromide, triphenylphosphorous dibromide and oxalyl bromide.

Exemplary synthetic methods, starting materials, and intermediates useful in various aspects of the invention for producing novel compounds of the present invention are described in the examples.

For the purposes of describing the invention, including the novel compounds and synthetic methods disclosed herein, the following terms and definitions are provided by way of example.

The term "halogen" as used herein refers to bromine, chlorine, fluorine or iodine. In one embodiment, the halogen is chlorine. In another embodiment, the halogen is bromine.

The term "hydroxy" as used herein refers to —OH or

The term "alkyl" as used herein refers to straight- or branched-chain aliphatic groups containing 1-20 carbon atoms, preferably 1-7 carbon atoms and most preferably 1-4 carbon atoms. This definition applies as well to the alkyl portion of alkoxy, alkanoyl and aralkyl groups. In one embodiment, the alkyl is a methyl group.

The term "alkoxy" includes substituted and unsubstituted alkyl, alkenyl, and alkynyl groups covalently linked to an oxygen atom. In one embodiment, the alkoxy group contains 1 to 4 carbon atoms. Embodiments of alkoxy groups include, but are not limited to, methoxy, ethoxy, isopropyloxy, propoxy, butoxy, and pentoxy groups. Embodiments of substituted alkoxy groups include halogenated alkoxy groups. In a further embodiment, the alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alk sulfonato, sulfamoyl, sulfonamido, nitro, trifluoromethyl, cyano, azido, heterocyclyl, alkylaryl, or an aromatic or heteroaromatic moieties. Exemplary halogen substituted alkoxy groups include, but are not limited to, fluoromethoxy, difluoromethoxy, trifluoromethoxy, chloromethoxy, dichloromethoxy, and trichloromethoxy.

The term "nitro", as used herein alone or in combination, refers to a —NO$_2$ group.

The term "amino" as used herein refers to the group —NRR', where R and R' may independently be hydrogen, alkyl, aryl, alkoxy, or heteroaryl. The term "aminoalkyl" as used herein represents a more detailed selection as compared to "amino" and refers to the group —NRR', where R and R' may independently be hydrogen or (C$_1$-C$_4$)alkyl.

The term "trifluoromethyl" as used herein refers to —CF$_3$.

The term "trifluoromethoxy" as used herein refers to —OCF$_3$.

The term "cycloalkyl" as used herein refers to a saturated cyclic hydrocarbon ring system containing from 3 to 7 carbon atoms that may be optionally substituted. Exemplary embodiments include, but are not limited to, cyclopropyl, cyclobutyl, cyclopentyl and cyclohexyl. In certain embodiments, the cycloalkyl group is cyclopropyl. In another embodiment, the (cycloalkyl)alkyl groups contain from 3 to 7 carbon atoms in the cyclic portion and 1 to 4 carbon atoms in the alkyl portion. In certain embodiments, the (cycloalkyl)alkyl group is cyclopropylmethyl. The alkyl groups are optionally substituted with from one to three substituents selected from the group consisting of halogen, hydroxy and amino.

The terms "alkanoyl" and "alkanoyloxy" as used herein refer, respectively, to —C(O)-alkyl groups and —O—C(O)-alkyl groups, each optionally containing 2-5 carbon atoms. Specific embodiments of alkanoyl and alkanoyloxy groups are acetyl and acetoxy, respectively.

The term "aryl" as used herein refers to monocyclic or bicyclic aromatic hydrocarbon groups having from 6 to 12 carbon atoms in the ring portion, for example, phenyl, naphthyl, biphenyl and diphenyl groups, each of which may be substituted with, for example, one to four substituents such as alkyl, substituted alkyl as defined above, halogen, trifluoromethyl, trifluoromethoxy, hydroxy, alkoxy, cycloalkyloxy, alkanoyl, alkanoyloxy, amino, alkylamino, dialkylamino, nitro, cyano, carboxy, carboxyalkyl, carbamyl, carbamoyl and aryloxy. Specific embodiments of aryl groups in accordance with the present invention include phenyl, substituted phenyl, naphthyl, biphenyl, and diphenyl.

The term "aroyl," as used alone or in combination herein, refers to an aryl radical derived from an aromatic carboxylic acid, such as optionally substituted benzoic or naphthoic acids.

The term "aralkyl" as used herein refers to an aryl group bonded to the 4-pyridinyl ring through an alkyl group, preferably one containing 1-4 carbon atoms. A preferred aralkyl group is benzyl.

The term "nitrile" or "cyano" as used herein refers to the group —CN.

The term "dialkylamino" refers to an amino group having two attached alkyl groups that can be the same or different.

The term "alkenyl" refers to a straight or branched alkenyl group of 2 to 10 carbon atoms having 1 to 3 double bonds. Preferred embodiments include ethenyl, 1-propenyl, 2-propenyl, 1-methylethenyl, 1-butenyl, 2-butenyl, 3-butenyl, 2-methyl-2-propenyl, 1-pentenyl, 2-pentenyl, 4-pentenyl, 3-methyl-2-butenyl, 1-hexenyl, 2-hexenyl, 1-heptenyl, 2-heptenyl, 1-octenyl, 2-octenyl, 1,3-octadienyl, 2-nonenyl, 1,3-nonadienyl, 2-decenyl, etc.

The term "alkynyl" as used herein refers to a straight or branched alkynyl group of 2 to 10 carbon atoms having 1 to 3 triple bonds. Exemplary alkynyls include, but are not limited to, ethynyl, 1-propynyl, 2-propynyl, 1-butynyl, 2-butynyl, 3-butynyl, 1-pentynyl, 2-pentynyl, 4-pentynyl, 1-octynyl, 6-methyl-1-heptynyl, and 2-decynyl.

The term "hydroxyalkyl" alone or in combination, refers to an alkyl group as previously defined, wherein one or several hydrogen atoms, preferably one hydrogen atom has been replaced by a hydroxyl group. Examples include hydroxymethyl, hydroxyethyl and 2-hydroxyethyl.

The term "aminoalkyl" as used herein refers to the group —NRR', where R and R' may independently be hydrogen or (C$_1$-C$_4$)alkyl.

The term "alkyl aminoalkyl" refers to an alkylamino group linked via an alkyl group (i.e., a group having the general structure —alkyl-NH-alkyl or —alkyl-N(alkyl)(alkyl)). Such groups include, but are not limited to, mono- and di-(C$_1$-C$_8$ alkyl)aminoC$_1$-C$_8$ alkyl, in which each alkyl may be the same or different.

The term "dialkylaminoalkyl" refers to alkylamino groups attached to an alkyl group. Examples include, but are not limited to, N,N-dimethylarninomethyl, N,N-dimethylaminoethyl, N,N-dimethylaminopropyl, and the like. The term dialkylaminoalkyl also includes groups where the bridging alkyl moiety is optionally substituted.

The term "haloalkyl" refers to an alkyl group substituted with one or more halo groups, for example chloromethyl, 2-bromoethyl, 3-iodopropyl, trifluoromethyl, perfluoropropyl, 8-chlorononyl and the like.

The term "carboxyalkyl" as used herein refers to the substituent —R'—COOH wherein R' is alkylene; and carbalkoxyalkyl refers to —R'—COOR wherein R' and R are alkylene and alkyl respectively. In certain embodiments, alkyl refers to a saturated straight- or branched-chain hydrocarbyl radical of 1-6 carbon atoms such as methyl, ethyl, n-propyl, isopropyl, n-butyl, t-butyl, n-pentyl, 2-methylpentyl, n-hexyl, and so forth. Alkylene is the same as alkyl except that the group is divalent.

The term "alkoxyalkyl" refers to an alkylene group substituted with an alkoxy group. For, example, methoxyethyl [$CH_3OCH_2CH_2$—] and ethoxymethyl ($CH_3CH_2OCH_2$—] are both $C_3$ alkoxyalkyl groups.

The term "carboxy", as used herein, represents a group of the formula —COOH.

The term "alkartoylamino" refers to alkyl, alkenyl or alkynyl groups containing the group —C(O)— followed by —N(H)—, for example acetylamino, propanoylamino and butanoylamino and the like.

The term "carbonylamino" refers to the group —NR—CO—$CH_2$—R', where R and R' may be independently selected from hydrogen or ($C_1$-$C_4$)alkyl.

The term "carbamoyl" as used herein refers to —O—C(O)$NH_2$.

The term "carbamyl" as used herein refers to a functional group in which a nitrogen atom is directly bonded to a carbonyl, i.e., as in —NRC(=O)R or —C(=O)NRR', wherein R and R' can be hydrogen, alkyl, substituted alkyl, alkenyl, substituted alkenyl, alkoxy, cycloalkyl, aryl, heterocyclo, or heteroaryl.

The term "heterocyclo" refers to an optionally substituted, unsaturated, partially saturated, or fully saturated, aromatic or nonaromatic cyclic group that is a 4 to 7 membered monocyclic, or 7 to 11 membered bicyclic ring system that has at least one heteroatom in at least one carbon atom-containing ring. The substituents on the heterocyclo rings may be selected from those given above for the aryl groups. Each ring of the heterocyclo group containing a heteroatom may have 1, 2 or 3 heteroatoms selected from nitrogen atoms, oxygen atoms and sulfur atoms. Plural heteroatoms in a given heterocyclo ring may be the same or different. The heterocyclo group may be attached to the 4-pyridinyl ring at any heteroatom or carbon atom. In one embodiment, two R groups form a fused ring with the carbons at position 2 and 3 of the pyridinyl ring, there is formed a 7-quinolin-4-yl moiety.

As used herein, the term "stereoisomers" is a general term for all isomers of individual molecules that differ only in the orientation of their atoms in space. It includes enantiomers and isomers of compounds with more than one chiral center that are not mirror images of one another (diastereomers).

The term "chiral center" refers to a carbon atom to which four different groups are attached.

The term "enantiomer" or "enantiomeric" refers to a molecule that is nonsuperimposeable on its mirror image and hence optically active wherein the enantiomer rotates the plane of polarized light in one direction and its mirror image rotates the plane of polarized light in the opposite direction.

The term "racemic" refers to a mixture of equal parts of enantiomers and which is optically inactive.

The term "resolution" refers to the separation or concentration or depletion of one of the two enantiomeric forms of a molecule.

In additional embodiments, the invention provides pharmaceutical compositions and methods for treating CNS disorders, including but not limited to neuropsychiatric conditions, such as depression and anxiety. Suitable forms of the compounds of the invention for use in biologically active compositions and methods of the invention include the compounds exemplified herein, as well as their pharmaceutically acceptable salts, polymorphs, solvates, hydrates, and prodrugs.

Within related embodiments, the invention provides methods for treating CNS disorders responsive to the inhibition of biogenic amine transporters, in particular, one or more, or any combination of, the norepinephrine, serotonin and dopamine transporters, in mammalian subjects. In more detailed embodiments, the invention provides methods for using the novel compounds disclosed herein for treating CNS disorders, including a range of neuropsychiatric disorders, such as depression and anxiety. In various embodiments, the compositions and methods are formulated, and administered, effectively as anti-depressants, or as anxiolytic agents.

In accordance with the invention, compounds disclosed herein, optionally formulated with additional ingredients in a pharmaceutically acceptable composition, are administered to mammalian subjects, for example a human patient, to treat or prevent one or more symptom(s) of a CNS disorder alleviated by inhibiting dopamine reuptake, and/or norepinephrine reuptake, and/or serotonin reuptake. In certain embodiments, "treatment" or "treating" refers to amelioration of one or more symptom(s) of a CNS disorder, whereby the symptom(s) is/are alleviated by inhibiting dopamine and/or norepinephrine and/or serotonin reuptake. In other embodiments, "treatment" or "treating" refers to an amelioration of at least one measurable physical parameter associated with a CNS disorder. In yet another embodiment, "treatment" or "treating" refers to inhibiting or reducing the progression or severity of a CNS disorder (or one or more symptom(s) thereof) alleviated by inhibiting dopamine and/or norepinephrine and/or serotonin reuptake, e.g., as discerned based on physical, physiological, and/or psychological parameters. In additional embodiments, "treatment" or "treating" refers to delaying the onset of a CNS disorder (or one or more symptom(s) thereof) alleviated by inhibiting dopamine and/or norepinephrine and/or serotonin reuptake.

In certain embodiments, a compound of the present invention or a pharmaceutically acceptable salt thereof is administered to a mammalian subject, for example a human patient, as a preventative or prophylactic treatment against a CNS disorder (or one or more symptom(s) thereof) alleviated by inhibiting dopamine and/or norepinephrine and/or serotonin reuptake. As used herein, "prevention", "preventing", and prophylaxis refers to a reduction in the risk or likelihood that the subject will acquire a CNS disorder or one or more symptom(s) thereof, which risk or likelihood is reduced in the subject by inhibiting dopamine and/or norepinephrine and/or serotonin reuptake. Alternatively, prevention and prophylaxis may correlate with a reduced risk of recurrence of the CNS disorder or symptom(s) thereof in the subject once the subject has been cured, restored to a normal state, or placed in remission from the subject CNS disorder. In related embodiments, a compound or pharmaceutical composition of the invention is administered as a preventative measure to the subject. Exemplary subjects amenable to prophylactic treatment in this context may have a genetic predisposition to a CNS disorder amenable to treatment by inhibiting dopamine, and/or serotonin, and/or norepinephrine reuptake, such as a family history of a biochemical imbalance in the brain, or a non-genetic predisposition to a disorder alleviated by inhibiting dopamine and/or norepinephrine and/or serotonin reuptake.

A compound of the present invention and pharmaceutically acceptable salts thereof are useful for treating or preventing endogenous disorders alleviated by inhibiting dopamine and/or norepinephrine and/or serotonin reuptake. Such disorders include, but are not limited to, attention-deficit disorder, depression, anxiety, obesity, Parkinson's disease, tic disorders, and addictive disorders.

Disorders alleviated by inhibiting dopamine and/or norepinephrine and/or serotonin reuptake are not limited to the specific disorders described herein, and the compositions and methods of the invention will be understood or readily ascertained to provide effective treatment agents for treating and/or preventing a wide range of additional CNS disorders and associated symptoms. For example, the compounds of the invention will provide promising candidates for treatment and/or prevention of attention deficit hyperactivity disorder and related symtoms, as well as forms and symptoms of alcohol abuse, drug abuse, obsessive compulsive behaviors, learning disorders, reading problems, gambling addiction, manic symptoms, phobias, panic attacks, oppositional defiant behavior, conduct disorder, academic problems in school, smoking, abnormal sexual behaviors, schizoid behaviors, somatization, depression, sleep disorders, general anxiety, stuttering, and tics disorders (see for example, U.S. Pat. No. 6,132,724). These and other symptoms, regardless of the underlying CNS disorder, are each prospective therapeutic targets for the novel compositions and methods of the invention that mediate therapeutic benefits by inhibiting dopamine and/or norepinephrine and/or serotonin reuptake. Additional CNS disorders contemplated for treatment employing the compositions and methods of the invention are described, for example, in the Quick Reference to the Diagnostic Criteria. From DSM-IV (Diagnostic and Statistical Manual of Mental Disorders, Fourth Edition), The American Psychiatric Association, Washington, D.C., 1994. These target disorders for treatment and/or prevention according to the invention, include, but are not limited to, Attention-Deficit/Hyperactivity Disorder, Predominately Inattentive Type; Attention-Deficit/Hyperactivity Disorder, Predominately Hyperactivity-Impulsive Type; Attention-Deficit/Hyperactivity Disorder, Combined Type; Attention-Deficit/Hyperactivity Disorder not otherwise specified (NOS); Conduct Disorder; Oppositional Defiant Disorder; and Disruptive Behavior Disorder not otherwise specified (NOS).

Depressive disorders amenable for treatment and/or prevention according to the invention include, but are not limited to, Major Depressive Disorder, Recurrent; Dysthymic Disorder; Depressive Disorder not otherwise specified (NOS); and Major Depressive Disorder, Single Episode.

Addictive disorders amenable for treatment and/or prevention employing the methods and compositions of the invention include, but are not limited to, eating disorders, impulse control disorders, alcohol-related disorders, nicotine-related disorders, amphetamine-related disorders, cannabis-related disorders, cocaine-related disorders, hallucinogen use disorders, inhalant-related disorders, and opioid-related disorders, all of which are further sub-classified as listed below.

Eating disorders include, but are not limited to, Bulimia Nervosa, Nonpurging Type; Bulimia. Nervosa, Purging Type; and Eating Disorder not otherwise specified (NOS).

Impulse control disorders include, but are not limited to, Intermittent Explosive Disorder, Kleptomania, Pyromania, Pathological Gambling, Trichotillomania, and Impulse Control Disorder not otherwise specified (NOS).

Alcohol-related disorders include, but are not limited to, Alcohol-Induced Psychotic Disorder, with delusions; Alcohol Abuse; Alcohol Intoxication; Alcohol Withdrawal; Alcohol Intoxication Delirium; Alcohol Withdrawal Delirium; Alcohol-Induced Persisting Dementia; Alcohol-Induced Persisting Amnestic Disorder; Alcohol Dependence; Alcohol-Induced Psychotic Disorder, with hallucinations; Alcohol-Induced Mood Disorder; Alcohol-Induced Anxiety Disorder; Acohol-Induced Sexual Dysfunction; Alcohol-Induced Sleep Disorders; Alcohol-Related Disorders not otherwise specified (NOS); Alcohol Intoxication; and Alcohol Withdrawal.

Nicotine-related disorders include, but are not limited to, Nicotine Dependence, Nicotine Withdrawal, and Nicotine-Related Disorder not otherwise specified (NOS).

Amphetamine-related disorders include, but are not limited to, Amphetamine Dependence, Amphetamine Abuse, Amphetamine Intoxication, Amphetamine Withdrawal, Amphetamine Intoxication Delirium, Amphetamine-Induced Psychotic Disorder with delusions, Amphetamine-Induced Psychotic Disorders with hallucinations, Amphetamine-Induced Mood Disorder, Amphetamine-Induced Anxiety Disorder, Amphetamine-Induced Sexual Dysfunction, Amphetamine-Induced Sleep Disorder, Amphetamine Related Disorder not otherwise specified (NOS), Amphetamine Intoxication, and Amphetamine Withdrawal.

Cannabis-related disorders include, but are not limited to, Cannabis Dependence; Cannabis Abuse; Cannabis Intoxication; Cannabis Intoxication Delirium; Cannabis-Induced Psychotic Disorder, with delusions; Cannabis-Induced Psychotic Disorder with hallucinations; Cannabis-Induced Anxiety Disorder; Cannabis Related Disorder not otherwise specified (NOS); and Cannabis intoxication.

Cocaine-related disorders include, but are not limited to, Cocaine Dependence, Cocaine Abuse, Cocaine Intoxication, Cocaine Withdrawal, Cocaine Intoxication Delirium, Cocaine-Induced Psychotic Disorder with delusions, Cocaine-Induced Psychotic Disorders with hallucinations, Cocaine-Induced Mood Disorder, Cocaine-Induced Anxiety Disorder, Cocaine-Induced Sexual Dysfunction, Cocaine-Induced Sleep Disorder, Cocaine Related Disorder not otherwise specified (NOS), Cocaine Intoxication, and Cocaine Withdrawal.

Hallucinogen-use disorders include, but are not limited to, Hallucinogen Dependence, Hallucinogen Abuse, Hallucinogen Intoxication, Hallucinogen Withdrawal, Hallucinogen Intoxication Delirium, Hallucinogen-Induced Psychotic Disorder with delusions, Hallucinogen-Induced Psychotic Disorders with hallucinations, Hallucinogen-Induced Mood Disorder, Hallucinogen-Induced Anxiety Disorder, Hallucinogen-Induced Sexual Dysfunction, Hallucinogen-Induced Sleep Disorder, Hallucinogen Related Disorder not otherwise specified (NOS), Hallucinogen Intoxication, and Hallucinogen Persisting Perception Disorder (Flashbacks).

Inhalant-related disorders include, but are not limited to, Inhalant Dependence; Inhalant Abuse; Inhalant Intoxication; Inhalant Intoxication Delirium; Inhalant-Induced Psychotic Disorder, with delusions; Inhalant-Induced Psychotic Disorder with hallucinations; Inhalant-Induced Anxiety Disorder; Inhalant Related Disorder not otherwise specified (NOS); and Inhalant Intoxication.

Opioid-related disorders include, but are not limited to, Opioid Dependence, Opioid Abuse, Opioid Intoxication, Opioid Intoxication Delirium, Opioid-Induced Psychotic Disorder with delusions, Opioid-Induced Psychotic Disorder with hallucinations, Opioid-Induced Anxiety Disorder, Opioid Related Disorder not otherwise specified (NOS), Opioid Intoxication, and Opioid Withdrawal.

Tic disorders include, but are not limited to, Tourette's Disorder, Chronic Motor or Vocal Tic Disorder, Transient Tic Disorder, Tic Disorder not otherwise specified (NOS), Stuttering, Autistic Disorder, and Somatization Disorder.

By virtue of their multiple reuptake inhibitory activity, the novel compounds of the present invention are thus useful in a wide range of veterinary and human medical applications, in particular for treating and/or preventing a wide array of CNS disorders and/or associated symptom(s) alleviated by by inhibiting dopamine and/or norepinephrine and/or serotonin reuptake.

Within additional aspects of the invention, combinatorial formulations and coordinate administration methods are provided which employ an effective amount of a compound of the invention (or a pharmaceutically effective enantiomer, salt, solvate, hydrate, polymorph, or prodrug thereof), and one or more additional active agent(s) that is/are combinatorially formulated or coordinately administered with the compound of the invention—yielding a combinatorial formulation or coordinate administration method that is effective to modulate, alleviate, treat or prevent a targeted CNS disorder, or one or more symptom(s) thereof, in a mammalian subject. Exemplary combinatorial formulations and coordinate treatment methods in this context a therapeutic compound of the invention in combination with one or more additional or adjunctive treatment agents or methods for treating the targeted CNS disorder or symptom(s), for example one or more antidepressant or anxiolytic agent(s) and/or therapeutic method(s).

In related embodiments of the invention, the compounds disclosed herein can be used in combination therapy with at least one other therapeutic agent or method. In this context, compounds of the invention can be administered concurrently or sequentially with administration of a second therapeutic agent, for example a second agent that acts to treat or prevent the same, or different, CNS disorder or symptom(s) for which the compound of the invention is administered. The compound of the invention and the second therapeutic agent can be combined in a single composition or adminstered in different compositions. The second therapeutic agent may also be effective for treating and/or preventing a CNS disorder or associated symptom(s) by inhibiting dopamine and/or norepinephrine and/or serotonin reuptake. The coordinate administration may be done simultaneously or sequentially in either order, and there may be a time period while only one or both (or all) active therapeutic agents, individually and/or collectively, exert their biological activities and therapeutic effects. A distinguishing aspect of all such coordinate treatment methods is that the compound of the invention exerts at least some detectable therapeutic activity toward alleviating or preventing the targeted CNS disorder or symptom(s), as described herein, and/or elicit a favorable clinical response, which may or may not be in conjunction with a secondary clinical response provided by the secondary therapeutic agent. Often, the coordinate administration of a compound of the invention with a secondary therapeutic agent as contemplated herein will yield an enhanced therapeutic response beyond the therapeutic response elicited by either or both the compound of the invention and/or secondary therapeutic agent alone.

As many of the CNS disorders and symptoms treatable or preventable using compounds of the present invention are chronic, in one embodiment combination therapy involves alternating between administering a compound of the present invention and a second therapeutic agent (i.e., alternating therapy regimens between the two drugs, e.g., at one week, one month, three month, six month, or one year intervals). Alternating drug regimens in this context will often reduce or even eliminate adverse side effects, such as toxicity, that may attend long-term administration of one or both drugs alone.

In certain embodiments of combinatorial formulations and coordinate treatment methods of the invention, the secondary therapeutic is a norepinephrine reuptake inhibitor. Examples of norepinephrine reuptake inhibitors useful in this context include tertiary amine tricyclics such as amitriptyline, clomipramine, doxepin, imipramine, (+)-trimipramine, and secondary amine tricyclics including amoxapine, atomoxetine, desipramine, maprotiline, nortriptyline, and protriptyline.

In certain embodiments of combinatorial formulations and coordinate treatment methods of the invention, the secondary therapeutic is a serotonin reuptake inhibitor. Examples of other serotonin reuptake inhibitors useful in this context include citalopram, fluoxetine, fluvoxamine, (−)-paroxetine, sertraline, and venlafaxine.

In other embodiments of combinatorial formulations and coordinate treatment methods provided herein, the secondary therapeutic agent is an anti-attention-deficit-disorder treatment agent. Examples of useful anti-attention-deficit-disorder agents for use in these embodiments include, but are not limited to, methylphenidate; dextroamphetamine; tricyclic antidepressants, such as imipramine, desipramine, and nortriptyline; and psychostimulants, such as pemoline and deanol.

In additional embodiments of combinatorial formulations and coordinate treatment methods provided herein, the secondary therapeutic agent is an anti-addictive-disorder agent. Examples of useful anti-addictive-disorder agents include, but are not limited to, tricyclic antidepressants; glutamate antagonists, such as ketamine HCl, dextromethorphan, dextrorphan tartrate and dizocilpine (MK801); degrading enzymes, such as anesthetics and aspartate antagonists; GABA agonists, such as baclofen and muscimol reuptake blockers; degrading enzyme blockers; glutamate agonists, such as D-cycloserine, carboxyphenylglycine, L-glutamic acid, and cis-piperidine-2,3-dicarboxylic acid; aspartate agonists; GABA antagonists such as gabazine (SR-95531), saclofen, bicuculline, picrotoxin, and (+) apomorphine HCl; and dopamine antagonists, such as spiperone HCl, haloperidol, and (−) sulpiride.

In other embodiments of combinatorial formulations and coordinate treatment methods provided herein, the secondary therapeutic agent is an anti-alcohol agent. Examples of useful anti-alcohol agents include, but are not limited to, disulfiram and naltrexone.

In other embodiments of combinatorial formulations and coordinate treatment methods provided herein, the secondary therapeutic agent is an anti-nicotine agent. Examples of useful anti-nicotine agents include, but are not limited to, clonidine.

In other embodiments of combinatorial formulations and coordinate treatment methods provided herein, the secondary therapeutic agent is an anti-opiate agent. Examples of useful anti-opiate agents include, but are not limited to, methadone, clonidine, lofexidine, levomethadyl acetate HCl, naltrexone, and buprenorphine.

In other embodiments of combinatorial formulations and coordinate treatment methods provided herein, the secondary therapeutic agent is anti-cocaine agent. Examples of useful anti-cocaine agents include, but are not limited to, desipramine, amantadine, fluoxidine, and buprenorphine.

In other embodiments of combinatorial formulations and coordinate treatment methods provided herein, the secondary therapeutic agent is an anti-lysergic acid diethylamide ("anti-LSD") agent. Examples of useful anti-LSD agents include, but are not limited to, diazepam.

In other embodiments of combinatorial formulations and coordinate treatment methods provided herein, the secondary therapeutic agent is an anti-phencyclidine ("anti-PCP") agent. Examples of useful anti-PCP agents include, but are not limited to, haloperidol.

In other embodiments of combinatorial formulations and coordinate treatment methods provided herein, the secondary therapeutic agent is an appetite suppressant. Examples of useful appetite suppressants include, but are not limited to, fenfluramine, phenylpropanolamine, and mazindol.

In yet additional embodiments of combinatorial formulations and coordinate treatment methods provided herein, the secondary therapeutic agent is an anti-Parkinson's-disease agent. Examples of useful anti-Parkinson's-disease agents include, but are not limited to dopamine precursors, such as levodopa, L-phenylalanine, and L-tyrosine; neuroprotective agents; dopamine agonists; dopamine reuptake inhibitors; anticholinergics such as amantadine and memantine; and 1,3,5-trisubstituted adamantanes, such as 1-amino-3,5-dimethyl-adamantane (See, U.S. Pat. No. 4,122,193).

Mammalian subjects amenable for treatment according to the methods of the invention include, but are not limited to, human and other mammalian subjects suffering from a CNS disorder that is amenable to treatment or beneficial intervention using an active agent capable of inhibiting reuptake of norepinephrine, serotonin, and/or dopamine by interfering with the CNS conditions that are subject to treatment according to the methods and compositions of the invention include depression, as well as a variety of other neuropsychiatric conditions and disorders. Other disorders for which the compounds of the present invention may be useful include irritable bowel syndrome; inflammatory bowel disease; bulimia; anorexia; obesity and related eating disorders; urinary tract disorders, such as stress urinary incontinence; addictive disorders (including addiction to nicotine, stimulants, alcohol, and opiates); degenerative diseases, including Alzheimers disease, amyotrophic lateral sclerosis, and Parkinson's disease; and pyretic conditions (including fevers, and post- and peri-menopausal hot flashes). For each of the foregoing disorders, combinatorial formulations and coordinate treatment methods are provided within the scope of the invention comprising compounds of the invention coordinately administered or combinatorially formulated with a second therapeutic agent or method known for treating the subject disorder, and/or one or more symptom(s) associated therewith.

Subjects are effectively treated prophylactically and/or therapeutically by administering to the subject an effective amount of a compound of the invention, which is effective to treat, alleviate, prevent or eliminate a targeted CNS disorder in the subject, and/or one or more symptom(s) associated therewith, for example depression.

Administration of an effective amount of a compound of the present invention to a mammalian subject presenting with one or more of the foregoing CNS disorders and/or symptom(s) will detectably decrease, eliminate, or prevent the targeted CNS disorder and/or associated symptom(s). In certain embodiments, administration of a compound of the present invention to a suitable test subject will yield a reduction in the targeted CNS disorder, or one or more targeted symptom(s) associated therewith, such as depression, by at least 10%, 20%, 30%, 50% or greater, up to a 75-90%, or 95% or greater, reduction in the one or more target symptom(s), compared to placebo-treated or other suitable control subjects. Comparable levels of efficacy are contemplated for the entire range of CNS disorders described herein, including all contemplated neurological and psychiatric disorders, as well as all other CNS conditions and symptoms identified herein for treatment or prevention using the compositions and methods of the invention.

The active compounds of the invention may be optionally formulated with a pharmaceutically acceptable carrier and/or various excipients, vehicles, stabilizers, buffers, preservatives, etc. An "effective amount," "therapeutic amount," "therapeutically effective amount," or "effective dose" is an effective amount or dose of an active compound as described herein sufficient to elicit a desired pharmacological or therapeutic effect in a mammalian subject—typically resulting in a measurable reduction in an occurrence, frequency, or severity of one or more symptom(s) associated with or caused by a CNS disorder, including a neurological or psychological disease, condition, or disorder in the subject. In certain embodiments, when a compound of the invention is administered to treat a CNS disorder, for example depression, an effective amount of the compound will be an amount sufficient in vivo to delay or eliminate onset of symptoms of the targeted condition or disorder. Therapeutic efficacy can alternatively be demonstrated by a decrease in the frequency or severity of symptoms associated with the treated condition or disorder, or by altering the nature, recurrence, or duration of symptoms associated with the treated condition or disorder. Therapeutically effective amounts, and dosage regimens, of the compositions of the invention, including pharmaceutically effective salts, solvates, hydrates, polymorphs or prodrugs thereof, will be readily determinable by those of ordinary skill in the art, often based on routine clinical or patient-specific factors.

Suitable routes of administration for a compound of the present invention include, but are not limited to, oral, buccal, nasal, aerosol, topical, transdermal, mucosal, injectable, slow release, controlled release, iontophoresis, sonophoresis, and other conventional delivery routes, devices and methods. Injectable delivery methods are also contemplated, including but not limited to, intravenous, intramuscular, intraperitoneal, intraspinal, intrathecal, intracerebroventricular, intraarterial, and subcutaneous injection.

Suitable effective unit dosage amounts of 1-aryl-3-azabicyclo[3.1.0]hexanes of the present invention for mammalian subjects may range from about 1 to 1200 mg, 50 to 1000 mg, 75 to 900 mg, 100 to 800 mg, or 150 to 600 mg. In certain embodiments, the effective unit dosage will be selected within narrower ranges of, for example, 10 to 25 mg, 30 to 50 mg, 75 to 100 mg, 100 to 150 mg, 1.50 to 250 mg or 250 to 500 mg. These and other effective unit dosage amounts may be administered in a single dose, or in the form of multiple daily, weekly or monthly doses, for example in a dosing regimen comprising from 1 to 5, or 2-3, doses administered per day, per week, or per month. In exemplary embodiments, dosages of 10 to 25 mg, 30 to 50 mg, 75 to 100 mg, 100 to 200 (anticipated dosage strength) mg, or 250 to 500 mg, are administered one, two, three, or four times per day. In more detailed embodiments, dosages of 50-75 mg, 100-150 mg, 150-200 mg, 250-400 mg, or 400-600 mg are administered once, twice daily or three times daily. In alternate embodiments, dosages are calculated based on body weight, and may be administered, for example, in amounts from about 0.5 mg/kg to about 30 mg/kg per day, 1 mg/kg to about 15 mg/kg per day, 1 mg/kg to about 10 mg/kg per day, 2 mg/kg to about 20 mg/kg per day, 2 mg/kg to about 10 mg/kg per day or 3 mg/kg to about 15 mg/kg per day.

The amount, timing and mode of delivery of compositions of the invention comprising an effective amount of a compound of the present invention will be routinely adjusted on an individual basis, depending on such factors as weight, age, gender, and condition of the individual, the acuteness of the targeted CNS disorder and/or related symptoms, whether the administration is prophylactic or therapeutic, and on the basis of other factors known to effect drug delivery, absorption, pharmacokinetics, including half-life, and efficacy. An effective dose or multi-dose treatment regimen for the compounds of the invention will ordinarily be selected to approximate a minimal dosing regimen that is necessary and sufficient to substantially prevent or alleviate one or more symptom(s) of a neurological or psychiatric condition in the subject, as described herein. Thus, following administration of a compound of the present invention, test subjects will exhibit a 10%, 20%, 30%, 50% or greater reduction, up to a 75-90%, or 95% or greater, reduction, in one or more symptoms associated with a targeted CNS disorder, including any targeted neuropsychiatric disorder, such as depression, compared to placebo-treated or other suitable control subjects.

Within additional aspects of the invention, combinatorial formulations and coordinate administration methods are provided which employ an effective amount of a compound of the present invention—yielding an effective formulation or method to alleviate or prevent one or more symptom(s) of a CNS disorder in a mammalian subject.

Pharmaceutical dosage forms of a compound of the present invention may optionally include excipients recognized in the art of pharmaceutical compounding as being suitable for the preparation of dosage units as discussed above. Such excipients include, without intended limitation, binders, fillers, lubricants, emulsifiers, suspending agents, sweeteners, flavorings, preservatives, buffers, wetting agents, disintegrants, effervescent agents and other conventional excipients and additives.

The compositions of the invention for treating CNS disorders, including depression, can thus include any one or combination of the following: a pharmaceutically acceptable carrier or excipient; other medicinal agent(s); pharmaceutical agent(s); adjuvants; buffers; preservatives; diluents; and various other pharmaceutical additives and agents known to those skilled in the art. These additional formulation additives and agents will often be biologically inactive and can be administered to patients without causing deleterious side effects or interactions with the active agent.

If desired, a compound of the present invention can be administered in a controlled release form by use of a slow release carrier, such as a hydrophilic, slow release polymer. Exemplary controlled release agents in this context include, but are not limited to, hydroxypropyl methyl cellulose, having a viscosity in the range of about 100 cps to about 100,000 cps.

A compound of the present invention will often be formulated and administered in an oral dosage form, optionally in combination with a carrier or other additive(s). Suitable carriers common to pharmaceutical formulation technology include, but are not limited to, microcrystalline cellulose, lactose, sucrose, fructose, glucose dextrose, or other sugars, di-basic calcium phosphate, calcium sulfate, cellulose, methylcellulose, cellulose derivatives, kaolin, mannitol, lactitol, maltitol, xylitol, sorbitol, or other sugar alcohols, dry starch, dextrin, maltodextrin or other polysaccharides, inositol, or mixtures thereof. Exemplary unit oral dosage forms for use in this invention include tablets, which may be prepared by any conventional method of preparing pharmaceutical oral unit dosage forms can be utilized in preparing oral unit dosage forms. Oral unit dosage forms, such as tablets, may contain one or more conventional additional formulation ingredients, including, but are not limited to, release modifying agents, glidants, compression aides, disintegrants, lubricants, binders, flavors, flavor enhancers, sweeteners and/or preservatives. Suitable lubricants include stearic acid, magnesium stearate, talc, calcium stearate, hydrogenated vegetable oils, sodium benzoate, leucine carbowax, magnesium lauryl sulfate, colloidal silicon dioxide and glyceryl monostearate. Suitable glidants include colloidal silica, fumed silicon dioxide, silica, talc, fumed silica, gypsum and glyceryl monostearate. Substances which may be used for coating include hydroxypropyl cellulose, titanium oxide, talc, sweeteners and colorants. The aforementioned effervescent agents and disintegrants are useful in the formulation of rapidly disintegrating tablets known to those skilled in the art. These typically disintegrate in the mouth in less than one minute, and preferably in less than thirty seconds. By effervescent agent is meant a couple, typically an organic acid and a carbonate or bicarbonate. Such rapidly acting dosage forms would be useful, for example, in the prevention or treatment of acute attacks of panic disorder.

The compounds and compositions of the invention can be prepared and administered in any of a variety of inhalation or nasal delivery forms known in the art. Devices capable of depositing aerosolized formulations of a compound of the present invention in the sinus cavity or pulmonary alveoli of a patient include metered dose inhalers, nebulizers, dry powder generators, sprayers, and the like. Pulmonary delivery to the lungs for rapid transit across the alveolar epithelium into the blood stream may be particularly useful in treating impending episodes of seizures or panic disorder. Methods and compositions suitable for pulmonary delivery of drugs for systemic effect are well known in the art. Suitable formulations, wherein the carrier is a liquid, for administration, as for example, a nasal spray or as nasal drops, may include aqueous or oily solutions of a compound of the present invention, and any additional active or inactive ingredient(s).

Intranasal delivery permits the passage of active compounds of the invention into the blood stream directly after administering an effective amount of the compound to the nose, without requiring the product to be deposited in the lung. In addition, intranasal delivery can achieve direct, or enhanced, delivery of the active compound to the CNS. In these and other embodiments, intranasal administration of the compounds of the invention may be advantageous for treating a variety of CNS disorders, including depression, by providing for rapid absorption and CNS delivery.

For intranasal and pulmonary administration, a liquid aerosol formulation will often contain an active compound of the invention combined with a dispersing agent and/or a physiologically acceptable diluent. Alternative, dry powder aerosol formulations may contain a finely divided solid form of the subject compound and a dispersing agent allowing for the ready dispersal of the dry powder particles. With either liquid or dry powder aerosol formulations, the formulation must be aerosolized into small, liquid or solid particles in order to ensure that the aerosolized dose reaches the mucous membranes of the nasal passages or the lung. The term "aerosol particle" is used herein to describe a liquid or solid particle suitable of a sufficiently small particle diameter, e.g., in a range of from about 2-5 microns, for nasal or pulmonary distribution to targeted mucous or alveolar membranes. Other considerations include the construction of the delivery device, additional components in the formulation, and particle characteristics. These aspects of nasal or pulmonary administration of drugs are well known in the art, and manipulation of formulations, aerosolization means, and construction of delivery devices, is within the level of ordinary skill in the art.

Yet additional compositions and methods of the invention are provided for topical administration of a compound of the present invention for treating CNS disorders, including depression. Topical compositions may comprise a compound of the present invention and any other active or inactive component(s) incorporated in a dermatological or mucosal acceptable carrier, including in the form of aerosol sprays, powders, dermal patches, sticks, granules, creams, pastes, gels, lotions, syrups, ointments, impregnated sponges, cotton applicators, or as a solution or suspension in an aqueous liquid, non-aqueous liquid, oil-in-water emulsion, or water-in-oil liquid emulsion. These topical compositions may comprise a compound of the present invention dissolved or dispersed in a portion of a water or other solvent or liquid to be incorporated in the topical composition or delivery device. It can be readily appreciated that the transdermal route of administration may be enhanced by the use of a dermal penetration enhancer known to those skilled in the art. Formulations suitable for such dosage forms incorporate excipients commonly utilized therein, particularly means, e.g. structure or matrix, for sustaining the absorption of the drug over an extended period of time, for example 24 hours. A once-daily transdermal patch is particularly useful for a patient suffering from generalized anxiety disorder.

Yet additional formulations of a compound of the present invention are provided for parenteral administration, including aqueous and non-aqueous sterile injection solutions which may optionally contain anti-oxidants, buffers, bacteriostats and/or solutes which render the formulation isotonic with the blood of the mammalian subject; aqueous and non-aqueous sterile suspensions which may include suspending agents and/or thickening agents; dispersions; and emulsions. The formulations may be presented in unit-dose or multi-dose containers. Pharmaceutically acceptable formulations and ingredients will typically be sterile or readily sterilizable, biologically inert, and easily administered. Parenteral preparations typically contain buffering agents and preservatives, and may be lyophilized for reconstitution at the time of administration.

Parental formulations may also include polymers for extended release following parenteral administration. Such polymeric materials are well known to those of ordinary skill in the pharmaceutical compounding arts. Extemporaneous injection solutions, emulsions and suspensions may be prepared from sterile powders, granules and tablets of the kind previously described. Preferred unit dosage formulations are those containing a daily dose or unit, daily sub-dose, as described herein above, or an appropriate fraction thereof, of the active ingredient(s).

In more detailed embodiments, a compound of the present invention may be encapsulated for delivery in microcapsules, microparticles, or microspheres, prepared, for example, by coacervation techniques or by interfacial polymerization, for example, hydroxymethylcellulose or gelatin-microcapsules and poly(methylmethacylate) microcapsules, respectively, in colloidal drug delivery systems (for example, liposomes, albumin microspheres, microemulsions, nano-particles and nanocapsules) or in macroemulsions.

The invention also provides pharmaceutical packs or kits comprising one or more containers holding a compound of the present invention, or any composition comprising a compound of the present invention as described herein, including pharmaceutically acceptable salts and other forms of a compound of the present invention, in a pharmaceutically acceptable, stable form. Optionally packaged with these packs and kits can be a notice, e.g., in a form prescribed by a governmental agency regulating pharmaceuticals or biological products, reflecting approval by the agency of the manufacture, use and/or sale of the product contained in the pack or kit for human administration (optionally specifying one or more approved treatment indications as described herein).

The following examples illustrate certain embodiments of the present invention, and are not to be construed as limiting the present disclosure.

Example I

Synthetic Methods for Preparing Substituted 1-aryl-3-azabicyclo[3.1.0]hexanes

Although many of the novel 1-aryl-3-azabicyclo[3.1.0] hexanes of the invention may be prepared according to methods known to those skilled in the art, they may also be generated, for example, according to the exemplary reaction schemes set forth below. While these novel schemes employ various intermediates and starting materials, it is to be understood that the illustrated processes are also applicable to compounds having alternative structure, substituent patterns, or stereochemistry depicted in these schemes.

With regard to the following synthetic schemes, and as otherwise used herein unless specified differently, Ar is a phenyl group substituted with two substituents independently selected from halogen, $C_{1-3}$ alkyl, $C_{2-4}$ alkenyl, $C_{2-4}$ alkynyl, halo($C_{1-3}$)alkyl, cyano, hydroxy, $C_{3-5}$ cycloalkyl, $C_{1-3}$ alkoxy, $C_{1-3}$ alkoxy($C_{1-3}$)alkyl, carboxy($C_{1-3}$)alkyl, $C_{1-3}$ alkanoyl, halo($C_{1-3}$)alkoxy, nitro, amino, $C_{1-3}$ alkylamino, and di($C_{1-3}$) alkylamino, an unsubstituted napthyl group or a napthyl group having 1-4 substituents independently selected from halogen, $C_{1-3}$ alkyl, $C_{2-4}$ alkenyl, $C_{2-4}$ alkynyl, halo($C_{1-3}$) alkyl, cyano, hydroxy, $C_{3-5}$ cycloalkyl, $C_{1-3}$ alkoxy, $C_{1-3}$ alkoxy($C_{1-3}$)alkyl, carboxy($C^{1-3}$)alkyl, $C_{1-3}$ alkanoyl, halo ($C_{1-3}$)alkoxy, nitro, amino, $C_{1-3}$ alkylamino, and di($C_{1-3}$) alkylamino, and R and $R_1$ are selected from, for example, hydrogen, $C_{1-6}$ alkyl, halo($C_{1-6}$)alkyl, $C_{3-9}$ cycloalkyl, $C_{1-5}$ alkoxy($C_{1-6}$)alkyl, carboxy($C_{1-3}$)alkyl, $C_{1-3}$ alkanoyl, carbamate, halo($C_{1-3}$)alkoxy($C_{1-6}$)alkyl, $C_{1-3}$ alkylamino($C_{1-6}$) alkyl, and di($C_{1-3}$)alkylamino($C_{1-6}$)alkyl, cyano($C_{1-6}$)alkyl, methyl, ethyl, trifluoromethyl, trifluoroethyl and 2-methoxyethyl.

Reaction Scheme 1 below generally sets forth an exemplary process for preparing 1-aryl-3-azabicyclo[3.1.0]hexane analogs from the corresponding 2-bromo-2-arylacetate or 2-chloro-2-arylacetate. The bromo or chloro acetate react with acrylonitrile to provide the methyl 2-cyano-1-arylcyclopropanecarboxylate, which is then reduced to the amino alcohol by reducing agents such as lithium aluminum hydride (LAH) or sodium aluminum hydride (SAH) or $NaBH_4$ with $ZnCl_2$. Cyclization of the amino alcohol with $SOCl_2$ or $POCl_3$ will provide the 1-aryl-3-azabicyclo[3.1.0]hexane. The cyclization of substituted 4-aminobutan-1-ol by $SOCl_2$ or $POCl_3$ into the pyrrolidine ring system was reported by Armarego et al., J. Chem. Soc. [Section C: Organic] 19:3222-9, (1971), and in Szalecki et al., patent publication PL 120095B2, CAN 99:158251. Oxalyl chloride, phosphorous tribromide, triphenylphosphorous dibromide and oxalyl bromide may be used for the same purpose. The methyl 2-bromo-2-arylacetate or methyl 2-chloro-2-arylacetate may be synthesized from substituted benzoylaldehyde or methyl-2-arylacetate as shown in Reaction Scheme 1A.

Reaction Scheme 1

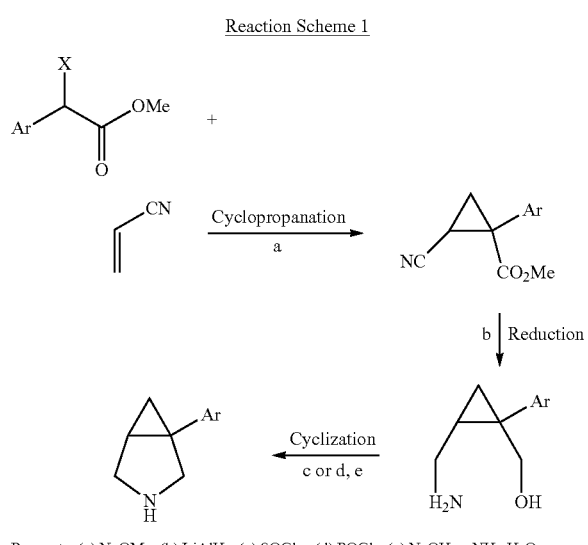

Reagents: (a) NaOMe; (b) LiAlH₃; (c) SOCl₂; (d) POCl₃; (e) NaOH or NH₃·H₂O

Reaction Scheme 1A

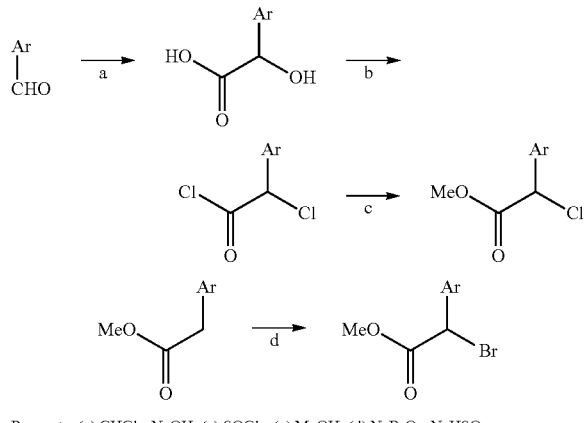

Reagents: (a) CHCl₃, NaOH; (c) SOCl₂; (c) MeOH; (d) NaBrO₃, NaHSO₃

Reaction Scheme 2 below illustrates another exemplary process for transforming methyl 2-cyano-1-arylcyclopropanecarboxylate to a desired compound or intermediate of the invention. Hydrolysis of the cyano ester provides the potassium salt which can then be converted into the cyano acid. Reduction and cyclization of the 2-cyano-1-arylcyclopropanecarboxylic acid with LAH or LiAlH(OMe)₃ according to the procedure outlined in Tetrahedron 45:3683 (1989), will generate 1-aryl-3-azabicyclo[3.1.0]hexane. In addition, the cyano-1-arylcyclopropanecarboxylic acid can be hydrogenated and cyclized into an amide, which is then reduced to 1-aryl-3-azabicyclo[3.1.0]hexane.

Reaction Scheme 2

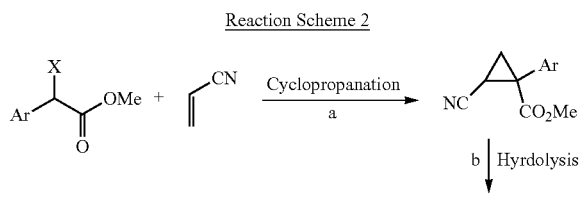

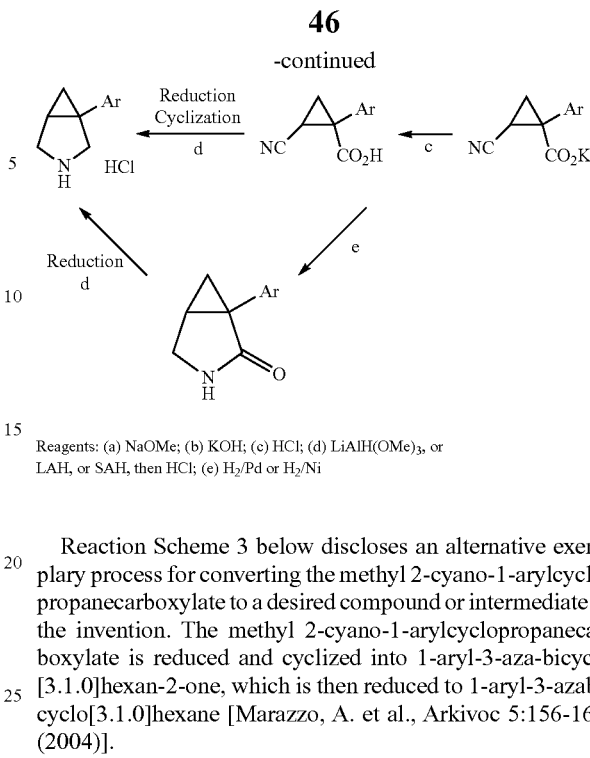

Reagents: (a) NaOMe; (b) KOH; (c) HCl; (d) LiAlH(OMe)₃, or LAH, or SAH, then HCl; (e) H₂/Pd or H₂/Ni Reaction Scheme 3 below discloses an alternative exemplary process for converting the methyl 2-cyano-1-arylcyclopropanecarboxylate to a desired compound or intermediate of the invention. The methyl 2-cyano-1-arylcyclopropanecarboxylate is reduced and cyclized into 1-aryl-3-aza-bicyclo[3.1.0]hexan-2-one, which is then reduced to 1-aryl-3-azabicyclo[3.1.0]hexane [Marazzo, A. et al., Arkivoc 5:156-169, (2004)].

Reaction Scheme 3

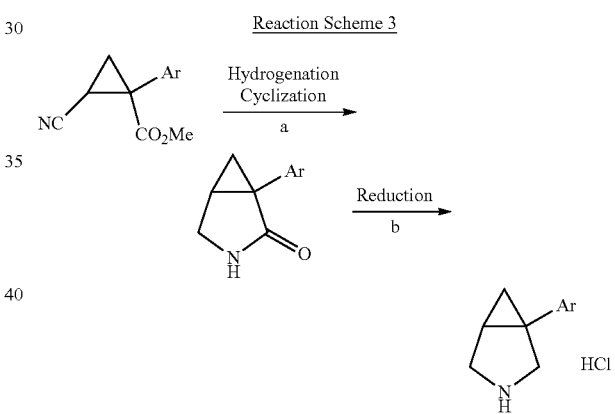

Reagents: (a) H₂/Pd or H₂/Ni; (b) B₂H₆ or BH₃ or LAH, then HCl

Reaction Scheme 4 below provides another exemplary process to prepare 1-aryl-3-azabicyclo[3.1.0]hexane analogs. Reaction of 2-arylacetonitrile with (±)-epichlorohydrin gives approximately a 65% yield of 2-(hydroxymethyl)-1-arylcyclopropanecarbonitrile (85% cis) with the trans isomer as one of the by-products [Cabadio et al., Fr. Bollettino Chimico Farmaceutico 117:331-42 (1978); Mouzin et al., Synthesis 4:304-305 (1978)]. The methyl 2-cyano-1-arylcyclopropanecarboxylate can then be reduced into the amino alcohol by a reducing agent such as LAH, SAH or NaBH₄ with ZnCl₂ or by catalytic hydrogenation. Cyclization of the amino alcohol with SOCl₂ or POCl₃ provides the 1-aryl-3-azabicyclo[3.1.0]hexane. The cyclization of substituted 4-aminobutan-1-ol by SOCl₂ or POCl₃ into the pyrrolidine ring system has been reported previously [Armarego et al., J. Chem. Soc. [Section C: Organic] 19:3222-9 (1971); patent publication PL 120095 B2, CAN 99:158251).

Reaction Scheme 4

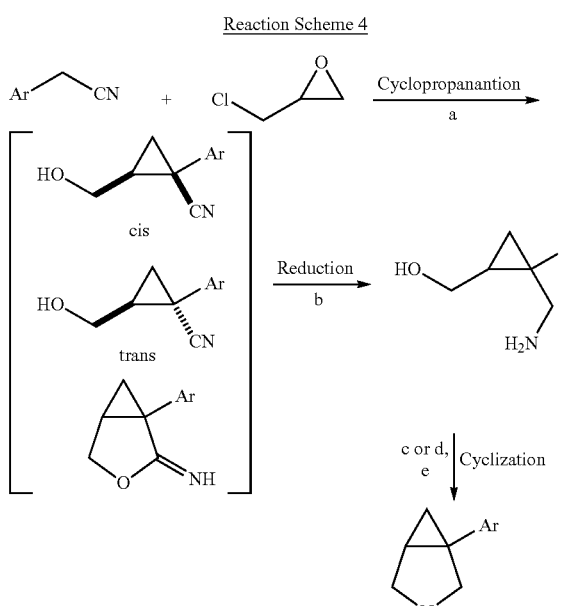

Reagents: (a) NaHMDS; (b) LAH or catalytic hydrogenation; (c) SOCl₂; (d) POCl₃; (e) NaOH Reaction Scheme 5 provides an exemplary process for synthesizing the (1R,5S)-(+)-1-aryl-3-azabicyclo[3.1.0]hexanes. Using (S)-(+)-epichlorohydrin as a starting material in the same process described in Scheme 4 will ensure a final product with 1-R chirality [Cabadio, S. et al., Fr. Bollettino Chimico Farmaceutico 117:331-42 (1978)].

Reaction Scheme 5

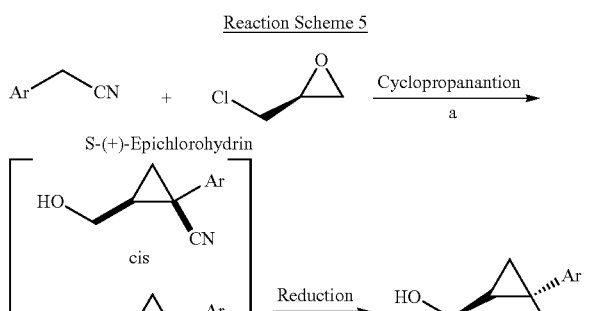

Reagents: (a) NaHMDS; (b) LAH or catalytic hydrogenation; (c) SOCl₂; (d) POCl₃; (e) NaOH Reaction Scheme 6 provides an exemplary process to prepare the (1S,5R)-(−)-1-aryl-3-azabicyclo[3.1.0]hexanes. Using (R)-(−)-epichlorohydrin as a starting material in the same process described in Scheme 4 will ensure a final product with 1-S chirality [Cabadio, S. et al., Fr. Bollettino Chimico Farmaceutico 117:331-42 (1978)].

Reaction Scheme 6

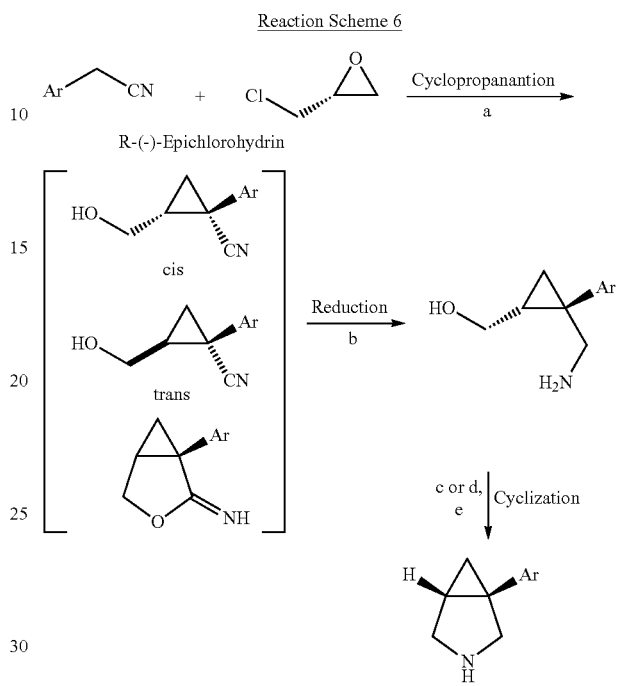

Reagents: (a) NaHMDS; (b) LAH or catalytic hydrogenation; (c) SOCl₂; (d) POCl₃; (e) NaOH Reaction Scheme 7 provides an alternative exemplary process for transforming the 2-(hydroxymethyl)-1-arylcyclopropanecarbonitrile to a desired compound or intermediate of the invention via an oxidation and cyclization reaction. Utilizing chiral starting materials (+)-epichlorohydrin or (−)-epichlorohydrin will lead to the corresponding (+)- or (−)-enantiomers and corresponding chiral analogs through the same reaction sequences.

Reaction Scheme 7

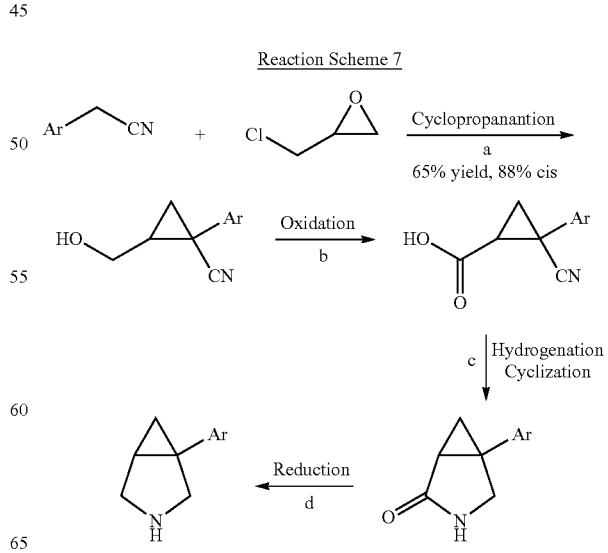

Reagents: (a) NaNH$_2$; (b) KMnO$_4$; (c) H$_2$/Ni or Pt; (d) B$_2$H$_6$ or BH$_3$ or LAH, then HCl

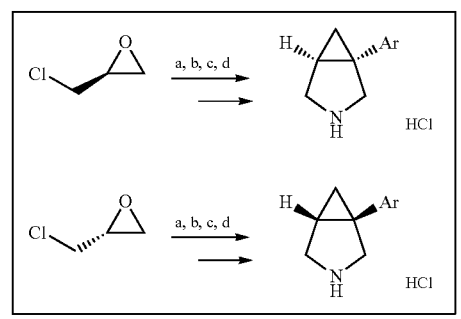

Reaction Scheme 8 provides an exemplary process for transforming the epichlorohydrin to a desired compound or intermediate of the invention via a replacement and cyclization reaction. The reaction of methyl 2-arylacetate with epichlorohydrin gives methyl 2-(hydroxymethyl)-1-arylcyclopropanecarboxylate with the desired cis isomer as the major product. The alcohol is converted into an OR$_3$ group such as —O-mesylate, —O-tosylate, —O-nosylate, —O-brosylate, —O-trifluoromethanesulfonate. Then OR$_3$ is replaced by a primary amine NH$_2$R$_4$, where R$_4$ is a nitrogen protection group such as a 3,4-dimethoxy-benzyl group or other known protection group. Nitrogen protecting groups are well known to those skilled in the art, see for example, "Nitrogen Protecting Groups in Organic Synthesis", John Wiley and Sons, New York, N.Y., 1981, Chapter 7; "Nitrogen Protecting Groups in Organic Chemistry", Plenum Press, New York, N.Y., 973, Chapter 2; T. W. Green and P. G. M. Wuts in "Protective Groups in Organic Chemistry", 3rd edition, John Wiley & Sons, Inc. New York, N.Y., 1999. When the nitrogen protecting group is no longer needed, it may be removed by methods well known in the art. This replacement reaction is followed by a cyclization reaction which provides the amide, which is then reduced into an amine by a reducing agent such as LAH. Finally the protection group is removed to yield the 1-aryl-3-azabicyclo[3.1.0]hexane analogs. Utilizing chiral (S)-(+)-epichlorohydrin as a starting material leads to the (1R,5S)-(+)-1-aryl-3-azabicyclo[3.1.0]hexane analogs with the same reaction sequence. Similarly, the (R)-(−)-epichlorohydrin will lead to the (1S,5R)-(−)-1-aryl-3-azabicyclo[3.1.0]hexane analogs.

Reaction Scheme 8

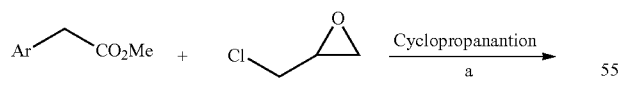

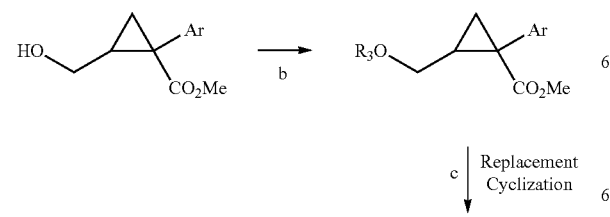

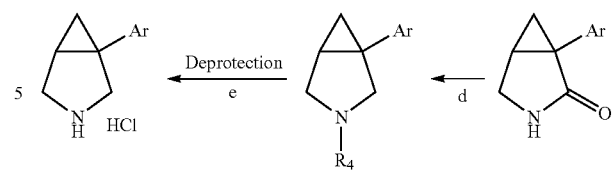

Reagents: (a) NaNH$_2$; (b) MsCl; (c) R$_4$NH$_2$; (d) LAH or SAH or BH$_3$; (e) HCl

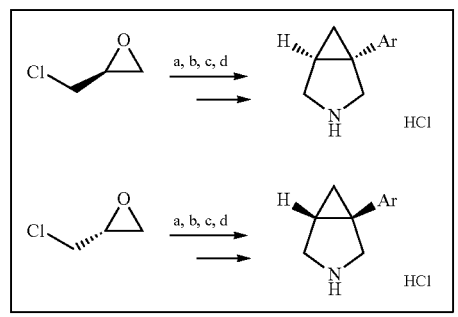

Reaction Scheme 9 provides an exemplary process for transforming the diol to a desired compound or intermediate of the invention. Reduction of the diester provides the diol which is then converted into an OR$_3$ group such as —O-mesylate, —O-tosylate, —O-nosylate, —O-brosylate, —O-trifluoromethanesulfonate. Then OR$_3$ is replaced by a primary amine NH$_2$R$_6$, where R$_6$ is a nitrogen protection group such as a 3,4-dimethoxy-benzyl group or other protection groups known in the art (e.g., allyl amine, tert-butyl amine). When the nitrogen protecting group is no longer needed, it may be removed by methods known to those skilled in the art.

Reaction Scheme 9

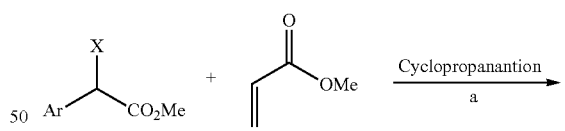

X = Cl or Br

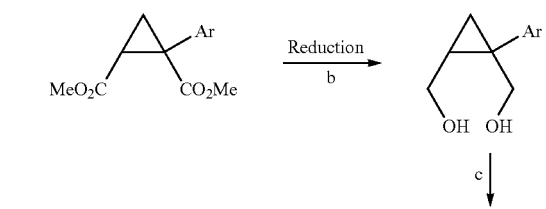

-continued

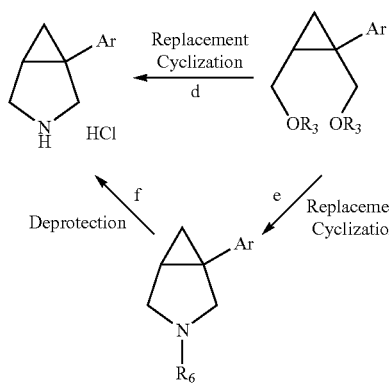

Reagents: (a) NaOMe; (b) NaBH₄; (c) MsCl; (d) NH₃, then HCl;
(e) R₆NH₂; (f) H₂/Pd or acid deprotection, then HCl Reaction Scheme 10 provides an exemplary process for resolving the racemic 1-aryl-3-aza-bicyclo[3.1.0]hexane to enantiomers. The resolution of amines through tartaric salts is generally known to those skilled in the art. For example, using O,O-Dibenzoyl-2R,3R-Tartaric Acid (made by acylating L(+)-tartaric acid with benzoyl chloride) in dichloroethane/methanol/water, racemic methamphetamine can be resolved in 80-95% yield, with an optical purity of 85-98% [Synthetic Communications 29:4315-4319 (1999)].

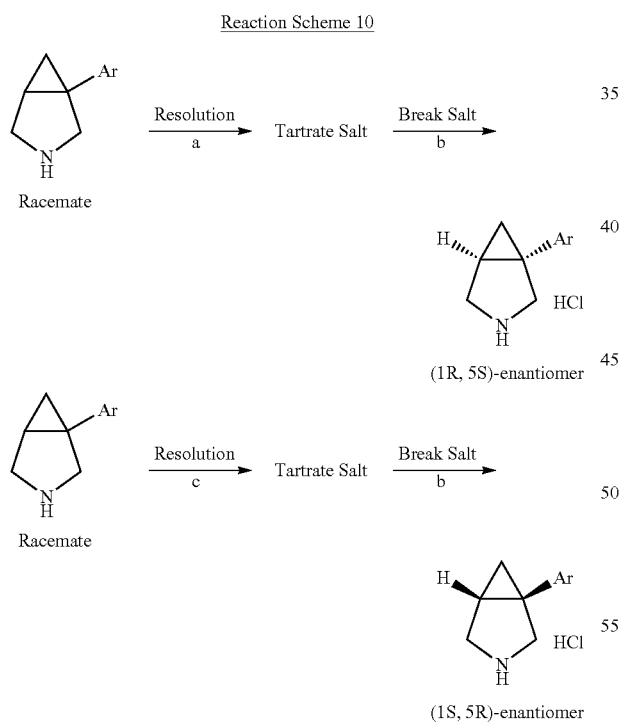

Reagents: (a) L-(-)-DBTA; (b) NaOH, then HCl in IPA; (c) D-(+)-DBTA

Reaction Scheme 11 provides an exemplary process for the preparation of 3-alkyl-1-aryl-3-azabicyclo[3.1.0]hexane analogs. These alkylation or reductive amination reaction reagents and conditions are generally well known to those skilled in the art.

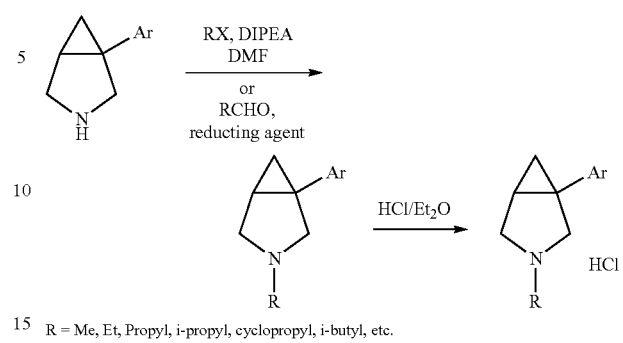

R = Me, Et, Propyl, i-propyl, cyclopropyl, i-butyl, etc.

Enantiomers of compounds within the present invention can be prepared as shown in Reaction Scheme 12 by separation through a chiral chromatography.

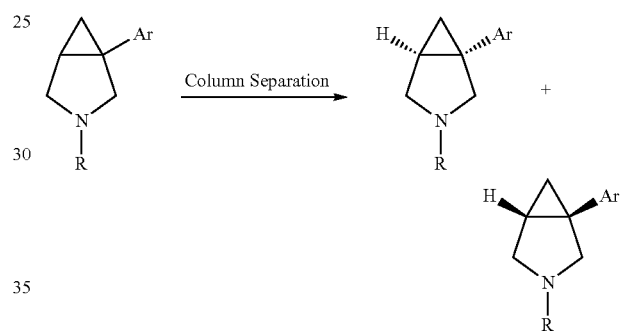

Alternatively, enantiomers of the compounds of the present invention can be prepared as shown in Reaction Scheme 13 using alkylation reaction conditions exemplified in scheme 11.

Reaction Scheme 14 provides an exemplary process for preparing some N-methyl 1-aryl-3-aza-bicyclo[3.1.0]hexane analogs. The common intermediate N-methyl bromomaleide is synthesized in one batch followed by Suzuki couplings with the various substituted aryl boronic acids. Cyclopropanations are then carried out to produce the imides, which are then reduced by borane to provide the desired compounds.

Reaction Scheme 14

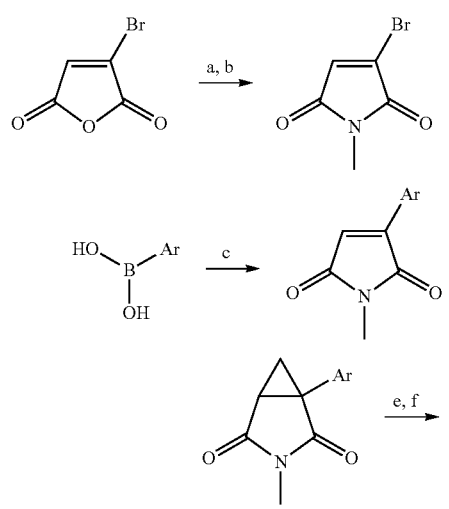

Reagents and conditions: (a) MeNH₂, THF, 10° C., 1.5 hr; (b) NaOAc, Ac₂O, 60° C., 2 hr; (c) PdCl₂(dppf), CsF, dioxane, 40° C., 1-6 hr; (d) Me₃SOCl, NaH, THF, 50-65° C., 2-6 hr; (e) 1M BH₃/THF, 0° C.; 60° C. 2 hr (f) HCl, Et₂O Reaction Scheme 15 provides an additional methodology for producing 1-aryl-3-azabicyclo[3.1.0]hexanes.

Reaction Scheme 15

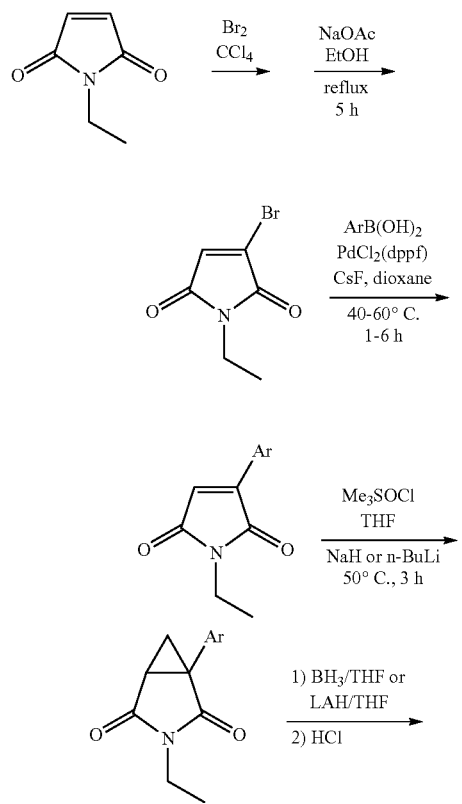

Reaction Scheme 16 provides an additional methodology for producing 1-aryl-3-azabicyclo[3.1.0]hexanes.

Reaction scheme 16

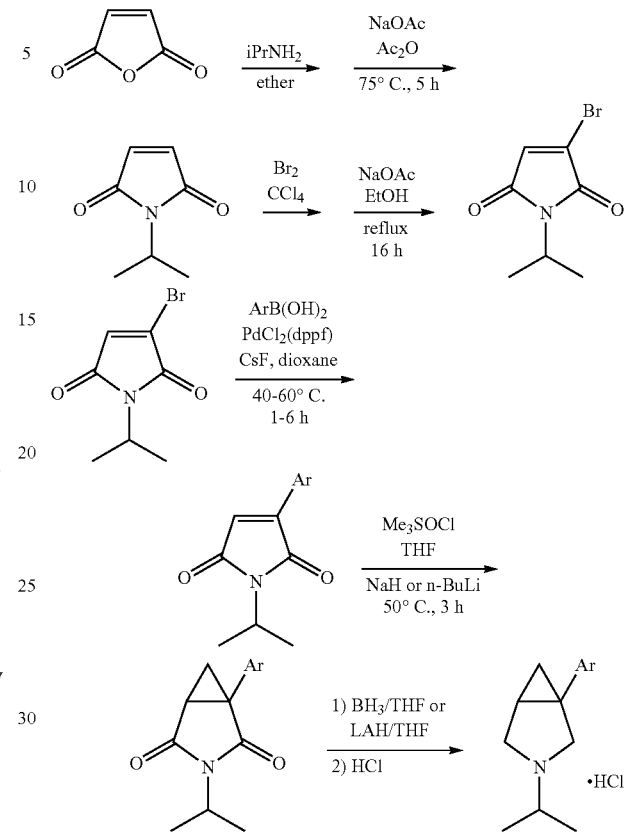

Reaction Scheme 17 provides an additional methodology for producing 1-aryl-3-azabicyclo[3.1.0]hexanes.

Reaction Scheme 17

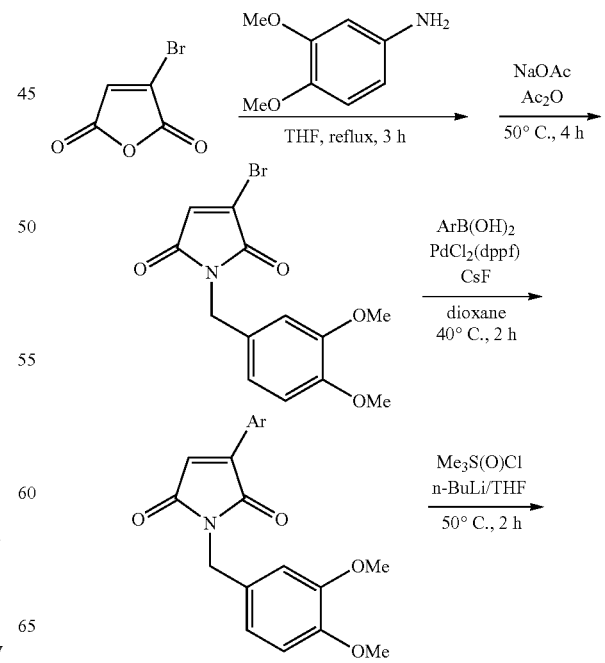

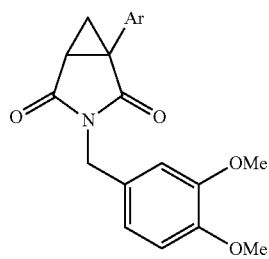
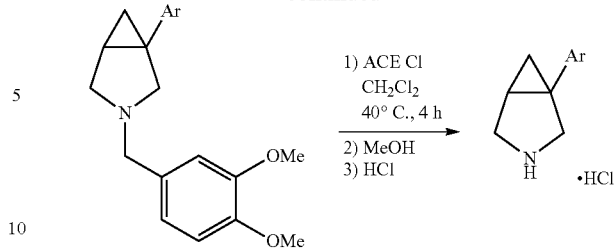
Reaction Scheme 18 provides an additional methodology for producing 1-aryl-3-azabicyclo[3.1.0]hexanes. Utilizing chiral starting materials (+)-epichlorohydrin or (−)-epichlorohydrin will lead to the corresponding chiral analogs through the same reaction sequences.
Reaction Scheme 18
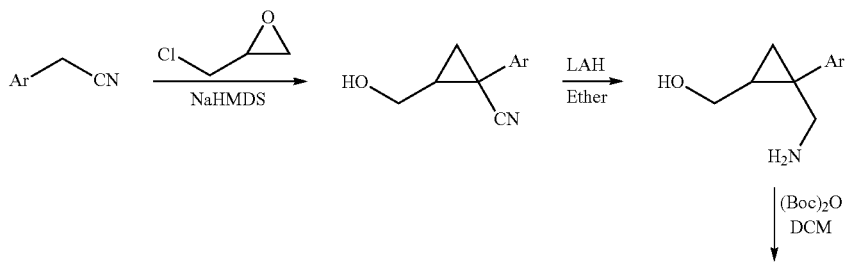
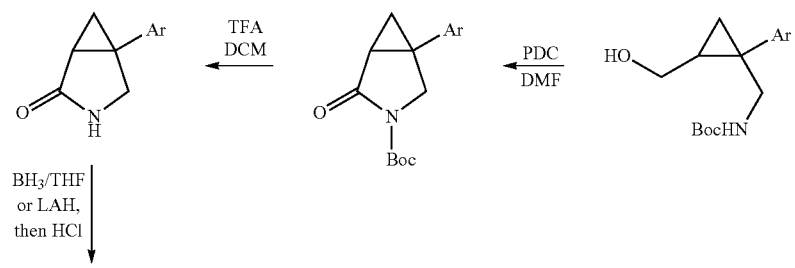
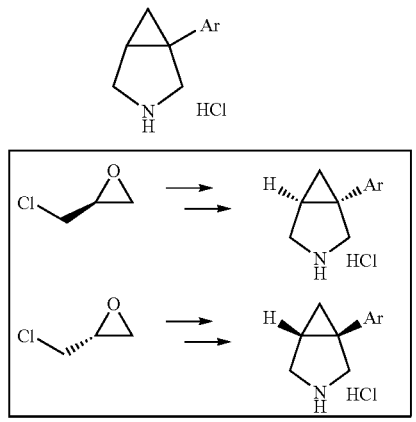

Reaction Scheme 19 provides an additional methodology for producing 1-aryl-3-azabicyclo[3.1.0]hexanes.
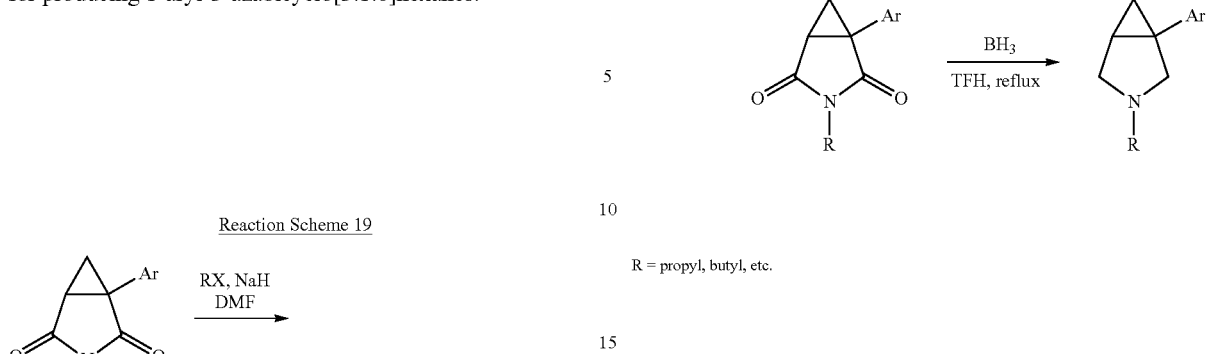
R = propyl, butyl, etc.
Reaction Scheme 20 provides an additional methodology for producing 1-aryl-3-azabicyclo[3.1.0]hexanes.
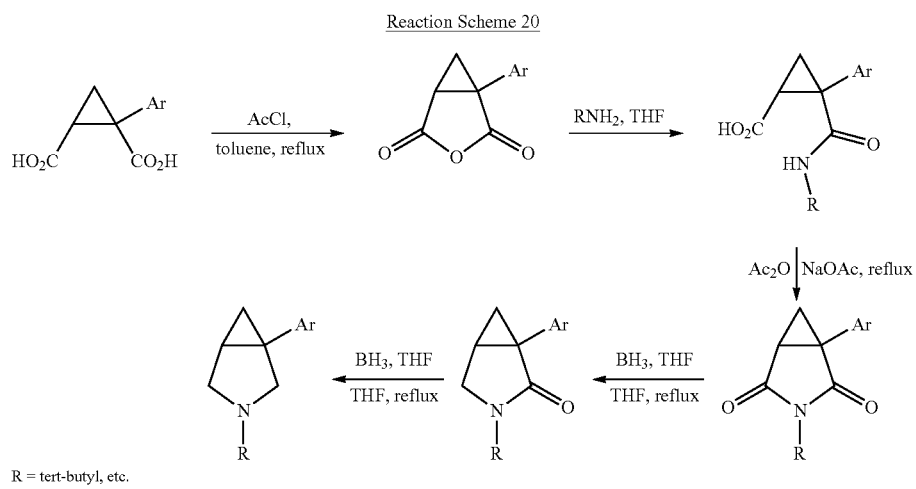
R = tert-butyl, etc.
Reaction Scheme 21 provides an additional methodology for producing 3- and/or 4-substituted 1-aryl-3-azabicyclo[3.1.0]hexanes.
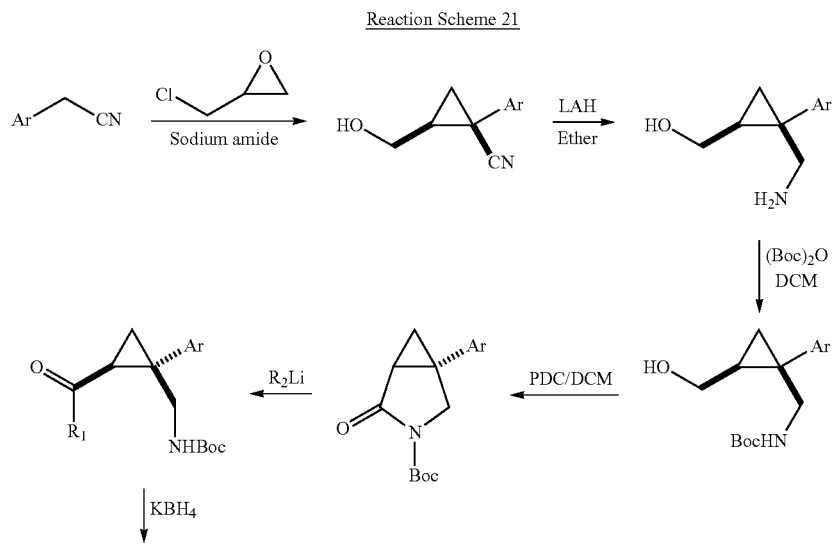

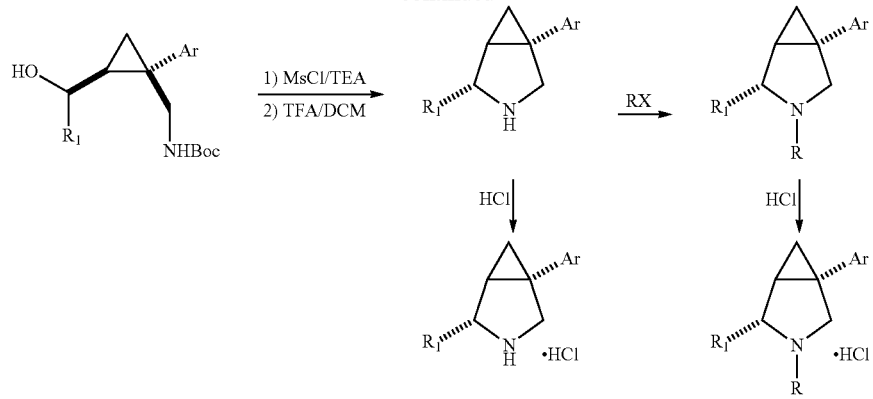
R = methyl, etc.
R₁ = methyl, etc.
Reaction Scheme 22 provides an additional methodology for producing 3and/or 4-substituted 1-aryl-3-azabicyclo[3.1.0]hexanes.
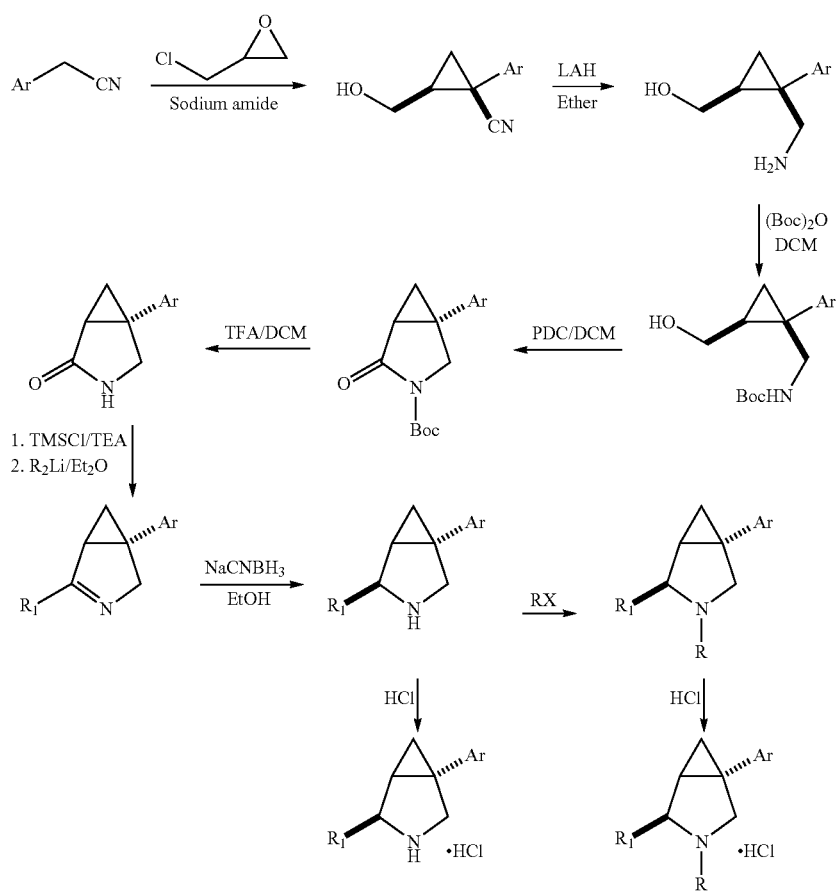
R = methyl, etc.
R₁ = methyl, etc.
Reaction Scheme 23 provides an additional methodology for producing 3and/or 2-substituted 1-aryl-3-azabicyclo[3.1.0]hexanes.

Reaction Scheme 23
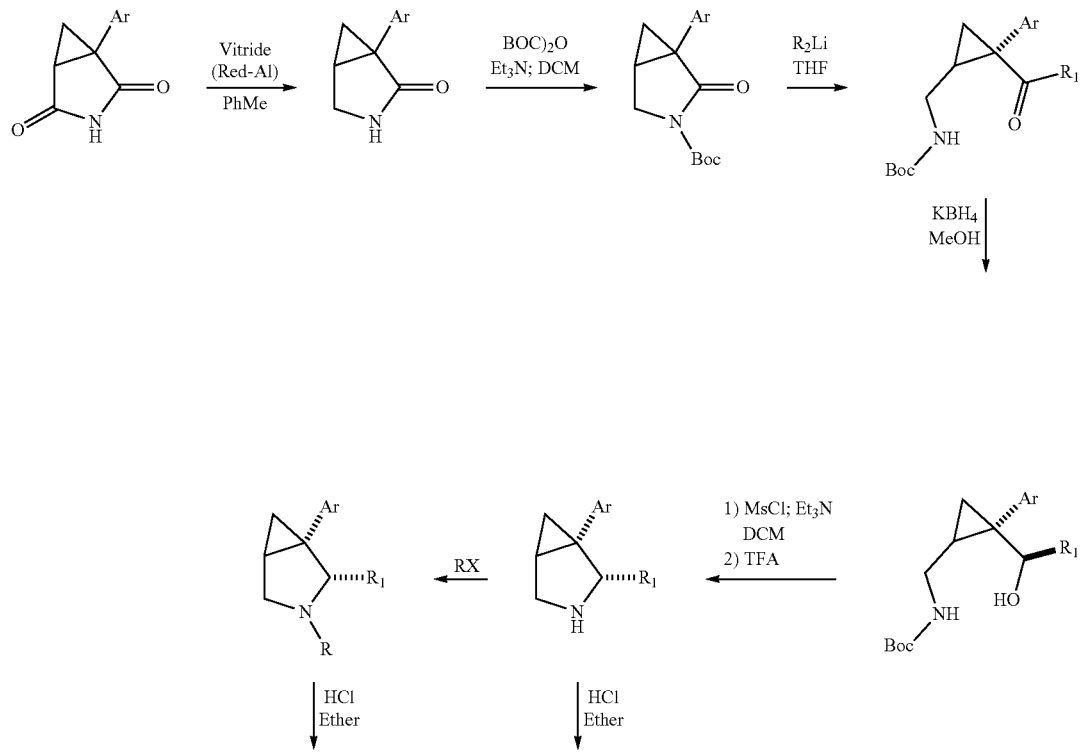
R = Me, etc.
R₁ = Me, etc.
Reaction Scheme 24 provides an additional methodology for producing 2- and/or 3-substituted 1-aryl-3-azabicyclo[3.1.0]hexanes.
Reaction Scheme 24
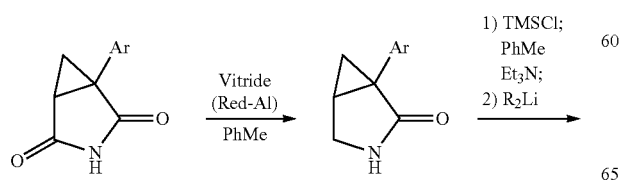

-continued
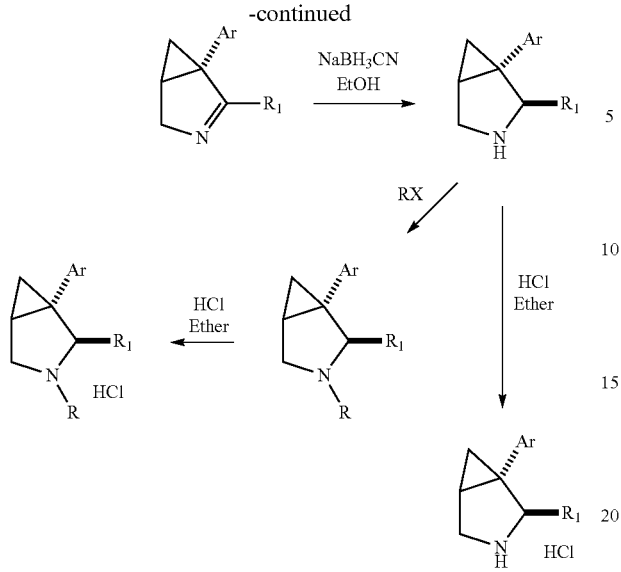
R = Me, etc.
R₁ = Me, etc.
Reaction Scheme 25 provides an additional generic methodology for producing 1-aryl-3-azabicyclo[3.1.0]hexanes.
Reaction Scheme 26 provides another generic methodology for producing 1-aryl-3-azabicyclo[3.1.0]hexanes.
Reaction Scheme 26
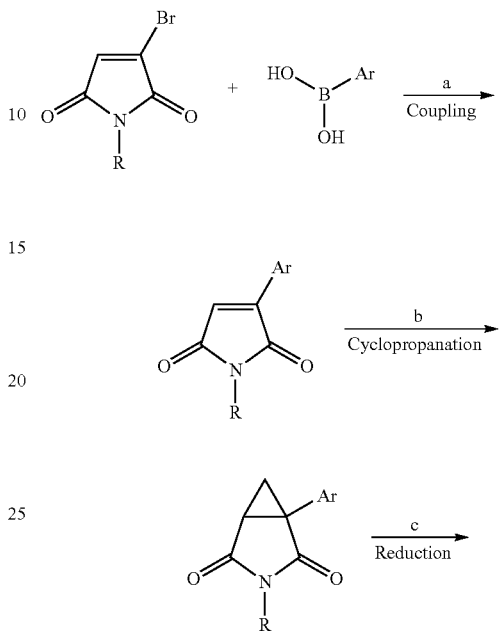
Reaction Scheme 25
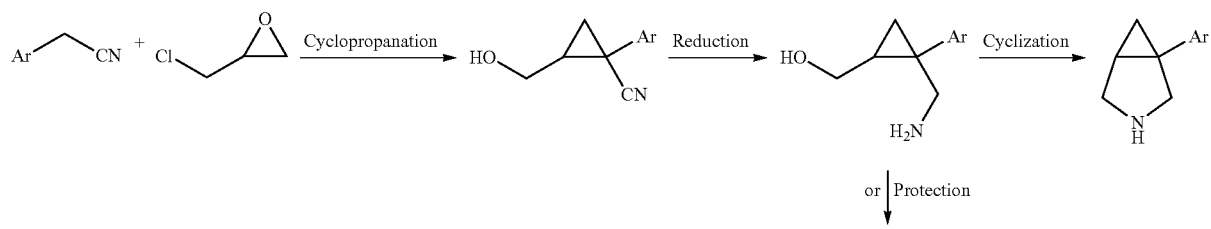
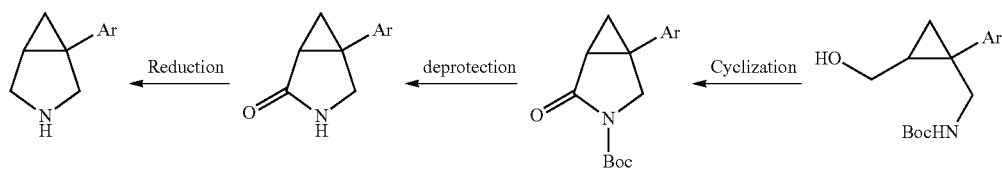

-continued

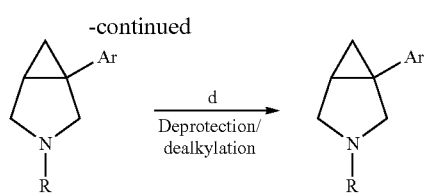

Example II

Preparation of aza-substituted-1-(3,4-dichlorophenyl)-3-aza-bicyclo[3.1.0]hexane hydrochloride compounds and enantiomers thereof

A. Synthesis of 1-(3,4-dichlorophenyl)-3-methyl-3-aza-bicyclo[3.1.0]hexane

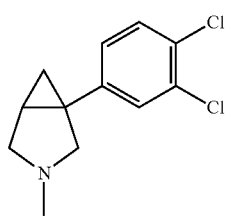

To a stirred solution of 1-(3,4-dichlorophenyl)-3-aza-bicyclo[3.1.0]hexane hydrochloride (30.0 g, 132 mmol) in 37% aqueous formaldehyde (25.8 mL) was added formic acid (32.4 mL). The resulting solution was stirred at 90° C. for 6 h. The reaction was then diluted with water (100 mL) and 2N aqueous sodium hydroxide added until the pH was greater than 9. The resulting mixture was extracted with $CH_2Cl_2$ (2×200 mL) and the combined organic extracts were washed with brine (200 mL), dried ($MgSO_4$) and concentrated under vacuum to provide the title compound (25.0 g, 79% yield) as an orange oil: LC (ELS)/MS: >99%, m/z 242.1 $[C_{12}H_{13}Cl_2N+H]^+$; $^1H$ NMR (300 MHz, $CDCl_3$): δ 0.94 (dd, 1H, J=5.3 Hz, J=7.9 Hz), 1.73 (t, 1H, J=4.7 Hz), 1.80 (m, 1H), 2.55 (s, 3H), 2.78 (d, 2H, J=9.2 Hz), 3.35 (d, 1H, J=9.6 Hz), 3.54 (d, 1H, J=9.3 Hz), 6.99 (dd, 1H, J=2.1 Hz, J=8.3 Hz), 7.24 (d, 1H, J=2.1 Hz), 7.35 (d, 1H, J=8.3 Hz).

B. Synthesis of 1(3,4-dichlorophenyl)-3-ethyl-3-aza-bicyclo[3.1.0]hexane

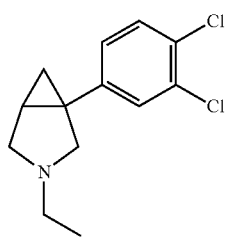 [SMILES: CCN1CC2CC2(c2ccc(Cl)c(Cl)c2)C1]

A stirred solution of 1-(3,4-dichlorophenyl)-3-aza-bicyclo[3.1.0]hexane hydrochloride (19.3 g, 72.9 mmol) in $CH_2Cl_2$ (100 mL) was rendered basic with 2N NaOH (100 mL). The resulting mixture was extracted with $CH_2Cl_2$ (2×100 mL) and the combined extracts dried, filtered and concentrated under reduced pressure. The residue was dissolved in acetonitrile (200 mL) and bromoethane (15.9 g, 146 mmol) added at room temperature. The mixture was stirred for 4 h during which time a white precipitate formed. After this time the reaction was concentrated under reduced pressure then treated with 2N NaOH (200 mL). Subsequent extraction with $CH_2Cl_2$ (3×100 mL) drying the combined extracts ($MgSO_4$), filtration and concentration under reduced pressure afforded a crude residue. This residue was purified by passing through a silica gel plug, eluting with ether, to yield the title compound (12.4 g, 66%) as a clear, viscous oil. This material was then used directly for either chiral separation or hydrochloride salt formation as provided in Example II, Section D hereinbelow.

C. Synthesis of 1-(3,4-dichlorophenyl)-3-isopropyl-3-aza-bicyclo[3.1.0]hexane

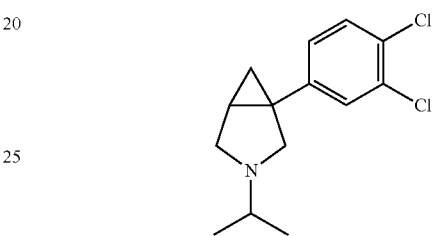

To a stirred solution of 1-(3,4-dichlorophenyl)-3-aza-bicyclo[3.1.0]hexane hydrochloride (10.0 g, 43.8 mmol) in DMF (20 mL) was added 2-iodoethane (9.67 g, 56.9 mmol) and DIPEA (7.35 g, 56.9 mmol). The resulting solution was stirred at ambient temperature for 6 h. After this time, the solvent was removed under vacuum and the residue was dissolved in $CH_2Cl_2$ (50 mL). The organic layer was washed with water (2×50 mL), 2N sodium hydroxide (50 mL) and brine (50 mL). The organics were dried ($Na_2SO_4$) and concentrated under vacuum. Three reactions were run in parallel and then combined for purification via column chromatography (silica gel, EtOAc) to provide the title compound (17.3 g, 49% yield) as a yellow oil: LC (ELS)/MS: 91%, m/z 271.6 $[C_{14}H_{17}Cl_2N+H]^+$; $^1H$ NMR (300 MHz, $CDCl_3$): δ 0.75 (dd, 1H, J=4.2 Hz, J==8.1 Hz), 1.05 (dd, 6H, J=4.7 Hz, J=6.3 Hz), 1.44 (t, 1H, J=4.2 Hz), 1.67 (td, 1H, J=3.9 Hz, J=8.0 Hz), 2.50 (m, 3H), 3.11 (d, 1H, J=8.6 Hz), 3.31 (d, 1H, J=8.4 Hz), 6.96 (dd, 1H, J=2.1 Hz, J=8.3 Hz), 7.22 (d, 1H, J=2.1 Hz), 7.32 (d, 1H, J=8.3 Hz).

D. Chiral Separation Conditions and Hydrochloride Salt Formation

The 3 racemic mixtures synthesized above in Sections A, B and C of this Example II were subjected to chiral chromatography using the following conditions:

1: Chiralcel OD column, 4.6 mm×250 mm; 99:1 heptanes/i-propanol with 0.1% DEA added; 100 mL/min; 275 nm; 50 mg/mL loading. Peak A eluted at 13 minutes and peak B eluted at 14.5 minutes.

2: Chiralcel OD column, 4.6 mm×250 mm; 90:10 heptanes/ethanol with 0.1% TFA added; 100 mL/min; 275 nm; 50 mg/mL loading. Peak A eluted at 9 minutes and peak B eluted at 27 minutes.

3: Chiralcel OD column, 4.6 mm×250 mm; 93:7 heptanes/ethanol with 0.1% TFA added; 100 mL/min; 275 nm; 50 mg/mL loading. Peak A eluted at 12 minutes and peak B eluted at 19 minutes.

The appropriate fractions were collected and concentrated under reduced pressure. The resulting residue was dissolved in $CH_2Cl_2$, washed with 2N sodium hydroxide, dried ($Na_2SO_4$) and the solvent removed under vacuum to yield the corresponding freebase.

To a stirred solution of the appropriate freebase in $CH_2Cl_2$ (1 g/mL) was added 2 M HCl in ether (2 eq.). The mixture was stirred at ambient temperature for 16 h. The solvent was then removed under reduced pressure and the resulting salt was slurried in ether and collected on a glass frit. Subsequent washing with ether and drying under vacuum provided the desired hydrochloride salt set forth below.

(1) (1S,5R)-1-(3,4-dichlorophenyl)-3-methyl-3-azabicyclo[3.1.0]hexane hydrochloride

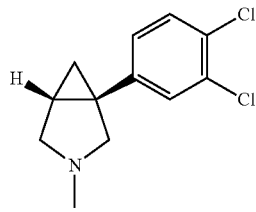

7.72 g (88%), white solid: LC (ELS)/MS: 98.8%, m/z 242 $[C_{12}H_{13}Cl_2N]^+$; $^1H$ NMR (300 MHz, $CDCl_3$): δ 1.21 (1, 1H, J=7.8 Hz), 2.04 (td, 1H, J=4.3 Hz, J=8.6 Hz), 2.32 (dd, 1H, J=4.8 Hz, J=6.9 Hz), 2.92 (d, 3H, J=4.5 Hz), 3.30 (m, 2H), 3.94 (dd, 1H, J=5.1 Hz, J=11.0 Hz), 4.11 (dd, 1H, J=5.2 Hz, J=10.9 Hz), 7.03 (dd, 1H, J=2.2 Hz, J=8.3 Hz), 7.29 (d, 1H, J=2.2 Hz), 7.42 (d, 1H, J=8.3 Hz); $^{13}C$ NMR (75 MHz, $CDCl_3$): δ 136.1, 131.6, 130.3, 129.6, 127.6, 124.5, 58.5, 55.2, 39.3, 28.5, 22.0, 14.5; $[\alpha]^{25}_D$-65.8° (c 1.00, methanol); Anal. Calcd. for $C_{12}H_{14}Cl_3N$: C, 51.73; H, 5.06; N, 5.03. Found: C, 51.68; H, 5.14; N, 4.92.

(2) (1R,5S)-1-(3,4-dichlorophenyl)-3-methyl-3-azabicyclo[3.1.0]hexane hydrochloride

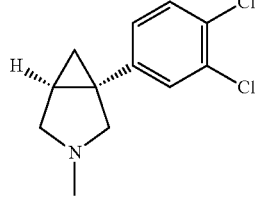

7.74 g (88%), white solid: LC (ELS)/MS: 99.3%, m/z 242 $[C_{12}H_{13}Cl_2N]^+$; $^1H$ NMR (300 MHz, $CDCl_3$): δ 1.21 (t, 1H, J=7.8 Hz), 2.04 (td, 1H, J=4.3 Hz, J=8.6 Hz), 2.33 (m, 1H), 2.91 (m, 3H), 3.27 (m, 2H), 3.94 (dd, 1H, J=5.2 Hz, J=11.0 Hz), 4.12 (dd, 1H, J=5.2 Hz, J=10.9 Hz), 7.02 (dd, 1H, J=2.2 Hz, J=8.3 Hz), 7.27 (m, 1H), 7.42 (d, 1H, J=8.3 Hz); $^{13}C$ NMR (75 MHz, $CDCl_3$): δ 138.6, 133.4, 132.2, 131.4, 129.6, 127.0, 60.3, 57.4, 41.6, 31.1, 23.9, 16.7; $[\alpha]^{25}_D$+67.0° (c 1.00, methanol); Anal. Calcd. for $C_{12}H_{14}Cl_3N$: C, 51.73; H, 5.06; N, 5.03. Found: C, 51.78; H, 4.96; N, 4.97.

(3) (1S,5R)-1-(3,4-dichlorophenyl)-3-ethyl-3-azabicyclo[3.1.0]hexane hydrochloride

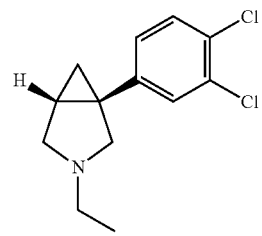

2.31 g (45%), white solid: LC (ELS) 1 MS: >99%, m/z 256 $[C_{13}H_{15}Cl_2N+H]^+$; $^1H$ NMR (300 MHz, $CDCl_3$): δ 1.19 (t, 1H, J=7.7 Hz), 1.52 (t, 3H, J=7.1 Hz), 2.03 (td, 1H, J=4.1 Hz, J=8.3 Hz), 2.39 (dd, 1H, J=4.7 Hz, J=6.7 Hz), 3.23 (m, 4H), 3.93 (dd, 1H, J=5.2 Hz, J=10.8 Hz), 4.12 (dd, 1H, J=5.3 Hz, J=10.8 Hz), 7.02 (dd, 1H, J=2.0 Hz, J=8.3 Hz), 7.27 (m, 1H), 7.42 (d, 1H, J=8.3 Hz); $^{13}C$ NMR (75 MHz, $CDCl_3$): δ 136.8, 131.3, 130.1, 129.6, 127.7, 125.0, 56.4, 53.4, 49.9, 28.7, 21.5, 15.0, 9.4; $[\alpha]^{25}_D$-62.7° (c 1.096, methanol); Anal. Calcd. for $C_{13}H_{16}Cl_3N$: C, 53.36; H, 5.51; N, 4.79. Found: C, 52.78; H, 5.24; N, 4.71.

(4) (1R,5S)-1-(3,4-dichlorophenyl)-3-ethyl-3-azabicyclo[3.1.0]hexane hydrochloride 3.64 g (56%), white solid: LC (ELS)/MS: 97%, m/z 256 $[C_{13}H_{15}Cl_2N+H]^+$; $^1H$ NMR (300 MHz, $CDCl_3$): δ 1.18 (t, 1H, J=7.3 Hz), 1.52 (t, 3H, J=7.2 Hz), 2.02 (m, 1H), 2.38 (m, 1H), 3.21 (m, 4H), 3.92 (d, 1H, J=10.9 Hz), 4.11 (d, 1H, J=10.8 Hz), 7.02 (d, 1H, J=8.1 Hz), 7.27 (m, 1H), 7.42 (d, 1H, J=8.3 Hz); $^{13}C$ NMR (75 MHz, $CDCl_3$): δ 137.5, 131.7, 130.1, 129.8, 128.2, 125.6, 57.2, 54.0, 50.5, 29.4, 22.2, 15.8, 9.8; [α]$^{25}_D$+69.2° (c 1.1, methanol); Anal. Calcd. for C$_{13}$H$_{16}$Cl$_3$N: C, 53.36; H, 5.51; N, 4.79. Found: C, 52.71; H, 5.23; N, 4.65.

(5) (1S,5R)-1-(3,4-dichlorophenyl)-3-isopropyl-3-aza-bicyclo[3.1.0]hexane hydrochloride

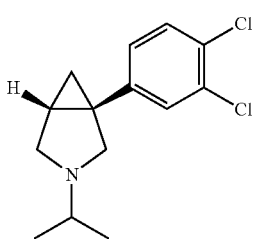 [SMILES: CC(C)N1C[C@@H]2C[C@]2(c2ccc(Cl)c(Cl)c2)C1]

5.61 g, white solid: LC (ELS)/MS: >99%, m/z 270 [C$_{14}$H$_{17}$Cl$_2$N+H]$^+$; $^1$H NMR (300 MHz, CDCl$_3$): δ 1.15 (t, LH, J=7.7 Hz), 1.55 (d, 6H, J=6.5 Hz), 2.02 (td, 1H, J=4.4 Hz, J=8.7 Hz), 2.50 (dd, 1H, J=4.8 Hz, J=6.7 Hz), 3.28 (m, 3H), 3.89 (dd, 1H, J=5.5 Hz, J=11.0 Hz), 4.08 (dd, 1H, J=5.5 Hz, J=10.9 Hz), 7.03 (dd, 1H, J=2.2 Hz, J=8.3 Hz), 7.27 (d, 1H, J=3.0 Hz), 7.42 (d, 1H, J=8.3 Hz); $^{13}$C NMR (75 MHz, CDCl$_3$): δ 136.9, 131.7, 130.1, 129.6, 127.7, 125.3, 58.6, 55.1, 52.2, 28.8, 21.7, 17.1, 14.9; [α]$^{25}_D$-74.1° (c 1.00, methanol); Anal. Calcd. for C$_{14}$H$_{18}$C$_{13}$N: C, 54.83; H, 5.92; N, 4.57. Found: C, 54.50; H, 5.85; N, 4.42.

(6) (1R,5S)-1(3,4-dichlorophenyl)-3-isopropyl-3-aza-bicyclo[3.1.0]hexane hydrochloride

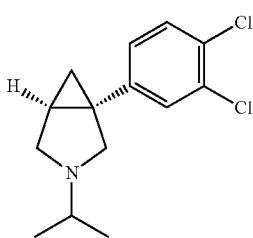 [SMILES: CC(C)N1C[C@H]2C[C@@]2(c2ccc(Cl)c(Cl)c2)C1]

5.20 g, white solid: LC (ELS)/MS: >99%, m/z 270 [C$_{14}$H$_{17}$Cl$_2$N+H]$^+$; $^1$H NMR (300 MHz, CDCl$_3$): δ 1.15 (t, 1H, J=7.7 Hz), 1.55 (d, 6H, J=6.5 Hz), 2.01 (td, 1H, J=4.4 Hz, J=8.7 Hz), 2.50 (dd, 1H, J=4.8 Hz, J=6.7 Hz), 3.26 (ddd, 1H, J=7.0 Hz, J=14.6 Hz, J=28.8 Hz), 3.90 (dd, 1H, J=5.5 Hz, J=11.0 Hz), 4.08 (dd, 1H, J=5.5 Hz, J=10.9 Hz), 7.02 (dd, 1H, J=2.2 Hz, J=8.3 Hz), 7.27 (d, 1H, J=2.4 Hz), 7.42 (d, 1H, J=8.3 Hz); $^{13}$C NMR (75 MHz, CDCl$_3$): δ 137.0, 131.2, 129.9, 128.5, 127.3, 124.0, 58.0, 55.0, 50.7, 29.1, 20.9, 17.4, 14.2; [α]$^{25}_D$+76.8° (c 1.00, methanol); Anal. Calcd. For C$_{14}$H$_{18}$Cl$_3$N: C, 54.83; H, 5.92; N, 4.57. Found: C, 54.69; H, 5.82; N, 4.44.

Example III

Preparation of 1-(3,4-dichlorophenyl)-3-propyl-3-azabicyclo[3.1.0]hexane Hydrochloride Using Reaction Scheme 19

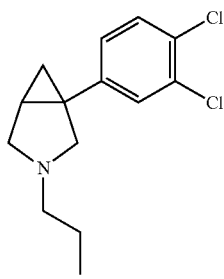 [SMILES: CCCN1CC2CC2(c2ccc(Cl)c(Cl)c2)C1]

To a 3-necked flask under nitrogen was added 1-(3,4-dichlorophenyl)-3-aza-bicyclo[3.1.0]hexane-2,4-dione (30 g) and anhydrous DMF (220 mL). The mixture was then cooled to between 0 and 10° C. using an ice/salt/water bath. At this point sodium hydride (4.68 g) was added portionwise over approximately 1 h. Significant gas evolution was noted on addition of the sodium hydride. On completion of the addition the reaction was allowed to stir for 30 rains at room temperature before the addition of bromopropane (17 mL). The reaction was then allowed to stir overnight at room temperature. TLC of the reaction mixture revealed no starting material. The reaction was quenched by adding the reaction mixture dropwise to cold water (<10° C.). This led to the formation of a slurry; the solid was dissolved on addition of ethyl acetate (500 mL). The organics were separated and aqueous re-extracted with ethyl acetate (1 L). The organics were again separated and washed with water (2×500 mL) and brine (2×500 mL), leading to the formation of an emulsion. The emulsion was separated after the addition of more water (500 mL) and ethyl acetate (500 mL). The organics were then separated, dried over magnesium sulphate, filtered and concentrated in vacuo to give a brown oil (36.8 g). A sample was sent for $^1$H NMR (GMCP408A) and this showed the crude product (36.8 g, 94% yield, purity >90%). This was used directly in the reduction stage.

To a 3-necked flask under nitrogen was added the imide (36.8 g) in THF (300 mL). The mixture was cooled to 0° C. and 1M BH$_3$ in THF was added dropwise. On completion of the addition the reaction was heated to reflux for 4 h. TLC of the reaction mixture showed that no starting material remained. The reaction mixture was cooled to 0° C. and quenched with 6N HCl (470 mL). The quenched mixture was then concentrated in vacuo to a volume of approximately 300 mL. The mixture was again cooled to 0° C. and made basic with 750 mL of 5M NaOH solution. The mixture was then extracted with DCM (2×1 L). The organics were then dried, filtered and concentrated in vacuo. The material was subjected to column chromatography (98% DCM: 2% methanol: 0.1% ammonia). However this led to the isolation of only mixed fractions. An alternative solvent system using 20% ethyl acetate: 80% hexane was employed. Three sets of fractions were obtained. Samples of each set of fractions were analysed via $^1$H NMR and showed that two sets of fractions (designated A and C) contained mostly product with small amounts of impurities present. The third set of fractions (designated B) was shown to contain only a small amount of product with significant other impurities present. The A and C sets of fractions were combined (7.7 g) and dissolved in diethyl ether (8 mL) before being cooled to 0° C. At this point 1M HCl in ether (143 mL) was added carefully to the mixture to form the salt. The slurry was stirred for 30 mins at 0° C. before being filtered. The salt was then dried in the oven overnight at ambient temperature. This gave the product as a white solid (6.08 g, 18.2%). NMR (300 MHz, $d_6$-DMSO) δ 11.28 (1H, brs, $NH^+$), 7.62-7.59 (2H, m, ArH), 7.28-7.25 (1H, m, ArH), 3.97-3.90 (1H, m, $NCH_2$), 3.63-3.44 (3H, m, $NCH_2$), 3.09-3.01 (2H, m, $NCH_2$), 2.21-2.16 (1H, m, CH), 1.88 (1H, t, J=5.4 Hz, $CH_2$), 1.77-1.69 (2H, m, $CH_2CH_3$), 1.11 (1H, obs t, J=7.3 Hz, $CH_2$), 0.87 (3H, obs t, J=7.3 Hz, $CH_3$); $^{13}C$ NMR (75 MHz, δ-$CDCl_3$) δ 140.5, 131.1, 130.4, 129.1, 128.9, 127.1, 56.5, 55.8, 54.5, 29.3, 23.4, 18.2, 15.9, 10.8; MS (m/z) 270 ($MH^+$, 100).

Example IV

Preparation of (1R,5S)-1-(3,4-dichlorophenyl)-3-propyl-3-azabicyclo[3.1.0]hexane Hydrochloride Using Reaction Scheme 13

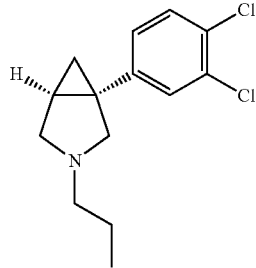 [SMILES: CCCN1C[C@H]2C[C@@]2(c2ccc(Cl)c(Cl)c2)C1]

To a stirred solution of (1R,5S)-1-(3,4-dichlorophenyl)-3-aza-bicyclo[3.1.0]hexane hydrochloride (10 g) in anhydrous DMF (70 mL) under nitrogen was added DIPEA (8.48 mL, 1.3 eq). The reaction was allowed to stir for 30 mins before the addition of propyl bromide (6.15 mL). The reaction was stirred at room temperature for 2 h. TLC of the reaction revealed a mixture of starting material and product. Therefore the reaction was continued with a further addition of 0.7 eq of DIPEA, heated to 40° C. and allowed to stir for 4 h. The reaction was then allowed to stand overnight at room temperature. TLC of the reaction revealed mainly product with a small amount of starting material and baseline material present. The reaction mixture was then concentrated in vacuo under reduced pressure to remove the DMF. This gave a liquid, which solidified on standing (pink solid). This was taken up in DCM (150 mL) and washed with water (100 mL). The organics were then separated, dried over magnesium sulphate, filtered and concentrated in vacuo. Once again a pink solid was obtained. This material was purified via column chromatography eluted using 98% DCM: 2% methanol: 0.1% ammonia. This gave pure compound (15.3 g) as a solid (15% DMF present). The solid was slurried in ethyl acetate (150 mL) and mixed with saturated aqueous $NaHCO_3$ solution (75 mL). The solid dissolved on addition of the base. The organics were separated and washed with water (2×200 mL) before drying over magnesium sulphate, filtering and concentrating in vacuo to give an oil (8.8 g). The oil was taken up in diethyl ether (9 mL) before being cooled to 0° C. At this point 1M HCl in ether (163 mL) was added carefully to the mixture to form the salt. The slurry was stirred for 30 mins at 0° C. before being filtered. The salt was then dried in the oven overnight at ambient temperature. This gave the product as a white solid (7.73 g, 66.7%). $^1H$ NMR (300 MHz, $d_6$-DMSO) δ 11.19 (1H, brs, $NH^+$), 7.62-7.57 (2H, m, ArH), 7.29-7.25 (1H, m, ArH), 3.95-3.90 (1H, dd, J=11.1, 4.5 Hz, $NCH_2$), 3.64-3.59 (1H, dd, J=11.1, 4.5 Hz, $NCH_2$), 3.55-3.41 (2H, m, $NCH_2$), 3.07-3.04 (2H, m, $NCH_2$), 2.21-2.16 (1H, m, CH), 1.88 (1H, t, J=5.4 Hz, $CH_2$), 1.77-1.69 (2H, m, $CH_2CH_3$), 1.11 (1H, obs t, J=7.3 Hz, $CH_2$), 0.87 (3H, obs t, J=7.3 Hz, $CH_3$); $^{13}C$ NMR (75 MHz, δ-$CDCl_3$) δ 140.5, 131.1, 130.4, 129.1, 128.9, 127.1, 56.5, 55.8, 54.5, 29.3, 23.4, 18.2, 15.9, 10.8; MS (m/z) 270 ($MH^+$, 100).

Example V

Preparation of (1S,5R)-1-(3,4-Dichlorophenyl)-3-propyl-3-azabicyclo[3.1.0]hexane Hydrochloride Using Reaction Scheme 13

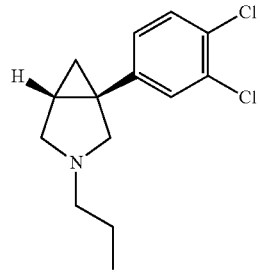 [SMILES: CCCN1C[C@@H]2C[C@]2(c2ccc(Cl)c(Cl)c2)C1]

To a stirred solution of (1S,5R)-1-(3,4-dichlorophenyl)-3-aza-bicyclo[3.1.0]hexane hydrochloride (10 g) in anhydrous DMF (70 mL) under nitrogen was added DIPEA (8.48 mL, 1.3 eq). The reaction was allowed to stir for 30 mins before the addition of propyl bromide (6.15 mL). The reaction was stirred at room temperature for 2 h. TLC of the reaction revealed a mixture of starting material and product. Therefore the reaction was continued with a further addition of 0.7 eq of DIPEA, heated to 40° C. and allowed to stir for 4 h. The reaction was then allowed to stand overnight at room temperature. TLC of the reaction revealed mainly product with a small amount of starting material and baseline material present. The reaction mixture was then concentrated in vacuo under reduced pressure to remove the DMF. This gave a liquid, which solidified on standing (pink solid). This was taken up in DCM (150 mL) and washed with water (100 mL). The organics were then separated, dried over magnesium sulphate, filtered and concentrated in vacuo. Once again a pink solid was obtained. This material was purified via column chromatography eluted using 98% DCM: 2% methanol: 0.1% ammonia. This gave pure compound (15.9 g) as a solid (15% DMF present). The solid was slurried in ethyl acetate (150 mL) and mixed with saturated aqueous $NaHCO_3$ solution (75 mL). The solid dissolved on addition of the base. The organics were separated and washed with water (2×200 mL) before drying over magnesium sulphate, filtering and concentrating in vacuo to give an oil (8.9 g). The oil was taken up in diethyl ether (9 mL) before being cooled to 0° C. At this point 1M HCl in ether (165 mL) was added carefully to the mixture to form the salt. The slurry was stirred for 30 mins at 0° C. before being filtered. The salt was then dried in the oven overnight at ambient temperature. This gave the product as a white solid (8.61 g, 75%). $^1$H NMR (300 MHz, $d_6$-DMSO) δ 11.20 (1H, brs, NH$^+$), 7.62-7.57 (2H, m, ArH), 7.29-7.25 (1H, m, 3.94-3.90 (1H, dd, J=11.1, 4.5 Hz, NCH$_2$), 3.64-3.59 (1H, dd, J=11.1, 4.5 Hz, NCH$_2$), 3.55-3.41 (2H, m, NCH$_2$), 3.07-3.04 (2H, m, NCH$_2$), 2.21-2.16 (1H, m, CH), 1.89 (1H, obs t, J=5.4 Hz, CH$_2$), 1.80-1.67 (2H, m, CH$_2$CH$_3$), 1.11 (1H, obs t, J=7.3 Hz, CH$_2$), 0.87 (3H, t, J=7.3 Hz, CH$_3$); $^{13}$C NMR (75 MHz, δ-CDCl$_3$) δ 140.5, 131.1, 130.4, 129.1, 128.9, 127.1, 56.5, 55.8, 54.5, 29.3, 23.4, 18.3, 15.9, 10.9; MS (m/z) 270 (MH$^+$, 100).

Example VI

Preparation of 3-Butyl-1-(3,4-dichlorophenyl)-3-aza-bicyclo[3.1.0]hexane

Hydrochloride Using Reaction Scheme 19

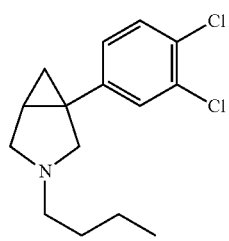 [SMILES: CCCCN1CC2CC2(c2ccc(Cl)c(Cl)c2)C1]

To a stirred solution of 1-(3,4-dichlorophenyl)-3-aza-bicyclo[3.1.0]hexane-2,4-dione (15.8 g) in DMF (63 ml) was added sodium hydride (60 wt. % in oil; 2.5 g) with the temperature kept below 20° C. The suspension was then stirred at room temperature for 20 mins before 1-bromobutane (9.9 ml) was added. The solution was then stirred at room temperature for 24 h when TLC (20% ethyl acetate in hexanes) indicated complete reaction. The solution was quenched into water (500 ml), extracted with ether (2×250 ml) and the extracts washed with water (2×250 ml), saturated brine (2×250 ml), dried (MgSO$_4$) and evaporated, yielding 15.6 g (81%) imide.

The imide above (15.6 g) was dissolved in THF (310 ml) and a solution of borane in THF (1M; 225 ml) was added with the temperature kept below 5° C. The solution was then heated to reflux for 4 h when TLC (20% ethyl acetate in hexane) indicated complete reaction. The solution was cooled to 0° C. and quenched by the addition of dilute HCl (6M; 200 ml) with the temperature kept below 10° C. The solution was then extracted with ether (2×200 ml), the aqueous made basic with sodium hydroxide (5M; 480 ml), extracted with ether (3×150 ml), the extracts combined, dried (MgSO$_4$) and evaporated, to give a crude oil with a yield of 3.2 g.

The oil was added to HCl in ether (2M; 20 ml), stored overnight at −20° C. and the resultant solid filtered off and washed with ether (2×10 ml). TLC (20% ethyl acetate in hexanes) indicated two components so the solid was dissolved in water (50 ml) made basic with solid K$_2$CO$_3$ to pH 10 and extracted with ether (3×100 ml). The extracts were dried (MgSO$_4$) and evaporated. The product was then purified by chromatography [SiO$_2$ (22.7 g): (25% EtOAc in hexanes)] to give the required material as a yellow oil, 0.7 g (5%); $^1$H NMR (300 MHz, CDCl$_3$) δ 7.16-7.06 (m, 41-1, ArH), 3.97 (t, 1H, J=6.3 Hz, NCH$_2$), 3.78 (s, 3H, NCH$_2$), 2.34 (s, 3H, ArCH$_3$), 1.87 (m, 1H, CHCH$_2$), 1.19 (t, 1H, J=5.5 Hz, CHCH$_2$), 0.87 (m, 1H, CHCH$_2$); MS (m/z) 188 (MH$^+$, 100).

Example VII

Preparation of 3-tert-butyl-1-(3,4-dichlorophenyl)-3-aza-bicyclo[3.1.0]hexane

Using Reaction Scheme 20

A. Synthesis of 1-(3,4-Dichlorophenyl-3-oxa-bicyclo[3.1.0]hexane-2,4-dione

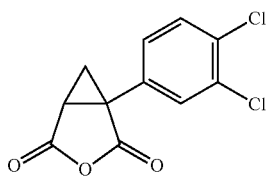 [SMILES: O=C1OC(=O)C2(c3ccc(Cl)c(Cl)c3)CC12]

To a stirred solution of the 1-(3,4-dichlorophenyl)cyclopropane-1,2-dicarboxylic acid (28.3 g) in acetyl chloride (142 ml) was heated to reflux for 3 h, cooled to room temperature and evaporated. The oil was dissolved in toluene (100 ml) and evaporated to dryness. This was then repeated twice before triturating the semi-solid in hexane (100 ml). The solid was filtered off, washed with hexane and pulled dry under a nitrogen atmosphere to give a brown solid, yield=26.7 g (101%); $^1$HNMR (300 MHz, CDCl$_3$) δ 7.52-7.46 (m, 2H, ArH), 7.27-7.24 (m, 1H, ArH), 3.35-3.30 (m, 1H, CH), 2.13-2.10 (m, 1H, CH), 1.97-1.95 (m, 1H, CH).

B. Synthesis of 2-(tert-Butylcarbamoyl)-2-(3,4-dichlorophenyl)-cyclopropane-1-carboxylic acid

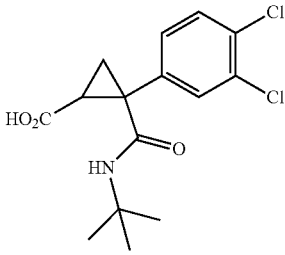 [SMILES: CC(C)(C)NC(=O)C1(c2ccc(Cl)c(Cl)c2)CC1C(=O)O]

To a stirred solution of the anhydride prepared as described in Example VII, Section A above (26.7 g) in THF (365 ml) was added tert-butylamine (23 ml) with the temperature kept below 20° C. The suspension was then stirred at room temperature for 1 h when TLC (50% ethyl acetate in hexane)

indicated complete reaction. The solvent was evaporated off and the resultant sticky mass used crude in the next reaction.

C. Synthesis of 3-tert-Butyl-1-(3,4-dichlorophenyl)-3-aza-bicyclo[3.1.0]hexane-2,4-dione

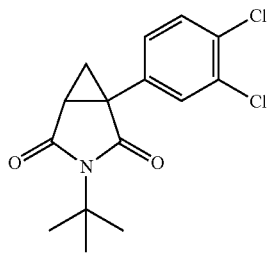 [SMILES: CC(C)(C)N1C(=O)C2CC2(c2ccc(Cl)c(Cl)c2)C1=O]

A stirred suspension of the amide prepared as described in Example VII, Section B above and sodium acetate (4.3 g) in acetic anhydride (145 ml) was heated to reflux for 4 h where TLC (50% ethyl acetate in hexanes) indicated complete reaction so the solvent was evaporated off and the oil absorbed onto silica (49.7 g). The product was then purified by chromatography [SiO$_2$ (503.7 g): (10% EtOAc in hexanes)] to give the required material as a yellow oil, in a yield of 23.7 g (73%); $^1$H NMR (300 MHz, CDCl$_3$) δ 7.52-7.46 (m, 2H, ArH), 7.23-7.20 (m, 1H, ArH), 2.64-2.60 (m, 1H, CH), 1.72-1.66 (m, 2H, CH), 1.52 (s, 9H, Bu$^t$).

D. Synthesis of 3-tert-Butyl-1-(3,4-dichlorophenyl)-3-aza-bicyclo[3.1.0]hexane-2-one

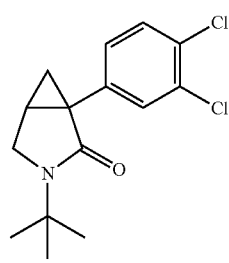 [SMILES: CC(C)(C)N1CC2CC2(c2ccc(Cl)c(Cl)c2)C1=O]

To a stirred solution of the imide prepared as described in Example VII, Section C above (23.7 g) in THF (395 ml) at 5° C. was added a solution of borane in THF (1M; 304 ml) with the temperature kept below 5° C. The solution was then heated to reflux for 2 h when TLC (20% ethyl acetate in hexane) indicated complete reaction. The solution was cooled to 0° C. and quenched by the addition of dilute HCl (6M; 400 ml) with the temperature kept below 10° C. The THF was evaporated off and the white solid filtered off and dried at 45° C. in vacuo overnight, yielding 17.0 g (75%) of the desired product. $^1$HNMR (300 MHz, CDCl$_3$) δ 7.71 (d, 1H, J=2.4 Hz, ArH), 7.57 (d, HI, =8.4 Hz, ArH), 7.36 (dd, 1H, J=8.4 Hz, J=2.4 Hz, ArH), 4.86 (br s, 2I-1, CH$_2$), 3.69-3.63 (m, 1H, CH), 3.46-3.43 (m, 1H, CH), 2.37-2.31 (m, 1H, CH), 1.45-1.42 (m, 1H, CH), 1.32 (s, 9H, Bu$^t$); MS (m/z) 299 (MH$^+$, 100).

E. Synthesis of 3-tert-butyl-1-(3,4-dichlorophenyl)-3-aza-bicyclo[3.1.0]-hexane maleate salt

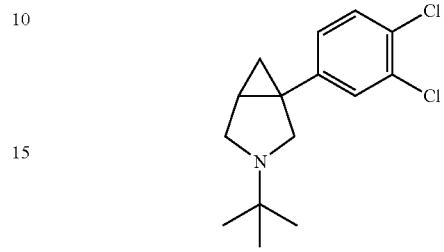

To a stirred solution of the amide prepared as described in Example VII, Section D above (15.1 g) in THF (270 ml) was added a solution of borane in THF (1M; 203 ml) at 20° C. The solution was then heated to reflux for 16 h when TLC (20% ethyl acetate in hexane) indicated incomplete reaction so the solution was cooled to room temperature and a further portion of borane in THF (1M; 130 ml) was added at 20° C. The solution was then again heated to reflux and held for 24 h. TLC indicated approximately 50% reaction so the solution was cooled to 0° C. and quenched by the addition of dilute HCl (6M; 400 ml) with the temperature kept below 10° C. The THF was evaporated off, the white solid filtered off, and the aqueous extracted with ethyl acetate (3×250 ml). The aqueous was made basic with NaOH (5M; 500 ml) and the product extracted into ether (3×200 ml), dried (MgSO$_4$) and evaporated to give a colourless oil, in a yield of 5.9 g (41%).

The crude amine was added to a solution of maleic acid (2.3 g) in methanol (11.5 ml) and stored at −20° C. overnight. The solid was filtered off, washed with methanol (2.5 ml) and dried at 45° C. in vacuo overnight, yielding the title compound (1.1 g, 5%); $^1$H NMR (300 MHz, CDCl$_3$) δ 7.31-7.19 (m, 2H, ArH), 6.95-6.91 (m, 1H, ArH), 3.28 (d, 1H, J=8.4 Hz, CH), 3.10 (d, 1H, J=8.4 Hz, CH), 2.48-2.40 (m, 4H, CH), 1.68-1.62 (m, 1H, CH), 1.47-1.33 (m, 5H, CH), 0.92-0.87 (m, 3H, CH$_3$), 0.77-0.74 (m, 1H, CH); MS (m/z) 284 (M$^+$, 100).

Example VIII

Preparation of 1-Aryl-3-methyl-3-aza-bicyclo[3.1.0]hexane hydrochlorides Using Reaction Scheme 14

A. Synthesis of 3-Bromo-1-methyl-1H-pyrrole-2,5-dione

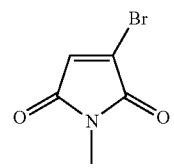

Pursuant to steps a and b of Reaction Scheme 14, a solution of bromomaleic anhydride (52.8 g, 0.298 mol) in diethyl ether (250 mL) was cooled to 5° C. A 2 M solution of methylamine in THF (298 mL, 0.596 mol, 2 eq.) was added dropwise over 1 hour and the reaction stirred for a further 30 minutes, maintaining the temperature below 10° C. The resulting precipitate was filtered, washed with diethyl ether (2×100 mL) and air-dried for 30 minutes, then suspended in acetic anhydride (368 mL) and sodium acetate (12.2 g, 0.149 mol, 0.5 eq.) added. The reaction was heated to 60° C. for 2 hours and solvent was then removed in vacuo. The residue was taken up in DCM (500 mL) and washed with saturated sodium bicarbonate solution (2×500 mL) and water (2×300 mL). Organics were dried over MgSO$_4$ (89 g), filtered and reduced in vacuo. The resulting oil was azeotroped with toluene (4×100 mL) to give N-methyl bromomaleimide as a beige solid. Yield=41.4 g (73%); $^1$H NMR (300 MHz, CDCl$_3$) δ 6.95 (1H, s, CH), 3.07 (3H, s, NCH$_3$).

B. General Synthetic procedure for preparation of 3-Aryl-1-methyl-pyrrole-2,5-diones Pursuant to step c of Reaction Scheme 14, the following provides a general procedure for synthesis of 3-aryl-1-methyl-pyrrole-2,5-diones. N-Methyl bromomaleimide (20 mL of a 0.5 M solution in 1,4-dioxane, 1.96 g net, 10 mmol), aryl boronic acid (11 mmol, 1.1 eq.), cesium fluoride (3.4 g, 22 mmol, 2.2 eq.) and [1,1'-bis-(diphenylphosphino)ferrocene] palladium (II) chloride (0.4 g, 0.5 mmol, 5 mol %) were stirred at 40° C. for between 1 and 6 hours. Reactions were filtered, solids washed with 1,4-dioxane (5 mL) and solvents removed in vacuo (two of the solids required an extra wash with dichloromethane at this stage). Residues were taken up in DCM (5 mL) then purified either by passing through a flash silica chromatography cartridge (20 g silica) or by column chromatography (30 g silica, eluted with 4:1 hexane:ethyl acetate then 2:1 hexane:ethyl acetate). Solvents were removed in vacuo to give the required crude products as solids. The compounds shown below (NMR data also listed below) were prepared using the foregoing general procedure:

(1) 3-(3,4-Difluorophenyl)-1-methyl-pyrrole-2,5-dione

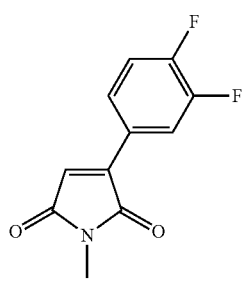 [SMILES: CN1C(=O)C=C(c2ccc(F)c(F)c2)C1=O]

Yield=1.4 g (61%); $^1$H NMR (300 MHz, CDCl$_3$) δ 7.88-7.81 (1H, m, ArH), 7.72-7.68 (1H, m, ArH), 7.29-7.20 (1H, m, ArH), 6.71 (1H, s, CH), 3.07, (3H, s, NCH$_3$); MS (m/z) 224 [MH$^+$].

(2) 3-(3-Fluoro-4-methylphenyl)-1-methyl-pyrrole-2,5-dione

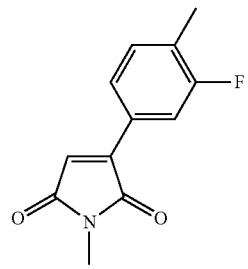 [SMILES: Cc1ccc(C2=CC(=O)N(C)C2=O)cc1F]

Yield=1.2 g (53%); $^1$H NMR (300 MHz, CDCl$_3$) δ 7.65-7.59 (2H, m, ArH), 7.28-7.21 (1H, obs t, J=8.1 Hz, ArH), 6.69 (1H, s, CH), 3.06 (3H, s, NCH$_3$), 2.32-2.31 (3H, d, J=2.3 Hz, ArCH$_3$); MS (m/z) 220 [MH$^+$].

(3) 3-(4-Fluoro-3-methylphenyl)-1-methyl-pyrrole-2,5-dione

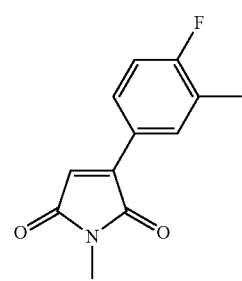 [SMILES: Cc1cc(C2=CC(=O)N(C)C2=O)ccc1F]

Yield=1.4 g (62%); $^1$H NMR (300 MHz, CDCl$_3$) δ 7.80-7.76 (21-1, m, ArH), 7.12-7.06 (1H, obs t, J=8.9 Hz, ArH), 6.67 (1H, s, CH), 3.08 (3H, s, NCH$_3$), 2.33 (3H, d, J=1.8 Hz, ArCH$_3$); MS (m/z) 220 [MH$^+$].

(4) 3-(2,4-Difluorophenyl)-1-methyl-pyrrole-2,5-dione

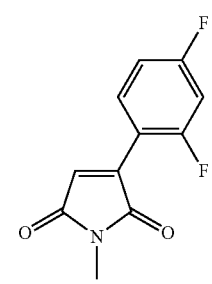 [SMILES: CN1C(=O)C=C(c2ccc(F)cc2F)C1=O]

Yield=1.8 g (78%); $^1$H NMR (300 MHz, CDCl$_3$) δ 8.39-8.31 (1H, m, ArH), 7.02-6.89 (3H, m, 2×ArH, CH), 3.08 (3H, s, NCH$_3$); MS (m/z) 236 [MH]$^+$.

(5) 3-(2,4-Dichlorophenyl)-1-methyl-pyrrole-2,5-dione

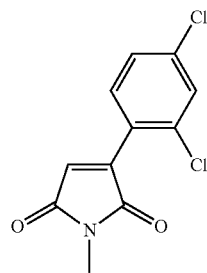 [SMILES: CN1C(=O)C=C(c2ccc(Cl)cc2Cl)C1=O]

Yield=2.0 g (76%); $^1$H NMR (300 MHz, CDCl$_3$) δ 7.70-7.67 (1H, d, J 8.4 Hz, ArH), 7.52 (1H, d, J=1.9 Hz, ArH), 7.37-7.33 (1H, m, ArH), 7.02 (1H, s. CH), 3.09 (3H, s, NCH$_3$); MS (m/z) 256 [MH$^+$].

(6) 3-(2-methoxynaphthalen-6-yl)-1-methyl-pyrrole-2,5-dione

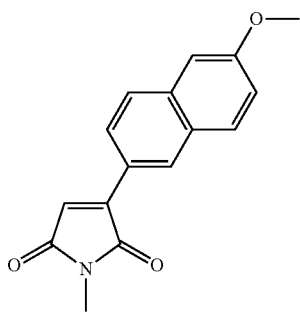 [SMILES: COc1ccc2cc(C3=CC(=O)N(C)C3=O)ccc2c1]

Yield=1.30 g, (65%); $^1$H NMR (300 MHz, CDCl$_3$) δ 8.62 (br s, 1H), 7.83 (m, 1H), 7.76 (m, 2H), 7.18 (m, 1H), 7.12 (m, 1H), 6.75 (s, 1H), 3.94 (s, 3H), 3.09 (s, 3H).

(7) 3-(2-ethoxynaphthalen-6-yl)-1-methyl-pyrrole-2,5-dione

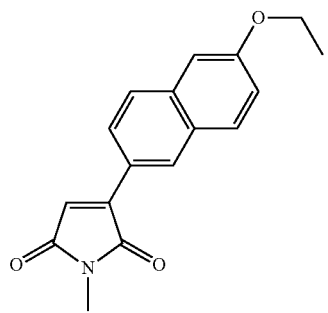 [SMILES: CCOc1ccc2cc(C3=CC(=O)N(C)C3=O)ccc2c1]

Yield=1.02 g, (48%); $^1$H NMR (300 MHz, CDCl$_3$) δ 8.62 (m, 1H), 7.83 (m, 1H), 7.75 (m, 2H), 7.18 (m, 1H), 7.11 (m, 1H), 6.76 (s, 1H), 4.17 (q, 2H, J=7 Hz), 3.10 (s, 3H), 1.49 (t, 3H, J=7 Hz); MS (M+1) 282.1.

C. General Synthetic procedure for preparation of 1-Aryl-3-methyl-3-aza-bicyclo[3.1.0]hexane-2,4-diones Pursuant to step d of Reaction Scheme 14, trimethylsulphoxonium chloride (1.2 eq.) and sodium hydride (60% dispersion in mineral oil, 1.2 eq.) were suspended in THF (50 vol) and heated at reflux (66° C.) for 2 hours. The reactions were cooled to 50° C. and a solution of 1-methyl-3-(aryl)pyrrole-2,5-dione (1 eq.) in THF (10 mL) was added in one portion. The reactions were heated at 50° C. for between 2 and 4 hours and then at 65° C. for a further 2 hours if required (as judged by disappearance of starting material by TLC), and then cooled to room temperature. Reactions were quenched by the addition of IMS (5 mL) and the solvents removed in vacuo. The residues were taken up in DCM (35 mL) and washed with water (3×35 mL). Combined aqueous washes were back-extracted with DCM (15 mL), organic portions combined and solvent removed in vacuo. The reactions were purified by column chromatography (30 g silica, eluting with increasingly polar fractions of ethyl acetate in hexane) and solvents removed in vacuo to give the 3-methyl-1-(aryl)-3-aza-bicyclo[3.1.0]hexane-2,4-diones as crude solids. The compounds shown below (NMR data also listed below) were prepared using the foregoing general procedure:

(1) 1-(3,4-Difluorophenyl)-3-methyl-3-aza-bicyclo[3.1.0]hexane-2,4-dione

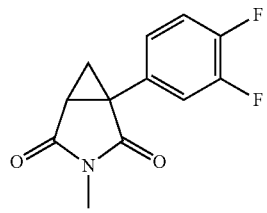 [SMILES: CN1C(=O)C2CC2(c2ccc(F)c(F)c2)C1=O]

Yield=0.6 g (40%); $^1$H NMR (300 MHz, CDCl$_3$) δ 7.32-7.26 (1H, m, ArH), 7.20-7.07 (2H, m, ArH), 2.92 (3H, s, NCH$_3$), 2.75-2.71 (1H, dd, J=8.1 Hz, 3.7 Hz, CH), 1.87-1.85 (1H, obs t, J=4.2 Hz, CH$_2$), 1.81-1.77 (1H, dd, J=8.1 Hz, 4.8 Hz, CH$_2$); MS (m/z) 238 [MH$^+$].

(2) 1-(3-Fluoro-4-methylphenyl)-3-methyl-3-aza-bicyclo[3.1.0]hexane-2,4-dione

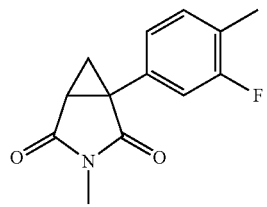 [SMILES: Cc1ccc(C23CC2C(=O)N(C)C3=O)cc1F]

Yield=0.2 g (16%); $^1$H NMR (300 MHz, CDCl$_3$) δ 7.19-7.14 (1H, t, J 7.8 Hz, ArH), 7.10-7.02 (2H, m, ArH), 2.91 (3H, s, NCH$_3$), 2.71-2.67 (1H, dd, J=8.1 Hz, 4.0 Hz, CH), 2.25 (3H, d, J=1.9 Hz, ArCH$_3$), 1.87-1.78 (2H, m, CH$_2$); MS (m/z) 234 [MH$^+$].

(3) 1-(4-Fluoro-3-methylphenyl)-3-methyl-3-aza-bicyclo[3.1.0]hexane-2,4-dione

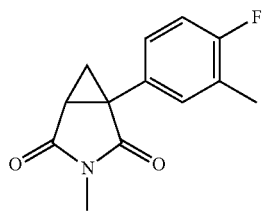 [SMILES: Cc1cc(C23CC2C(=O)N(C)C3=O)ccc1F]

Yield=0.5 g (33%); $^1$H NMR (300 MHz, CDCl$_3$) δ 7.25-7.21 (1H, m, ArH), 7.19-7.14 (1H, m, ArH), 7.02-6.96 (1H, t, J=9.0 Hz), 2.92 (3H, s, NCH$_3$), 2.69-2.65 (1H, dd, J=7.8 Hz, 4.1 Hz, CH), 2.27-2.26 (3H, d, J=2.2 Hz, ArCH$_3$), 1.84-1.77 (2H, m, CH$_2$); MS (m/z) 234 [MH$^+$].

(4) 1-(2,4-Difluorophenyl)-3-methyl-3-aza-bicyclo[3.1.0]hexane-2,4-dione

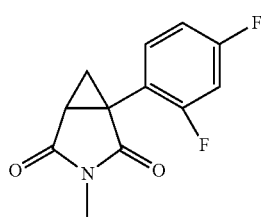 [SMILES: CN1C(=O)C2CC2(c2ccc(F)cc2F)C1=O]

Yield=0.7 g (36%); $^1$H NMR (300 MHz, CDCl$_3$) δ 7.35-7.20 (1H, m, ArH), 6.94-6.79 (2H, m, ArH), 2.92 (3H, s, NCH$_3$), 2.65-2.61 (1H, dd, J=7.7 Hz, 4.1 Hz, CH), 1.89-1.83 (2H, m, CH$_2$); MS (m/z) 238 [MH$^+$].

(5) 1-(2,4-Dichlorophenyl)-3-methyl-3-aza-bicyclo[3.1.0]hexane-2,4-dione

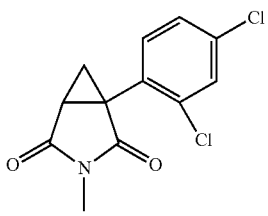 [SMILES: CN1C(=O)C2CC2(c2ccc(Cl)cc2Cl)C1=O]

Yield=1.0 g (47%); $^1$H NMR (300 MHz, CDCl$_3$) δ 7.45-7.44 (1H, s, ArH), 7.29-7.28 (2H, m, ArH), 2.94 (3H, s, NCH$_3$), 2.62-2.58 (1H, dd, J=7.7 Hz, 4.8 Hz, CH), 1.95-1.91 (2H, m, CH$_2$); MS (m/z) 270 [MH$^+$].

(6) 1-(2-methoxynaphthalen-6-yl)-3-methyl-3-aza-bicyclo[3.1.0]hexane-2,4-dione

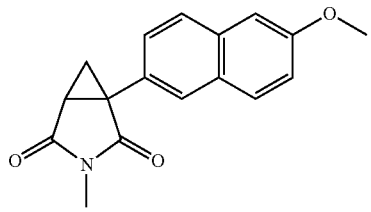 [SMILES: COc1ccc2cc(C34CC3C(=O)N(C)C4=O)ccc2c1]

Yield=580 mg, (41%)); MS (M+1) 282.1. $^1$H NMR (CDCl3) δ 7.79 (m, 1H), 7.69-7.76 (m, 2H), 7.44 (m, 1H), 7.16 (m, 1H), 7.12 (m, 1H), 3.92 (s, 3H), 2.96 (s, 3H), 2.78 (m, 1H), 1.87-1.97 (m, 2H).

(7) 1-(2-ethoxynaphthalen-6-yl)-3-methyl-3-aza-bicyclo[3.1.0]hexane-2,4-dione

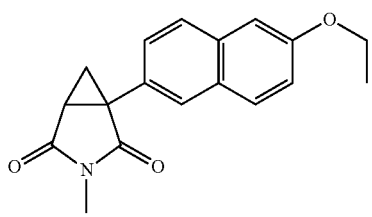 [SMILES: CCOc1ccc2cc(C34CC3C(=O)N(C)C4=O)ccc2c1]

Yield=360 mg, (39%)); $^1$H NMR (CDCl3) δ 7.78 (m, 1H), 7.71 (m, 2H), 7.43 (m, 1H), 7.16 (m, 1H), 7.11 (m, 1H), 4.15 (q, 2H, 0.1=7 Hz), 2.95 (s, 3H), 2.78 (m, 1H), 1.91 (m, 2H); MS (M+1) 296.1.

D. General Synthetic procedure for preparation of 1-Aryl-3-methyl-3-aza-bicyclo[3.1.0]hexane hydrochlorides Pursuant to steps e and f of Reaction Scheme 14, borane (1 M complex in THF, 5 eq.) was cooled to <0° C. and a solution of 3-methyl-1-(aryl)-3-aza-bicyclo[3.1.0]hexane-2,4-dione (1 eq.) in THF (10 vol.) added dropwise, maintaining the temperature <0° C. The reactions were warmed to room temperature for 15 minutes then heated to reflux (67° C.) for 2 hours. The reactions were cooled to <0° C. and quenched with the dropwise addition of 6 M HCl (5 vol., temperature maintained <0° C.). Solvents were removed in vacuo and the resulting white residues made basic with the addition of 5 M NaOH (25 mL) and extracted with DCM (2×20 mL). The organics were washed with water (3×30 mL) then concentrated in vacuo to ~1 mL volume. The resulting oils were purified by column chromatography (15 g silica, eluting with DCM then 5% MeOH in DCM) to give the crude free bases. Samples were dissolved in diethyl ether (1 mL) and 1 M HCl in ether (10 mL) was added. The resulting white precipitates were stored at −20° C. for 16 hours then centrifuged. Ether was decanted and the solids washed with a further three portions of ether (material isolated by centrifugation and ether decanted after each wash). Materials were dried in vacuo at 30° C. to give the required products as white solids. The compounds shown below (NMR data also listed below) were prepared using the general procedures described above:

(1) 1-(3,4-Difluorophenyl)-3-methyl-3-aza-bicyclo[3.1.0]hexane

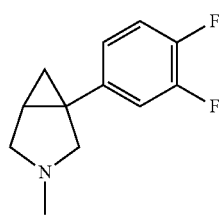

Free base: $^1$H NMR (300 MHz, CDCl$_3$) δ 7.07-6.95 (1H, m, ArH), 6.92-6.79 (2H, m, ArH), 3.23-3.20 (1H, d, J=8.8 Hz, CH$_2$), 3.04-3.01 (1H, d, J=8.8 Hz, CH$_2$), 2.48-2.42 (2H, m, CH$_2$), 2.32 (3H, s, NCH$_3$), 1.62-1.58 (1H, m, CH), 1.39-1.38 (1H, m, CH$_2$) 0.74-0.70 (1H, dd, J=8.1 Hz, 4.4 Hz, CH$_2$)

Hydrochloride salt: Yield=175 mg (28%); $^1$H NMR (300 MHz, CDCl$_3$) δ 12.16 (1H, br-s, N$^+$H), 7.26-6.95 (3H, m, ArH), 3.95 (1H, br-s, CH$_2$), 3.80 (1H, br-s, CH$_2$), 3.53 (1H, br-s, CH$_2$), 3.42 (1H, br-s, CH$_2$), 2.92 (3H, s, NCH$_3$), 2.10 (1H, br-s, CH$_2$), 1.95 (1H, br-s, CH$_2$), 113 (1H, br-s, CH$_2$); $^{13}$C NMR (75 MHz, CDCl$_3$) δ 151.67, 151.03, 148.51, 147.90, 134.70, 123.77, 123.64, 117.64, 117.42, 116.88, 116.65, 60.10, 56.96, 41.12, 30.63, 23.26, 15.29; MS (m/z) 210 [MH$^+$]; LC purity 96.3%.

(2) 1-(3-Fluoro-4-methylphenyl)-3-methyl-3-aza-bicyclo[3.1.0]hexane

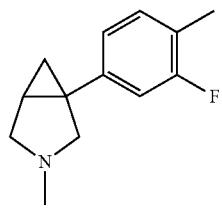

Free base: $^1$H NMR (300 MHz, CDCl$_3$) δ 7.13-7.03 (2H, m, ArH), 6.80-6.75 (1H, m, ArH), 3.28-3.25 (1H, d, J=8.9 Hz, CH$_2$), 3.08-3.05 (1H, d, J=8.8 Hz, CH$_2$), 2.55-2.52 (1H, d, J=8.5 Hz, CH$_2$), 2.47-2.43 (1H, dd, J=8.8 Hz, 3.3 Hz, CH$_2$) 2.36 (3H, s, NCH$_3$), 2.22 (3H, s, ArCH$_3$), 1.67-1.62 (1H, m, CH), 1.43-1.39 (1H, m, CH$_2$) 0.79-0.75 (1H, dd, J=8.1 Hz, 4.4 Hz, CH$_2$).

Hydrochloride salt: Yield=66 mg (30%); $^1$H NMR (300 MHz, CDCl$_3$) δ 12.12 (1H, br-s, N$^+$H), 7.07-7.02 (1H, t, J=7.9 Hz, ArH), 6.87-6.80 (2H, m, ArH), 3.94-3.91 (1H, d, J=9.2 Hz, CH$_2$), 3.78-3.75 (1H, d, J=8.8 Hz, CH$_2$), 3.44-3.39 (1H, m, CH$_2$), 3.36-3.34 (1H, m, CH$_2$), 2.88 (3H, s, NCH$_3$), 2.14 (3H, s, ArCH$_3$), 2.07-2.04 (1H, m, CH$_2$), 1.91-1.88 (1H, m, CH), 1.10-1.05 (1H, obs t, J=7.6 Hz, CH$_2$); $^{13}$C NMR (75 MHz, CDCl$_3$) δ 162.68, 159.43, 137.39, 137.29, 131.69, 131.61, 124.01, 123.79, 122.44, 122.40, 113.92, 113.63, 59.88, 56.85, 40.75, 30.71, 23.17, 15.48, 13.91; MS (m/z) 206 [MH$^+$]; LC purity 93.1%.

(3) 1-(4-Fluoro-3-methylphenyl)-3-methyl-3-aza-bicyclo[3.1.0]hexane

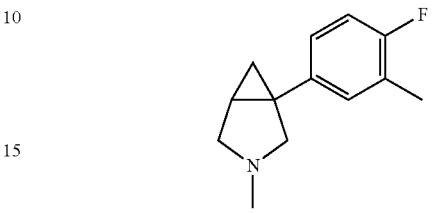

Free base: $^1$H NMR (300 MHz, CDCl$_3$) δ 6.97-6.94 (1H, m, ArH), 6.93-6.88 (2H, m, ArH), 3.28-3.25 (1H, d, J=8.4 Hz, CH$_2$), 3.08-3.05 (1H, d, J=8.5 Hz, CH$_2$), 2.52-2.45 (2H, m, CH$_2$), 2.35 (3H, s, NCH$_3$), 2.24 (3H, s, ArCH$_3$), 1.64-1.59 (1H, m, CH), 1.38-1.35 (1H, obs t, J=4.3 Hz, CH$_2$) 0.76-0.72 (1H, dd, J=8.1 Hz, 4.4 Hz, CH$_2$).

Hydrochloride salt: Yield=134 mg (26%); $^1$H NMR (300 MHz, CDCl$_3$) δ 12.21 (1H, br-s, N$^+$H), 6.99-6.93 (2H, m, ArH), 6.90-6.84 (1H, t, J=8.8 Hz, ArH), 3.98-3.93 (1H, dd, J=10.6 Hz, 5.1 Hz, CH$_2$), 3.83-3.78 (11-1, dd, J=10.8 Hz, 4.9 Hz, CH$_2$), 3.41-3.34 (1H, m, CH$_2$), 3.27-3.21 (1H, obs t, J=9.4 Hz CH$_2$), 2.87-2.85 (3H, d, J=4.5 Hz, NCH$_3$), 2.18 (3H, s, ArCH$_3$) 2.07-2.03 (1H, m, CH$_2$), 1.92-1.87 (1H, m, CH), 1.09-1.04 (1H, obs t, J=7.5 Hz, CH$_2$); $^{13}$C NMR (75 MHz, CDCl$_3$) δ 162.00, 158.75, 133.04, 132.99, 130.45, 130.37, 126.18, 126.08, 125.33, 125.09, 115.32, 115.02, 60.37, 56.99, 40.85, 30.71, 22.73, 15.25, 14.28; MS (m/z) 206 [MH$^+$]; LC purity 98.6%.

(4) 1-(2,4-Difluorophenyl)-3-methyl-3-aza-bicyclo[3.1.0]hexane

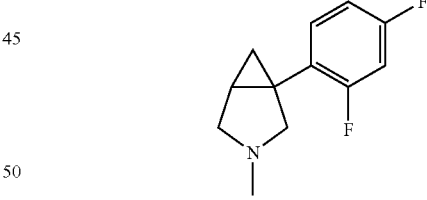

Free base: $^1$H NMR (300 MHz, CDCl$_3$) δ 7.18-7.13 (1H, m, ArH), 6.78-6.68 (2H, m, ArH), 3.20-3.16 (1H, dd, J=8.5 Hz, 1.4 Hz, CH$_2$), 3.08-3.05 (1H, d, J=8.5 Hz, CH$_2$), 2.55-2.51 (1H, dd, J=8.8 Hz, 3.3 Hz, CH$_2$), 2.40-2.37 (1H, d, J=8.4 Hz, CH$_2$), 2.32 (3H, s, NCH$_3$), 1.65-1.60 (11-1, m, CH), 1.35-1.32 (1H, obs t, J=4.3 Hz, CH$_2$) 0.72-0.68 (1H, dd, J=8.1 Hz, 4.4 Hz, CH$_2$).

Hydrochloride salt: Yield=136 mg (19%); $^1$H NMR (300 MHz, CDCl$_3$) δ 12.20 (1H, br-s, N$^+$H), 7.22-7.17 (1H, m, ArH), 6.89-6.75 (2H, m, 3.94-3.85 (2H, m, CH$_2$), 3.37-3.35 (1H, d, J=8.1 Hz, CH$_2$), 3.17-3.14 (1H, d, J=10.6 Hz, CH$_2$), 2.85 (3H, s, NCH$_3$), 2.13 (1H, br-s, CH$_2$), 1.92-1.87 (1H, m, CH), 1.18-1.13 (1H, obs t, J 7.9 Hz, CH$_2$); $^{13}$C NMR (75 MHz, CDCl$_3$) δ 164.29, 164.13, 163.75, 163.59, 160.97, 160.81, 160.45, 160.29, 131.91, 131.85, 120.51, 120.27, 111.84, 111.50, 104.47, 104.13, 103.79, 59.76, 56.90, 41.03, 26.69, 22.42, 13.37; MS (m/z) 210 [MH+]; LC purity 95.1%.

(5) 1-(2,4-Dichlorophenyl)-3-methyl-3-aza-bicyclo[3.1.0]hexane

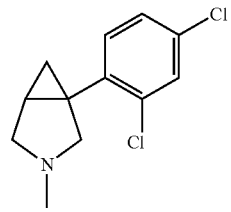

Free base: $^1$H NMR (300 MHz, CDCl$_3$) δ 7.37-7.16 (311, m, ArH), 3.16-3.13 (1H, d, J=8.8 Hz, CH$_2$), 3.11-3.08 (11-1, d, J=8.8 Hz, CH$_2$), 2.70-2.66 (1H, 8.8 Hz, 3.7 Hz, CH$_2$), 2.45-2.43 (1H, d, J=8.5 Hz, CH$_2$), 2.35 (3H, s, NCH$_3$), 1.66-1.61 (1H, m, CH), 1.41-1.38 (1H, obs t, J=4.4 Hz, CH$_2$) 0.74-0.70 (1H, dd, J=8.1 Hz, 4.4 Hz, CH$_2$).

(6) 1-(2-methoxynaphthalen-6-yl)-3-methyl-3-aza-bicyclo[3.1.0]hexane

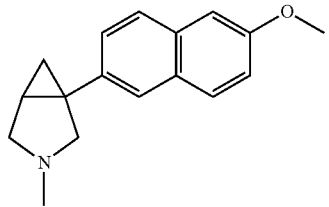 [SMILES: COc1ccc2cc(C34CC3CN(C)C4)ccc2c1]

Free base: Yield=276 mg, (61%) as a white solid. MS(M+1) 254.2. $^1$H NMR (CDCl3) δ 7.62-7.68 (m, 2H), 7.54 (m, 1H), 7.22 (m, 1H), 7.08-7.14 (m, 2H), 3.90 (s, 3H), 3.42 (m, 1H), 3.15 (m, 1H), 2.70 (m, 1H), 2.56 (m, 1H), 2.42 (s, 3H), 1.77 (m, 1H), 1.48 (m, 1H), 0.91 (m, 1H).

Hydrochloride salt: Yield=155 mg, (77%) as a white solid. MS (M+1) 254.2. $^1$H NMR (CDCl3) δ☐ 12.56 (br s, 1H), ☐ 7.67 (m, 2H), 7.55 (m, 1H), 7.21 (m, 1H), 7.14 (m, 1H), 7.08 (m, 1H), 4.14 (m, 1H), 3.93 (m, 1H), 3.89 (s, 3H), 3.34 (m, 2H), 2.90 (d, 2H, J=5 Hz), 2.24 (m, 1H), 2.06 (m, 1H), 1.26 (m, 1H). $^{13}$C NMR (CDCl3) δ 158.18, 133.92, 132.89, 129.22, 128.87, 127.83, 126.15, 125.43, 119.81, 105.85, 60.76, 57.52, 55.55, 41.45, 31.77, 23.23, 16.11.

(7) 1-(2-ethoxynaphthalen-6-yl)-3-methyl-3-aza-bicyclo[3.1.0]hexane

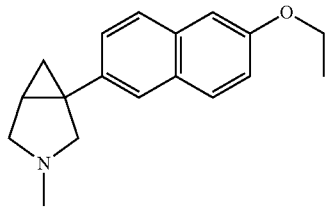 [SMILES: CCOc1ccc2cc(C34CC3CN(C)C4)ccc2c1]

Free base: Yield=192 mg, (65%) as a white solid. $^1$H NMR (CDCl3) δ 7.64 (m, 2H), 7.54 (m, 1H), 7.21 (m, 1H), 7.07-7.15 (m, 2H), 4.13 (q, 2H, J=7 Hz), 3.41 (m, 1H), 3.15 (m, 1H), 2.69 (m, 1H), 2.56 (m, 1H), 2.42 (s, 3H), 1.77 (m, 1H), 1.48 (m, 1H), 1.47 (t, 3H, J=7 Hz), 0.91 (m, 1H); MS (M+1) 268.2.

Hydrochloride salt: Yield=172 mg, (81%) as a white solid. $^1$H NMR (CDCl3) δ☐ 12.50 (br s, 1H), 7.66 (m, 2H), 7.54 (m, 1H), 7.20 (m, 1H), 7.14 (m, 1H), 7.07 (m, 1H), 4.14 (m, 1H), 4.10 (t, 2H, J=7 Hz), 3.93 (m, 1H), 3.34 (m, 2H), 2.90 (d, 3H, J=5 Hz), 2.22 (m, 1H), 2.06 (m, 1H), 1.45 (t, 3H, J=7 Hz), 1.26 (m, 1H). 13C NMR (CDCl3) δ 157.50, 133.96, 132.76, 129.17, 128.81, 127.79, 126.14, 125.37, 120.09, 106.61, 63.75, 60.77, 57.54, 41.46, 31.77, 23.21, 16.09, 14.98; MS (M+1) 268.2.

Example IX

Preparation of 1-Aryl-3-ethyl-3-aza-bicyclo[3.1.0]hexane Hydrochlorides Using Reaction Scheme 15

A. Synthesis of 3-Bromo-1-ethylmaleimide

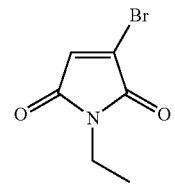

A cooled (5° C.) solution of N-ethylmaleimide (20 g, 0.16 mole) in carbon tetrachloride (20 mL) under nitrogen was treated dropwise over 45 min with bromine (23 g, 0.14 mole) at a rate to keep pot temp <10° C. The mixture was stirred at 5° C. for 2 hours. Dichloromethane (20 mL) was added to the reaction and N$_2$ was bubbled through the reaction for 15 min to remove excess bromine. The reaction was blown dry with a steady stream of N$_2$ and then brought up in ethanol. Anhydrous sodium acetate (12.3 g, 0.15 mole) was added and the reaction was refluxed for 4 hours. The mixture was concentrated in vacuo and the residue taken up in methylene chloride (300 mL), filtered and concentrated in vacuo to yield an orange oil. Pure 3-bromo-1-ethylmaleimide was obtained from recrystallization in chloroform to yield a yellowish solid (26 g, 82%). NC) MS (M+1) peak observed. $^1$H NMR (CDCl$_3$) δ 1.20 (t, J=7.22 Hz, 3H), 3.62 (q, J=7.22 Hz, 2H), 6.85 (s, 1H).

B. Synthesis of 1-(3,4-Difluorophenyl)-3-ethyl-3-azabicyclo[3.1.0]hexane Hydrochloride

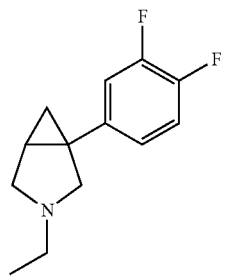 [SMILES: CCN1CC2CC2(c2ccc(F)c(F)c2)C1]

A stirred solution/suspension of 3-bromo-1-ethylmaleimide (1.0 g, 5 mmol) and 3,4-difluorophenylboronic acid (850 mg, 5.4 mmol) in dioxane (15 mL) under nitrogen was degassed with a stream of nitrogen for 10 min, treated with cesium fluoride (1.6 g, 10.8 mmol) and Cl$_2$Pd(dppf).CH$_2$Cl$_2$ (0.25 g, 0.3 mmol), then stirred at room temperature for 1 h and at 40° C. for 45 min. The mixture was then cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride) to afford a pale yellow solid, which was triturated from cold petroleum ethers to afford arylmaleimide intermediate (973 mg, 84%) as a pale yellow solid.

A stirred suspension of sodium hydride oil dispersion (60%, 160 mg, 4.0 mmol) in anhydrous tetrahydrofuran (30 mL) under nitrogen was treated with trimethyl-sulfoxonium chloride (0.58 g, 4.5 mmol), then refluxed for 2.5 h and cooled (50° C.). The above arylmaleimide (937 mg, 4.0 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane and loaded onto a silica gel column and eluted with 1:1, 2:1, then 3:1 methylene chloride/heptane to afford bicyclic diimide intermediate (429 mg, 42%) as a very pale yellow oil. $^1$H NMR (CDCl$_3$) δ 1.09-1.16 (m, 3H) 1.21-1.31 (m, 1H) 1.73-1.87 (m, 2H) 2.72 (dd, J=8.00, 3.90 Hz, 1H) 3.40-3.53 (m, 2H) 7.05-7.22 (m, 2H) 7.26-7.34 (m, 1H).

A stirred ice-cooled solution of 1.0N borane/THF (16 mL, 16 mmol) under nitrogen was treated dropwise with a solution of the above bicyclic diimide intermediate (429 mg, 1.7 mmol) in anhydrous THF (10 mL). The solution was stirred at room temperature for 15 min, refluxed for 4 h, cooled on an ice bath, and carefully treated dropwise with 6N HCl (10 mL, vigorous evolution of gas). The solution was concentrated to a white solid, which was partitioned between 5N sodium hydroxide (25 mL) and ether (50 mL). The organic layer was separated and the aqueous extracted with ether (50 mL). The combined organic solution was washed with water (25 mL), dried (Mg$_2$SO$_4$), and concentrated in vacuo. The residue was dissolved in methanol (23 mL), treated with 4N HCl/dioxane (7 mL), then stirred at room temperature for 16 h and at 55° C. for 4 h. The solution was concentrated in vacuo and the residue triturated from ether to afford 1-(3,4-difluorophenyl)-3-ethyl-3-azabicyclo[3.1.0]hexane, hydrochloride (105 mg, 21%) as a white solid. MS (M+1) 224. $^1$H NMR (CDCl$_3$) δ 1.08-1.19 (m, J=6.64, 6.64 Hz, 1H) 1.49 (t, 3H) 1.71-1.86 (m, 1H) 1.90-2.03 (m, 1H) 2.30 (dd, 1H) 3.00-3.42 (m, 4H) 3.89 (dd, 1H) 4.06 (dd, 1H) 6.69-7.20 (m, 3H). $^{13}$C NMR (CDCl$_3$) δ 10.99, 16.31, 22.96, 30.42, 51.17, 55.07, 58.31, 116.85, 117.75, 123.82, 135.79, 148.65, 149.29, 150.63, 151.28.

C. Synthesis of 1-(3-Chloro-4-fluorophenyl)-3-ethyl-3-azabicyclo[3.1.0]hexane Hydrochloride

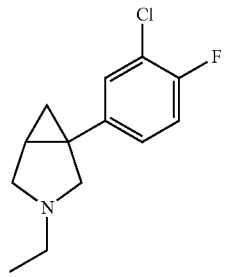 [SMILES: CCN1CC2CC2(c2ccc(F)c(Cl)c2)C1]

A stirred solution/suspension of 3-bromo-1-ethylmaleimide (1.09 g, 5 mmol) and 3-chloro-4-fluorophenylboronic acid (945 mg, 5.4 mmol) in dioxane (15 mL) under nitrogen was degassed with a stream of nitrogen for 10 min, treated with cesium fluoride (1.6 g, 10.8 mmol) and Cl$_2$Pd (dppf).CH$_2$Cl$_2$ (0.25 g, 0.3 mmol), then stirred at room temperature for 1 h and at 40° C. for 45 min. The mixture was then cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride) to afford a pale yellow solid, which was triturated from cold petroleum ethers to afford arylmaleimide intermediate (1.0 g, 83%) as a pale yellow solid.

A stirred suspension of sodium hydride oil dispersion (60%, 160 mg, 3.95 mmol) in anhydrous tetrahydrofuran (30 mL) under nitrogen was treated with trimethyl-sulfoxonium chloride (0.56 g, 4.3 mmol), then refluxed for 2.5 h and cooled (50° C.). The above arylmaleimide (1.0 g, 3.95 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane and loaded onto a silica gel column and eluted with 1:1, 2:1, then 3:1 methylene chloride/heptane to afford bicyclic diimide intermediate (567 mg, 54%) as a very pale yellow oil. $^1$H NMR (CDCl$_3$) δ 1.09-1.16 (m, 3H) 1.21-1.31 (m, 1H) 1.73-1.87 (m, 2H) 2.72 (dd, J=8.00, 3.90 Hz, 1H) 3.40-3.53 (m, 2H) 7.05-7.22 (m, 2H) 7.26-7.34 (m, 1H).

A stirred ice-cooled solution of 1.0N borane/THF (10.5 mL, 10.5 mmol) under nitrogen was treated dropwise with a solution of the above bicyclic diimide intermediate (560 mg, 2.1 mmol) in anhydrous THF (10 mL). The solution was stirred at room temperature for 15 min, refluxed for 4 h, cooled on an ice bath, and carefully treated dropwise with 6N HCl (10 mL, vigorous evolution of gas). The solution was concentrated to a white solid, which was partitioned between 5N sodium hydroxide (25 mL) and ether (50 mL). The organic layer was separated and the aqueous extracted with ether (50 mL). The combined organic solution was washed with water (25 mL), dried (Mg$_2$SO$_4$), and concentrated in vacuo. The residue was dissolved in methanol (23 mL), treated with 4N HCl/dioxane (7 mL), then stirred at room temperature for 16 h and at 55° C. for 4 h. The solution was concentrated in vacuo and the residue triturated from ether to afford 1-(3-chloro-4-fluorophenyl)-3-ethyl-3-azabicyclo[3.1.0]hexane, hydrochloride (100 mg, 20%) as a white solid. MS (M+1) 240.1. $^1$H NMR (CDCl$_3$) δ 1.13-1.20 (m, 1H) 1.51 (t, J=7.22 Hz, 3H) 1.93-2.02 (m, 1H) 2.36 (dd, J=6.64, 4.69 Hz, 1H) 2.95-3.30 (m, 4H) 3.92 (dd, J=10.84, 5.17 Hz, 1H) 4.10 (dd, J=10.93, 5.27 Hz, 1H) 7.01-7.15 (m, 2H) 7.23 (dd, J=6.74, 2.25 Hz, 1H). $^{13}$C NMR (CDCl$_3$) δ 11.22, 16.63, 22.99, 31.42, 55.52, 58.68, 124.82, 126.25, 126.49, 126.96, 127.82, 129.06, 132.68, 133.44, 135.59.

D. Synthesis of 1-(3-Fluoro-4-methylphenyl)-3-ethyl-3-azabicyclo[3.1.0]hexane Hydrochloride

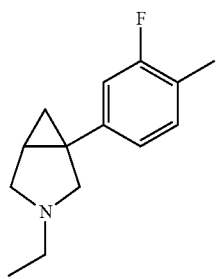 [SMILES: CCN1CC2CC2(c2ccc(C)c(F)c2)C1]

A stirred solution/suspension of 3-bromo-1-ethylmaleimide (1.0 g, 5 mmol) and 3-fluoro-4-methylphenyl boronic acid (830 mg, 5.4 mmol) in dioxane (15 mL) under nitrogen was degassed with a stream of nitrogen for 10 min, treated with cesium fluoride (1.6 g, 10.8 mmol) and Cl$_2$Pd(dppf).CH$_2$Cl$_2$ (0.25 g, 0.3 mmol), then stirred at room temperature for 1 h and at 40° C. for 45 min. The mixture was then cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride) to afford a pale yellow solid, which was triturated from cold petroleum ethers to afford arylmaleimide intermediate (888 mg, 80%) as a pale yellow solid.

A stirred suspension of sodium hydride oil dispersion (60%, 152 mg, 3.8 mmol) in anhydrous tetrahydrofuran (30 mL) under nitrogen was treated with trimethyl-sulfoxonium chloride (0.59 g, 4.2 mmol), then refluxed for 2.5 h and cooled (50° C.). The above arylmaleimide (888 mg, 3.81 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane, loaded onto a silica gel column and eluted with 1:1, 2:1, then 3:1 methylene chloride/heptane to afford bicyclic diimide intermediate (297 mg, 31%) as a very pale yellow oil. $^1$H NMR (CDCl$_3$) δ 1.13 (t, J=7.13 Hz, 3H) 1.73-1.84 (m, 2H) 2.24-2.29 (m, J=1.95 Hz, 1H) 2.68 (dd, J=8.00, 3.90 Hz, 1H) 3.42-3.53 (m, 2H) 7.01-7.12 (m, 2H) 7.18 (t, J=7.91 Hz, 1H).

A stirred ice-cooled solution of 1.0N borane/Tl-IF (9.6 mL, 9.6 mmol) under nitrogen was treated dropwise with a solution of the above bicyclic diimide intermediate (297 mg, 1.2 mmol) in anhydrous THF (10 mL). The solution was stirred at room temperature for 15 min, refluxed for 4 h, cooled on an ice bath, and carefully treated dropwise with 6N HCl (10 mL, vigorous evolution of gas). The solution was concentrated to a white solid, which was partitioned between 5N sodium hydroxide (25 mL) and ether (50 mL). The organic layer was separated and the aqueous extracted with ether (50 mL). The combined organic solution was washed with water (25 mL), dried (Mg$_2$SO$_4$), and concentrated in vacuo. The residue was dissolved in methanol (23 mL), treated with 4N HCl/dioxane (7 mL), then stirred at room temperature for 16 h and at 55° C. for 4 h. The solution was concentrated in vacuo and the residue triturated from ether to afford 1-(3-fluoro-4-methylphenyl)-3-ethyl-3-azabicyclo[3.1.0]hexane hydrochloride (165 mg, 63%) as a white solid. MS (M+1) 220. $^1$H NMR (CDCl$_3$) □ 1.13 (t, J=7.61 Hz, 1H) 1.48 (t, J=7.22 Hz, 3H) 1.91-2.00 (m, 1H) 2.20-2.23 (in, J=1.76 Hz, 3H) 2.25 (dd, J=6.64, 4.69 Hz, 1H) 3.13-3.24 (m, 3H) 3.24-3.36 (m, 1H) 3.87 (dd, J=10.93, 5.27 Hz, 1H) 4.05 (dd, J=10.84, 5.37 Hz, 1H) 6.76-6.88 (m, 2H) 7.03-7.16 (m, 1H). $^{13}$C NMR (CDCl$_3$) δ 11.13, 14.40, 16.54, 23.05, 30.69, 51.49, 55.26, 58.39, 113.92, 122.62, 124.36, 132.11, 137.89, 160.27, 162.72.

E. Synthesis of 1-(3-Methyl-4-fluorophenyl)-3-ethyl-3-azabicyclo[3.1.0]hexane Hydrochloride

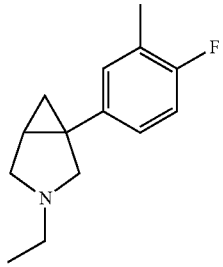 [SMILES: CCN1CC2CC2(c2ccc(F)c(C)c2)C1]

A stirred solution/suspension of 3-bromo-1-ethylmaleimide (1.0 g, 5 mmol) and 3-methyl-4-fluorophenyl boronic acid (830 mg, 5.4 mmol) in dioxane (15 mL) under nitrogen was degassed with a stream of nitrogen for 10 min, treated with cesium fluoride (1.6 g, 10.8 mmol) and Cl$_2$Pd(dppf).CH$_2$Cl$_2$ (0.25 g, 0.3 mmol), then stirred at room temperature for 1 h and at 40° C. for 45 min. The mixture was then cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride) to afford a pale yellow solid, which was triturated from cold petroleum ethers to afford arylmaleimide intermediate (982 mg, 88%) as a pale yellow solid.

A stirred suspension of sodium hydride oil dispersion (60%, 170 mg, 4.2 mmol) in anhydrous tetrahydrofuran (30 mL) under nitrogen was treated with trimethyl-sulfoxonium chloride (0.60 g, 4.6 mmol), then refluxed for 2.5 h and cooled (50° C.). The above arylmaleimide (982 mg, 4.2 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane, loaded onto a silica gel column and eluted with 1:1, 2:1, then 3:1 methylene chloride/heptane to afford bicyclic diimide intermediate (460 mg, 50%) as a very pale yellow oil. $^1$H NMR (CDCl$_3$) δ 1.13 (t, J=7.13 Hz, 3H) 1.73-1.84 (m, 2H)

2.24-2.29 (m, J=1.95 Hz, 1H) 2.68 (dd, J=8.00, 3.90 Hz, 1H, 3.42-3.53 (m, 2H) 7.01-7.12 (m, 2H) 7.18 (t, J=7.91 Hz, 1H).

A stirred ice-cooled solution of 1.0N borane/THF (15 mL, 15 mmol) under nitrogen was treated dropwise with a solution of the above bicyclic diimide intermediate (470 mg, 1.9 mmol) in anhydrous THF (10 mL). The solution was stirred at room temperature for 15 min, refluxed for 4 h, cooled on an ice bath, and carefully treated dropwise with 6N HCl (10 mL, vigorous evolution of gas). The solution was concentrated to a white solid, which was partitioned between 5N sodium hydroxide (25 mL) and ether (50 mL). The organic layer was separated and the aqueous extracted with ether (50 mL). The combined organic solution was washed with water (25 mL), dried (Mg$_2$SO$_4$), and concentrated in vacuo. The residue was dissolved in methanol (23 mL), treated with 4N HCl/dioxane (7 mL), then stirred at room temperature for 16 h and at 55° C. for 4 h. The solution was concentrated in vacuo and the residue triturated from ether to afford 1-(3-methyl-4-fluorophenyl)-3-ethyl-3-azabicyclo[3.1.0]hexane, hydrochloride (400 mg, 89%) as a white solid. MS (M+1) 220. $^1$H NMR (CDCl$_3$) δ 1.10 (t, J=7.61 Hz, 1H) 1.47 (t, J=7.22 Hz, 3H) 1.88-1.97 (m, 1H) 2.18-2.21 (m, 1H) 2.21-2.23 (m, J=2.54, 2.54 Hz, 3H) 3.10-3.22 (m, 3H) 3.23-3.33 (m, 1H) 3.86 (dd, J=11.03, 5.37 Hz, 1H) 4.03 (dd, J=10.93, 5.47 Hz, 1H) 6.87-7.03 (m, 3H). $^{13}$C NMR (CDCl$_3$) δ 11.13, 14.76, 16.05, 22.60, 30.71, 51.47, 55.39, 58.87, 115.61, 125.67, 126.44, 130.74, 133.59, 159.54, 161.98.

F. Synthesis of 1-(2,4-Difluorophenyl)-3-ethyl-3-azabicyclo[3.1.0]hexane Hydrochloride

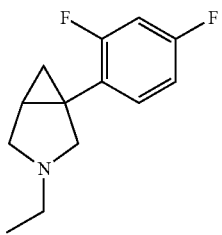 [SMILES: CCN1CC2CC2(c2ccc(F)cc2F)C1]

A stirred solution/suspension of 3-bromo-1-ethylmaleimide (0.7 g, 3.43 mmol) and 2,4-difluorophenyl boronic acid (0.85 g, 5.4 mmol) in dioxane (15 mL) under nitrogen was degassed with a stream of nitrogen for 10 min, treated with cesium fluoride (1.6 g, 10.8 mmol) and Cl$_2$Pd(dppf).CH$_2$Cl$_2$ (0.25 g, 0.3 mmol), then stirred at room temperature for 0.5 h and at 45° C. for 30 min then at 65° C. for 45 min. The mixture was cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride 60% and ethyl acetate 40%) to afford a yellowish solid, which was triturated from cold petroleum ethers to afford arylmaleimide intermediate (922 mg, 80%) as yellowish solid.

A stirred suspension of sodium hydride oil dispersion (60%, 155 mg, 3.89 mmol) in anhydrous tetrahydrofuran (30 mL) under nitrogen was treated with trimethyl-sulfoxoniurn chloride (0.55 g, 4.25 mmol), then refluxed for 2.5 h and cooled (50° C.). The above arylmaleimide (922 mg, 3.89 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane, loaded onto a silica gel column and eluted with 1:1, 2:1, then 3:1 methylene chloride/heptane to afford bicyclic diimide intermediate (460 mg, 59%) as a very pale yellow oil. $^1$H NMR (CDCl$_3$) δ 1.14 (t, J=7.13 Hz, 3H) 1.76-1.83 (m, 1H) 1.83-1.93 (m, 1H) 2.61 (dd, J=8.40, 3.71 Hz, 1H) 3.41-3.55 (m, 2H) 6.77-6.95 (m, 2H) 7.27-7.37 (m, 1H).

A stirred ice-cooled solution of 1.0N borane/THF (16 mL, 16 mmol) under nitrogen was treated dropwise with a solution of the above bicyclic diimide intermediate (460 mg, 2.2 mmol) in anhydrous THF (10 mL). The solution was stirred at room temperature for 15 min, refluxed for 4 h, cooled on an ice bath, and carefully treated dropwise with 6N HCl (10 mL, vigorous evolution of gas). The solution was concentrated to a white solid, which was partitioned between 5N sodium hydroxide (25 mL) and ether (50 mL). The organic layer was separated and the aqueous extracted with ether (50 mL). The combined organic solution was washed with water (25 mL), dried (Mg$_2$SO$_4$), and concentrated in vacuo. The residue was dissolved in methanol (23 mL), treated with 4N HCl/dioxane (7 mL), then stirred at room temperature for 16 h and at 55° C. for 4 h. The solution was concentrated in vacuo and the residue triturated from ether to afford 1-(2,4-difluorophenyl)-3-ethyl-3-azabicyclo[3.1.0]hexane, hydrochloride (250 mg, 62%) as a white solid. MS (M+1) 224. $^1$H NMR (CDCl$_3$) δ 1.15 (t, J=7.71 Hz, 1H) 1.46 (t, J=7.22 Hz, 3H) 1.84-1.93 (m, 1H) 2.17-2.25 (m, 1H) 3.06-3.21 (m, 3H) 3.27-3.36 (m, 1H) 3.84-3.99 (m, 2H) 6.68-6.88 (m, 2H) 7.14-7.25 (m, 1H). $^{13}$C NMR (CDCl$_3$) δ 11.04, 13.78, 22.38, 26.60, 51.46, 55.16, 58.09, 104.50, 112.05, 132.29.

G. Synthesis of 1-(2,4-Dichlorophenyl)-3-ethyl-3-azabicyclo[3.1.0]hexane Hydrochloride

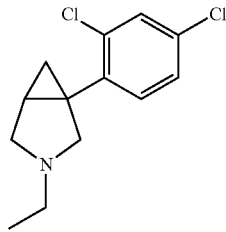 [SMILES: CCN1CC2CC2(c2ccc(Cl)cc2Cl)C1]

A stirred solution/suspension of 3-bromo-1-ethylmaleimide (0.7 g, 3.43 mmol) and 2,4-diclorophenylboronic acid (1.03 g, 5.4 mmol) in dioxane (15 mL) under nitrogen was degassed with a stream of nitrogen for 10 min, treated with cesium fluoride (1.6 g, 10.8 mmol) and Cl$_2$Pd(dppf).CH$_2$Cl$_2$ (0.25 g, 0.3 mmol), then stirred at room temperature for 0.5 h and at 45° C. for 30 min then at 65° C. for 45 min. The mixture was cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride 60% and ethyl acetate 40%) to afford a yellowish solid, which was triturated from cold petroleum ethers to afford arylmaleimide intermediate (1.32 g, 87%) as yellowish solid.

A stirred suspension of sodium hydride oil dispersion (60%, 165 mg, 4.1 mmol) in anhydrous tetrahydrofuran (30 mL) under nitrogen was treated with trimethyl-sulfoxonium chloride (0.58 g, 4.5 mmol), then refluxed for 2.5 h and cooled (50° C.). The above arylmaleimide (1.1 g, 4.1 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane, loaded onto a silica gel column and eluted with 1:1, 2:1, then 3:1 methylene chloride/heptane to afford bicyclic diimide intermediate (603 mg, 52%) as a very pale yellow oil. $^1$H NMR (CDCl$_3$) δ 1.15 (t, 3H) 1.86 (dd, J=4.88, 3.71 Hz, 1H) 1.93 (dd, J=8.20, 4.88 Hz, 1H) 2.57 (dd, J=8.30, 3.81 Hz, 1H) 3.44-3.53 (m, 2H) 7.29 (d, J=1.17 Hz, 2H) 7.45 (t, J=1.17 Hz, 1H).

A stirred ice-cooled solution of 1.0N borane/THF (5 mL, 5 mmol) under nitrogen was treated dropwise with a solution of the above bicyclic diimide intermediate (200 mg, 0.7 mmol) in anhydrous THF (10 mL). The solution was stirred at room temperature for 15 min, refluxed for 4 h, cooled on an ice bath, and carefully treated dropwise with 6N HCl (10 mL, vigorous evolution of gas). The solution was concentrated to a white solid, which was partitioned between 5N sodium hydroxide (25 mL) and ether (50 mL). The organic layer was separated and the aqueous extracted with ether (50 mL). The combined organic solution was washed with water (25 mL), dried (Mg$_2$SO$_4$), and concentrated in vacuo. The residue was dissolved in methanol (23 mL), treated with 4N HCl/dioxane (7 mL), then stirred at room temperature for 16 h and at 55° C. for 4 h. The solution was concentrated in vacuo and the residue triturated from ether to afford 1-(2,4-dichlorophenyl)-3-ethyl-3-azabicyclo[3.1.0]hexane, hydrochloride (115 mg, 47%) as a white solid. MS (M+1) 256.1. $^1$H NMR (CDCl$_3$) δ 1.16-1.23 (m, 1H) 1.47 (t, J=6.44 Hz, 3H) 1.87-1.93 (m, 1H) 2.23-2.31 (m, 1H) 3.10-3.28 (m, 3H) 3.36-3.48 (m, 1H) 3.81-3.98 (m, 2H) 7.19-7.32 (m, 3H). $^{13}$C NMR (CDCl$_3$) δ 11.13, 14.34, 23.43, 30.37, 51.57, 55.36, 57.48, 128.15, 129.96, 133.00, 133.69, 135.27, 136.11.

H. Synthesis of 1-(Naphthalen-2-yl)-3-ethyl-3-azabicyclo[3.1.0]hexane Hydrochloride

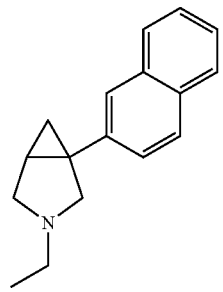 [SMILES: CCN1CC2CC2(c2ccc3ccccc3c2)C1]

A stirred solution/suspension of 3-bromo-1-ethylmaleimide (1.0 g, 5 mmol) and naphthalene-2-boronic acid (930 mg, 5.4 mmol) in dioxane (15 mL) under nitrogen was degassed with a stream of nitrogen for 10 min, treated with cesium fluoride (1.6 g, 10.8 mmol) and Cl$_2$Pd(dppf).CH$_2$Cl$_2$ (0.25 g, 0.3 mmol), then stirred at room temperature for 1 h and at 40° C. for 45 min. The mixture was then cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride) to afford a pale yellow solid, which was triturated from cold petroleum ethers to afford arylmaleimide intermediate (925 mg, 75%) as a pale yellow solid.

A stirred suspension of sodium hydride oil dispersion (60%, 145 mg, 3.68 mmol) in anhydrous tetrahydrofuran (30 mL) under nitrogen was treated with trimethyl-sulfoxonium chloride (0.52 g, 4.05 mmol), then refluxed for 2.5 h and cooled (50° C.). The above arylmaleimide (925 mg, 3.68 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane and loaded onto a silica gel column and eluted with 1:1, 2:1, then 3:1 methylene chloride/heptane to afford bicyclic diimide intermediate (466 mg, 48%) as a very pale yellow oil. $^1$H NMR (CDCl$_3$) δ 1.16 (t, J=7.13 Hz, 3H) 1.82-1.90 (m, 1H) 1.95 (dd, J=8.20, 4.69 Hz, 1H) 2.80 (dd, J=8.20, 3.71 Hz, 1H) 3.43-3.59 (m, 2H) 7.43-7.54 (m, 3H) 7.73-7.92 (m, 4H).

A stirred ice-cooled solution of 1.0N borane/THF (16 mL, 16 mmol) under nitrogen was treated dropwise with a solution of the above bicyclic diimide intermediate (466 mg, 1.76 mmol) in anhydrous THF (10 mL). The solution was stirred at room temperature for 15 min, refluxed for 4 h, cooled on an ice bath, and carefully treated dropwise with 6N HCl (10 mL, vigorous evolution of gas). The solution was concentrated to a white solid, which was partitioned between 5N sodium hydroxide (25 mL) and ether (50 mL). The organic layer was separated and the aqueous extracted with ether (50 mL). The combined organic solution was washed with water (25 mL), dried (Mg$_2$SO$_4$), and concentrated in vacuo. The residue was dissolved in methanol (23 mL), treated with 4N HCl/dioxane (7 mL), then stirred at room temperature for 16 h and at 55° C. for 4 h. The solution was concentrated in vacuo and the residue triturated from ether to afford 1-(naphthalene-2-yl)-3-ethyl-3-azabicyclo[3.1.0]hexane, hydrochloride (110 mg, 20%) as a white solid. MS (M+1) 238. $^1$H NMR (CDCl$_3$) δ 1.29 (t, J=7.42 Hz, 1H) 1.53 (t, J=6.44 Hz, 3H) 2.07-2.14 (m, 1H) 2.33-2.41 (m, 1H) 3.16-3.26 (m, 2H) 3.26-3.38 (m, 2H) 3.95 (d, 1H) 4.20 (d, J=7.22 Hz, 1H) 7.23 (s, 1H) 7.42-7.54 (m, 2H) 7.63 (s, 1H) 7.73-7.86 (m, 3H). $^{13}$C NMR (CDCl$_3$)

δ 158.83, 156.34, 135.62, 129.93, 127.57, 121.54, 117.17, 59.78, 57.35, 53.99, 30.68, 23.06, 19.05, 16.29.

Example X

Preparation of
1-Aryl-3-isopropyl-3-aza-bicyclo[3.1.0]hexane hydrochlorides Using Reaction Scheme 16

A. Synthesis of
3-Bromo-1-(1-methylethyl)maleimide

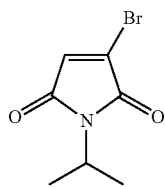

A cooled (5° C.) stirred solution of maleic anhydride (29.4 g, 0.30 mole) in anhydrous ether (150 mL) under nitrogen was treated dropwise over 45 min with a solution of isopropylamine (35.5 g, 0.60 mole) in anhydrous ether (100 mL) at a rate to keep the pot temp <20° C. The mixture was then stirred at 10° C. for 15 min, filtered, and the filter cake rinsed with anhydrous ether and dried in vacuo to afford a white solid. This was taken up in acetic anhydride (250 mL), treated with anhydrous sodium acetate (12.3 g, 0.15 mole), and heated to 75° C. with stirring for 4.5 h, then at 100° C. for 1.5 h. The mixture was concentrated in vacuo and the residue taken up in methylene chloride (300 mL), washed with saturated aqueous sodium bicarbonate (200 mL), water (200 mL), dried (MgSO$_4$), and concentrated in vacuo. The residue was distilled (approx. 5 mm pressure) to afford two products; one an N-isopropylmaleimide that distilled at 82° C. (13.0 g), the other an acetate adduct of N-isopropylmaleimide that distilled at 154° C. (12.9 g). The acetate adduct was dissolved in 4:1 acetonitrile/triethylamine (100 mL), heated to 65° C. for 4 h, then concentrated in vacuo. The residue was dissolved in methylene chloride and filtered through a pad of silica gel (eluted with methylene chloride) to afford an additional 3.5 g of N-isopropylmaleimide. Total yield was 16.5 g of N-isopropylmaleimide (40%).

A stirred ice-cold solution of N-isopropylmaleimide (16.4 g, 0.118 mole) in carbon tetrachloride (12 mL) under nitrogen was treated dropwise with bromine (6.41 mL, 0.25 mole) at a rate to keep the pot temp <9° C., then stirred at 3° C. for 2 h, during which time the mixture formed a solid cake. The cake was maintained under a stream of nitrogen to allow excess bromine and CCl$_4$ to evaporate. The reaction mixture was then placed under vacuum to remove the remaining solvent. Ethanol (100 mL) was added to the flask, followed by sodium acetate (11 g, 0.134 mole), and the mixture was refluxed for 16 h with stirring. The cooled solution was filtered through Celite® (filter cake rinsed with methylene chloride), and the filtrate concentrated in vacuo, dissolved in methylene chloride, filtered through a pad of alumina (eluted with methylene chloride), and re-concentrated in vacuo. The residue was dissolved in 2:1 petroleum ether/methylene chloride, loaded onto a column of silica gel, and eluted successively with 2:1 petroleum ethers/CH$_2$Cl$_2$, 1:1 petroleum ethers/CH$_2$Cl$_2$, and CH$_2$Cl$_2$ alone to afford the subject compound (16.45 g, 64% yield) as a pale yellow, low melting solid. No MS (M+1) peak observed. $^1$H NMR (CDCl$_3$) δ 6.78 (s, 1H), 4.30-4.40 (m, 1H), 1.37 (d, 6H, J=8 Hz))

B. Synthesis of 1-(2,4-dichlorophenyl)-3-ethyl-3-azabicyclo[3.1.0]hexane Hydrochloride

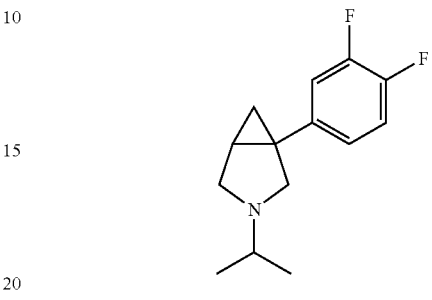

A stirred solution/suspension of 3-bromo-1-(1-methylethyl)maleimide (1.09 g, 5 mmol) and 3,4-difluorophenylboronic acid (987 mg, 6.25 mmol) in dioxane (15 mL) under nitrogen was degassed with a stream of nitrogen for 10 min, treated with cesium fluoride (1.8 g, 11.8 mmol) and Cl$_2$Pd (dppf).CH$_2$Cl$_2$ (0.25 g, 0.3 mmol), then stirred at room temperature for 1 h and at 40° C. for 3 h. The mixture was then cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride) to afford a pale yellow solid, which was triturated from cold petroleum ethers to afford arylmaleimide intermediate (1.024 g, 82%) as a very pale yellow solid. No MS (M+1) peak. $^1$H NMR (CDCl$_3$) δ 7.83 (m, 1H), 7.67 (m, 1H), 7.24 (m, 1H), 6.64 (s, 1H), 4.39 (m, 1H), 1.43 (d, 6H, J=7 Hz).

A stirred suspension of sodium hydride oil dispersion (60%, 140 mg, 3.5 mmol) in anhydrous tetrahydrofuran (30 mL) under nitrogen was treated with trimethylsulfoxonium chloride (0.55 g, 4.25 mmol), then refluxed for 2.5 h and cooled (50° C.). The above arylmaleimide (879 mg, 3.5 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane and loaded onto a silica gel column and eluted with 1:1, 2:1, then 3:1 methylene chloride/heptane to afford bicyclic diimide intermediate (793 mg, 85%) as a white solid. No MS (M+1) peak. $^1$H NMR (CDCl$_3$) δ 7.29 (m, 1H), 7.07-7.20 (m, 2H), 4.24 (m, 1H), 2.68 (m, 1H), 1.71-1.76 (m, 2H), 1.34 (m, A stirred ice-cooled solution of 1.0N borane/THF (21 mL, 21 mmol) under nitrogen was treated dropwise with a solution of the above bicyclic diimide intermediate (780 mg, 2.94 mmol) in anhydrous THF (14 mL). The solution was stirred at room temperature for 15 min, refluxed for 4 h, cooled on an ice bath, and carefully treated dropwise with 6N HCl (12 mL, vigorous evolution of gas). The solution was concentrated to a white solid, which was partitioned between 5N sodium hydroxide (30 mL) and ether (60 mL). The organic layer was separated and the aqueous extracted with ether (60 mL). The combined organic solution was washed with water (2×35 mL), dried (Mg$_2$SO$_4$), and concentrated in vacuo. The residue was dissolved in methanol (30 mL), treated with 4N HCl/dioxane (10 mL), stirred at room temperature for 60 h (only 16 h needed), and at 55° C. for 4 h. The solution was concentrated in vacuo and the residue was triturated from ether containing a little acetonitrile to afford 1-(3,4-difluorophenyl)-3-(2-propyl)-3-azabicyclo[3.1.0]hexane, hydrochloride (585 mg, 73%) as a white solid. MS (M+1) 238.2. $^1$H NMR (CDCl$_3$) δ 7.08 (m, 2H), 6.92 (m, 1H), 4.02 (m, 1H), 3.84 (m, 1H), 3.35 (m, 2H), 3.22 (m, 1H), 2.39 (m, 1H), 1.96 (m, 1H), 1.51 (d, 6H, J=6 Hz), 1.10 (m, 1H). $^{13}$C NMR (CDCl$_3$) δ 151.82, 149.34, 135.59, 123.85, 118.08, 116.89, 59.75, 57.30, 53.97, 30.80, 23.19, 19.04, 16.34.

C. Synthesis of 1-(3-chloro-4-fluorophenyl)-3-(2-propyl)-3-azabicyclo[3.1.0]hexane Hydrochloride

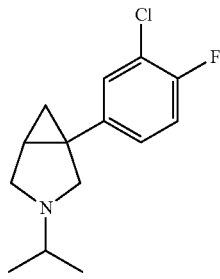 [SMILES: CC(C)N1CC2CC2(c2ccc(F)c(Cl)c2)C1]

A stirred solution/suspension of 3-bromo-1-(1-methylethyl)maleimide (1.09 g, 5 mmol) and 3-chloro-4-fluorophenylboronic acid (1.09 g, 6.25 mmol) in dioxane (15 mL) under nitrogen was degassed with a stream of nitrogen for 10 min, treated with cesium fluoride (1.8 g, 11.8 mmol) and Cl$_2$Pd(dppf).CH$_2$Cl$_2$ (0.25 g, 0.3 mmol), then stirred at room temperature for 1 h and at 40° C. for 45 min. The mixture was then cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride) to afford a pale yellow solid, which was triturated from cold petroleum ethers to afford arylmaleimide intermediate (1.10 g, 82%) as a pale yellow solid. No MS (M+1) peak. $^1$H NMR (CDCl$_3$) δ 8.03 (m, 1H), 7.80 (m, 1H), 7.20-7.30 (m, 1H), 6.65 (s, 1H), 4.40 (m, 1H), 1.43 (d, 6H, J=7 Hz).

A stirred suspension of sodium hydride oil dispersion (60%, 140 mg, 3.5 mmol) in anhydrous tetrahydrofuran (30 mL) under nitrogen was treated with trimethyl-sulfoxonium chloride (0.55 g, 4.25 mmol), then refluxed for 2.5 h and cooled (50° C.). The above arylmaleimide (937 mg, 3.5 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual solid was dissolved in 1:1 methylene chloride/heptane, loaded onto a silica gel column and eluted with 1:1, 2:1, then 3:1 methylene chloride/heptane to afford bicyclic diimide intermediate (628 mg, 64%) as a very pale yellow oil. No MS (M+1) peak. $^1$H NMR (CDCl$_3$) δ 7.48 (m, 1H), 7.27 (m, 1H), 7.14 (m, 1H), 4.23 (m, 1H), 2.69 (m, 1H), 1.74 (m, 2H), 1.34 (m, 6H).

A stirred ice-cooled solution of 1.0N borane/THF (16 mL, 16 mmol) under nitrogen was treated dropwise with a solution of the above bicyclic diimide intermediate (620 mg, 2.2 mmol) in anhydrous THF (10 mL). The solution was stirred at room temperature for 15 min, refluxed for 4 h, cooled on an ice bath, and carefully treated dropwise with 6N HCl (10 mL, vigorous evolution of gas). The solution was concentrated to a white solid, which was partitioned between 5N sodium hydroxide (25 mL) and ether (50 mL). The organic layer was separated and the aqueous extracted with ether (50 mL). The combined organic solution was washed with water (25 mL), dried (Mg$_2$SO$_4$), and concentrated in vacuo. The residue was dissolved in methanol (23 mL), treated with 4N HCl/dioxane (7 mL), then stirred at room temperature for 16 h and at 55° C. for 4 h. The solution was concentrated in vacuo and the residue triturated from ether to afford 1-(3-chloro-4-fluorophenyl)-3-(2-propyl)-3-azabicyclo[3.1.0]hexane hydrochloride (520 mg, 81%) as a white solid. MS (M+1) 254.1. $^1$H NMR (CDCl$_3$) δ 7.25 (m, 1H), 7.08 (m, 2H), 4.04 (m, 1H), 3.85 (m, 1H), 3.35 (m, 2H), 3.21 (m, 1H), 2.39 (m, 1H), 1.97 (m, 1H), 1.50 (d, 6H, J=7 Hz), 1.10 (m, 1H). $^{13}$C NMR (CDCl$_3$) δ 158.83, 156.34, 135.62, 129.93, 127.57, 121.54, 117.17, 59.78, 57.35, 53.99, 30.68, 23.06, 19.05, 16.29.

D. Synthesis of 1-(3-Fluoro-4-methylphenyl)-3-(2-propyl)-3-azabicyclo[3.1.0]hexane Hydrochloride

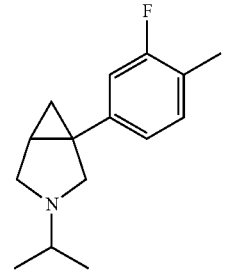 [SMILES: Cc1ccc(C23CC2CN(C(C)C)C3)cc1F]

A stirred solution/suspension of 3-bromo-1-(1-methylethyl)maleimide (1.09 g, 5 mmol) and 3-fluoro-4-methylphenylboronic acid (962 mg, 6.25 mmol) in dioxane (15 mL) under nitrogen was degassed with a stream of nitrogen for 10 min, treated with cesium fluoride (1.8 g, 11.8 mmol) and Cl$_2$Pd(dppf).CH$_2$Cl$_2$ (0.25 g, 0.3 mmol), then stirred at room temperature for 1 h and at 40° C. for 1 h. The mixture was then cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride) to afford a yellow solid, which was triturated from petroleum ethers to afford arylmaleimide intermediate (1.11 g, 90%) as a pale yellow solid. No MS (M+1) peak. $^1$H NMR (CDCl$_3$) δ 7.60 (m, 2H), 7.24 (m, 1H), 6.62 (s, 1H), 4.39 (m, 1H), 2.32 (br s, 3H), 1.43 (d, 6H, J=7 Hz).

A stirred suspension of sodium hydride oil dispersion (60%, 140 mg, 3.5 mmol) in anhydrous tetrahydrofuran (30 mL) under nitrogen was treated with trimethyl-sulfoxonium chloride (0.55 g, 4.25 mmol), then refluxed for 2.5 h and cooled (50° C.). The above arylmaleimide (866 mg, 3.5 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual oil was dissolved in 1:1 methylene chloride/heptane and loaded onto a silica gel column and eluted with 1:1, 2:1, and 3:1 methylene chloride/heptane to afford bicyclic diimide intermediate (633 mg, 69%) as a white solid. MS (M+1) 262.1. $^1$H NMR (CDCl$_3$) δ 7.17 (m, 1H), 7.09 (m, 1H), 7.04 (m, 1H), 4.24 (m, 1H), 2.64 (m, 1H), 2.26 (br s, 3H), 1.70-1.80 (m, 2H), 1.34 (m, 6H).

A stirred ice-cooled solution of 1.0N borane/THF (17 mL, 17 mmol) under nitrogen was treated dropwise with a solution of the above bicyclic diimide intermediate (619 mg, 2.37 mmol) in anhydrous THF (11 mL). The solution was stirred at room temperature for 15 min, refluxed for 4 h, cooled on an ice bath, and carefully treated dropwise with 6N HCl (10 mL, vigorous evolution of gas). The solution was concentrated to a white solid, which was partitioned between 5N sodium hydroxide (25 mL) and ether (50 mL). The organic layer was separated and the aqueous extracted with ether (50 mL). The combined organic solution was washed with water (2×30 mL), dried (Mg$_2$SO$_4$), and concentrated in vacuo. The residue was dissolved in methanol (23 mL), treated with 4N HCl/dioxane (7 mL), then stirred at room temperature for 60 h (only requires 14 h) and at 55° C. for 4 h. The solution was concentrated in vacuo and the residue triturated from ether to afford 1-(3-fluoro-4-methylphenyl)-3-(2-propyl)-3-azabicyclo[3.1.0]hexane, hydrochloride (538 mg, 84%) as a white solid. MS (M+1) 234.2. $^1$H NMR (CDCl$_3$) δ 7.11 (m, 1H), 6.82 (m, 2H), 4.02 (m, 1H), 3.83 (m, 1H), 3.32 (m, 2H), 3.23 (m, 1H), 2.35 (m, 1H), 2.21 (s, 3H), 1.94 (s, 1H), 1.51 (d, 6H, J=7 Hz), 1.10 (m, 1H). $^{13}$C NMR (CDCl$_3$) δ 132.13, 124.39, 124.22, 122.68, 114.06, 113.84, 59.68, 57.22, 53.98, 30.88, 23.16, 19.02, 16.58, 14.41.

E. Synthesis of 1-(4-Fluoro-3-methylphenyl)-3-(2-propyl)-3-azabicyclo[3.1.0]hexane Hydrochloride

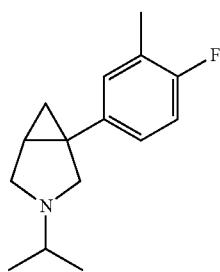 [SMILES: Cc1cc(C23CC2CN(C(C)C)C3)ccc1F]

A stirred solution/suspension of 3-bromo-1-(1-methylethyl)maleimide (1.09 g, 5 mmol) and 4-fluoro-3-methylphenylboronic acid (962 mg, 6.25 mmol) in dioxane (15 mL) under nitrogen was degassed with a stream of nitrogen for 10 min, treated with cesium fluoride (1.8 g, 11.8 mmol) and Cl$_2$Pd(dppf).CH$_2$Cl$_2$ (0.25 g, 0.3 mmol), then stirred at room temperature for 1 h and at 40° C. for 1 h. The mixture was then cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride) to afford a yellow solid, which was triturated from cold petroleum ethers to afford arylmaleimide intermediate (1.14 g, 92%) as a very pale yellow solid. No MS (M+1) peak. $^1$H NMR (CDCl$_3$) δ 7.77 (m, 1H), 7.72 (m, 1H), 7.06 (m, 1H), 6.58 (s, 1H), 4.38 (m, 1H), 2.32 (br s, 3H), 1.43 (d, 6H, J=7 Hz).

A stirred suspension of sodium hydride oil dispersion (60%, 140 mg, 3.5 mmol) in anhydrous tetrahydrofuran (30 mL) under nitrogen was treated with trimethyl-sulfoxonium chloride (0.55 g, 4.25 mmol), then refluxed for 2.5 h and cooled (50° C.). The above arylmaleimide (866 mg, 3.5 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual oil was dissolved in 1:1 methylene chloride/heptane and loaded onto a silica gel column and eluted with 1:1, then 2:1 methylene chloride/heptane to afford bicyclic diimide intermediate (510 mg, 56%) as a colorless oil. No MS (M+1) peak. $^1$H NMR (CDCl$_3$) δ 7.23 (m, 1H), 7.16 (m, 1H), 6.99 (m, 1H), 4.23 (m, 1H), 2.63 (m, 1H), 2.27 (br s, 3H), 1.72 (m, 2H), 1.34 (m, 6H).

A stirred ice-cooled solution of 1.0N borane/THF (7.5 mL, 7.5 mmol) under N$_2$ was treated dropwise with a solution of the above bicyclic diimide intermediate (268 mg, 1.026 mmol) in anhydrous THF (5 mL). The solution was stirred at room temperature for 15 min, refluxed for 4 h, cooled on an ice bath, and carefully treated dropwise with 6N HCl (5 mL, vigorous evolution of gas). The solution was concentrated to a white solid, which was partitioned between 5N sodium hydroxide (15 mL) and ether (30 mL). The organic layer was separated and the aqueous extracted with ether (30 mL). The combined organic solution was washed with water (2×15 mL), dried (Mg$_2$SO$_4$), and concentrated in vacuo. The residue was dissolved inmethanol (12 mL), treated with 4N HCl/dioxane (4 mL), and stirred at room temperature for 14 h and at 55° C. for 4 h. The solution was concentrated in vacuo and the residue triturated from ether to afford 1-(4-fluoro-3-methylphenyl)-3-(2-propyl)-3-azabicyclo[3.1.0]hexane, hydrochloride (230 mg, 83%) as a white solid. MS (M+1) 234.2. $^1$H NMR (CDCl$_3$) δ 6.96 (m, 3H), 4.03 (m, 1H), 3.86 (m, 1H), 3.29 (m, 2H), 3.17 (m, 1H), 2.34 (m, 1H), 2.24 (s, 3H), 1.93 (m, 1H), 1.52 (d, 6H, J=7 Hz), 1.09 (m, 1H). $^{13}$C NMR (CDCl$_3$) δ 161.52, 159.56, 133.69, 130.66, 126.39, 125.50, 115.48, 59.48, 57.57, 53.98, 30.70, 22.57, 18.87, 15.83, 14.58.

F. Synthesis of 1-(2,4-Difluorophenyl)-3-(2-propyl)-3-azabicyclo[3.1.0]hexane Hydrochloride

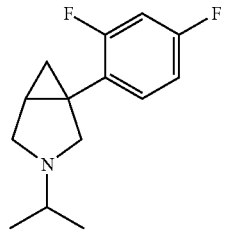 [SMILES: CC(C)N1CC2CC2(c2ccc(F)cc2F)C1]

A stirred solution/suspension of 3-bromo-1-(1-methylethyl)maleimide (1.09 g, 5 mmol) and 2,4-difluorophenylboronic acid (987 mg, 6.25 mmol) in dioxane (15 mL) under nitrogen was degassed with a stream of nitrogen for 10 min, treated with cesium fluoride (1.8 g, 11.8 mmol) and Cl$_2$Pd(dppf).CH$_2$Cl$_2$ (0.25 g, 0.3 mmol), then stirred at room temperature for 1 h and at 60° C. for 1 h. The mixture was then cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride) to afford a pale yellow solid, which was triturated from cold petroleum ethers to afford arylmaleimide intermediate (941, 75%) as a very pale yellow solid. No MS (M+1) peak. $^1$H NMR (CDCl$_3$) δ 8.33 (m, 1H), 6.88-7.02 (m, 2H), 6.85 (m, 1H), 4.40 (m, 1H), 1.43 (d, 6H, J=7 Hz).

A stirred suspension of sodium hydride oil dispersion (60%, 140 mg, 3.5 mmol) in anhydrous tetrahydrofuran (30 mL) under nitrogen was treated with trimethyl-sulfoxonium chloride (0.55 g, 4.25 mmol), then refluxed for 2.5 h and cooled (50° C.). The above arylmaleimide (879 mg, 3.5 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residue was dissolved in 1:1 methylene chloride/heptane and loaded onto a silica gel column and eluted with 1:1, 3:2, and 2:1 methylene chloride/heptane to afford bicyclic diimide intermediate (292 mg, 32%) as a pale yellow solid. MS (M+1) 266.1. $^1$H NMR (CDCl$_3$) δ 7.31 (m, 1H), 6.82-6.92 (m, 2H), 4.24 (m, 1H), 2.57 (m, 1H), 1.84 (m, 1H), 1.74 (m, 1H), 1.35 (m, 6H).

A stirred ice-cooled solution of 1.0N borane/THF (8 mL, 8 mmol) under nitrogen was treated dropwise with a solution of the above bicyclic diimide intermediate (290 mg, 1.093 mmol) in anhydrous THF (5 mL). The solution was stirred at room temperature for 15 min, refluxed for 4 h, cooled on an ice bath, and carefully treated dropwise with 6N HCl (5 mL, vigorous evolution of gas). The solution was concentrated to a white solid, which was partitioned between 5N sodium hydroxide (15 mL) and ether (30 mL). The organic layer was separated and the aqueous extracted with ether (30 mL). The combined organic solution was washed with water (20 mL), dried (Mg$_2$SO$_4$), and concentrated in vacuo. The residue was dissolved in methanol (15 mL), treated with 4N HCl/dioxane (5 mL), and stirred at room temperature for 60 h (needed only 14 h) and at 55° C. for 4 h. The solution was concentrated in vacuo and the residue triturated from ether to afford 1-(2,4-difluorophenyl)-3-(2-propyl)-3-azabicyclo[3.1.0]hexane, hydrochloride (280 mg, 94%) as a white solid. MS (M+1) 238.2. $^1$H NMR (CDCl$_3$) δ 7.21 (m, 1H), 6.82 (m, 2H), 3.88 (m, 2H), 3.39 (m, 1H), 3.31 (m, 1H), 3.18 (m, 1H), 2.32 (m, 1H), 1.86 (m, 1H), 1.49 (m, 6H), 1.14 (m, 1H). $^{13}$C NMR (CDCl$_3$) δ 164.19, 161.70, 132.36, 121.03, 112.13, 104.48, 59.33, 56.71, 53.61, 26.77, 22.61, 18.82, 13.69

G. Synthesis of 1-(2,4-Dichlorophenyl)-3-(2-propyl)-3-azabicyclo[3.1.0]hexane Hydrochloride

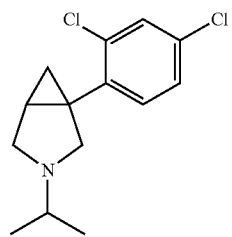 [SMILES: CC(C)N1CC2CC2(c2ccc(Cl)cc2Cl)C1]

A stirred solution/suspension of 3-bromo-1-(1-methylethyl)maleimide (1.09 g, 5 mmol) and 2,4-dichlorophenylboronic acid (1.19 g, 6.25 mmol) in dioxane (15 mL) under nitrogen was degassed with a stream of nitrogen for 10 min, treated with cesium fluoride (1.8 g, 11.8 mmol) and Cl$_2$Pd (dppf).CH$_2$Cl$_2$ (0.25 g, 0.3 mmol), then stirred at room temperature for 1 h and at 60° C. for 1 h. The mixture was then cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride) to afford a pale yellow oil, which was triturated from cold petroleum ethers to afford arylmaleimide intermediate (1.038 g, 73%) as a white solid. No MS (M+1) peak. $^1$H NMR (CDCl$_3$) δ 7.68 (m, 1H), 7.52 (m, 1H), 7.34 (m, 1H), 6.94 (s, 1H), 4.40 (m, 1H), 1.44 (d, 6H, J=7 Hz).

A stirred suspension of sodium hydride oil dispersion (60%, 140 mg, 3.5 mmol) in anhydrous tetrahydrofuran (30 mL) under nitrogen was treated with trimethyl-sulfoxonium chloride (0.55 g, 4.25 mmol), then refluxed for 2.5 h and cooled (50° C.). The above arylmaleimide (995 mg, 3.5 mmol) was added in one portion and the mixture stirred at 50° C. for 3 h, cooled on an ice bath, and quenched with saturated ammonium chloride (10 mL). The product mixture was extracted with ether (2×50 mL), and the combined extracts washed with water (30 mL), dried (MgSO$_4$), and concentrated in vacuo. The residual oil was dissolved in 1:1 methylene chloride/heptane, loaded onto a silica gel column and eluted with 1:1, then 2:1 methylene chloride/heptane to afford bicyclic diimide intermediate (523 mg, 50%) as a pale yellow solid. No MS (M+1) peak. $^1$H NMR (CDCl$_3$) δ 7.44 (m, 1H), 7.28 (m, 2H), 4.25 (m, 1H), 2.51 (m, 1H), 1.90 (m, 1H), 1.81 (m, 1H), 1.35 (d, 6H, J=7 Hz).

A stirred ice-cooled solution of 1.0N borane/THF (12 mL, 12 mmol) under nitrogen was treated dropwise with a solution of the above bicyclic diimide intermediate (498 mg, 1.67 mmol) in anhydrous THF (8 mL). The solution was stirred at room temperature for 15 min, refluxed for 4 h, cooled on an ice bath, and carefully treated dropwise with 6N HCl (7 mL, vigorous evolution of gas). The solution was concentrated to a white solid, which was partitioned between 5N sodium hydroxide (20 mL) and ether (40 mL). The organic layer was separated and the aqueous extracted with ether (40 mL). The combined organic solution was washed with water (2×25 mL), dried (Mg$_2$SO$_4$), and concentrated in vacuo. The residue was dissolved in methanol (15 mL), treated with 4N HCl/dioxane (5 mL), and stirred at room temperature for 60 h (needed only 14 h) and at 55° C. for 4 h. The solution was concentrated in vacuo and the residue triturated from ether to afford 1-(2,4-dichlorophenyl)-3-(2-propyl)-3-azabicyclo[3.1.0]hexane, hydrochloride (347 mg, 68%) as a white solid. MS (M+1) 270.1. $^1$H NMR (CDCl$_3$) δ 7.39 (d, 1H, J=2 Hz), 7.29 (d, 1H, J=8 Hz), 7.23 (dd, 1H, J=8 Hz, 2 Hz), 3.83 (m, 2H), 3.48 (m, 1H), 3.30 (m, 2H), 2.39 (m, 1H), 1.88 (m, 1H), 1.50 (m, 6H), 1.16 (m, 1H). $^{13}$C NMR (CDCl$_3$) δ 136.06, 135.20, 133.78, 133.76, 129.92, 128.12, 59.36, 56.03, 53.73, 30.46, 23.51, 18.94, 14.25.

H. Synthesis of 1-(2-Naphthyl)-3-(2-propyl)-3-azabicyclo[3.1.0]hexane Hydrochloride

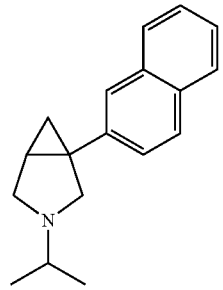 [SMILES: CC(C)N1CC2CC2(c2ccc3ccccc3c2)C1]

A stirred solution/suspension of 3-bromo-1-(1-methylethyl)maleimide (1.09 g, 5 mmol) and naphthalene-2-boronic acid (1.08 g, 6.25 mmol) in dioxane (15 mL) under nitrogen was degassed with a stream of nitrogen for 10 min, treated with cesium fluoride (1.8 g, 11.8 mmol) and Cl$_2$Pd (dppf).CH$_2$Cl$_2$ (0.25 g, 0.3 mmol), then stirred at room temperature for 1 h and at 40° C. for 2 h. The mixture was then cooled and diluted with methylene chloride (50 mL). The mixture was filtered through Celite® (rinse filter cake with methylene chloride) and the brown filtrate concentrated in vacuo. The residue was dissolved in methylene chloride and filtered through a column of silica gel (eluted with methylene chloride) to afford a solid, which was triturated from petroleum ethers to afford the arylmaleimide intermediate (1.045 g, 79%) as a bright yellow solid. No MS (M+1) peak. $^1$H NMR (CDCl$_3$) δ 8.67 (br s, 1H), 7.75-7.95 (m, 4H), 7.54 (m, 2H), 6.76 (s, 1H), 4.44 (m, 1H), 1.47 (d, 6H, J=7 Hz).

A stirred suspension of sodium hydride oil dispersion (60%, 120 mg, 3.0 mmol) in anhydrous tetrahydrofuran (25 mL) under nitrogen was treated with trimethyl-sulfoxonium chloride (0.52 g, 4.0 mmol), then refluxed for 2.5 h and cooled (50° C.). The above arylmaleimide (796 mg, 3.0 mmol) was added in one portion and the mixture stirred at 50° C. for 2 h, cooled on an ice bath, and quenched with saturated ammonium chloride (10 mL). The product mixture was extracted with ether (2×40 mL) and the combined extracts were rinsed with water (30 mL), dried (MgSO$_4$), and concentrated in vacuo. The residue was dissolved in petroleum ethers containing a little methylene chloride, loaded onto a silica gel column, and eluted with 15% ethyl acetate/petroleum ethers to afford bicyclic diimide intermediate (577 mg, 69%) as an orange solid. MS (M+1) 280.2. $^1$H NMR (CDCl$_3$) δ 7.80-7.90 (m, 4H), 7.50 (m, 3H), 4.28 (m, 1H), 2.77 (m, 1H), 1.90 (m, 1H), 1.81 (m, 1H), 1.38 (m, 6H).

A stirred ice-cooled solution of 1.0N borane/THF (16 mL, 16 mmol) under nitrogen was treated dropwise with a solution of the above bicyclic diimide intermediate (560 mg, 2.0 mmol) in anhydrous THF (10 mL). The solution was stirred at room temperature for 15 min, refluxed for 8 h, cooled on an ice bath, and carefully treated dropwise with 6N HCl (7 mL, vigorous evolution of gas). The solution was concentrated to a white solid, which was partitioned between 5N sodium hydroxide (25 mL) and ether (50 mL). The organic layer was separated and the aqueous extracted with ether (2×25 mL). The combined organic solution was washed with water (25 mL), dried (Mg$_2$SO$_4$), and concentrated in vacuo. The residue was dissolved in methanol (20 mL), treated with 4N HCl/dioxane (7 mL), and stirred at room temperature for 14 h and at 55° C. for 4 h. The solution was concentrated in vacuo and the residue triturated from ether to afford 1-(2-naphthyl)-3-(2-propyl)-3-azabicyclo[310]hexane, hydrochloride (337 mg, 67%) as a white solid. MS (M+1) 252.2. NMR (CDCl$_3$) δ 7.81 (m, 3H), 7.63 (br s, 1H), 7.50 (m, 2H), 7.24 (m, 1H), 4.18 (m, 1H), 3.94 (m, 1H), 3.35 (m, 3H), 2.49 (m, 1H), 2.11 (m, 1H), 1.57 (d, 6H, J=6 Hz), 1.27 (m, 1H). $^{13}$C NMR (CDCl$_3$) δ 135.66, 133.21, 132.41, 128.77, 127.65, 127.54, 126.67, 126.20, 126.07, 124.75, 59.49, 57.23, 54.01, 31.29, 22.93, 18.90, 16.31.

Example XI

Preparation of 1-Aryl-3-aza-bicyclo[3.1.0]hexane hydrochlorides Using Reaction Scheme 17

A. Synthesis of 3-Bromo-1-(3,4-dimethoxybenzyl)maleimide

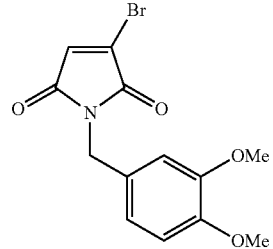 [SMILES: COc1ccc(CN2C(=O)C=C(Br)C2=O)cc1OC]

A solution of bromomaleic anhydride (Aldrich, 20.0 g, 0.113 mole) in anhydrous tetrahydrofuran (100 mL) under nitrogen was treated dropwise with a solution of 3,4-dimethoxybenzylamine (20.0 g, 0.1196 mole) in anhydrous THF (40 mL) over 30 min, and the stirred mixture was then refluxed for 3 h and maintained at room temperature for 20 h. The mixture was concentrated in vacuo, suspended in acetic anhydride (135 mL), treated with anhydrous sodium acetate (6.15 g, 75 mmol), and heated to 50° C. with stirring under nitrogen for 4 h (solids dissolved after a few minutes). The mixture was concentrated in vacuo and dissolved in methylene chloride (300 mL). The solution was washed with saturated aqueous sodium bicarbonate (150 mL), then with water (150 mL), dried (Na$_2$SO$_4$), and concentrated in vacuo to a brown residue. This was dissolved in methylene chloride and passed through a column of silica gel (~400 mL volume) and eluted with methylene chloride to afford a tan solid, which was recrystallized from ethyl acetate/heptane (2 crops) to afford 3-bromo-1-(3,4-dimethoxybenzyl)maleimide (24.75 g, 67%) as a pale tan solid. NO MS (M+1) peak. $^1$H NMR (CDCl₃) δ 6.89-6.94 (m, 2H), 6.84 (s, 1H), 6.78 (d, 1H, J=8 Hz), 4.63 (s, 2H), 3.86 (s, 3H), 3.84 (s, 3H).

B. Synthesis of 1-(3,4-Difluorophenyl)-3-azabicyclo[3.1.0]hexane Hydrochloride

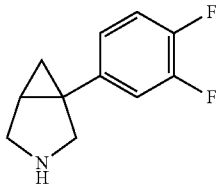

A stirred solution of 3-bromo-1-(3,4-dimethoxybenzyl)maleimide (1.14 g, 3.5 mmol) and 3,4-difluorophenylboronic acid (0.71 g, 4.5 mmol) in anhydrous dioxane (10 mL) under nitrogen was degassed over 10 min with a stream of nitrogen, then treated with cesium fluoride (1.3 g, 8.5 mmol) and Cl₂Pd(dppf).CH₂Cl₂ (Aldrich, 0.17 g, 0.21 mmol), stirred 1 h at room temperature, then 2 h at 40° C. The mixture was cooled, diluted with methylene chloride (50 mL), stirred a few minutes, filtered through Celite® (rinse with methylene chloride), and the filtrate concentrated in vacuo. The residue was dissolved in methylene chloride and loaded onto a silica gel column and the product eluted with 3% ethyl acetate/methylene chloride to afford a yellow solid, which was triturated from petroleum ethers to afford the intermediate arylmaleimide (954 mg, 76%) as a very pale yellow solid. NO MS (M+1) peak. ¹H NMR (CDCl₃) δ 7.84 (m, 1H), 7.68 (m, 1H), 7.24 (m, 1H), 6.93-6.99 (m, 2H), 6.80 (m, 1H), 6.70 (s, 1H), 4.66 (s, 2H), 3.87 (s, 3H), 3.84 (s, 3H).

A cooled (−20° C.) stirred solution of trimethylsulfoxonium chloride (431 mg, 3.35 mmol) in anhydrous tetrahydrofuran (10 mL) under nitrogen was treated dropwise with n-butyllithium/hexane (2.4N, 1.2 mL, 2.85 mmol) and gradually warmed to 50° C. over 30 minutes. Meanwhile, a solution of the intermediate arylmaleimide (900 mg, 2.5 mmol) in anhydrous THF (10 mL) was heated to 50° C., then added quickly in one portion to the above heated suspension. The mixture was then stirred at 50° C. for 2 h, and cooled on an ice bath. Saturated aqueous ammonium chloride (2 mL) was added to quench, and the mixture was diluted with methylene chloride (75 mL), dried (MgSO₄), filtered through Celite® (rinse with methylene chloride), and concentrated in vacuo. The residue was dissolved in methylene chloride, loaded onto a silica gel column, and the product eluted with 1%, 2%, then 3% ethyl acetate/methylene chloride to afford the intermediate bicyclic diimide (602 mg, 65%) as a pale yellow gum. MS (M+1) 374.2. ¹H NMR (CDCl₃) δ 7.28 (m, 1H), 7.15 (m, 1H), 7.08 (m, 1H), 6.87-6.92 (m, 2H), 6.78 (m, 1H), 4.50 (m, 2H), 3.85 (s, 2H), 3.84 (s, 2H), 2.72 (m, 1H), 1.72 (m, 2H).

A cooled (5° C.) stirred solution of 1N lithium aluminum hydride/THF (10.6 mL, 10.6 mmol) under nitrogen was treated slowly with a solution of the above intermediate bicyclic diimide (597 mg, 1.6 mmol) in anhydrous THF (7 mL), stirred 1 h at room temperature, refluxed for 6 h, and cooled (5° C.). Water (0.4 mL), 15% sodium hydroxide (0.4 mL), and water (1.2 mL) were carefully added dropwise, followed by additional THF to facilitate stirring. The suspension was shirred 15 min, filtered through Celite® (filter cake rinsed with THF), and the filtrate concentrated in vacuo. The residue was dissolved in methylene chloride, loaded onto a silica gel column, and eluted with 3:1 methylene chloride/ethyl acetate to afford the intermediate dimethoxybenzyl bicyclic amine (345 mg, 63%) as a colorless viscous oil. MS (M+1) 346.2. ¹H NMR (CDCl₃) 7.03 (m, 1H), 6.86-6.95 (m, 2H), 6.78-6.85 (m, 3H), 3.88 (s, 3H), 3.86 (s, 3H), 3.60 (m, 2H), 3.22 (m, 1H), 3.05 (m, 1H), 2.53 (m, 2H), 1.64 (m, 1H), 1.52 (m, 1H), 0.75 (m, 1H).

A mixture of the intermediate dimethoxybenzyl bicyclic amine (345 mg, 1.00 mmol) and anhydrous potassium carbonate (311 mg, 2.25 mmol) in anhydrous methylene chloride (8 mL) in a pressure tube equipped with a stirbar was treated with 1-chloroethyl chloroformate (322 mg, 2.25 mmol), closed, and stirred at 45° C. for 4 h. The tube was cooled, opened, and the contents filtered (rinse with methylene chloride), and the filtrate concentrated in vacuo. The residue was dissolved in methanol (10 mL), refluxed for 1 h, cooled, treated with DOWEX® 550A-OH resin (3.0 g, pre-rinsed with methanol), stirred a few minutes, filtered, and the filtrate concentrated in vacuo. The residue was taken up in ether, filtered through Celite®, and the filtrate treated with 2N HCl/ether (0.75 mL, 1.5 mmol). The suspension was stirred, the solid salt collected by filtration, rinsed with ether, and dried in vacuo to afford 1-(3,4-difluorophenyl)-3-azabicyclo[3.1.0]hexane, hydrochloride (118 mg, 51%) as a white solid. MS (M+1) 196.0. ¹H NMR (CDCl₃) δ 10.31 (br s, 1H), 9.83 (br s, 1H), 7.11 (m, 1H), 7.00 (m, 1H), 6.93 (m, 1H), 3.75 (m, 1H), 3.50-3.70 (m, 3H), 1.94 (m, 1H), 1.60 (m, 1H), 1.20 (m, 1H). ¹³C NMR (CDCl₃) δ 151.83, 149.30, 135.20, 123.66, 118.07, 116.84, 50.91, 47.73, 31.02, 23.61, 15.74.

C. Synthesis of 1-(4-Fluoro-3-trifluoromethylphenyl)-3-azabicyclo[3.1.0]hexane Hydrochloride

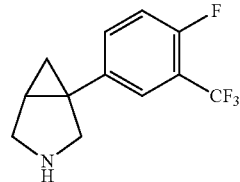 [SMILES: Fc1ccc(C23CNCC2C3)cc1C(F)(F)F]

A stirred solution of 3-bromo-1-(3,4-dimethoxybenzyl)maleimide (1.63 g, 5.0 mmol) and 4-fluoro-3-(trifluoromethyl)phenylboronic acid (1.35 g, 6.5 mmol) in anhydrous dioxane (15 mL) under nitrogen was degassed over 10 min with a stream of nitrogen, then treated with cesium fluoride (2.0 g, 13.2 mmol) and Cl₂Pd(dppf).CH₂Cl₂ (Aldrich, 0.25 g, 0.30 mmol), stirred 1 h at room temperature, then 2 h at 40° C. The mixture was cooled, diluted with methylene chloride (70 mL), stirred a few minutes, filtered through Celite® (rinse with methylene chloride), and the filtrate concentrated in vacuo. The residue was dissolved in methylene chloride and loaded onto a silica gel column and the product eluted with methylene chloride to afford product, which was triturated from petroleum ethers to afford the intermediate arylmaleimide (1.05 g, 51%) as a yellow solid. NO MS (M+1) peak. ¹H NMR (CDCl₃) δ 7.69 (m, 1H), 7.36 (m, 1H), 7.04 (m, 1H), 6.92-6.99 (m, 3H), 6.79 (m, 1H), 4.68 (s, 2H), 3.87 (s, 3H), 3.85 (s, 3H).

A cooled (−20° C.) stirred solution of trimethylsulfoxonium chloride (434 mg, 3.375 mmol) in anhydrous tetrahydrofuran (10 mL) under nitrogen was treated dropwise with n-butyllithium/hexane (2.4N, 1.17 mL, 2.80 mmol) and gradually warmed to 50° C. over 30 minutes. Meanwhile, a solution of the intermediate arylmaleimide (1.023 g, 2.5 mmol) in anhydrous THF (10 mL) was heated to 50° C. and added quickly in one portion to the above heated suspension. The mixture was then stirred at 50° C. for 2 h, and cooled on an ice bath. Saturated aqueous ammonium chloride (3 mL) was added to quench, and the mixture was diluted with methylene chloride (75 mL), dried (MgSO$_4$), filtered through Celite® (rinse with methylene chloride), and concentrated in vacuo. The residue was dissolved in methylene chloride, loaded onto a silica gel column, and the product eluted with 2% ethyl acetate/methylene chloride to afford the intermediate bicyclic diimide (602 mg, 65%) as a pale yellow foam. MS (M+1) 423.9. $^1$H NMR (CDCl$_3$) δ 7.64 (m, 1H), 7.56 (m, 1H), 7.28 (m, 1H), 6.88 (m, 2H), 6.79 (m, 1H), 4.53 (m, 2H), 3.85 (br s, 6H), 2.71 (m, 1H), 1.91 (m, 1H), 1.76 (m, 1H).

An ice-cooled, stirred solution of 1N borane/THF (7.5 mL, 7.5 mmol) under nitrogen was treated dropwise with a solution of the above intermediate bicyclic diimide (390 mg, 0.92 mmol) in anhydrous tetrahydrofuran (4 mL), then stirred for 45 min at room temperature and for 4 h at reflux and cooled on an ice bath. 6N HCl (5 mL) was carefully added dropwise, and the mixture was concentrated in vacuo and the white solid residue partitioned between 5N NaOH (15 mL) and ether (50 mL). The organic layer was separated and the aqueous was extracted with ether (2×30 mL). The combined organic solution was dried (MgSO$_4$), concentrated in vacuo, dissolved in methanol (15 mL), treated with 4N HCl/dioxane (5 mL), then stirred at room temperature for 18 h and at 60° C. for 4 h. The solution was concentrated in vacuo and the residue dissolved in methanol (25 mL), treated with DOWEX® 550A-OH resin (3 g), stirred for 15 min, filtered, and the filtrate concentrated in vacuo to afford the intermediate dimethoxybenzyl bicyclic amine (272 mg, 75%) as a colorless glass. MS (M+1) 396.2. $^1$H NMR (CDCl$_3$) δ 7.43 (m, 2H), 7.12 (m, 1H), 6.86 (m, 1H), 6.78-6.82 (m, 2H), 3.88 (s, 3H), 3.86 (s, 3H), 3.59 (m, 2H), 3.19 (m, 1H), 3.08 (m, 1H), 2.62 (m, 1H), 2.43 (m, 1H), 1.74 (m, 1H), 1.50 (m, 1H), 0.77 (m, 1H).

A mixture of the intermediate dimethoxybenzyl bicyclic amine (276 mg, 0.698 mmol) and anhydrous potassium carbonate (207 mg, 1.5 mmol) in anhydrous methylene chloride (5.5 mL) in a pressure tube equipped with a stirbar was treated with 1-chloroethyl chloroformate (0.21 mL, 1.93 mmol), closed, and stirred at 40° C. for 4 h. The tube was cooled, opened, and the contents filtered (rinse with methylene chloride), and the filtrate concentrated in vacuo. The residue was dissolved in methanol (10 mL), refluxed for 1 h, cooled, treated with DOWEX® 550A-OH resin (1.0 g, prerinsed with methanol), stirred a few minutes, filtered, and the filtrate concentrated in vacuo. The residue was dissolved in methylene chloride, loaded onto a silica gel column, and eluted with 5% ethanol/methylene chloride, then with 10% (9:1 ethanol/ammonia)/methylene chloride to afford an oil, which was dissolved in ether (3 mL), treated with 2N HCl/ether (0.5 mL, 1.0 mmol), stirred a few minutes, filtered, rinsed with ether, collected, and dried in vacuo to afford 1-(4-fluoro-3-trifluoromethylphenyl)-3-azabicyclo[3.1.0]hexane, hydrochloride (91 mg, 46%) as a white solid. MS (M+1) 246.0. $^1$H NMR (CDCl$_3$) δ 10.35 (br s, 1H), 9.87 (br s, 1H), 7.55 (m, 1H), 7.46 (m, 1H), 7.21 (m, 1H), 3.60-3.80 (m, 3H), 3.51 (m, 1H), 2.03 (m, 1H), 1.68 (m, 1H), 1.22 (m, 1H). $^{13}$C NMR (CDCl$_3$) δ 134.80, 126.95, 126.56, 124.44, 123.64, 120.93, 50.19, 47.27, 26.85, 22.28, 13.56.

D. Synthesis of 1-(3-Fluoro-4-methoxyphenyl)-3-azabicyclo[3.1.0]hexane Hydrochloride

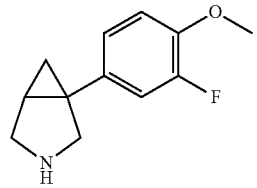

A stirred solution of 3-bromo-1-(3,4-dimethoxybenzyl) maleimide (1.14 g, 3.5 mmol) and 3-fluoro-4-methoxyphenylboronic acid (765 mg, 4.5 mmol) in anhydrous dioxane (10 mL) under nitrogen was degassed over 10 min with a stream of nitrogen, then treated with cesium fluoride (1.3 g, 8.5 mmol) and Cl$_2$Pd(dppf).CH$_2$Cl$_2$ (Aldrich, 0.17 g, 0.21 mmol), stirred 1 h at room temperature, then 2 h at 40° C. The mixture was cooled, diluted with methylene chloride (50 mL), stirred a few minute's, filtered through Celite® (rinse with methylene chloride), and the filtrate concentrated in vacuo. The residue was dissolved in methylene chloride and loaded onto a silica gel column and the product eluted with 3% ethyl acetate/methylene chloride to afford product, which was triturated from petroleum ethers to afford the intermediate arylmaleimide (1.123 g, 86%) as a yellow solid. MS (M+1) 372.1. $^1$H NMR (CDCl$_3$) δ 7.76 (m, 1H), 7.71 (m, 1H), 7.01 (m, 1H), 6.93-6.99 (m, 2H), 6.80 (m, 1H), 6.60 (s, 1H), 4.65 (s, 2H), 3.93 (s, 3H), 3.87 (s, 3H), 3.84 (s, 3H).

A cooled (−20° C.) stirred solution of trimethylsulfoxonium chloride (515 mg, 4.00 mmol) in anhydrous tetrahydrofuran (12 mL) under nitrogen was treated dropwise with n-butyllithium/hexane (2.4N, 1.42 mL, 3.4 mmol) and gradually warmed to 50° C. over 30 minutes. Meanwhile, a solution of the intermediate arylmaleimide (1.114 g, 3.0 mmol) in anhydrous THF (13 mL) was heated to 50° C., and added quickly in one portion to the above heated suspension. The mixture was then stirred at 50° C. for 1.5 h, and cooled on an ice bath. Saturated aqueous ammonium chloride (2 mL) was added to quench, and the mixture was diluted with methylene chloride (75 mL), dried (MgSO$_4$), filtered through Celite® (rinse with methylene chloride), and concentrated in vacuo. The residue was dissolved in methylene chloride, loaded onto a silica gel column, and the product eluted with 2%, then 3% ethyl acetate/methylene chloride to afford the intermediate bicyclic diimide (622 mg, 54%) as a pale beige solid. MS (M+1) 386.2. $^1$H NMR (CDCl$_3$) δ 7.14 (m, 1H), 7.07 (m, 1H), 6.94 (m, 1H), 6.87-6.92 (m, 2H), 6.78 (m, 1H), 4.50 (m, 2H), 3.87 (s, 3H), 3.85 (s, 3H), 3.84 (s, 3H), 2.67 (m, 1H), 1.74 (m, 1H), 1.67 (m, 1H).

A cooled (5° C.) stirred solution of 1N lithium aluminum hydride/THF (10.6 mL, 10.6 mmol) under nitrogen was treated slowly with a solution of the above intermediate bicyclic diimide (617 mg, 1.6 mmol) in anhydrous THF (7 mL), stirred 1 h at room temperature, refluxed for 6 h, and cooled (5° C.). Water (0.4 mL), 15% sodium hydroxide (0.4 mL), and water (1.2 mL) were carefully added dropwise, followed by additional THF to facilitate stirring. The suspension was stirred 20 min, filtered through Celite® (filter cake rinsed with THF), and the filtrate concentrated in vacuo. The residue was dissolved in methylene chloride, loaded onto a silica gel column, and eluted with 3:1 methylene chloride/ethyl acetate to afford the intermediate dimethoxybenzyl bicyclic amine (362 mg, 63%) as a colorless viscous oil. MS (M+1) 358.3. $^1$H NMR (CDCl$_3$) δ 6.78-6.88 (m, 6H), 3.88 (s, 3H), 3.86 (s, 3H), 3.84 (s, 3H), 3.59 (m, 2H), 3.20 (m, 1H), 3.04 (m, 1H), 2.53 (m, 2H), 1.61 (m, 1H), 1.46 (m, 1H), 0.73 (m, 1H).

A mixture of the intermediate dimethoxybenzyl bicyclic amine (358 mg, 1.00 mmol) and anhydrous potassium carbonate (311 mg, 2.25 mmol) in anhydrous methylene chloride (8 mL) in a pressure tube equipped with a stirbar was treated with 1-chloroethyl chloroformate (322 mg, 2.25 mmol), closed, and stirred at 45° C. for 4 h. The tube was cooled, opened, and the contents filtered (rinse with methylene chloride), and the filtrate concentrated in vacuo. The residue was dissolved in methanol (10 mL), refluxed for 1 h, cooled, treated with DOWEX® 550A-OH resin (3.0 g, pre-rinsed with methanol), stirred a few minutes, filtered, and the filtrate concentrated in vacuo. The residue was taken up in ether, filtered through Celite®, and the filtrate treated with 2N HCl/ether (0.75 mL, 1.5 mmol). The suspension was stirred for awhile, the solid salt collected by filtration, rinsed with ether, and dried in vacuo to afford 1-(3-fluoro-4-methoxyphenyl)-3-azabicyclo[3.1.0]hexane, hydrochloride (125 mg, 51%) as a white solid. MS (M+1) 208.0. $^1$H NMR (CDCl$_3$) δ 10.27 (br s, 1H), 9.76 (br s, 1H), 6.88-6.95 (m, 3H), 3.86 (s, 3H), 3.72 (m, 1H), 3.40-3.65 (m, 3H), 1.89 (m, 1H), 1.54 (m, 1H), 1.18 (m, 1H). $^{13}$C NMR (CDCl$_3$) δ 153.72, 147.27, 131.04, 123.51, 115.58, 113.92, 56.56, 51.08, 47.80, 30.95, 23.32, 15.39.

E. Synthesis of 1-(3-Fluoro-4-methylphenyl)-3-azabicyclo[3.1.0]hexane Hydrochloride

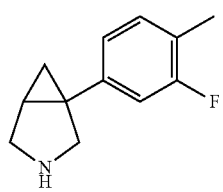

A stirred solution of 3-bromo-1-(3,4-dimethoxybenzyl) maleimide (1.31 g, 4.0 mmol) and 3-fluoro-4-methylphenyl-boronic acid (770 mg, 5.0 mmol) in anhydrous dioxane (12 mL) under nitrogen was degassed over 10 min with a stream of nitrogen, then treated with cesium fluoride (1.5 g, 9.9 mmol) and Cl$_2$Pd(dppf).CH$_2$Cl$_2$ (Aldrich, 0.20 g, 0.245 mmol), stirred 1 h at room temperature, then 2 h at 40° C. The mixture was cooled, diluted with methylene chloride (60 mL), stirred a few minutes, filtered through Celite® (rinse with methylene chloride), and the filtrate concentrated in vacuo. The residue was dissolved in methylene chloride and loaded onto a silica gel column and the product eluted with 2% ethyl acetate/methylene chloride to afford the intermediate arylmaleimide (1.12 g, 79%) as a yellow solid. MS (M+1) 356.1. $^1$H NMR (CDCl$_3$) δ 7.63 (m, 1H), 7.59 (m, 1H), 7.24 (m, 1H), 6.94-6.99 (m, 2H), 6.80 (m, 1H), 6.68 (s, 1H), 4.65 (s, 2H), 3.87 (s, 3H), 3.84 (s, 3H), 2.31 (s, 3H).

A cooled (-20° C.) stirred solution of trimethylsulfoxonium chloride (534 mg, 4.15 mmol) in anhydrous tetrahydrofuran (15 mL) under nitrogen was treated dropwise with n-butyllithium/hexane (2.5N, 1.4 mL, 3.45 mmol) and gradually warmed to 50° C. over 30 minutes. Meanwhile, a solution of the intermediate arylmaleimide (1.10 g, 3.1 mmol) in anhydrous THF (10 mL) was heated to 50° C., and added quickly in one portion to the above heated suspension. The mixture was then stirred at 50° C. for 2 h, and cooled on an ice bath. Saturated aqueous ammonium chloride (2 mL) was added to quench, and the mixture was diluted with methylene chloride (60 mL), dried (MgSO$_4$), filtered through Celite® (rinse with methylene chloride), and concentrated in vacuo. The residue was dissolved m methylene chloride, loaded onto a silica gel column, and the product eluted with 2% ethyl acetate/methylene chloride to afford the intermediate bicyclic diimide (615 mg, 54%) as a viscous pale yellow oil. MS (M+1) 370.2. $^1$H NMR (CDCl$_3$) δ 7.16 (m, 1H), 7.08 (m, 1H), 7.02 (m, 1H), 6.87-6.93 (m, 2H), 6.78 (m, 1H), 4.50 (m, 2H), 3.85 (s, 3H), 3.84 (s, 3H), 2.69 (m, 1H), 2.25 (br s, 3H), 1.76 (m, 1H), 1.68 (m, 1H).

A cooled (5° C.) stirred solution of 1N lithium aluminum hydride/THF (11.5 mL, 11.5 mmol) under nitrogen was treated slowly with a solution of the above intermediate bicyclic diimide (650 mg, 1.76 mmol) in anhydrous THF (10 mL), stirred 1 h at room temperature, refluxed for 6 h, and cooled (5° C.). Water (0.45 mL), 15% sodium hydroxide (0.45 mL), and water (1.35 mL) were carefully added dropwise, followed by additional THF to facilitate stirring. The suspension was stirred 15 min, filtered through Celite® (filter cake rinsed with THF), and the filtrate concentrated in vacuo. The residue was dissolved in methylene chloride, loaded onto a silica gel column, and eluted with 3:1 methylene chloride/ethyl acetate to afford the intermediate dimethoxybenzyl bicyclic amine (347 mg, 58%) as a colorless viscous oil. MS (M+1) 342.2. $^1$H NMR (CDCl$_3$) δ 7.05 (m, 1H), 6.88 (m, 1H), 6.73-6.83 (m, 4H), 3.88 (s, 3H), 3.87 (s, 3H), 3.59 (m, 2H), 3.23 (m, 1H), 3.04 (m, 3H), 2.54 (m, 2H), 2.21 (br s, 3H), 1.65 (m, 1H), 1.50 (m, 1H), 0.76 (m, 1H).

A mixture of the intermediate dimethoxybenzyl bicyclic amine (336 mg, 0.984 mmol) and anhydrous potassium carbonate (286rng, 2.07 mmol) in anhydrous methylene chloride (8 mL) in a pressure tube equipped with a stirbar was treated with 1-chloroethyl chloroformate (0.29 mL, 2.71 mmol), closed, and stirred at 40° C. for 4 h. The tube was cooled, opened, and the contents filtered (rinse with methylene chloride), and the filtrate concentrated in vacuo. The residue was dissolved in methanol (12 mL), refluxed for 1 h, cooled, treated with DOWEX® 550A-OH resin (2.0 g, prerinsed with methanol), stirred a few minutes, filtered, and the filtrate concentrated in vacuo. The residue was taken up in ether, filtered through Celite®, and the filtrate treated with 2N HCl/ether (0.50 mL, 1.0 mmol). The suspension was stirred, the solid salt collected by filtration, rinsed with ether, and dried in vacuo to afford 1-(3-fluoro-4-methylphenyl)-3-azabicyclo [3.1.0]hexane, hydrochloride (127 mg, 57%) as a white solid. MS (M+1) 192.1. $^1$H NMR (CDCl$_3$) δ 10.29 (br s, 1H), 9.80 (br s, 1H), 7.11 (m, 1H), 6.78-6.88 (m, 2H), 3.75 (m, 1H), 3.50-3.65 (m, 3H), 2.22 (s, 3H), 1.92 (m, 1H), 1.57 (m, 1H), 1.19 (m, 1H). $^{13}$C NMR (CDCl$_3$) δ 162.72, 137.90, 132.05, 124.30, 122.66, 114.08, 50.75, 47.72, 31.06, 23.57, 15.85, 14.38.

F. Synthesis of 1-(4-Fluoro-3-methylphenyl)-3-azabicyclo[3.1.0]hexane Hydrochloride

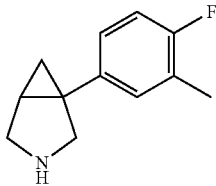

A stirred solution of 3-bromo-1-(3,4-dimethoxybenzyl)maleimide (1.0 g, 3.06 mmol) and 4-(4-fluoro-3-methyl)phenyl boronic acid (0.52 g, 3.4 mmol) in anhydrous dioxane (10 mL) under nitrogen was degassed over 10 min with a stream of nitrogen, then treated with cesium fluoride (1.3 g, 8.5 mmol) and Cl$_2$Pd(dppf).CH$_2$Cl$_2$ (Aldrich, 0.17 g, 0.21 mmol), stirred 1 h at room temperature, then 2 h at 40° C. The mixture was cooled, diluted with methylene chloride (50 mL), stirred a few minutes, filtered through Celite® (rinse with methylene chloride), and the filtrate concentrated in vacuo. The residue was dissolved in methylene chloride and loaded onto a silica gel column and the product eluted with 3% ethyl acetate/methylene chloride to afford a yellow solid, which was triturated from petroleum ethers to afford the intermediate arylmaleimide (940 g, 79%) as a pale yellow solid.

A cooled (−20° C.) stirred solution of trimethylsulfoxonium chloride (370 mg, 2.86 mmol) in anhydrous tetrahydrofuran (15 mL) under nitrogen was treated dropwise with n-butyllithium/hexane (2.4N, 1.1 mL, 2.03 mmol) and gradually warmed to 50° C. over 30 minutes. Meanwhile, a solution of the intermediate arylmaleimide (0.94 g, 2.6 mmol) in anhydrous THF (10 mL) was heated to 50° C., and added quickly in one portion to the above heated suspension. The mixture was then stirred at 50° C. for 2 h and cooled on an ice bath. Saturated aqueous ammonium chloride (1 mL) was added to quench, and the mixture was diluted with methylene chloride (75 mL), dried (MgSO$_4$), filtered through Celite® (rinse with methylene chloride), and concentrated in vacuo. The residue was dissolved in methylene chloride, loaded onto a silica gel column, and the product eluted with 3% ethyl acetate/methylene chloride to afford the intermediate bicyclic diimide (400 mg, 50%) as a very pale yellow viscous oil. $^1$H NMR (CDCl$_3$) δ 1.63-1.70 (m, 1H) 1.74 (dd, J=8.16, 4.63 Hz, 1H) 2.21-2.31 (m, J=1.87 Hz, 3H) 2.67 (dd, J=8.22, 3.58 Hz, 1H) 3.85 (d, J=2.76 Hz, 6H) 4.50 (dd, 2H) 6.82-7.03 (m, 2H) 7.08-7.24 (m, 1H).

A cooled (5° C.) stirred solution of 1N lithium aluminum hydride/THF (3.6 mL, 10 mmol) under nitrogen was treated slowly with a solution of the above intermediate bicyclic diimide (400 mg, 1.2 mmol) in anhydrous THF (7 mL), stirred 1 h at room temperature, refluxed for 6 h, and cooled (5° C.). Water (0.4 mL), 15% sodium hydroxide (0.4 mL), and water (1.2 mL) were carefully added dropwise, followed by additional THF to facilitate stirring. The suspension was stirred 15 min, filtered through Celite® (filter cake rinsed with THF), and the filtrate concentrated in vacuo. The residue was dissolved in methylene chloride, loaded onto a silica gel column, and eluted with 3:1 methylene chloride/ethyl acetate to afford the intermediate dimethoxybenzyl bicyclic amine (280 mg, 58%) as a colorless viscous oil.

A mixture of the intermediate dimethoxybenzyl bicyclic amine (280 mg, 0.76 mmol) and anhydrous potassium carbonate (215 mg, 1.55 mmol) in anhydrous methylene chloride (5 mL) in a pressure tube equipped with a stirbar was treated with 1-chloroethyl chloroformate (0.221 mL, 1.55 mmol), closed, and stirred at 45° C. for 4 h. The tube was cooled, opened, and the contents filtered (rinse with methylene chloride), and the filtrate concentrated in vacuo. The residue was dissolved in methanol (7 mL), refluxed for 1 h, cooled, treated with DOWEX® 550A-OH resin (2.0 g, pre-rinsed with methanol), stirred a few minutes, filtered, and the filtrate concentrated in vacuo. The residue was taken up in ether, filtered through Celite®, and the filtrate treated with 2N HCl/ether (0.6 mL, 1.2 mmol). The suspension was stirred a few minutes, the solid salt collected by filtration, rinsed with ether, and dried in vacuo to afford 1-(4-fluoro-3-methylphenyl)-3-azabicyclo[3.1.0]hexane, hydrochloride (100 mg, 47%) as a light beige solid. MS (M+1) 192.1. $^1$H NMR (CDCl$_3$) δ 1.10 (t, J=7.61 Hz, 1H) 1.88-1.97 (m, 1H) 2.18-2.21 (m, 1H) 2.21-2.23 (m, J=2.54, 2.54 Hz, 3H) 3.10-3.22 (m, 3H) 3.23-3.33 (m, 1H) 3.86 (dd, J=11.03, 5.37 Hz, 1H) 4.03 (dd, J=10.93, 5.47 Hz, 1H) 6.87-7.03 (m, 3H). $^{13}$C NMR (CDCl$_3$) δ 16.05, 22.60, 30.71, 51.47, 55.39, 58.87, 115.61, 125.67, 126.44, 130.74, 133.59, 159.54, 161.98.

G. Synthesis of 1-(Naphthalen-2-yl)-3-azabicyclo[3.1.0]hexane Hydrochloride

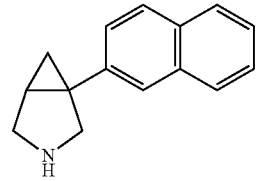 [SMILES: c1ccc2cc(C34CNCC3C4)ccc2c1]

A stirred solution of 3-bromo-1-(3,4-dimethoxybenzyl)maleimide (1.0 g, 3.06 mmol) and 2-naphthaleneboronic acid (0.59 g, 3.4 mmol) in anhydrous dioxane (10 mL) under nitrogen was degassed over 10 min with a stream of nitrogen, then treated with cesium fluoride (1.3 g, 8.5 mmol) and Cl$_2$Pd(dppf).CH$_2$Cl$_2$ (Aldrich, 0.17 g, 0.21 mmol), stirred 1 h at room temperature, then 2 h at 40° C. The mixture was cooled, diluted with methylene chloride (50 mL), stirred a few minutes, filtered through Celite® (rinse with methylene chloride), and the filtrate concentrated in vacuo. The residue was dissolved in methylene chloride and loaded onto a silica gel column and the product eluted with 3% ethyl acetate/methylene chloride to afford a yellow solid, which was triturated from petroleum ethers to afford the intermediate arylmaleimide (690 g, 83%) as a pale yellow solid.

A cooled (−20° C.) stirred solution of trimethylsulfoxonium chloride (261 mg, 2.03 mmol) in anhydrous tetrahydrofuran (15 mL) under nitrogen was treated dropwise with n-butyllithium/hexane (2.4N, 1.1 mL, 2.03mmol) and gradually warmed to 50° C. over 30 minutes. Meanwhile, a solution of the intermediate arylmaleimide (0.690 g, 2.6 mmol) in anhydrous THF (10 mL) was heated to 50° C. and added quickly in one portion to the above heated suspension. The mixture was then stirred at 50° C. for 2 h and cooled on an ice bath. Saturated aqueous ammonium chloride (1 mL) was added to quench, and the mixture was diluted with methylene chloride (75 mL), dried (MgSO$_4$), filtered through Celite® (rinse with methylene chloride), and concentrated in vacuo. The residue was dissolved in methylene chloride, loaded onto a silica gel column, and the product eluted with 3% ethyl acetate/methylene chloride to afford the intermediate bicyclic diimide (400 mg, 50%) as a very pale yellow viscous oil. $^1$H NMR (CDCl$_3$) δ 1.78 (dd, J=4.59, 3.61 Hz, 1H) 1.91 (dd, J=8.20, 4.69 Hz, 1H) 2.81 (dd, J=8.20, 3.71 Hz, 1H) 3.86 (d, J=4.30 Hz, 6H) 4.54 (dd, 2H) 7.38-7.55 (m, 3H) 7.74-7.90 (m, 4H).

A cooled (5° C.) stirred solution of 1N lithium aluminum hydride/THF (3.6 mL, 10 mmol) under nitrogen was treated slowly with a solution of the above intermediate bicyclic diamide (360 mg, 1.0 mmol) in anhydrous THF (7 mL), stirred 1 h at room temperature, refluxed for 6 h, and cooled (5° C.). Water (0.4 mL), 15% sodium hydroxide (0.4 mL), and water (1.2 mL) were carefully added dropwise, followed by additional THF to facilitate stirring. The suspension was stirred 15 min, filtered through Celite® (filter cake rinsed with THF), and the filtrate concentrated in vacuo. The residue was dissolved in methylene chloride, loaded onto a silica gel column, and eluted with 3:1 methylene chloride/ethyl acetate to afford the intermediate dimethoxybenzyl bicyclic amine (350 mg, 55%) as a colorless viscous oil.

A mixture of the intermediate dimethoxybenzyl bicyclic amine (340 mg, 0.95 mmol) and anhydrous potassium carbonate (290 mg, 2.1 mmol) in anhydrous methylene chloride (5 mL) in a pressure tube equipped with a stirbar was treated with 1-chloroethyl chloroformate (0.301 mL, 2.2 mmol), closed, and stirred at 45° C. for 4 h. The tube was cooled, opened, and the contents filtered (rinse with methylene chloride), and the filtrate concentrated in vacuo. The residue was dissolved in methanol (7 mL), refluxed for 1 h, cooled, treated with DOWEX® 550A-OH resin (2.0 g, prerinsed with methanol), stirred a few minutes, filtered, and the filtrate concentrated in vacuo. The residue was taken up in ether, filtered through Celite®, and the filtrate treated with 2N HCl/ether (0.6 mL, 1.2 mmol). The suspension was stirred a few minutes, the solid salt collected by filtration, rinsed with ether, and dried in vacuo to afford 1-(naphthalene-2-yl)-3-azabicyclo[3.1.0]hexane, hydrochloride (95 mg, 53%) as a light beige solid. MS (M+1) 210.1. $^1$H NMR (DMSO-d$_6$) δ☐ 1.14-1.23 (m, 1H) 1.49 (t, J=5.27 Hz, 1H) 2.13-2.27 (m, 1H) 3.30-3.43 (m, 1H) 3.57 (d, J=7.81 Hz, 2H) 3.62-3.81 (m, 1H) 7.35 (dd, J=8.59, 1.76 Hz, 1H) 7.39-7.53 (m, 2H) 7.71-7.91 (m, 4H). $^{13}$C NMR (DMSO-d$_6$) δ 16.44, 24.13, 31.37, 47.45, 49.92, 125.43, 125.74, 126.40, 127.03, 128.10, 128.74, 132.38, 133.55, 137.64, H. Synthesis of 1-(6-Methoxynaphthalen-2-yl)-3-azabicyclo[3.1.0]hexane Hydrochloride

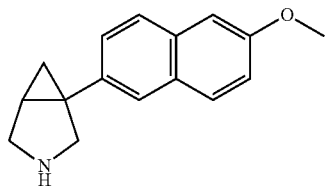 [SMILES: COc1ccc2cc(C34CNCC3C4)ccc2c1]

A stirred solution of 3-bromo-1-(3,4-dimethoxybenzyl) maleimide (1.31 g, 4.0 mmol) and 6-methoxynaphthalene-2-boronic acid (1.01 g, 5.0 mmol) in anhydrous dioxane (12 mL) under nitrogen was degassed over 10 min with a stream of nitrogen, then treated with cesium fluoride (1.5 g, 9.9 mmol) and Cl$_2$Pd(dppf).CH$_2$Cl$_2$ (Aldrich, 0.20 g, 0.245 mmol), stirred 1 h at room temperature, then 2 h at 40° C. The mixture was cooled, diluted with methylene chloride (60 mL), stirred a few minutes, filtered through Celite® (rinse with methylene chloride), and the filtrate concentrated in vacuo. The residue was dissolved in methylene chloride and loaded onto a silica gel column and the product eluted with 2% ethyl acetate/methylene chloride to afford the intermediate arylmaleimide (1.10 g, 68%) as a yellow solid. MS (M+1) 404.2. $^1$H NMR (CDCl$_3$) δ 8.62 (m, 1H), 7.82 (m, 1H), 7.75 (m, 2H), 7.18 (m, 1H), 7.12 (m, 1H), 6.97-7.02 (m, 2H), 6.81 (m, 1H), 6.76 (s, 1H), 4.69 (s, 2H), 3.94 (s, 3H), 3.88 (s, 3H), 3.85 (s, 3H).

A cooled (−20° C.) stirred solution of trimethylsulfoxonium chloride (482 mg, 3.75 mmol) in anhydrous tetrahydrofuran (12 mL) under nitrogen was treated dropwise with n-butyllithium/hexane (2.5N, 1.2 mL, 3.00 mmol) and gradually warmed to 50° C. over 30 minutes. Meanwhile, a solution of the intermediate arylmaleimide (1.09 g, 2.7 mmol) in anhydrous THF (12 mL) was heated to 50° C. and added quickly in one portion to the above heated suspension. The mixture was then stirred at 50° C. for 2 h and cooled on an ice bath. Saturated aqueous ammonium chloride (2 mL) was added to quench, and the mixture was diluted with methylene chloride (60 mL), dried (MgSO$_4$), filtered through Celite® (rinse with methylene chloride), and concentrated in vacuo. The residue was dissolved in methylene chloride, loaded onto a silica gel column, and the product eluted with 2% ethyl acetate/methylene chloride to afford the intermediate bicyclic diimide (543 mg, 48%) as a pale orange solid. MS (M+1) 418.2. $^1$H NMR (CDCl$_3$) δ 7.78 (m, 1H), 7.67-7.75 (m, 2H), 7.42 (m, 1H), 7.15 (m, 1H), 7.11 (m, 1H), 6.90-6.95 (m, 2H), 6.79 (m, 1H), 4.54 (m, 2H), 3.91 (s, 3H), 3.86 (s, 3H), 3.85 (s, 3H), 2.77 (m, 1H), 1.88 (m, 1H), 1.75 (m, 1H).

A cooled (5° C.) stirred solution of 1N lithium aluminum hydride/THF (8 mL, 8 mmol) under nitrogen was treated slowly with a solution of the above intermediate bicyclic diimide (534 mg, 1.28 mmol) in anhydrous THF (6 mL), stirred 1 h at room temperature, refluxed for 6 h, and cooled (5° C.). Water (0.3 mL), 15% sodium hydroxide (0.3 mL), and water (0.9 mL) were carefully added dropwise, followed by additional THF to facilitate stirring. The suspension was stirred 15 min, filtered through Celite® (filter cake rinsed with THF), and the filtrate concentrated in vacuo. The residue was dissolved in methylene chloride, loaded onto a silica gel column, and eluted with 3:1 methylene chloride/ethyl acetate to afford the intermediate dimethoxybenzyl bicyclic amine (345 mg, 69%) as a white solid. MS (M+1) 390.2. $^1$H NMR (CDCl) δ 7.64 (m, 2H), 7.52 (m, 1H), 7.20 (m, 1H), 7.07-7.13 (m, 2H), 6.92 (m, 1H), 6.79-6.87 (m, 2H), 3.90 (brs, 6H), 3.87 (s, 3H), 3.64 (m, 2H), 3.35 (m, 1H), 3.11 (m, 1H), 2.70 (m, 1H), 2.58 (m, 1H), 1.78 (m, 1H), 1.56 (m, 1H), 0.87 (m, 1H).

A mixture of the intermediate dimethoxybenzyl bicyclic amine (325 mg, 0.8344 mmol) and anhydrous potassium carbonate (243 mg, 1.76 mmol) in anhydrous methylene chloride (6.5 mL) in a pressure tube equipped with a stirbar was treated with 1-chloroethyl chloroformate (0.25 mL, 2.3 mmol), closed, and stirred at 40° C. for 4 h. The tube was cooled, opened, and the contents filtered (rinse with methylene chloride), and the filtrate concentrated in vacuo. The residue was dissolved in methanol (10 mL), refluxed for 1 h, cooled, treated with DOWEX® 550A-OH resin (1.0 g, prerinsed with methanol), stirred a few minutes, filtered, and the filtrate concentrated in vacuo. The residue was taken up in ether containing a little methylene chloride, filtered through Celite®, and the filtrate treated with 2N HCl/ether (0.60 mL, 1.2 mmol). The suspension was stirred and the solid salt collected by filtration, rinsed with ether, suspended in acetonitrile, filtered, collected and dried in vacuo to afford 1-(6-methoxynaphthalen-2-yl)-3-azabicyclo[3.1.0]hexane, hydrochloride (151 mg, 66%) as a white solid. MS (M+1) 240.1. $^1$H NMR (DMSO-d6) δδ 9.90 (br 5, 1H), 9.57 (br s, 1H), 7.73 (m, 3H), 7.31 (m, 1H), 7.26 (m, 1H), 7.13 (m, 1H), 3.83 (s, 3H), 3.71 (m, 1H), 3.45-3.55 (m, 2H), 3.39 (m, 1H), 2.14 (m, 1H), 1.43 (m, 1H), 1.14 (m, 1H). $^{13}$C NMR (DMSO-d6) δ 157.78, 134.96, 133.67, 129.58, 128.96, 127.66, 125.96, 125.74, 119.53, 106.41, 55.82, 50.17, 47.55, 31.24, 23.87, 16.09.

Synthesis of 1-(6-Ethoxynaphthalen-2-yl)-3-azabicyclo[3.1.0]hexane Hydrochloride

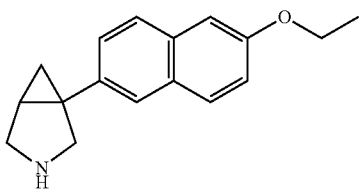 [SMILES: CCOc1ccc2cc(C34CNCC3C4)ccc2c1]

A stirred solution of 3-bromo-1-(3,4-dimethoxybenzyl)maleimide (1.31 g, 4.0 mmol) and 6-ethoxynaphthalene-2-boronic acid (1.08 g, 5.0 mmol) in anhydrous dioxane (12 mL) under nitrogen was degassed over 10 min with a stream of nitrogen, then treated with cesium fluoride (1.5 g, 9.9 mmol) and Cl$_2$Pd(dppf).CH$_2$Cl$_2$ (Aldrich, 0.20 g, 0.245 mmol), stirred 1 h at room temperature, then 2 h at 40° C. The mixture was cooled, diluted with methylene chloride (60 mL), stirred a few minutes, filtered through Celite® (rinse with methylene chloride), and the filtrate concentrated in vacuo. The residue was dissolved in methylene chloride and loaded onto a silica gel column and the product eluted with 2% ethyl acetate/methylene chloride to afford the intermediate arylmaleimide (1.36 g, 81%) as a yellow solid. No MS (M+1) peak observed. $^1$H NMR (CDCl$_3$) δ 8.62 (m, 1H), 7.81 (m, 1H), 7.74 (m, 2H), 7.17 (m, 1H), 7.10 (m, 1H), 6.96-7.02 (m, 2H), 6.81 (m, 1H), 6.75 (s, 1H), 4.69 (s, 2H), 4.16 (q, 2H, J=7 Hz), 3.88 (s, 3H), 3.84 (s, 3H), 1.48 (t, 3H, J=7 Hz).

A cooled (−20° C.) stirred solution of trimethylsulfoxonium chloride (515 mg, 4.00 mmol) in anhydrous tetrahydrofuran (15 mL) under nitrogen was treated dropwise with n-butyllithium/hexane (2.5N, 1.32 mL, 3.30 mmol) and gradually warmed to 50° C. over 30 minutes. Meanwhile, a solution of the intermediate arylmaleimide (1.23 g, 2.95 mmol) in anhydrous THF (10 mL) was heated to 50° C., then added quickly in one portion to the above heated suspension, and the mixture was stirred at 50° C. for 2 h, then cooled on an ice bath. Saturated aqueous ammonium chloride (3 mL) was added to quench, and the mixture was diluted with methylene chloride (70 mL), dried (MgSO$_4$), filtered through Celite® (rinse with methylene chloride), and concentrated in vacuo. The residue was dissolved in methylene chloride, loaded onto a silica gel column, and the product eluted with 2% ethyl acetate/methylene chloride to afford the intermediate bicyclic diimide (700 mg, 55%) as a pale orange viscous oil. MS (M+1) 432.2. $^1$H NMR (CDCl$_3$) δ 7.77 (m, 1H), 7.70 (m, 2H), 7.41 (m, 1H), 7.15 (m, 1H), 7.10 (m, 1H), 6.90-6.95 (m, 2H), 6.79 (m, 1H), 4.54 (m, 2H), 4.14 (q, 2H, J=7 Hz), 3.86 (s, 3H), 3.85 (s, 3H), 2.77 (m, 1H), 1.88 (m, 1H), 1.75 (m, 1H), 1.47 (t, 3H, J=7 Hz).

A cooled (5° C.) stirred solution of 1N lithium aluminum hydride/THF (11 mL, 11 mmol) under nitrogen was treated slowly with a solution of the above intermediate bicyclic dimide (690 mg, 1.60 mmol) in anhydrous THF (10 mL), stirred 1 h at room temperature, refluxed for 6 h, and cooled (5° C.). Water (0.45 mL), 15% sodium hydroxide (0.45 mL), and water (1.35 mL) were carefully added dropwise, followed by additional THF to facilitate stirring. The suspension was stirred 15 min, filtered through Celite® (filter cake rinsed with THF), and the filtrate concentrated in vacuo. The residue was dissolved in methylene chloride, loaded onto a silica gel column, and eluted with 4:1 methylene chloride/ethyl acetate to afford the intermediate dimethoxybenzyl bicyclic amine (415 mg, 64%) as a white solid. MS (M+1) 404.8. $^1$H NMR (CDCl$_3$) δ 7.63 (m, 2H), 7.51 (m, 1H), 7.19 (m, 1H), 7.06-7.13 (m, 2H), 6.91 (m, 1H), 6.85 (m, 1H), 6.81 (m, 1H), 4.13 (q, 2H, J=7 Hz), 3.89 (s, 3H), 3.87 (s, 3H), 3.63 (m, 2H), 3.35 (m, 1H), 3.10 (m, 1H), 2.70 (m, 1H), 2.58 (m, 1H), 1.77 (m, 1H), 1.56 (m, 1H), 1.46 (t, 3H, J=7 Hz), 0.87 (m, 1H).

A mixture of the intermediate dimethoxybenzyl bicyclic amine (403 mg, 1.00 mmol) and anhydrous potassium carbonate (290 mg, 2.1 mmol) in anhydrous methylene chloride (8 mL) in a pressure tube equipped with a stirbar was treated with 1-chloroethyl chloroformate (0.30 mL, 2.75 mmol), closed, and stirred at 40° C. for 4 h. The tube was cooled, opened, and the contents filtered (rinse with methylene chloride), and the filtrate concentrated in vacuo. The residue was dissolved in methanol (12 mL), refluxed for 1 h, cooled, treated with DOWEX® 550A-OH resin (1.5 g, prerinsed with methanol), stirred a few minutes, filtered, and the filtrate concentrated in vacuo. The residue was dissolved in methylene chloride, loaded onto a silica gel column, and eluted with 10% (9:1 ethanol/ammonia)/methylene chloride to afford a white solid. This was taken up in anhydrous ether containing a little methylene chloride, treated with 2N HCl/ether (0.6 mL, 1.2 mmol), stirred, filtered, collected, and dried in vacuo to afford 1-(6-ethoxynaphthalen-2-yl)-3-azabicyclo[3.1.0]hexane, hydrochloride (148 mg, 51%) as a white solid. MS (M+1) 254.1. $^1$H NMR (DMSO-d6) δ 9.93 (br s, 1H), 9.62 (br s, 1H), 7.73 (m, 3H), 7.31 (m, 1H), 7.25 (m, 1H), 7.12 (m, 1H), 4.10 (q, 2H, J=7 Hz), 3.71 (m, 1H), 3.51 (m, 2H), 3.38 (m, 1H), 2.15 (m, 1H), 1.44 (m, 1H), 1.36 (t, 3H, J=7 Hz), 1.14 (m, 1H). $^{13}$C NMR (DMSO-d6) δ 156.11, 133.98, 132.81, 128.71, 128.27, 127.98, 126.73, 125.04, 118.89, 106.21, 62.84, 49.27, 46.64, 30.36, 22.96, 15.38, 14.54.

J. Synthesis of 1-(4-Methylnaphthalen-1-yl)-3-azabicyclo[3.1.0]hexane Hydrochloride

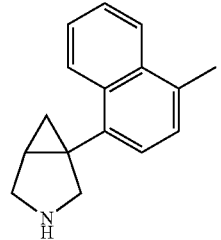 [SMILES: Cc1ccc(C23CNCC2C3)c2ccccc12]

A stirred solution of 3-bromo-1-(3,4-dimethoxybenzyl)maleimide (3.26 g, 10.0 mmol) and 4-methylnaphthalene-1-boronic acid (2.33 g, 12.5 mmol) in anhydrous dioxane (30 mL) under nitrogen was degassed over 10 min with a stream of nitrogen, then treated with cesium fluoride (4.0 g, 26 mmol) and Cl₂Pd(dppf).CH₂Cl₂ (Aldrich, 0.50 g, 0.61 mmol), stirred 1 h at room temperature, then 2 h at 40° C. The mixture was cooled, diluted with methylene chloride (125 mL), stirred a few minutes, filtered through Celite® (rinse with methylene chloride), and the filtrate concentrated in vacuo. The residue was dissolved in methylene chloride and loaded onto a silica gel column and the product eluted with 3% ethyl acetate/methylene chloride to afford a solid, which was triturated from petroleum ethers to afford the intermediate arylmaleimide (3.555 g, 92%) as a yellow solid. MS (M+1) 388.2. ¹H NMR (CDCl₃) δ 8.07 (tn, 1H), 8.00 (m, 1H), 7.50-7.62 (m, 2H), 7.39 (m, 1H), 7.00-7.05 (m, 2H), 6.82 (m, 1H), 6.78 (s, 1H), 4.74 (s, 2H), 3.89 (s, 3H), 3.86 (s, 3H), 2.73 (s, 3H).

A cooled (−20° C.) stirred solution of trimethylsulfoxonium chloride (1.48 g, 11.5 mmol) in anhydrous tetrahydrofuran (35 mL) under nitrogen was treated dropwise with n-butyllithium/hexane (2.5N, 4.0 mL, 10 mmol) and gradually warmed to 50° C. over 30 minutes. Meanwhile, a solution of the intermediate arylmaleimide (3.50 g, 9.0 mmol) in anhydrous THF (35 mL) was heated to 50° C. and added quickly in one portion to the above heated suspension. The mixture was then stirred at 50° C. for 2 h and cooled on an ice bath. Saturated aqueous ammonium chloride (5 mL) was added to quench, and the mixture was diluted with methylene chloride (200 mL), dried (MgSO₄), filtered through Celite® (rinse with methylene chloride), and concentrated in vacuo. The residue was dissolved in methylene chloride, loaded onto a silica gel column, and the product eluted with 2% ethyl acetate/methylene chloride to afford first recovered starting material (680 mg), then the intermediate bicyclic diimide (411 mg, 14% based on recovered starting material) as a pale tan solid. MS (M+1) 402.2. ¹H NMR (CDCl₃) δ 8.04 (m, 1H), 7.78 (m, 1H), 7.55 (m, 1H), 7.45 (m, 1H), 7.36 (m, 1H), 7.28 (m, 1H), 6.92-6.98 (m, 2H), 6.80 (m, 1H), 4.58 (m, 2H), 3.87 (s, 3H), 3.83 (s, 3H), 2.71 (m, 1H), 2.69 (s, 3H), 1.95 (m, 1H), 1.90 (m, 11H).

A cooled (5° C.) stirred solution of 1N lithium aluminum hydride/THF (6 mL, 6 mmol) under nitrogen was treated slowly with a solution of the above intermediate bicyclic diimide (370 mg, 0.922 mmol) in anhydrous THF (5 mL), stirred 1 h at room temperature, refluxed for 6 h, and cooled (5° C.). Water (0.23 mL), 15% sodium hydroxide (0.23 mL), and water (0.70 mL) were carefully added dropwise, followed by additional THF to facilitate stirring. The suspension was stirred 15 min, filtered through Celite® (filter cake rinsed with THF), and the filtrate concentrated in vacuo. The residue was dissolved in methylene chloride, loaded onto a silica gel column, and eluted with 3:1 methylene chloride/ethyl acetate to afford the intermediate dimethoxybenzyl bicyclic amine (252 mg, 73%) as a viscous colorless oil. MS (M+1) 374.3. ¹H NMR (CDCl₃) δ 8.35 (m, 1H), 8.00 (m, 1H), 7.51 (m, 2H), 7.37 (m, 1H), 7.24 (m, 1H), 6.90 (m, 1H), 6.76-6.84 (m, 2H), 3.88 (s, 3H), 3.86 (s, 3H), 3.62 (m, 2H), 3.32 (m, 1H), 3.20 (m, 1H), 2.82 (m, 1H), 2.67 (s, 3H), 2.55 (m, 1H), 1.76 (m, 1H), 1.62 (m, 1H), 0.80 (m, 1H).

A mixture of the intermediate dimethoxybenzyl bicyclic amine (240 mg, 0.643 mmol) and anhydrous potassium carbonate (187 mg, 1.35 mmol) in anhydrous methylene chloride (5 mL) in a pressure tube equipped with a stirbar was treated with 1-chloroethyl chloroformate (0.19 mL, 1.77 mmol), closed, and stirred at 40° C. for 4 h. The tube was cooled, opened, and the contents filtered (rinse with methylene chloride), and the filtrate concentrated in vacuo. The residue was dissolved in methanol (8 mL), refluxed for 1 h, cooled, treated with DOWEX® 550A-OH resin (1 g, prerinsed with methanol), stirred a few minutes, filtered, and the filtrate concentrated in vacuo. The residue was dissolved in ether, treated with 2.0N HCl/ether (0.4 mL, 0.8 mmol), the suspension stirred a few minutes, filtered, rinsed with ether, collected, and dried in vacuo to afford 1-(4-methylnaphthalen-1-yl)-3-azabicyclo[3.1.0]hexane, hydrochloride (149 mg, 89%) as a white solid. MS (M+1) 224.1. ¹H NMR (CDCl₃) δ 10.35 (br s, 1H), 9.93 (br s, 1H), 8.12 (m, 1H), 8.03 (m, 1H), 7.56 (m, 2H), 7.37 (m, 1H), 7.25 (m, 1H), 3.86 (m, 2H), 3.74 (m, 1H), 3.50 (m, 1H), 2.67 (s, 3H), 2.06 (m, 1H), 1.78 (m, 1H), 1.24 (m, 1H). ¹³C NMR (CDCl₃) δ 135.42, 133.17, 131.95, 126.68, 126.40, 126.15, 125.33, 124.70, 51.94, 48.04, 30.87, 22.44, 19.74, 14.76.

Example XII

Preparation of 1-Aryl-3-aza-bicyclo[3.1.0]hexane hydrochlorides Using Reaction Scheme 4

A. Synthesis of 1-(3-Fluoro-4-trifluoromethoxyphenyl)-3-azabicyclo[3.1.0]hexane Hydrochloride

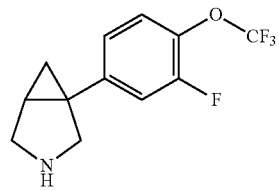 [SMILES: Fc1cc(C23CNCC2C3)ccc1OC(F)(F)F]

An ice-cooled (3° C.) stirred suspension of sodium amide (460 mg, 11.5 mmol) in anhydrous tetrahydrofuran (15 mL) under nitrogen was treated with a solution of 3-fluoro-4-(trifluoromethoxy)phenylacetonitrile (1.10 g, 5.0 mmol) in anhydrous THF (5 mL) and stirred at room temperature for 2 h, then recooled on an ice bath. Epichlorohydrin (0.52 mL, 6.0 mmol) was added via syringe in one portion, and the mixture was stirred at room temperature for 1 h, cooled on an ice bath, and quenched with saturated aqueous ammonium chloride (5 mL). The product mixture was taken up in ethyl acetate (70 mL) and the organic layer was separated. The aqueous was extracted with ethyl acetate (15 mL), and the combined organic solution was dried (MgSO₄), concentrated in vacuo, dissolved in methylene chloride, and loaded onto a silica gel column. The product was eluted with 3:1 methylene chloride/ethyl acetate to afford the intermediate hydroxymethylcyclopropylnitrile (887 mg, 65%) as a pale yellow viscous oil (3:1 syn/anti isomers by NMR). The compound was somewhat impure, but used as is.

An ice-cooled (3° C.) stirred solution of 1N LAH/THF (4.5 mL, 4.5 mtnol) under nitrogen was treated dropwise with a solution of the intermediate hydroxymethylcyclopropylnitrile (826 mg, 3.00 mmol) and the mixture was stirred on an ice bath for 2 h, then carefully quenched with water (0.17 mL), 15% sodium hydroxide (0.17 mL), and water (0.50 mL). The suspension was diluted with THF to facilitate stirring, then stirred 15 min, filtered through Celite® (filter cake rinsed with THF), and the filtrate concentrated in vacuo. The residue was dissolved in anhydrous 1,2-dichloroethane (14 mL) under nitrogen, cooled (3° C.), and treated dropwise with thionyl chloride (0.235 mL, 3.2 mmol). After stirring at room temperature for 3 h, the solution was concentrated in vacuo and the residue taken up in water (10 mL) and made basic with 5N sodium hydroxide (3 mL). The aqueous solution was extracted with methylene chloride (4×20 mL) and the combined organic solution washed with water (30 mL), dried (Na$_2$SO$_4$), and concentrated in vacuo. The residue was dissolved in methylene chloride and loaded onto a silica gel column and eluted with 10% (9:1 ethanol/ammonia)/methylene chloride to afford the bicyclic amine free base (149 mg, 19%) as a pale yellow oil. MS (M+1) 262.1. Compound carried through below was somewhat impure, but was used as is.

A stirred solution of the bicyclic amine (144 mg, 0.55 mmol) in anhydrous ether (5 mL) was treated with 2.0N HCl/ether (0.5 mL, 1.0 mmol), stirred a few minutes, filtered, rinsed with ether, collected, and dried in vacuo to afford 1-(3-fluoro-4-trifluoromethoxyphenyl)-3-azabicyclo[3.1.0]hexane, hydrochloride (107 mg, 65%) as a white solid. MS (M+1) 262.1. $^1$H NMR (CDCl$_3$) δ☐ 10.35 (br s, 1H), 9.89 (br s, 1H), 7.26 (m, 1H), 6.97-7.07 (m, 2H), 3.78 (m, 1H), 3.55-3.70 (m, 3H), 1.99 (m, 1H), 1.65 (m, 1H), 1.24 (m, 1H). $^{13}$C NMR (CDCl$_3$) δ 155.76, 153.23, 139.09, 124.15, 123.28, 116.30, 50.35, 47.44, 30.80, 23.74, 15.92.

B. Synthesis of 1-(Naphthalen-1-yl)-3-azabicyclo[3.1.0]hexane Hydrochloride

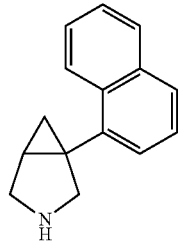 [SMILES: c1ccc2c(C34CNCC3C4)cccc2c1]

An ice-cooled (3° C.) stirred suspension of sodium amide (2.3 g, 60 mmol) in anhydrous tetrahydrofuran (15 mL) under nitrogen was treated with a solution of 1-naphthaleneacetonitrile (5 g, 30 mmol) in anhydrous THF (5 mL) and stirred at room temperature for 2 h, then recooled on an ice bath. Epichlorohydrin (2.3 mL, 30 mmol) was added via syringe in one portion, and the mixture was stirred at room temperature for 1 h, cooled on an ice bath, and quenched with saturated aqueous ammonium chloride (5 mL). The product mixture was taken up in ethyl acetate (70 mL) and the organic layer was separated. The aqueous was extracted with ethyl acetate (15 mL), and the combined organic solution was dried (MgSO$_4$), concentrated in vacuo, dissolved in methylene chloride, and loaded onto a silica gel column. The product was eluted with 3:1 methylene chloride/ethyl acetate to afford the intermediate hydroxymethylcyclopropyl-nitrile (2 g, 30%) as a pale yellow viscous oil (3:1 syn/anti isomers by NMR).

An ice-cooled (3° C.) stirred solution of 1N LAH/THF (5.6 mL, 11.2 mmol) under nitrogen was treated dropwise with a solution of the intermediate hydroxymethylcyclopropylnitrile (2.0 g, 8.97 mmol) and the mixture was stirred on an ice bath for 2 h, then carefully quenched with water (0.17 mL), 15% sodium hydroxide (0.17 mL), and water (0.50 mL). The suspension was diluted with THF to facilitate stirring, then stirred 15 min, filtered through Celite® (filter cake rinsed with THF), and the filtrate concentrated in vacuo. The residue was dissolved in anhydrous 1,2-dichloroethane (14 mL) under nitrogen, cooled (3° C.), and treated dropwise with thionyl chloride (0.235 mL, 3.2 mmol). After stirring at room temperature for 3 h, the solution was concentrated in vacuo and the residue taken up in water (10 mL) and made basic with 5N sodium hydroxide (3 mL). The aqueous solution was extracted with methylene chloride (4×20 mL) and the combined organic solution washed with water (30 mL), dried (Na$_2$SO$_4$), and concentrated in vacuo. The residue was dissolved in methylene chloride and loaded onto a silica gel column and eluted with 10% (9:1 ethanol/ammonia)/methylene chloride to afford the bicyclic amine free base (600 mg, 73%) as a pale yellow oil.

A stirred solution of the bicyclic amine (100 mg, 3.96 mmol) in anhydrous ether (5 mL) was treated with 2.0N HCl/ether (0.5 mL, 1.0 mmol), stirred a few minutes, filtered, rinsed with ether, collected, and dried in vacuo to afford 1-(naphthalen-1-yl)-3-azabicyclo[3.1.0]hexane, hydrochloride (100 mg, 85%) as a white solid. MS (M+1) 211.1. $^1$H NMR (400 MHz, DMSO-d$_6$) δ ppm 1.02-1.10 (m, 1H) 1.58 (t, J=5.08 Hz, 1H) 2.05-2.16 (m, 1H) 3.24 (d, J=10.93 Hz, 1H) 3.48 (dd, J=11.42, 5.95 Hz, 1H) 3.69 (dd, J=11.23, 5.95 Hz, 1H) 3.71-3.82 (m, 1H) 7.46 (dd, J=8.20, 7.03 Hz, 1H) 7.50-7.58 (m, 1H) 7.56-7.65 (m, 2H) 7.82-7.89 (m, 1H) 7.95 (d, J=7.42 Hz, 1H) 8.10 (d, J=8.40 Hz, 1H). $^{13}$C NMR (DMSO-d$_6$) δ 14.28, 22.74, 30.75, 47.76, 51.73, 124.72, 126.29, 126.62, 127.23, 128.89, 129.47, 132.81, 134.08, 135.16.

C. Synthesis of 1-(4-Fluoronaphthalen-1-yl)-3-azabicyclo[3.1.0]hexane Hydrochloride

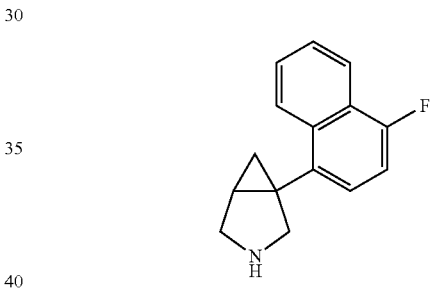

An ice-cooled (3° C.) stirred suspension of 1M sodium hexamethyldisilazane (17.2 mL, 17.2 mmol) in anhydrous tetrahydrofuran (15 mL) under nitrogen was treated with a solution of 4-fluoronaphthalen-1-acetonitrile (1.6 g, 8.6 mmol) in anhydrous THF (5 mL) and stirred at room temperature for 2 h, then recooled on an ice bath. Epichlorohydrin (0.75 mL, 9.5 mmol) was added via syringe in one portion, and the mixture was stirred at room temperature for 1 h, cooled on an ice bath, and quenched with saturated aqueous ammonium chloride (5 mL). The product mixture was taken up in ethyl acetate (70 mL) and the organic layer was separated. The aqueous was extracted with ethyl acetate (15 mL), and the combined organic solution was dried (MgSO$_4$), concentrated in vacuo, dissolved in methylene chloride, and loaded onto a silica gel column. The product was eluted with 3:1 methylene chloride/ethyl acetate to afford the intermediate hydroxymethylcyclopropylnitrile (1 g, 50%) as a pale yellow viscous oil (3:1 syn/anti isomers by NMR).

An ice-cooled (3° C.) stirred solution of 1N LAH/THF (2.6 mL, 5.2 mmol) under nitrogen was treated dropwise with a solution of the intermediate hydroxymethylcyclopropylnitrile (10 g, 4.2 mmol) and the mixture was stirred on an ice bath for 2 h, then carefully quenched with water (0.17 mL), 15% sodium hydroxide (0.17 mL), and water (0.50 mL). The suspension was diluted with THF to facilitate stirring, then stirred 15 min, filtered through Celite® (filter cake rinsed with THF), and the filtrate concentrated in vacuo. The residue was dissolved in anhydrous 1,2-dichloroethane (14 mL) under nitrogen, cooled (3° C.), and treated dropwise with thionyl chloride (0.235 mL, 3.2 mmol). After stirring at room temperature for 3 h, the solution was concentrated in vacuo and the residue taken up in water (10 mL) and basified with 5N sodium hydroxide (3 mL). The aqueous solution was extracted with methylene chloride (4×20 mL) and the combined organic solution washed with water (30 mL), dried ($Na_2SO_4$), and concentrated in vacuo. The residue was dissolved in methylene chloride and loaded onto a silica gel column and eluted with 10% (9:1 ethanol/ammonia)/methylene chloride to afford the bicyclic amine free base (400 mg, 40%) as a pale yellow oil.

A stirred solution of the bicyclic amine (100 mg, 0.44 mmol) in anhydrous ether (5 mL) was treated with 2.0N HCl/ether (0.5 mL, 1.0 mmol), stirred a few minutes, filtered, rinsed with ether, collected, and dried in vacuo to afford 1-(4-fluoronaphthalen-1-yl)-3-azabicyclo[3.1.0]hexane, hydrochloride (100 mg, 85%) as a white solid. MS (M+1) 228.1. $^1$H NMR (DMSO-$d_6$) δ 1.06 (t, J=6.93 Hz, 1H) 1.58 (t, J=5.08 Hz, 1H) 2.03-2.19 (m, 1H) 3.16-3.28 (m, 1H) 3.47 (dd, J=11.42, 5.95 Hz, 1H) 3.68 (dd, J=11.13, 5.86 Hz, 1H) 3.76 (s, 1H) 7.29 (dd, J=10.64, 7.91 Hz, 1H) 7.47-7.81 (m, 3H) 8.08 (d, J=8.00 Hz, 1H) 8.15 (d, J=8.40 Hz, 1H). $^{13}$C NMR (DMSO-$d_6$) δ 22.77, 30.27, 47.72, 51.66, 109.93, 121.39, 123.69, 125.06, 127.40, 128.44, 131.58, 134.08.

Example XIII

Preparation of 1-Aryl-3-methyl-3-aza-bicyclo[3.1.0]hexane Using Reaction Scheme 11

A. Synthesis of 3-Methyl-1-(naphthalen-1-yl)-3-azabicyclo[3.1.0]hexane Hydrochloride

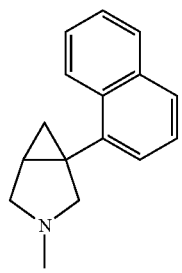 [SMILES: CN1CC2CC2(c2cccc3ccccc23)C1]

A stirred solution/suspension of 1-(1-naphthalen-1-yl)-3-azabicyclo[3.1.0]hexane (500 mg, 2.4 mmol) in 1,2-dichloromethane (12 mL) was treated with 37% aqueous formaldehyde (1.2 mL, 24 mmol), then with sodium triacetoxyborohydride (2.5 g, 12 mmol), stirred for 3 h, then treated with 1N sodium hydroxide (5 mL). The organic layer was separated and the aqueous solution was extracted with methylene chloride containing 2-propanol (2×10 mL). The combined organic solution was dried ($MgSO_4$) and concentrated in vacuo to afford 3-methyl-1-(naphthalen-1-yl)-3-azabicyclo[3.1.0]hexane (76 mg, 84%, essentially pure without chromatography). This was dissolved in anhydrous ether (5 mL) and treated with 2N HCl/ether (0.35 mL, 0.7 mmol), stirred a few minutes, filtered, rinsed with ether, collected, and dried in vacuo to afford 3-methyl-1-(naphthalen-1-yl)-3-azabicyclo[3.1.0]hexane, hydrochloride (72 mg, 82%) as a white solid. MS (M+1) 224.1. $^1$H NMR (DMSO-$d_6$) δ 0.97 (dd, J=7.71, 6.54 Hz, 1H) 1.97-2.10 (m, 1H) 2.14-2.24 (m, 1H) 2.77-2.81 (m, J=4.69, 4.69 Hz, 3H) 3.20-3.31 (m, 1H) 3.67-3.76 (m, 2H) 3.94 (dd, J=11.13, 5.08 Hz, 1H) 7.47 (dd, J=8.20, 7.03 Hz, 1H) 7.51-7.58 (m, 1H) 7.59-7.66 (m, 2H) 7.88 (d, J=8.20 Hz, 1H) 7.95 (d, J=7.61 Hz, 1H) 8.15 (d, J=8.40 Hz, 1H); $^{13}$C (DMSO-$d_6$) δ 14.53, 22.27, 30.45, 56.77, 60.55, 124.71, 126.25, 126.65, 127.30, 128.31, 128.94, 129.41, 132.98, 134.02, 134.97

B. Synthesis of 3-Methyl-1-(4-fluoronaphthalen-1-yl)-3-azabicyclo[3.1.0]hexane Hydrochloride

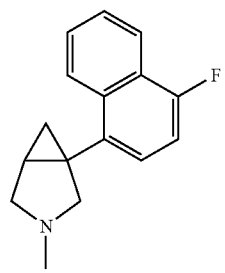 [SMILES: CN1CC2CC2(c2ccc(F)c3ccccc23)C1]

A stirred solution/suspension of 1-(4-fluoronaphthalen-1-yl)-3-azabicyclo[3.1.0]hexane (215 mg, 0.95 mmol) in 1,2-dichloromethane (12 mL) was treated with 37% aqueous formaldehyde (0.5 mL, 9.5 mmol), then with sodium triacetoxyborohydride (1.25 g, 4.75 mmol), stirred for 3 h, then treated with 1N sodium hydroxide (5 mL). The organic layer was separated and the aqueous solution was extracted with methylene chloride containing a little 2-propanol (2×10 mL). The combined organic solution was dried ($MgSO_4$) and concentrated in vacuo to afford 1-(4-fluoronaphthalen-1-yl)-3-methyl-3-azabicyclo[3.1.0]hexane (150 mg, 65%, essentially pure without chromatography). This was dissolved in anhydrous ether (5 mL) and treated with 2N HCl/ether (0.35 mL, 0.7 mmol), stirred a few minutes, filtered, rinsed with ether, collected, and dried in vacuo to afford 3-methyl-1-(4-fluoronaphthalen-1-yl)-3-aza-bicyclo[3.1.0]hexane, hydrochloride (150 mg, 82%) as a white solid. MS (M+1) 242.1. $^1$H NMR (DMSO-$d_6$) δ 0.91-1.01 (m, 1H) 2.01-2.09 (m, 1H) 2.13-2.24 (m, 1H) 2.72-2.84 (m, J=4.69 Hz, 3H) 3.16-3.30 (m, 1H) 3.72 (q, J=5.60 Hz, 2H) 3.93 (dd, J=11.23, 5.17 Hz, 1H) 7.31 (dd, J=10.74, 8.01 Hz, 1H) 7.48-7.79 (m, 3H) 8.07 (d, J=8.20 Hz, 1H) 8.20 (d, J=8.40 Hz, 1H). $^{13}$C (DMSO-$d_6$) δ 14.51, 22.36, 29.97, 56.72, 60.47, 109.90, 121.34, 123.61, 125.04, 127.43, 128.50, 131.39, 134.24 157.08.

C. Synthesis of 1-(4-Methylnaphthalen-1-yl)-3-methyl-3-azabicyclo[3.1.0]hexane Hydrochloride

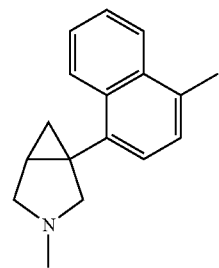 [SMILES: Cc1ccc(C23CC2CN(C)C3)c2ccccc12]

A stirred solution/suspension of 1-(4-methylnaphthalen-1-yl)-3-azabicyclo[3.1.0]hexane (85 mg, 0.38 mmol) in 1,2-dichloromethane (12 mL) was treated with 37% aqueous formaldehyde (0.23 mL, 3.0 mmol), then with sodium triacetoxyborohydride (318 mg, 1.5 mmol), stirred for 3 h, then treated with 1N sodium hydroxide (5 mL). The organic layer was separated and the aqueous solution was extracted with methylene chloride containing 2-propanol (2×10 mL). The combined organic solution was dried (MgSO$_4$) and concentrated in vacuo to afford 1-(4-methylnaphthalen-1-yl)-3-methyl-3-azabicyclo[3.1.0]hexane (76 mg, 84%, essentially pure without chromatography). This was dissolved in anhydrous ether (5 mL) and treated with 2N HCl/ether (0.35 mL, 0.7 mmol), stirred a few minutes, filtered, rinsed with ether, collected, and dried in vacuo to afford 1-(4-methylnaphthalen-1-yl)-3-methyl-3-azabicyclo[3.1.0]hexane, hydrochloride (72 mg, 82%) as a white solid. MS (M+1) 238.1. $^1$H NMR (CDCl$_3$) δ 12.70 (br s, 1H), 8.16 (m, 1H), 8.04 (m, 1H), 7.58 (m, 2H), 7.37 (m, 1H), 7.26 (m, 1H), 4.20 (m, 1H), 4.06 (m, 1H), 3.50 (m, 1H), 3.14 (m, 1H), 2.90 (d, 3H, J=5 Hz), 2.68 (s, 3H), 2.40 (m, 1H), 2.13 (m, 1H), 1.22 (m, 1H). $^{13}$C NMR (CDCl$_3$) δ 135.73, 133.21, 131.70, 126.81, 126.35, 126.33, 125.41, 124.54, 61.65, 57.62, 41.52, 30.97, 22.37, 19.75.

Example XIV

Preparation of 1-Aryl-3-aza-bicyclo[3.1.0]hexane and 1-Aryl-3-methyl-3-aza-bicyclo[3.1.0]hexane Using Reaction Schemes 5, 6 and 13

A. Synthesis of cyclopropanecarbonitriles (1) Synthesis of (1S,2R)-2-Hydroxymethyl-1-naphthyl-cyclopropancarbonitrile as Representative Procedure for (1)-(6)

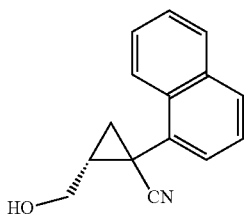 [SMILES: N#CC1(c2cccc3ccccc23)C[C@H]1CO]

To a stirring solution of 1-naphthylacetonitrile (15 g, 0.090 moles) in anhydrous THF (150 mL) at −15 to −10° C. under nitrogen, was added 90 mL of sodium bis (trimethylsilyl) amide (NaHMDS, 1M in THF) slowly via addition funnel while keeping the temperature below −5° C. The resulting brown mixture was stirred for 0.75 h between −10° C. and 0° C. R-epichlorohydrin (8.3 g, 0.090 moles in 10 mL of THF) was added slowly over 15 minutes while keeping the temperature below −10° C. The mixture was stirred between −10° C. and 0° C. for 0.5 h then NaHMDS (90 mL, 0.090 moles) was added while keeping the temperature between −10° C. and −15° C. The mixture was stirred for 45 minutes then warmed to room temperature, stirred 30 min and quenched with 40 mL of water. The mixture was stirred 5 minutes, allowed to settle and the layers were separated. The lower aqueous layer was re-extracted with EtOAc (~75 mL). The organics were combined, washed with 100 mL of saturated NaCl, dried over Na$_2$SO$_4$, filtered and concentrated to provide an oil. Chromatography through a short silica gel plug eluting with EtOAc/Heptane (5-50%) afforded 6.8 g of product. $^1$H NMR shows a mixture of diastereomers (~3:1 cis/trans). The product was carried forward to reduction without further characterization. $^1$H NMR (400 MHz, CDCl$_3$, partial assignment) δ 1.53-1.66 (m, 2H), 1.85-1.95 (m, 1H), 3.18 (br. s., 1H), 3.85-3.96 (m, 1H), 4.13-4.22 (m, 1H), 7.31-7.39 (m, 1H), 7.43-7.55 (m, 2H), 7.57-7.65 (m, 1H), 7.78-7.91 (m, 2H), 8.46-8.54 (m, 1H).

(2) (1R,2S)-2-Hydroxymethyl-1-naphthyl-cyclopropancarbonitrile

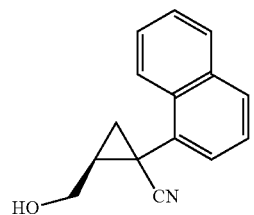 [SMILES: N#CC1(c2cccc3ccccc23)C[C@@H]1CO]

Yield==34%; H NMR (400 MHz, CDCl$_3$, partial assignment) δ 1.53-1.66 (m, 2H), 1.85-1.95 (m, 1H), 3.18 (br. s., 1H), 3.85-3.96 (m, 1H), 4.13-4.22 (m, 1H), 7.31-7.39 (m, 1H), 7.43-7.55 (m, 2H), 7.57-7.65 (m, 1H), 7.78-7.91 (m, 2H), 8.46-8.54 (m, 1H).

(3) (1S,2S)-2-Hydroxymethyl-2-naphthyl-cyclopropancarbonitrile

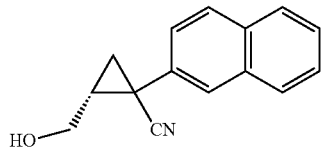 [SMILES: N#CC1(c2ccc3ccccc3c2)C[C@H]1CO]

Yield==63%; $^1$H NMR (400 MHz, CDCl$_3$, partial assignment) δ 1.59-1.66 (m, 1H), 1.68-1.74 (m, 1H), 1.98-2.07 (m, 1H), 2.41 (br. s., 1H), 3.85 (dd, J=12.10, 8.30 Hz, 1H), 4.07-4.13 (m, 1H), 7.33 (dd, J=8.49, 2.05 Hz, 1H), 7.45-7.53 (m, 2H), 7.77-7.87 (m, 4H).

(4) (1R,2S)-2-Hydroxymethyl-2-naphthyl-cyclopropancarbonitrile

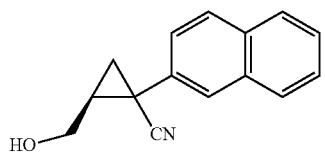

Yield=56%; $^1$H NMR (400 MHz, CDCl$_3$) δ 1.64-1.73 (m, 3H), 1.94-2.07 (m, 2H), 3.97 (dd, J=11.91, 8.69 Hz, 1H), 4.28

(dd, J=11.91, 5.08 Hz, 1H), 7.39-7.45 (m, 1H), 7.48-7.59 (m, 2H), 7.62-7.68 (m, 1H), 7.88 (dd, J=15.18, 8.15 Hz, 2H), 8.48 (dd, J=8.49, 0.78 Hz, 1H).

(5) (1S,2R)-2-Hydroxymethyl-1-(3-fluoro-4-methylphenyl)cyclopropancarbonitrile

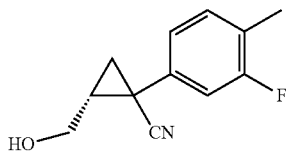

Yield—not isolated; ¹H NMR (400 MHz, CDCl₃, partial assignment) δ 1.44 (dd, J=6.98, 6.00 Hz, 1H), 1.72 (dd, J=9.42, 5.91 Hz, 1H), 1.83-1.93 (m, 1H), 2.19-2.44 (m, 4H), 3.77 (dd, J=12.10, 8.30 Hz, 1H), 4.00-4.08 (m, 1H), 6.88-7.01 (m, 2H), 7.08-7.21 (m, 1H).

(6) (1R,2S)-2-Hydroxymethyl-1-(3-fluoro-4-methylphenyl)cyclopropancarbonitrile

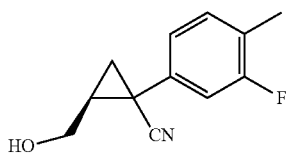

Yield=40%; ¹H NMR (400 MHz, CDCl₃) δ 1.24 (t, J=7.13 Hz, 1H), 1.56 (d, J=8.10 Hz, 1H), 1.83-1.92 (m, 1H), 2.23 (d, J=1.76 Hz, 3H), 2.46 (hr. s., 1H), 3.76 (dd, J=12.06, 8.25 Hz, 1H), 4.03 (dd, J=12.10, 5.17 Hz, 1H), 6.92 (dd, J=10.54, 1.85 Hz, 1H), 6.98 (dd, J=7.91, 1.95 Hz, 1H), 7.02-7.21 (m, 1H).

(7) Synthesis of (1S,2R)-2-Hydroxymethyl-1-(4-chloro-3-trifluoromethylphenyl)cyclopropancarbonitrile as Representative Procedure for (7)-(12)

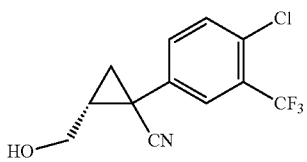 [SMILES: N#CC1(c2ccc(Cl)c(C(F)(F)F)c2)C[C@H]1CO]

To a stirring solution of 4-chloro-3-trifluoromethylphenylacetonitrile (11 g, 0.050 moles) in anhydrous THF (100 mL) at −18° C. under nitrogen, was added 1.95 g (0.050 mmoles 1 eq) of sodium amide in one portion. The resulting mixture was stirred for 1 h between −15° C. and −5° C. The dark mixture was cooled to −15° C. and R-epichlorohydrin (4.6 g, 0.050 moles in 10 mL of THF) was added slowly over 15 minutes while keeping the temperature below −10° C. The mixture was stirred between −15° C. and −5° C. for 0.75 h then cooled to −15° C. and another 1 equivalent (1.95 g) of sodium amide was added in one portion. The mixture was stirred for 3.5 h while allowing to warm to between −10 and +5° C. then allowed to warm to room temperature and quenched with 50 mL of saturated NH₄Cl. The mixture was stirred 5 minutes, allowed to settle and the layers were separated. The lower aqueous layer was re-extracted with EtOAc (2×50 mL). The organics were combined, washed with 100 mL of saturated NaCl, dried over Na₂SO₄, filtered and concentrated to a dark oil. Chromatography through a short silica gel plug eluting with EtOAc/Heptane (5-35%) afforded 5.5 g (40%) of product as a dark red oil. ¹H NMR shows a mixture of diastereomers. ¹H NMR (400 MHz, CDCl₃) δ 1.42-1.52 (m, 1H), 1.59-1.72 (m, 1H), 1.89-1.99 (m, 1H), 2.08 (br. s., 1H), 3.79 (dd, J=12.08, 8.33 Hz, 1H), 4.12 (dd, J=12.13, 4.90 Hz, 1H), 7.42-7.55 (m, 1H), 7.56-7.63 (m, 1H), 7.67-7.76 (m, 1H).

(8) (1R,2S)-2-Hydroxymethyl-1-(4-chloro-3-trifluoromethylphenyl)cyclopropancarbonitrile

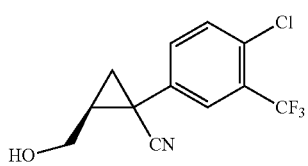

Yield==60%; ¹H NMR (400 MHz, CDCl₃) δ 1.42-1.52 (m, 1H), 1.59-1.72 (m, 1H), 1.89-1.99 (m, 1H), 2.08 (br. s., 1H), 3.79 (dd, J=12.08, 8.33 Hz, 1H), 4.12 (dd, J=12.13, 4.90 Hz, 1H), 7.42-7.55 (m, 1H), 7.56-7.63 (m, 1H), 7.67-7.76 (m, 1H).

(9) (1S,2S)-2-Hydroxymethyl-1-(4-chloro-3-fluorolphenyl)cyclopropancarbonitrile

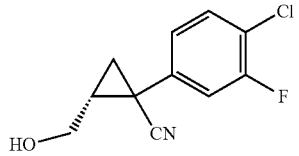

Yield=41%; ¹H NMR (400 MHz, CDCl₃) δ 1.57-1.65 (m, 2H), 1.84-1.95 (m, 1H), 2.61 (q, J=5.27 Hz, 1H), 3.68-3.78 (m, 1H), 4.01-4.11 (m, 1H), 7.02-7.10 (m, 1H), 7.29-7.40 (m, 1H).

(10) (1R,2S)-2-Hydroxymethyl-1-(4-chloro-3-fluorolphenyl)cyclopropancarbonitrile

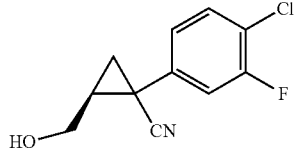 [SMILES: N#CC1(c2ccc(Cl)c(F)c2)C[C@@H]1CO]

Yield==39%; ¹H NMR (400 MHz, CDCl₃) δ 1.55-1.65 (m, 2H), 1.84-1.95 (m, 1H), 2.61 (q, J=5.27 Hz, 1H), 3.68-3.78 (m, 1H), 4.01-4.11 (m, 1H), 7.00-7.10 (m, 1H), 7.31-7.40 (m, 1H).

(11) (1S,2H)-2-Hydroxymethyl-1-(3-chloro-4-fluorolphenyl)cyclopropancarbonitrile

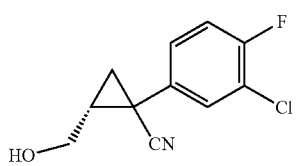 [SMILES: N#CC1(c2ccc(F)c(Cl)c2)C[C@H]1CO]

Yield==20%; ¹H NMR (400 MHz, CDCl₃) δ 1.36-1.46 (m, 1H), 1.55-1.64 (m, 1H), 1.84-1.94 (m, 1H), 2.07-2.20 (m, 1H), 3.76 (dd, J=12.10, 8.40 Hz, 1H), 4.05-4.12 (m, 1H), 7.10-7.15 (m, 1H), 7.17-7.23 (m, 1H), 7.33-7.37 (m, 1H)

(12) (1R,2S)-2-Hydroxymethyl-1(3-chloro,4-fluorophenyl)cyclopropancarbonitrile

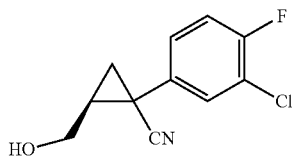 [SMILES: N#CC1(c2ccc(F)c(Cl)c2)C[C@@H]1CO]

Yield=34%; ¹H NMR (400 MHz, CDCl₃) δ 1.37-1.46 (m, 1H), 1.54-1.65 (m, 1H), 1.77 (dd, J=9.47, 5.95 Hz, 1H), 1.83-1.95 (m, 1H), 3.76 (dd, J=12.10, 8.40 Hz, 1H), 4.06-4.13 (m, 1H), 7.12-7.16 (m, 1H), 7.17-7.22 (m, 1H), 7.33-7.38 (m, 1H).

B. Synthesis of Cyclopropyl Methanol Compounds (1) Synthesis of (1R,2S)-(2-Aminomethyl-2-(1-naphthyl)cyclopropyl)-methanol as Representative Procedure for (1)-(6)

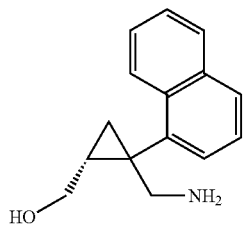 [SMILES: NCC1(c2cccc3ccccc23)C[C@H]1CO]

To a stirring slurry of lithium aluminum hydride (LAH), (2.31 g, 0.061 moles) in THF (30 mL) at 0-5° C. was added a solution of crude nitrile, A(1) (6.8 g, (0.030 moles) in 80 mL of THF), slowly via addition funnel while keeping the temperature below 10° C. The mixture was stirred for 45 minutes while warming to ~15° C., after which time, no starting material was observed by TLC analysis (SiO₂ plate, EtOAc/Heptane 1:1). The reaction was carefully quenched by the dropwise addition of H₂O (2.5 mL) followed by 2.5 mL of 15% NaOH and lastly 8 mL of H₂O. The resulting off white slurry was stirred for 1 h then filtered through a Celite pad, washing with 2×50 mL of EtOAc. The filtrate was concentrated to a pale yellow oil. Chromatography on silica gel eluting with CH₂Cl₂/MeOH/NH₄OH (20:1:0.1 to 10:1:0.1) afforded 3.3 g (47%) of pure amino alcohol as a light brown colored oil. ¹H NMR (400 MHz, CDCl₃) δ 1.01-1.09 (m, J=5.22, 5.22 Hz, 1H), 1.15 (dd, J=8.64, 4.93 Hz, 1H), 1.70 (br. s., 1H), 1.77-1.89 (m, 1H), 2.52 (br. s., 1H), 3.34-3.56 (m, J=11.52, 11.52 Hz, 2H), 3.58-3.69 (m, 1H), 4.17-4.30 (m, J=11.23 Hz, 2H), 7.39-7.55 (m, 3H), 7.56-7.62 (m, 1H), 7.77 (d, J=8.20 Hz, 1H), 7.84-7.91 (m, 1H), 8.28 (br. s., 1H).

(2) (1S,2R)-(2-Aminomethyl-2-(1-naphthyl)cyclopropyl)-methanol

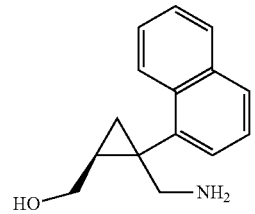 [SMILES: NCC1(c2cccc3ccccc23)C[C@@H]1CO]

Yield=47%; ¹H NMR (400 MHz, CDCl₃) 1.00-1.09 (m, 1H) 1.13 (dd, 0.1=8.59, 4.78 Hz, 1H) 1.81-1.93 (m, 1H) 2.61-3.05 (m, 4H) 3.41-3.51 (m, 1H) 3.55-3.64 (m, 1H) 4.17-4.28 (m, 1H) 7.39-7.57 (m, 3H) 7.65 (d, J=6.93 Hz, 1H) 7.73-7.80 (m, 1H) 7.85-7.91 (m, 1H) 8.30 (br. s., 1H).

(3) (1R,2S)-(2-Aminomethyl-2-(2-naphthyl)cyclopropyl-methanol

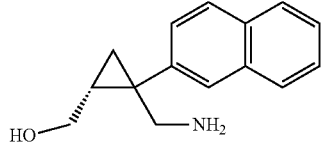 [SMILES: NCC1(c2ccc3ccccc3c2)C[C@H]1CO]

Yield=56%; ¹H NMR (400 MHz, CDCl₃) δ 0.79-0.79 (m, 1H), 1.03 (dd, J=8.59, 4.78 Hz, 1H), 1.83-1.93 (m, 1H), 2.54 (br. s., 3H), 2.64 (d, J=12.59 Hz, 1H), 3.40 (dd, J=12.15, 11.08 Hz, 1H), 3.53 (dd, J=12.59, 0.78 Hz, 1H), 4.17 (dd, J=12.20, 5.47 Hz, 1H), 7.41-7.54 (m, 3H), 7.77-7.83 (m, 3H), 7.85 (d, J=1.37 Hz, 1H).

(4) (1S,2R)-(2-Aminomethyl-2-(2'-naphthyl)cyclopropyl-methanol

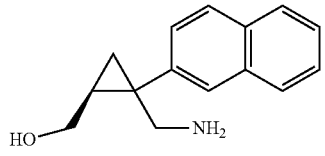 [SMILES: NCC1(c2ccc3ccccc3c2)C[C@@H]1CO]

Yield=55%; ¹H NMR (400 MHz, CDCl₃) δ 0.80 (t, J=5.12 Hz, 1H), 0.82 (m, 1H), 1.03 (dd, J=8.59, 4.78 Hz, 1H), 1.82-

1.94 (m, 1H), 2.47-2.70 (m, J=12.59 Hz, 4H), 3.40 (dd, J=12.15, 11.08 Hz, 1H), 3.53 (dd, J=12.59, 0.78 Hz, 1H), 4.17 (dd, J=12.20, 5.47 Hz, 1H), 7.41-7.54 (m, 3H), 7.77-7.84 (m, 3H), 7.85 (d, J=1.37 Hz, 1H).

(5) (1R,2S)-(2-Aminomethyl-2-(3-fluoro,4-methylphenyl)cyclopropyl) methanol

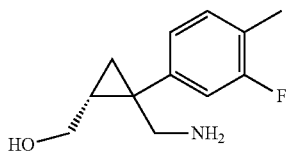

Yield=38%; ¹H NMR (400 MHz, CDCl₃) δ 0.67-0.75 (m, J=5.17, 5.17 Hz, 1H), 0.93 (dd, J=8.59, 4.78 Hz, 1H), 1.66-1.77 (m, 1H), 2.23 (d, J=1.85 Hz, 3H), 2.56 (d, J=12.59 Hz, 1H), 2.95 (br. s., 3H), 3.32 (dd, J=12.25, 10.98 Hz, 1H), 3.43 (dd, J=12.54, 0.83 Hz, 1H), 4.10 (dd, J=12.30, 5.47 Hz, 1H), 6.99-7.15 (m, 3H).

(6) (1S,2R)-(2-Aminomethyl-2-(3-fluoro,4-methylphenyl)cyclopropyl)-methanol

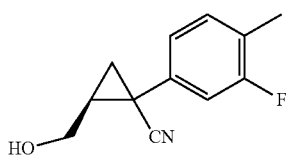

Yield=43%; ¹H NMR (400 MHz, CDCl₃) δ 0.72 (t, J=5.17 Hz, 1H), 0.93 (dd, J=8.59, 4.78 Hz, 1H), 1.65-1.77 (m, 1H), 2.23 (d, J=1.85 Hz, 3H), 2.56 (d, J=12.59 Hz, 1H), 2.95 (br. s., 3H), 3.32 (dd, J=12.25, 10.98 Hz, 1H), 3.43 (dd, J=12.54, 0.83 Hz, 1H), 4.10 (dd, J=12.30, 5.47 Hz, 1H), 6.95-7.17 (m, 3H).

(7) Synthesis of (1R,2S)-(2-Aminomethyl-2-(4-chloro-3-trifluoromethylphenyl)cyclopropyl)-methanol as Representative Procedure for (7)-(12)

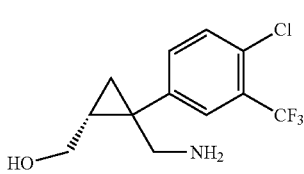

To a stirring solution of (1S,2R)-2-Hydroxymethyl-1-(4-chloro-3-trifluoromethylphenyl)cyclopropancarbonitrile prepared according to Example XIV.A(7) above (5.5 g mg, 20 mmoles) in THF (75 mL) at room temperature under nitrogen was added 29.9 mL (60 mmoles) of BH₃.Me₂S (2M in THF). The reaction flask was fitted with a Dean Stark trap and the mixture was heated to a gentle reflux. The mixture was refluxed for 3 h while distilling out solvent and Me₂S (about 20-25 mL was collected). No starting nitrile was observed by TLC analysis (SiO₂ plate, EtOAc/Heptane 1:1). The mixture was cooled to room temperature and carefully quenched with MeOH (10 mL) then added 20 mL of 6N HCl and refluxed for 0.5 h. The mixture was cooled to room temperature, basified with solid K₂CO₃. The resulting slurry was diluted with EtOAc (75 mL), filtered and concentrated to a pale yellow oil. Chromatography on silica gel eluting with CH₂Cl₂/MeOH/NH₄OH (50:1:0.1 to 10:1:0.1) afforded 2.35 g (42%) of the pure amino alcohol as a pale yellow oil. ¹H NMR (400 MHz, CDCl₃) δ 0.72-0.84 (m, 1H), 0.87-0.99 (m, J=7.86, 4.44 Hz, 1H), 1.57-1.78 (m, J=21.57 Hz, 2H), 2.60 (d, J=12.98 Hz, 1H), 2.92 (s, 3H), 3.24-3.48 (m, 2H), 3.53-3.71 (m, J=3.61 Hz, 1H), 4.02-4.17 (m, 1H), 7.37-7.55 (m, 2H), 7.66 (s, 1H).

(8) (1S,2R)-(2-Aminomethyl-2-(4-chloro,3-trifluormethylphenyl)cyclopropyl)-methanol

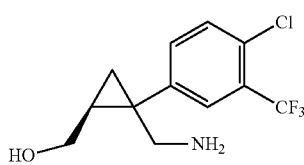 [SMILES: NCC1(c2ccc(Cl)c(C(F)(F)F)c2)C[C@@H]1CO]

Yield=35%; ¹H NMR (400 MHz, CDCl₃) δ 0.80 (t, J=5.31 Hz, 1H), 0.94 (dd, J=8.69, 5.03 Hz, 1H), 1.61-1.77 (m, 1H), 2.61 (d, J=12.90 Hz, 1H), 2.83 (br. s., 3H), 3.33 (dd, J=12.26, 10.98 Hz, 1H), 3.38-3.46 (m, 1 II), 4.10 (dd, J=12.31, 5.35 Hz, 1H), 7.40-7.46 (m, 1H), 7.47-7.53 (m, 1H), 7.67 (d, J=2.01 Hz, 1H).

(9) (1R,2S)-(2-Aminomethyl-2-(4-chloro-3-fluorophenyl)cyclopropyl)-methanol

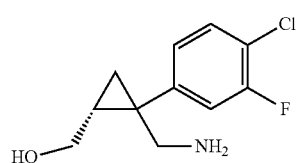

Yield=56%; ¹H NMR (400 MHz, CDCl₃) δ 0.73-0.79 (m, 1H), 0.94 (dd, J=8.71, 5.01 Hz, 1H), 1.65-1.77 (m, 1H), 2.54-2.62 (m, J=12.69 Hz, 1H), 2.78 (d, J=10.74 Hz, 3H), 3.32 (dd, J=12.30, 10.93 Hz, 1H), 3.40-3.48 (m, 1H), 4.10 (dd, J=12.40, 5.37 Hz, 1H), 7.09-7.20 (m, 2H), 7.28-7.36 (m, 1H).

(10) (1S,2R)-(2-Aminomethyl-2-(4-chloro,3-fluorophenyl)cyclopropyl)-methanol

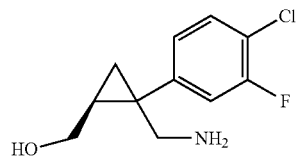 [SMILES: NCC1(c2ccc(Cl)c(F)c2)C[C@@H]1CO]

Yield=37%; ¹H NMR (400 MHz, CDCl₃) δ 0.74-0.80 (m, 1H), 0.95 (dd, J=8.69, 4.98 Hz, 1H), 1.66-1.78 (m, 1H), 2.01 (br. s., J=74.09 Hz, 3H), 2.59 (d, J=12.69 Hz, 1H), 3.3:3 (dd, J=12.30, 10.93 Hz, 1H), 3.44 (dd, J=12.74, 0.93 Hz, 1H), 4.11

(dd, J=12.35, 5.42 Hz, 1H), 7.11-7.15 (m, 1H), 7.18 (dd, J=10.01, 2.00 Hz, 1H), 7.33 (t, J=7.96 Hz, 1H).

(11) (1R,2S)-(2-Aminomethyl-2-(3-chloro,4-fluorophenyl)cyclopropyl)-methanol

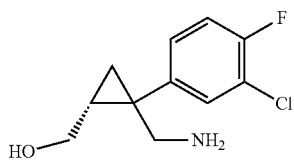 [SMILES: NCC1(c2ccc(F)c(Cl)c2)C[C@H]1CO]

Yield=47%; $^1$H NMR (400 MHz, CDCl$_3$) δ 0.74 (t, J=5.22 Hz, 1H), 0.93 (dd, J=8.69, 4.88 Hz, 1H), 1.61-1.75 (m, 1H), 2.57 (d, J=12.79 Hz, 1H), 2.72 (br. s., 3H), 3.31 (dd, J=12.30, 10.93 Hz, 1H), 3.39 (dd, J=12.79, 0.98 Hz, 1H), 4.10 (dd, J=12.30, 5.37 Hz, 1H), 7.07 (t, J=8.69 Hz, 1H), 7.22-7.29 (m, 1H), 7.43 (dd, J=7.08, 2.20 Hz, 1H).

(12) (1S,2R)-(2-Aminomethyl-2-(3-chloro,4-fluorophenyl)cyclopropyl) methanol

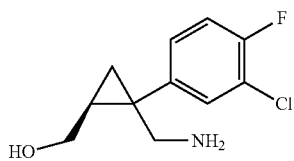 [SMILES: NCC1(c2ccc(F)c(Cl)c2)C[C@@H]1CO]

Yield=55%; $^1$H NMR (400 MHz, CDCl$_3$) δ 0.75 (m, 1H), 0.93 (dd, J=8.69, 4.88 Hz, 1H), 1.61-1.75 (m, 1H), 2.59 (d, J=12.79 Hz, 1H), 2.74 (hr. s., 3H), 3.31 (dd, J=12.30, 10.93 Hz, 1H), 3.39 (dd, J=12.79, 0.98 Hz, 1H), 4.10 (dd, J=12.30, 5.37 Hz, 1H), 7.07 (t, J=8.69 Hz, 1H), 7.23-7.28 (m, 1H), 7.45 (dd, J=7.08, 2.20 Hz, 1H).

C. Synthesis of various naphthyl and phenyl 3-azabicyclo[3.1.0]hexane Hydrochlorides (1) Synthesis of 1S,5R-(−)-1-(1-naphthyl)-3-azabicyclo[3.1.0]hexane Hydrochloride as Representative Procedure for (1)-(6)

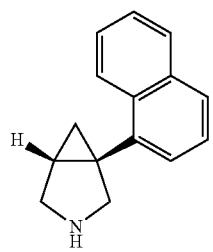 [SMILES: c1ccc2c([C@@]34CNC[C@@H]3C4)cccc2c1]

To a stirring solution of (1R,2S)-(2-Aminomethyl-2-(1-naphthyl)cyclopropyl)-methanol prepared according to Example XIVB(1) above (3.2 g, 0.014 moles) in 35 mL of dichloroethane (DCE), at room temperature under nitrogen, was added 1.2 mL (0.017 moles, 1.2 eq) of SOCl$_2$ slowly via syringe while keeping the temperature below 50° C. (Note: The reaction exotherms from 22° C. to 45° C.) The resulting mixture was stirred for 3.5 h at room temperature after which time, TLC analysis (SiO$_2$ plate, CH$_2$Cl$_2$/MeOH/NH$_4$OH (10:1:0.1)) showed no starting material remaining. The mixture was quenched with 40 mL of water and the layers were separated. The organic layer was washed with H$_2$O (2×50 mL). The aqueous layers were combined, made basic with 10N NaOH to pH=10 (pH paper) and extracted with 2×100 mL of CH$_2$Cl$_2$. The combined organics were dried over Na$_2$SO$_4$, filtered and concentrated to an oil. The oil was dissolved in MeOH (20 mL), treated with 15 mL of 2M HCl/Et$_2$O and concentrated in vacuo to a suspension. The slurry was diluted with 25 mL of Et$_2$O, filtered and washed with 35 mL of Et$_2$O. The solid product was dried overnight (~29 mmHg, 50° C.) to give 1 g (29%) of pure product as a white solid. $^1$H NMR (400 MHz, CDCl$_3$) δ 1.22 (t, J=7.37 Hz, 1H), 1.58 (dd, J=6.00, 4.73 Hz, 1H), 2.03-2.10 (m, 1H), 3.25-3.27 (m, 1H), 3.42 (d, 11.52 Hz, 1H), 3.64 (d, J=11.62 Hz, 1H), 3.74-3.85 (m, 2H), 7.32-7.39 (m, 1H), 7.40-7.48 (m, 2H), 7.48-7.55 (m, 1H), 7.75 (d, J=8.20 Hz, 1H), 7.79-7.85 (m, 1H), 8.04 (d, J=8.30 Hz, 1H), $^{13}$C NMR (101 MHz, CDCl$_3$) δ 14.54, 22.43, 30.89, 48.01, 51.89, 123.92, 125.60, 126.24, 126.93, 129.04, 129.17, 133.55, 134.04, LC/MS (m/z M$^{+1}$) 210.0, [α]$_D$ (c=1, MeOH), =−54.4.

(2) 1R,5S-(+)-1-(1-naphthyl)-3-azabicyclo[3.1.0]hexane Hydrochloride

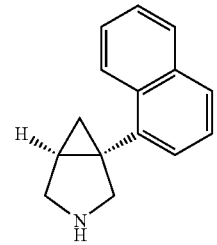 [SMILES: c1ccc2c([C@]34CNC[C@H]3C4)cccc2c1]

Yield=29%; $^1$H NMR (400 MHz, METHANOL-d$_4$) δ 1.24-1.32 (m, 1H), 1.32-1.37 (m, 1H), 2.23-2.31 (m, 1H), 3.47 (d, J=11.71 Hz, 1H), 3.66 (d, J=11.71 Hz, 1H), 3.85 (d, J=11.62 Hz, 1H), 3.93 (dd, J=11.67, 3.95 Hz, 1H), 7.46 (dd, J=8.25, 7.08 Hz, 1H), 7.50-7.57 (m, 1H), 7.57-7.65 (m, 2H), 7.86 (d, J=8.30 Hz, 1H), 7.89-7.95 (m, 1H), 8.17 (d, J=8.49 Hz, 1H), $^{13}$C NMR (101 MHz, METHANOL-d$_4$) δ 22.36, 30.65, 30.65, 48.09, 51.99, 123.78, 125.47, 125.89, 126.50, 128.65, 128.88, 133.87, 134.28, LC/MS (m/z M$^{+1}$ 210.0), [α]$_D$ (c=1, MeOH), =+55.6.

(3) 1S,5R-(−)-1-(2-naphthyl)-3-azabicyclo[3.1.0]hexane Hydrochloride

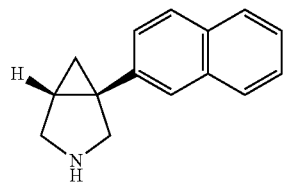 [SMILES: c1ccc2cc([C@@]34CNC[C@@H]3C4)ccc2c1]

Yield=32%; $^1$H NMR (400 MHz, CDCl$_3$) δ 1.33-1.40 (m, J=7.52, 7.52 Hz, 1H), 1.67 (dd, J=6.64, 4.69 Hz, 1H), 2.03-

2.11 (m, 1H), 3.63-3.80 (m, 3H), 3.85-3.94 (m, J=11.23, 5.95 Hz, 1H), 7.23-7.29 (m, 1H), 7.43-7.52 (m, 2H), 7.66 (d, J=1.56 Hz, 1H), 7.75-7.83 (m, 3H), 9.81-9.98 (m, J=7.81 Hz, 1H), 10.38 (s, 1H), $^{13}$C NMR (101 MHz, CDCl$_3$) δ 15.56, 23.47, 31.79, 47.87, 50.99, 125.01, 126.38, 126.42, 126.84, 127.78, 127.86, 128.95, 132.67, 133.46, 135.50, LC/MS (m/z M$^{+1}$ 210.1), [α]$_D$ (c=1, MeOH), =−82.2.

(4) 1R,5S-(+)-1-(2-naphthyl)-3-azabicyclo[3.1.0] hexane Hydrochloride

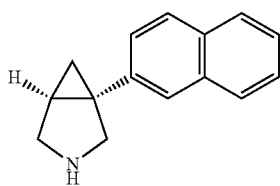 [SMILES: c1ccc2cc([C@]34CNC[C@H]3C4)ccc2c1]

Yield=30%; $^1$H NMR (400 MHz, DMSO-d$_6$) δ 1.14-1.23 (m, 1H), 1.44-1.50 (m, 1H), 2.17-2.26 (m, 1H), 3.36-3.43 (m, 1H), 3.47-3.61 (m, 2H), 3.75 (d, J=11.23 Hz, 1H), 7.36 (dd, J=8.59, 1.85 Hz, 1H), 7.42-7.53 (m, 2H), 7.80 (d, J=1.56 Hz, 1H), 7.82-7.90 (m, 3H), 9.76 (br. s., 1H), $^{13}$C NMR (101 MHz, DMSO-d$_6$) δ 16.41, 24.11, 31.36, 47.50, 49.97, 125.43, 125.76, 126.41, 127.04, 128.07, 128.15, 128.74, 132.39, 133.55, 137.62), LC/MS (m/z M$^{+1}$ 210.1, [α]$_D$ (c=1, MeOH), =+66.0.

(5) 1S,5R-(−)-1-(3-fluoro, 4-methylphenyl)-3-azabicyclo[3.1.0]hexane Hydrochloride

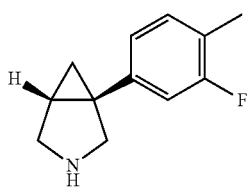

Yield=64%; $^1$H NMR (400 MHz, DMSO-d$_6$) δ 0.99-1.08 (m, 1H), 1.39-1.45 (m, 1H), 2.05-2.13 (m, 1H), 2.17 (d, J=1.37 Hz, 3H), 3.28-3.35 (m, 1H), 3.35-3.48 (m, 2H), 3.63 (d, J=10.64 Hz, 1H), 6.97 (dd, J=7.81, 1.76 Hz, 1H), 7.05 (dd, J=11.32, 1.76 Hz, 1H), 7.19 (t, J=8.10 Hz, 1H), 9.70 (br. s., 1H), 9.96 (br. s., 2H), $^{13}$C NMR (101 MHz, DMSO-d$_6$) δ 14.43 (d, J=3.16 Hz) 16.59, 24.15, 30.72 (d, J=2.01 Hz) 47.30, 49.70, 113.87 (d, J=22.92 Hz) 122.91 123.01, 132.18 (d, J=5.66 Hz) 140.21 (d, J=7.86 Hz) 161.31 (d, J=242.57 Hz), LC/MS (m/z M$^{+1}$ 192.1), [α]$_D$ (c=1, MeOH), =−58.4.

(6) 1R,5S-(+)-1-(3-fluoro,4-methylphenyl)-3-azabicyclo[3.1.0]hexane Hydrochloride

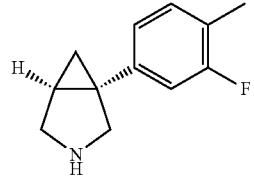

Yield=95% * crude; $^1$H NMR (400 MHz, DMSO-d$_6$) δ 1.00-1.09 (m, 1H), 1.36-1.44 (m, 1H), 2.05-2.14 (m, 1H), 2.17 (d, J=1.46 Hz, 3H), 3.32 (d, J=11.13 Hz, 1H), 3.37-3.47 (m, 2H), 3.63 (d, J=11.13 Hz, 1H), 6.97 (dd, J=7.81, 1.85 Hz, 1H), 7.05 (dd, J=11.32, 1.76 Hz, 1H), 7.20 (t, J=8.15 Hz, 1H), 9.74 (br. s., 2H), $^{13}$C NMR (101 MHz, DMSO-d$_6$) δ 14.44 (d, J=3.16 Hz), 16.54, 24.13, 30.71 (d, J=2.11 Hz, 1C) 47.34, 49.73, 113.89 (d, J=22.91 Hz) 122.92 (d, J=13.90 Hz), 123.03, 132.19 (d, J=5.75 Hz), 140.19 (d, J=7.86 Hz), 161.32 (d, J=242.47 Hz), LC/MS (m/z M$^{+1}$ 192.1), [α]$_D$ (c=1, MeOH), =±55.8

(7) Synthesis of 1S,5R-(−)-1-(4-chloro-3-trifluoromethylphenyl)-3-azabicyclo[3.1.0]hexane Hydrochloride as Representative Procedure for (7)-(12)

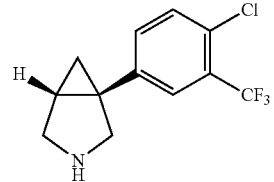 [SMILES: FC(F)(F)c1cc([C@@]23CNC[C@@H]2C3)ccc1Cl]

To a stirring solution of (1R,2S)-(2-aminomethyl-2-(4-chloro-3-trifluoromethylphenyl)cyclopropyl)-methanol prepared according to Example XIV B(7) above (2.35 g, 8.4 mmoles) in 50 mL of dichloroethane (DCE), at room temperature under nitrogen, was added 0.8 mL (10.1 mmoles, 1.3 eq) of SOCl$_2$ slowly via syringe while keeping the temperature below 40° C. The resulting mixture was stirred for 2 h at room temperature after which time, TLC analysis (SiO$_2$ plate, CH$_2$Cl$_2$/MeOH/NH$_4$OH (10:1:0.1)) showed remaining no starting material. The mixture was quenched with 125 mL of water, diluted with CH$_2$Cl$_2$ (75 mL) stirred 2-3 minutes, allowed to settle and the layers were separated. The organic layer was washed with H$_2$O (75 mL). The aqueous layers were combined, made basic with 10N NaOH to pH=10 (pH paper) and extracted with 2×100 mL of CH$_2$Cl$_2$. The combined organics were dried over Na$_2$SO$_4$, filtered and concentrated to an oil. The oil was dissolved in MeOH (40 mL), treated with 20 mL of 2M HCl/Et$_2$O, concentrated to ~5-10 mL total volume and then diluted with 30 mL of Et$_2$O and 5 mL of heptane. The resulting slurry was filtered and washed with 35 mL of cold Et$_2$O. The solid product was dried overnight (~29 mmHg, 50° C.) to give 1.8 g (72%) of pure product as a white solid. $^1$H NMR (400 MHz, CDCl$_3$) δ 1.01-1.07 (m, 1H), 1.13-1.18 (m, 1H), 1.77-1.85 (m, 1H), 3.19-3.33 (m, 3H), 3.42 (d, J=11.13 Hz, 1H), 5.10 (br.s, 2H), 7.29 (dd, J=8.20, 2.15 Hz, 1H), 7.42 (d, J=8.40 Hz, 1H), 7.47 (d, J=2.34 Hz, 1H); $^{13}$C NMR (101 MHz, CDCl$_3$) δ 15.81, 23.59, 31.02, 47.75, 50.68, 121.35, 124.07, 126.38, 129.14 (d, J=31.45 Hz), 131.63 (d, J=1.72 Hz), 131.94 (d, J=0.96 Hz), 132.21, 137.50, LC/MS (m/z M$^{+1}$ 262.0), [α]$_D$ (c=1, MeOH), =−54.2.

(8) 1R,5S-(+)-1-(4-chloro,3-trifluormethylphenyl)-3-azabicyclo[3.1.0]hexane Hydrochloride

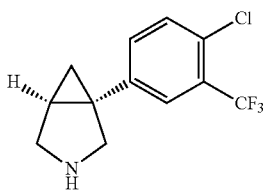 [SMILES: FC(F)(F)c1cc([C@]23CNC[C@H]2C3)ccc1Cl]

Yield=43%; $^1$H NMR (400 MHz, CDCl$_3$) δ 1.17-1.26 (m, 1H), 2.03-2.11 (m, J=6.64 Hz, 1H), 2.30-2.38 (m, J=6.30, 4.44 Hz, 1H), 2.87-2.98 (m, J=2.15 Hz, 3H), 3.20-3.29 (m, 1H), 3.31-3.41 (m, 1H), 3.89-4.00 (m, 1H), 4.09-4.18 (m, 1H), 7.28-7.35 (m, 1H), 7.44-7.52 (m, 2H), 12.78 (br. s., 1H); $^{13}$C NMR (101 MHz, CDCl$_3$) δ 15.95, 23.64, 31.02, 47.75, 50.68, 121.35, 124.07, 126.51, 129.12 (d, J=31.45 Hz), 131.62 (d, J=1.72 Hz), 131.96 (d, J=0.96 Hz), 132.21, 137.50, LC/MS (m/z M$^{+1}$ 262.0), [α]$_D$ (c=1, MeOH), =+58.3.

(9) 1S,5R-(−)-1-(4-chloro-3-fluorophenyl)-3-azabicyclo[3.1.0]hexane Hydrochloride

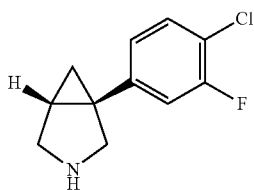 [SMILES: Fc1cc([C@@]23CNC[C@@H]2C3)ccc1Cl]

Yield=68%; $^1$H NMR (400 MHz, CDCl$_3$) δ 1.16-1.27 (m, J=7.52, 7.52 Hz, 1H), 1.58-1.69 (m, 1H), 1.91-2.04 (m, 1H), 3.49-3.69 (n, J=5.47 Hz, 3H), 3.72-3.83 (m, J=11.03, 5.76 Hz, 1H), 6.87-7.01 (m, 2H), 7.34 (t, J=7.91 Hz, 1H), 9.86 (s, 1H), 10.32 (s, 1H); $^{13}$C NMR (101 MHz, CDCl$_3$) δ 16.14, 23.91, 30.99 (d, J=1.82 Hz), 47.67, 50.55, 115.67 (d, J=21.76 Hz), 120.32 (d, J=17.55 Hz), 123.72 (d, J=3.64 Hz), 131.25, 139.17 (d, J=6.71 Hz) 158.35 (d, J=250.24 Hz), LC/MS (m/z M$^{+1}$ 212.0), [α]$_D$ (c=1, MeOH), =−76.0.

(10) 1R,5S-(+)-1-(4-chloro,3-fluorophenyl)-3-azabicyclo[3.1.0]hexane Hydrochloride

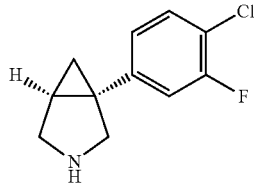

Yield=31%; $^1$H NMR (400 MHz, METHANOL-d$_4$) δ 1.20 (dd, J=6.54, 4.90 Hz, 1H), 1.26-1.32 (m, 1H), 2.17-2.24 (m, 1H), 3.51 (d, J=11.53 Hz, 1H), 3.59-3.71 (m, 2H), 3.76 (d, J=11.35 Hz, 1H), 7.09-7.15 (m, 1H), 7.23 (dd, J=10.48, 2.15 Hz, 1H), 7.43 (t, J=8.05 Hz, 1H); $^{13}$C NMR (101 MHz, METHANOL-d$_4$) δ 15.34, 23.74, 30.60 (d, J=1.92 Hz), 50.31, 115.43 (d, J=22.05 Hz), 119.25 (d, J=17.74 Hz), 123.90 (d, J=3.55 Hz), 130.79, 140.30 (d, Hz), 158.16 (d, J=247.84 Hz), LC/MS (m/z M$^{+1}$ 212.0), [α]$_D$ (c=1, MeOH), =+64.0.

(11) 1S,5R+)-1-(3-chloro,4-fluorophenyl)-3-azabicyclo[3.1.0]hexane Hydrochloride

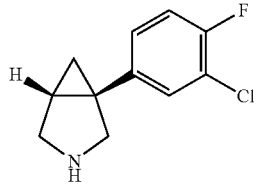 [SMILES: Fc1ccc([C@@]23CNC[C@@H]2C3)cc1Cl]

Yield=34%; $^1$H NMR (400 MHz, CDCl$_3$) δ 1.21 (t, J=7.42 Hz, 1H), 1.59 (dd, J=6.64, 4.88 Hz, 1H), 1.91-1.99 (m, 1H), 3.45-3.68 (m, 3H), 3.75 (dd, J=11.23, 6.15 Hz, 1H), 7.05-7.14 (m, 2H), 7.21-7.27 (m, 1H), 9.84 (s, 1H), 10.32 (s, 1H); $^{13}$C NMR (101 MHz, CDCl$_3$) δ 15.62, 23.53, 30.92, 47.76, 50.99, 117.20 (d, J=21.29 Hz), 121.63 (d, J=18.03 Hz), 127.46 (d, J=7.29 Hz), 129.99, 135.29 (d, J=3.93 Hz), 157.58 (d, J=249.76 Hz), LC/MS (m/z M$^{+1}$ 212.1); [α]$_D$ (c=1, MeOH), =−42.8.

(12) 1R,5S-(+)-1-(3-chloro,4-fluorophenyl)-3-azabicyclo[3.1.0]hexane Hydrochloride

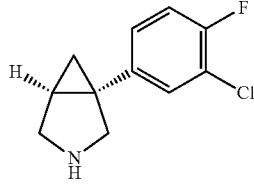 [SMILES: Fc1ccc([C@]23CNC[C@H]2C3)cc1Cl]

Yield=59%; $^1$H NMR (400 MHz, CDCl$_3$) δ 1.15-1.24 (m, 1H), 1.60 (dd, J=6.54, 4.78 Hz, 1H), 1.90-1.97 (m, 1H), 3.47-3.69 (m, 3H), 3.74 (dd, J=11.27, 6.10 Hz, 1H), 7.04-7.12

(m, 2H), 7.21-7.26 (m, 1H), 9.81 (br. s., 1H), 10.26 (br. s., 1H); $^{13}$C NMR (101 MHz, CDCl$_3$) δ 19.22, 27.40, 34.82, 51.77, 54.96, 121.04 (d, J=21.38 Hz), 125.37 (d, J=18.03 Hz), 131.53 (d, J=7.29 Hz), 133.94, 139.23 (d, J=3.93 Hz), 161.48 (d, J=249.38 Hz), LC/MS (m/z M$^{+1}$ 212.1), [α]$_D$ (c=1, MeOH), =+41.4.

D. Synthesis of various napthyl and phenyl-3-methyl-3-azabicyclo[3.1.0]hexane Hydrochloride using the representative procedure shown in Example XIV(C)(7)

(1) 1S,5R+)-1-(1-naphthyl)-3-methyl-3-azabicyclo [3.1.0]hexane Hydrochloride

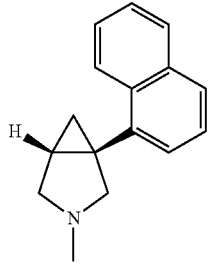 [SMILES: CN1C[C@@H]2C[C@]2(c2cccc3ccccc23)C1]

$^1$H NMR (400 MHz, CDCl$_3$) δ 1.22-1.31 (m, 1H), 2.14-2.21 (m, 1H), 2.45 (d, J=6.50 Hz, 1H), 2.91 (d, J=4.76 Hz, 3H), 3.11-3.23 (m, 1H), 3.46-3.55 (m, 1H), 4.08 (dd, J=11.07, 5.31 Hz, 1H), 4.19-4.27 (m, 1H), 7.39-7.64 (m, 4H), 7.83 (d, J=8.14 Hz, 1H), 7.87-7.93 (m, 1H), 8.11-8.20 (m, 1H), 12.85 (br. s, 1H); $^{13}$C NMR (101 MHz, CDCl$_3$) δ 15.05, 22.11-22.56 (m, 1C) 30.92, 41.35, 57.25-57.70 (m, 1C) 61.37, 124.02, 125.67, 126.41, 127.12, 129.18, 132.72, 133.51, 134.03, LC/MS (m/z. M$^{+1}$ 224.1); [α]$_D$ (c=1, MeOH), =-60.6.

(2) 1R,5S-(+)-1-(1-naphthyl)-3-methyl-3-azabicyclo [3.1.0]hexane Hydrochloride

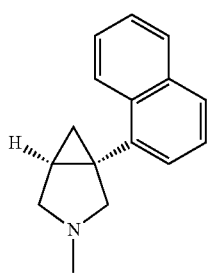 [SMILES: CN1C[C@H]2C[C@@]2(c2cccc3ccccc23)C1]

Yield=58%; $^1$H NMR (400 MHz, DMSO-d$_6$) δ 0.93-1.03 (m, 1H), 2.01 (br. s., 1H), 2.14-2.25 (m, 1H), 2.79 (s, 3H), 3.19-3.34 (m, 1H), 3.89-4.01 (m, 1H), 7.48 (dd, J=8.10, 7.22 Hz, 1H), 7.52-7.58 (m, 1H), 7.59-7.66 (m, 2H), 7.88 (d, J=8.20 Hz, 1H), 7.96 (d, J=7.61 Hz, 1H), 8.16 (d, J=8.40 Hz, 1H), 11.30 (br. s., 1H); $^{13}$C NMR (101 MHz, DMSO-d$_6$) δ 14.56, 22.27, 30.46, 40.33, 56.83, 60.63, 124.73, 126.25, 126.65, 127.29, 128.92, 129.41, 132.98, 134.02, [α]$_D$ (c=1, MeOH), =+64.2.

(3) 1S,5R-(-)-1-(2-naphthyl)-3-methyl-3-azabicyclo [3.1.0]hexane Hydrochloride

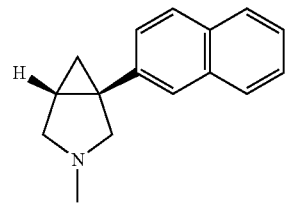

Yield=60%; $^1$H NMR (400 MHz, CDCl$_3$) δ 1.27-1.34 (m, 1H), 2.08-2.15 (m, 1H), 2.29 (dd, J=6.88, 4.73 Hz, 1H), 2.92 (d, J=4.69 Hz, 3H), 3.31-3.42 (m, 2H), 3.95 (dd, J=11.03, 5.27 Hz, 1H), 4.18 (dd, J=10.84, 5.27 Hz, 1H), 7.20-7.27 (m, 1H), 7.43-7.53 (m, 2H), 7.62 (d, J=1.66 Hz, 1H), 7.74-7.85 (m, 3H), 12.64 (br. s., 1H); $^{13}$C NMR (101 MHz, CDCl$_3$) δ 16.40, 23.41, 31.85, 41.48, 57.47, 60.56, 124.70, 126.19, 126.52, 126.99, 127.73, 127.90, 129.08, 132.69, 1:33.43, 135.34, LC/MS (m/z M$^{+1}$ 224.1, [α]$_D$) (c=1, =-88.6.

(4) 1R,5S-(+)-1-(2-naphthyl)-3-methyl-3-azabicyclo [3.1.0]hexane Hydrochloride

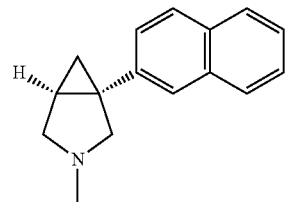 [SMILES: CN1C[C@H]2C[C@@]2(c2ccc3ccccc3c2)C1]

Yield=80%; $^1$H NMR (400 MHz, DMSO-d$_6$) δ 1.14-1.22 (m, 1H), 1.89 (dd, J=5.91, 5.03 Hz, 1H), 2.17-2.24 (m, 1H), 2.81 (d, J=4, 49 Hz, 3H), 3.45-3.54 (m, 1H), 3.60-3.69 (m, 2H), 3.95 (dd, J=10.88, 5.03 Hz, 1H), 7.35-7.53 (m, 3H), 7.76-7.89 (m, 4H); $^{13}$C NMR (101 MHz, DMSO-d$_6$) δ 16.13-16.48 (m, 1C) 24.17, 31.18, 40.32, 56.68, 58.96-59.19 (m, 1C) 125.38, 125.78, 126.45, 127.08, 128.04, 128.17, 128.73, 132.42, 133.51H, 137.43, LC/MS (m/z M$^{+1}$ 210.1), [α]$_D$) (c=1, MeOH), =+77.8.

(5) 1S,5R-(-)-1-(3-fluoro,4-methylphenyl)-3-methyl-3-azabicyclo[3.1.0]hexane Hydrochloride

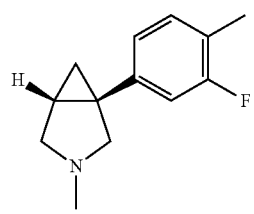

Yield=63%; ¹H NMR (400 MHz, DMSO-d₆) δ 1.01-1.09 (m, 1H) 1.76-1.84 (m, 1H) 2.05-2.12 (m, 1H) 2.17 (d, J=1.37 Hz, 3H) 2.76 (d, J=4.20 Hz, 3H) 3.38-3.53 (m, 2H) 3.56 (dd, J=10.98, 4.83 Hz, 1H) 3.83 (dd, J=10.93, 4.88 Hz, 1H) 6.98 (dd, J=7.86, 1.71 Hz, 1H) 7.08 (dd, J=11.32, 1.56 Hz, 1H) 7.19-7.25 (m, 1H) 11.35 (br. s., 1H); ¹³C NMR (101 MHz, DMSO-d₆) δ ppm 14.44 (d, J=3.1 Hz) 16.22, 24.24, 30.54 (d, J=1.2 Hz) 56.55, 58.86, 113.94 (d, J=22.7 Hz) 122.96, 123.19-132.18 (d, J=5.7 Hz) 139.95 (d, J=7.8 Hz) 161.32 (d, 1=242.8 Hz), LC/MS (m/z M⁺¹ 206.0), [α]_D (c=1, MeOH), =−69.6.

(6) 1R,5S-(+)-1-(3-fluoro,4-methylphenyl)-3-methyl-3-azabicyclo[3.1.0]hexane Hydrochloride

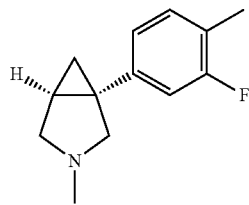

Yield==63%; ¹H NMR (400 MHz, DMSO-d₆) δ 1.02-1.10 (m, 1H) 1.68-1.74 (m, 1H), 2.05-2.12 (m, 1H), 2.18 (d, J=1.56 Hz, 3H), 2.77 (d, J=4.30 Hz, 3H), 3.38-3.52 (m, 2H), 3.58 (dd, J=11.08, 4.83 Hz, 1H), 3.84 (dd, J=10.98, 4.93 Hz, 1H), 6.98 (dd, J=7.81, 1.76 Hz, 1H), 7.08 (dd, J=11.32, 1.66 Hz, 1H), 7.21 (t, J=8.10 Hz, 1H), 11.09 (br. s., 1H); ¹³C NMR (101 MHz, DMSO-d₆) δ 14.45 (d, J=3.16 Hz), 16.22, 24.22, 30.51, 40.30, 56.65, 58.94, 113.93 (d, J=22.9 Hz), 123.05 (d, J=3.26 Hz), 123.18, 132.19 (d, J=5.6 Hz), 139.90 (d, J=8.0 Hz), 161.32 (d, J=242.5 Hz), LC/MS (m/z 206.1), [α]_D (c=1, MeOH), =+48.0.

(7) Synthesis of 1S,5R-(−)-1-(4-chloro-3-trifluoromethylphenyl)-3-methyl-3-azabicyclo[3.1.0]hexane Hydrochloride

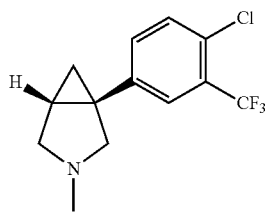 [SMILES: CN1C[C@@H]2C[C@]2(c2ccc(Cl)c(C(F)(F)F)c2)C1]

To a stirring solution of amine hydrochloride (0.8 g, 3 mmoles) in 75 mL of dichloroethane (DCE), at room temperature under nitrogen, was added 2.1 mL (28 mmoles, 9.2 eq) of formaldehyde (37%) followed by 2.98 g (14 mmoles) of sodium triacetoxyborohydride. The resulting mixture was stirred for 1-2 h at room temperature after which time, LC/NIS analysis showed one main peak corresponding to the desired product. The mixture was quenched with 20 mL of 1M NaOH, allowed to settle and the layers were separated. The aqueous layer was washed with 40 mL of CH₂Cl₂. The combined organic layers were dried over Na₂SO₄, filtered and concentrated to an oil. The oil was dissolved in MeOH (5 mL) and treated with an excess of 2M HCl/Et₂O. An additional 15 mL of Et₂O/acetonitrile/heptane (2:1:1) was added. The resulting suspension was cooled to 0-5° C. and filtered, washing the product cake with Et₂O (10 mL). The product was dried overnight (~29 mmHg, 50° C.) to give 520 mg (62%) of pure product as a white solid. ¹H NMR (400 MHz, CDCl₃) δ 1.17-1.23 (m, 1H), 2.03-2.09 (m, 1H), 2.33 (dd, J=6.93, 4.78 Hz, 1H), 2.92 (d, J=4.59 Hz, 3H), 3.22-3.31 (m, 1H), 3.34-3.42 (m, 1H), 3.92 (dd, J=11.03, 5.27 Hz, 1H), 4.11 (dd, J=10.84, 5.27 Hz, 1H), 7.31 (dd, J=8.30, 2.05 Hz, 1H), 7.47 (d, J=8.20 Hz, 1H), 7.51 (d, J=2.05 Hz, 1H), 12.74 (br. s., 1H); ¹³C NMR (101 MHz, CDCl₃) δ 15.76-15.97 (m, 1C) 23.64-23.81 (m, 1C) 30.90-31.04 (m, 1C) 47.56-47.70 (m, 1C) 50.56-50.72 (m, 1C) 121.25-121.44 (m, 1C) 123.97-124.16 (m, 1C) 126.35-126.74 (m, 1C) 129.01-129.41 (m, 1C), 131.69, 131.93, 137.42, LC/MS (m/z M⁺¹ 276.0), [α]_D (c=1, MeOH), =−60.2

(8) 1R,5S-(+)-1-(4-chloro,3-trifluormethylphenyl)-3-methyl-3-azabicyclo[3.1.0]hexane Hydrochloride

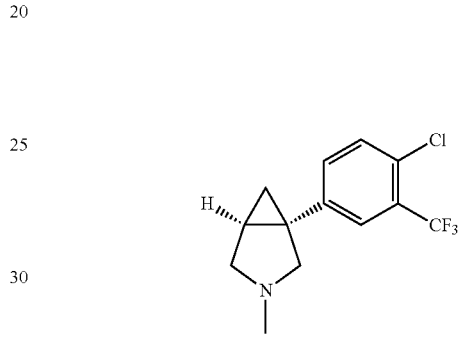

Yield 80%; ¹H NMR (400 MHz, CDCl₃) δ 1.17-1.25 (m, 1H), 2.03-2.10 (m, 1H), 2.33 (dd, J=6.98, 4.73 Hz, 1H), 2.92 (d, J=4.69 Hz, 3H), 3.23-3.31 (m, 1H), 3.34-3.44 (m, 1H), 3.92 (dd, J=10.98, 5.22 Hz, 1H), 4.11 (dd, J=10.84, 5.27 Hz, 1H), 7.32 (dd, J=8.30, 2.05 Hz, 1H), 7.44-7.55 (m, 2H), 12.74 (br. s., 1H); ¹³C NMR (101 MHz, CDCl₃) δ 16.31, 23.59, 31.04, 41.35, 57.16, 60.04, 121.34, 124.06, 126.53 (q, J=5.27 Hz), 129.20 (d, J=31.54 Hz), 131.82, 132.01, 132.35 (m), LC/MS (m/z 276.1), [α]_D (c=1, MeOH), =+41.4.

(9) 1S,5R-(−)-1-(4-chloro-3-fluorophenyl)-3-methyl-3-azabicyclo[3.1.0]hexane Hydrochloride

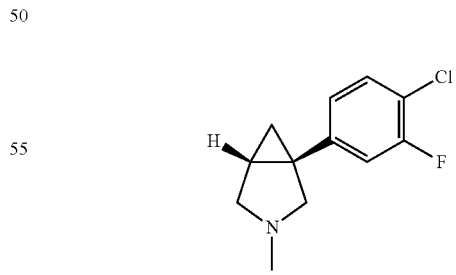

Yield=81%; ¹H NMR (400 MHz, CDCl₃) δ 1.10-1.27 (1H), 1.97-2.07 (m, 1H), 2.29 (br. s., 1H), 2.91 (s, 3H), 3.19-3.39 (m, 2H), 3.90 (br. s., 1H), 4.02-4.17 (m, 1H), 6.91 (d, 0.1=7.81 Hz, 1H), 7.00 (d, J=9.66 Hz, 1H), 7.35 (t, J=7.71 Hz, 1 H); ¹³C NMR (101 MHz, CDCl₃) δ 16.09-17.22 (m, 1C) 23.85, 31.04, 41.65, 57.32-60.14, 115.67 (d, J=21.8 Hz), 120.48 (d, J=17.5 Hz) 123.72, 131.36, 138.97, 158.37 (d, J=250.3 Hz), LC/MS (m/z M$^{+1}$ 226.0), [α]$_D$ (c=1, MeOH), =−79.8.

(10) 1R,5S-(+)-1-(4-chloro,3-fluorophenyl)-3-methyl-3-azabicyclo[3.1.0]hexane Hydrochloride

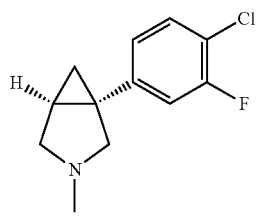

Yield=87%; $^1$H NMR (400 MHz, METHANOL-d$_4$) δ 1.27 (t, J=7.71 Hz, 1H), 1.47 (dd, J=6.78, 4.83 Hz, 1H), 2.17-2.26 (m, 1H), 2.98 (s, 3H), 3.61 (d, J=11.32 Hz, 1H), 3.80 (d, J=11.32 Hz, 1H), 4.03 (d, J=11.23 Hz, 1H), 7.10-7.16 (m, 1H), 7.26 (dd, J=10.45, 2.05 Hz, 1H), 7.43 (t, J=8.10 Hz, 1H); $^{13}$C NMR (101 MHz, METHANOL-d$_4$) δ 14.25, 15.29, 23.70, 39.83, 57.24, 59.59, 115.42 (d, J=22.24 Hz, 1C) 119.36 (d, J=17.74 Hz, 1C) 123.87 (d, J=3.64 Hz, 1C) 130.81, 140.03, 158.16 (d, J=247.84 Hz, 1C), LC/MS (m/z M$^{+1}$ 226.0), [α]$_D$ (c=1, MeOH), =+61.6.

(11) 1S,5R-(−)-1-(3-chloro,4-fluorophenyl)-3-methyl-3-azabicyclo[3.1.0]hexane Hydrochloride

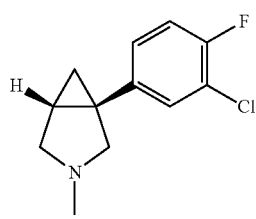

Yield=78%; $^1$H NMR (400 MHz, CDCl$_3$) δ 1.03-1.16 (m, 1H) 1.84-2.01 (m, 2H) 2.84 (s, 3H) 3.17-3.30 (m, 1H) 3.29-3.41 (m, 1H) 3.80 (d, J=10.84 Hz, 1H) 3.97 (d, J=10.84 Hz, 1H) 6.97-7.11 (m, 2H) 7.18-7.29 (m, 1H); $^{13}$C NMR (101 MHz, CDCl$_3$) δ 15.88, 18.47, 23.27, 30.72, 40.96, 57.26, 60.30, 117.17 (d, J=21.4 Hz), 121.50 (d, J=17.9 Hz), 127.51 (d, J=7.2 Hz), 129.90, 134.98 (d, J=3.7 Hz), 157.56 (d, J=249.8 Hz), LC/MS (m/z M$^{+1}$ 225.7), [α]$_D$ (c=1, MeOH), =−46.2.

(12) 1R,5S-(+)-1-(3-chloro,4-fluorophenyl)-3-methyl-3-azabicyclo[3.1.0]hexane Hydrochloride

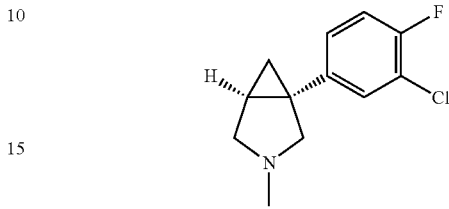

Yield 59%; $^1$H NMR (400 MHz, CDCl$_3$) δ 1.14 (t, J=7.81 Hz, 1H) 1.93-2.01 (m, 1H) 2.19 (dd, J=6.74, 4.69 Hz, 1H) 2.91 (d, J=4.59 Hz, 3H) 3.23-3.32 (m, 1H) 3.37-3.46 (m, 1H) 3.86 (dd, J=10.88, 5.12 Hz, 1H) 4.02 (dd, J=10.84, 5.17 Hz, 1H) 7.06-7.11 (m, 2H) 7.26-7.31 (m, 1H); $^{13}$C NMR (101 MHz, CDCl$_3$) δ 15.83, 23.43, 30.91, 41.26, 57.23, 60.20-60.54 (m, J=0.6 Hz), 117.26 (d, J=21.3 Hz), 121.61 (d, J=18.1 Hz), 127.61 (d, J=7.3 Hz), 130.00, 135.14 (d, J=3.9 Hz), 157.61 (d, J=249.9 Hz), 157.63, LC/MS (m/z M$^{+1}$ 225.9), [α]$_D$ (c=1, MeOH), =+60.5.

Example XV

Preparation of 1-Aryl-4-methyl-3-aza-bicyclo[3.1.0]hexane Using Reaction Scheme 21

A. Preparation of (±)-1-(3,4-dichloro-phenyl)-(r/s)-2-hydroxymethyl-cyclopropanecarbonitrile

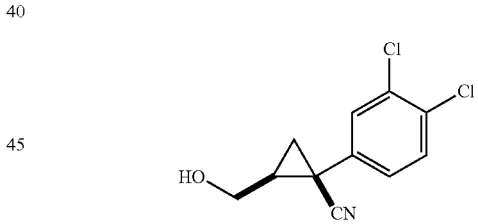

To an oven-dried, three-necked, 500 mL round-bottomed flask was added the compound 3,4-dichlorobenzonitrile and THF with stirring under argon. The solution was cooled to −25° C. in a dry ice/MeCN bath and charged with 5.3 g of sodium amide. The resulting yellow suspension became orange upon stirring and was warmed to ambient temperature over 2 hours. The brown mixture was cooled to −25° C. and epichlorohydrin was added drop-wise over 10 minutes followed by a second equivalent of sodium amide in one portion. The golden brown mixture was stirred at −25° C. and warmed to 15° C. over 8 h. The dark red-colored mixture was poured (with stirring) into 500 mL of saturated ammonium chloride. The organic phase was separated and dried over magnesium sulfate for 12 h. The mixture was filtered and concentrated under reduced pressure and dried to afford 31 g of red oil. Half of the material was loaded onto a silica gel (250 g) column and eluted first with hexane. Later the polarity was increased to 10% EtOAc in hexanes and finally to 20% EtOAc in hexanes. Tubes containing the product were combined and concentrated, and dried under a high vacuum to give the product as a mixture of diastereomers. Yield: 6.8 g (42%); LCMS: (+) ESI: m/z=242 [M]+; $^1$H NMR (300 MHz, CDCl$_3$, peaks corresponding to syn isomer listed) δ 7.43 (m, 2H, ArH), 7.7.14 (m, 1H, ArH), 4.09 (dd, 1H, CHOH, J=12 Hz and 4.8 Hz), 3.74 (dd, 1H, CHOH, J=12 Hz and 8.4 Hz), 2.73 (bs, 1H, OH), 1.91 (m, 1H, ArCCH$_2$CH), 1.62 (m, 2H, ArCCH$_2$CH).

B. Preparation of (±))-1-aminomethyl-1-(3',4'-dichlorophenyl) cylcopropyl-(r/s)-2-methanol

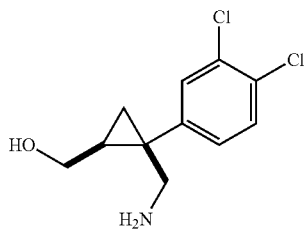 [SMILES: NC[C@]1(c2ccc(Cl)c(Cl)c2)C[C@@H]1CO]

An oven-dried, 500 mL round-bottomed flask was charged with LAH (2.13 g, 0.056 mole) and diethyl ether (210 mL). The mixture was cooled to <5° C. by ice bath, and after 10 min, a solution of carbonitrile (6.8 g, 0.028 mole) in diethyl ether (90 mL) was added via addition funnel over 30 min after which the contents were stirred at ice-bath temperature for 3 h. The reaction slurry was quenched carefully by slow addition of 25% aq. NaOH solution (5.5 mL) and stirred at ice-bath temperature for 45 min. Water (5 mL) was added and the contents filtered and washed with ether (2×50 mL). The combined filtrate was concentrated under reduced pressure and dried under a high vacuum pump overnight to afford a colorless thick liquid. Yield: 6.0 g (87%); LCMS: (+) ESI: m/z=246 [M]+; $^1$H NMR (300 MHz, CDCl$_3$) δ☐: 7.50 (d, 1H, ArH), 7.40 (d, 1H, ArH), 7.24 (dd, 1H, ArH), 4.32 (dd, 1H, CHOH), 3.43 (d, 1H, CH$_2$N), 3.34 (dd, 1H, CHOH), 2.60 (d, 1H, CH$_2$N), 1.71 (m, 1H, ArCCH$_2$CH), 0.94 (dd, 1H, ArCCH$_2$CH), 0.77 (m, 1H, ArCCH$_2$CH).

C. Preparation of (±)-2-hydroxymethyl-1-(3',4'-dichlorophenyl)-cyclopropylmethyl-(r/s)-carbamic acid tert-butylester

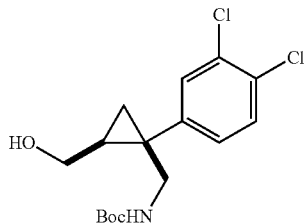 [SMILES: CC(C)(C)OC(=O)NC[C@]1(c2ccc(Cl)c(Cl)c2)C[C@@H]1CO]

Boc anhydride (5.91 g, 0.026 mole) was added in one portion to a stirred solution of amino alcohol in anhydrous DCM (150 mL), and the reaction mixture stirred at ambient temperature under argon for 4.5 h. Water (200 mL) was added to the reaction mixture and the organic layer separated. The organic layer was washed with brine (100 mL), dried (Na$_2$SO$_4$), filtered, and concentrated to give N-boc amino alcohol as a colorless liquid that became a colorless glass upon standing. The material was used without further purification. Yield: 9.0 g (quantitative); LCMS: (+) ESI: m/z=368 [M+Na]+.

D. Preparation of (±)-4-oxo-1-(3',4',-dichlorophenyl)-3-aza-bicyclo[3.1.0]hexan-3-carboxylic acid tert-butyl ester

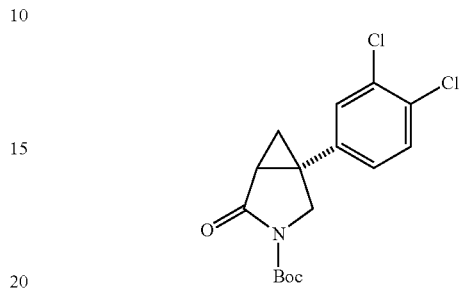

PDC (23 g, 0.06 mole) was added in one portion to a stirred mixture of N-boc amino alcohol (9.0 g, 0.026 mole) and molecular sieves (23 g) in anhydrous DCM (200 mL). The resulted dark brown reaction mixture was stirred at ambient temperature under argon for 3.5 h. The reaction mixture was diluted with diethyl ether (50 mL), filtered through a plug of Celite® using a sintered funnel and washed with dichloromethane (3×50 mL). The dark brown filtrate was concentrated to give a thick brown liquid which was purified via column chromatography using approximately 250 g silica. The column was first eluted with 100% hexanes, changing the gradient to 9:1 hexanes:EtOAc, then 8:2 hexanes: EtOAc. Tubes containing the product were combined, concentrated, and dried on a high vacuum pump overnight to give the desired product. Yield: 4.1 g (49%); LCMS: (+) ESI: m/z=364 [M+Na]+; $^1$H NMR (300 MHz, CDCl$_3$) δ☐: 7.43 (d, 1H, ArH), 7.36 (d, 1H, ArH), 7.09 (dd, 1H, ArH), 4.03 (dd, 1H, CH$_2$N), 3.91 (d, 1H, CH$_2$N), 2.30 (d, 1H, ArCCH$_2$CH), 1.60 (m, 1H, ArCCH$_2$CH), 1.54 (s, 9H, tert-Bu), 1.34 (m, 1H, ArCCH$_2$CH).

E. Preparation of (±)-1-tert-butyloxycarbonylaminomethyl-(r/s)-2-acetyl-1-(3',4'-dichlorophenyl)-cyclopropane

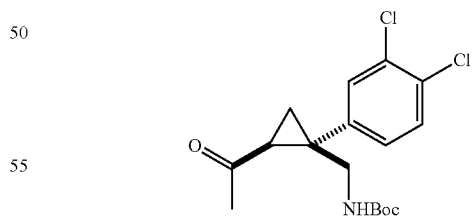

A solution of methyl lithium-ether (3.4 mL, 5.42 mmole, 1.6M) was added drop wise via a syringe to a stirred solution of N-boc lactam (1.6 g, 4.7 mmole) in anhydrous THF cooled at dry-ice/acetone bath temperature. The reaction mixture was stirred with cooling (<−78° C.) for 3 h and then warmed to ambient temperature. The reaction mixture was quenched with 1N aq HCl solution (20 mL) and then extracted with ethyl acetate (2×20 mL). The combined organic layer was washed with brine (20 mL), dried (Na$_2$SO$_4$), filtered, and concentrated to result in a yellow liquid. The compound was purified via column chromatography on silica (~100 g) eluting with 10% EtOAc-hexane and increasing to 20% EtOAc-hexanes. The desired fractions were combined, concentrated under reduced pressure, and dried to afford the desired product. Yield: 1.17 g (70%); LCMS: (+) ESI: m/z=380 [M+Na]⁺; ¹H NMR (300 MHz, CDCl₃) δ☐: 7.39 (m, 2H, ArH), 7.17 (dd, 1H, ArH), 4.50 (bs, 1H, NH), 3.52 (m, 2H, CH₂N), 2.42 (s, 3H, CH₃), 2.30 (d, 1H, ArCCH₂C$\underline{H}$), 1.66 (m, 1H, ArCC$\underline{H}$₂CH), 1.34 (s, 9H, tert-Bu), 1.24 (m, 1H, ArCC$\underline{H}$₂CH).

F. Preparation of erythreo and threo[1-(3,4-dichloro-phenyl)-2-(1-hydroxy-ethyl)-cyclopropylmethyl]-carbamic acid tert-butyl esters

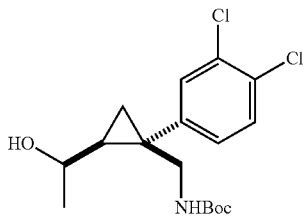

The product from Example XV E above was added to methanol and stirred at ambient temperature under Ar (g) in a 50 mL round-bottomed flask. Potassium borohydride was added portion-wise and the resulting suspension stirred overnight. A clear solution was obtained. The resulting solution was partitioned between EtOAc (10 mL) and water (10 mL). The aqueous layer was extracted with EtOAc (2×10 mL) and the combined layers washed with brine (10 mL). The organic layer was dried over sodium sulfate for 2 hours and filtered, concentrated under reduced pressure, and dried for 1 hour to afford a solid. The solid was purified on a filterpad of 20 g of silica eluting with 4/1 hexanes/EtOAc (v/v), switching to 1/1 hexanes/EtOAc (v/v) upon collection of the major spot. The second (desired) diastereomer was collected, including undesired diastereomer, yield: 0.321 g, 40%; and desired diastereomer, yield: 0.254 g, 32%; ¹H NMR, Undesired diastereomer: (300 MHz, CDCl₃) δ☐: 7.34-40 (m, 2H, ArH), 7.15 (m, 1H, ArH), 4.93 (bs, 1H, NH), 3.50-61 (m, 3H, CH₃), 3.25 (m, 2H, CH₂N), 1.2-1.4 (m, 9H, tert-Bu), 0.95-1.0 (m, 1H, ArCCH₂), 0.54 (m, 1H, ArCCH₂); Desired diastereomer 1-7: (300 MHz, CDCl₃) δ☐: 7.37 (d, 1H, J=18 Hz, ArH), 7.35 (m, 1-H, ArH), 7.11 (m, 1H, ArH), 4.48 (bs, 1H, NH), 3.78 (m, 3H, CH₃), 3.57 (m, 1H, CH₂N), 3.37 (d, 1H, J=5 Hz, CH₂N), 3.32 (d, 1H, J==5 Hz, CHOH), 1.4 (s, 9H, tert-Bu), 1.23 (m, 1H, CH), 1.03 (m, 2H, ArCCH₂).

G. Preparation of (±)-1-(3,4-dichloro-phenyl)-(r)-4-methyl-3-aza-bicyclo[3.1.0]hexane

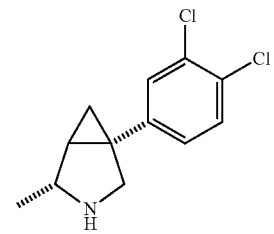

The compound from Example XV F above was added to DCM and triethylamine and cooled in an ice bath under Ar (g) with stirring. Methanesulfonyl chloride was added dropwise with stirring over 10 min, and the resulting suspension warmed to ambient temperature overnight. The resulting yellow solution was washed with water (2×10 mL) and the DCM layer dried over magnesium sulfate. The mixture was filtered and concentrated under reduced pressure to afford a yellow oil. This oil was dissolved in 0.8 mL of DCM and cooled in an ice bath under Ar (g). To this was added 0.8 mL of TFA and the resulting solution was stirred at ambient temperature for 1 hour. The solution was concentrated under reduced pressure, quenched with concentrated NaOH, and extracted with ether (2×10 mL). The organic extracts were combined and dried over magnesium sulfate, filtered, and concentrated under reduced pressure. The oil was purified on a 2000 micron prep plate eluting with 10/1 CHCl₃/MeOH (v/v) to afford the desired free base. Yield: 0.030 g 15%; LCMS (+) ESI: m/z=242 [M+H]⁺ (100); 244 [M+H]⁺ (65); UV (λ$_{max}$=218)=97%; ¹H NMR (300 MHz, CDCl₃) δ☐ 7.32-36 (m, 1H, ArH), 7.23-26 (m, 1H, ArH), 7.01-04 (m, 1H, ArH), 3.37 (q, 1H, J=7 Hz, CHCH₃), 3.20-25 (m, 2H, CH₂N), 1.55 (m, 1H, CHCH₂), 1.22 (m, 3H, CHCH₃), 0.96 (m, 2H, ArCCH₂); ¹³C NMR (75 MHz, CDCl₃) δ☐ 130.3, 129.3, 126.7, 55.7, 50.7, 32.4, 21.1, 15.8

H. Preparation of the Hydrochloride Salt of (±)-1-(3,4-dichloro-phenyl)-(r)-4-methyl-3-aza-bicyclo[3.1.0]hexane To a vial was added 30 mg of the compound from Example XV F above, 1 mL diethyl ether, and 0.2 mL 2N HCl in diethyl ether. A white precipitate appeared in minutes and the suspension was stirred at ambient temperature for 1 hour. The suspension was filtered, collected, and dried to afford 18 mg of a white solid. LCMS (+) ESI: m/z=242 [MH]⁺ (100); 244 [MH+2]⁺ (65); UV (λ$_{max}$=218)=95%; ¹H NMR (300 MHz, MeOH-d₄) OD 7.48-52 (m, 2H, ArH), 7.23-26 (m, 1H, ArH), 4.63 (s(br), 2H, NH₂) 3.93 (q, 1H, J=7 Hz, CHCH₃), 3.68 (m, 2H, CH$_2$N), 2.08 (dd, 1H, J=8 Hz, 5 Hz, CHCH$_2$), 1.45 (m, 3H, CHCH$_3$), 1.29 (m, 1H, CH), 1.16 (m, 2H, ArCCH$_2$).

Example XVI

Preparation of 1-Aryl-4-methyl-3-aza-bicyclo[3.1.0] hexane and 1-Aryl-3,4-dimethyl-3-aza-bicyclo[3.1.0] hexane Using Reaction Scheme 22

A. Preparation of (±)-5(3',4'-dichlorophenyl)-3-aza-bicyclo[3.1.0]hexan-2-one

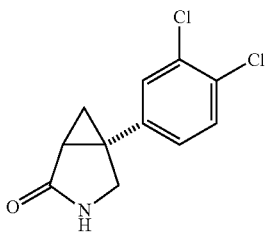

TFA (7.5 mL, 96 mmole) was added drop wise via a syringe over a period of 10 min to a stirred and colorless solution of N-boc lactam prepared according to Example XV, D above (4.1 g, 12 mmole) in anhydrous DCM (100 mL) at ice-bath temperature. The resulting light brown solution was stirred at ambient temperature for 6 h. The reaction mixture was concentrated and dissolved in dichloromethane (100 mL). This solution was washed with saturated aqueous NaHCO$_3$ solution (50 mL), brine (50 mL), dried (Na$_2$SO$_4$), filtered, and concentrated to give an off-white solid. It was dried on a high vacuum pump overnight. Yield: 2.7 g (93%); LC MS: (+) ESI: m/z=242 [MH]$^+$.

B. Preparation of (±)-4-methyl-1-(3',4'-dichlorophenyl)-2,4-dehydro-3-aza-bicyclo[3.1.0]hexan-2-one

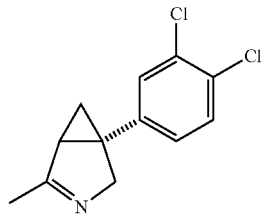

A solution of TMSCl (0.52 mL, 4.1 mmole) in toluene (2 mL) was added drop wise via syringe to a stirred suspension of lactam (0.9 g, 3.72 mmole) and triethylamine (0.64 mL, 4.46 mmole) in anhydrous toluene (12 mL) that was cooled in an ice-bath. The resulting white turbid solution was stirred at 50° C. for 4 h and then cooled in an ice-bath. The mixture was filtered through a plug of Celite® eluting with hexanes:diethyl ether (1:1, 10 mL) and washed with additional hexanes: diethyl ether (1:1, 10 mL). The combined filtrates were concentrated and dried under high vacuum for 30 min. The residue was dissolved in anhydrous diethyl ether (10 mL) and cooled using a dry-ice/acetone bath to a temperature of approximately −30° C. A solution of MeLi (0.64 mL, 4.46 mmole) solution was added drop wise and continued stirring at −30° C. (bath temp) for 30 min. The cold bath was removed and the contents stirred at ambient temperature for 1 h. The reaction mixture was quenched with addition to an aqueous ammonium chloride solution (0.5 g in 12 mL) and the contents stirred at ambient temperature for 30 min. The organic layer was separated, washed with brine (25 mL), dried (Na$_2$SO$_4$), filtered, and concentrated under reduced pressure. The oil was dried under high vacuum for 2 h to give a yellow oil. The oil was purified via chromatography on silica (100 g), first eluting with hexanes: EtOAc (8:2), and gradually increasing the polarity to 7:3, 1:1, and finally 2:8 hexanes: EtOAc. Tubes containing the desired product were combined and concentrated under reduced pressure and dried under high vacuum overnight to afford the product. Yield: 0.6 g (71%); LCMS: (+) ESI: m/z=240 [M]$^+$.

C. Preparation of (±)-trans-4-methyl-1-(3',4'-dichlorophenyl)-3-azabicyclo[3.1.0]hexane

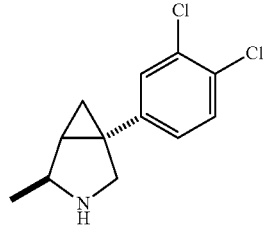

Sodium cyanoborohydride (0.24 g, 3.83 mmole) was added to a stirred solution of imine (0.6 g, 2.5 mmole) in ethanol (8 mL). To this mixture was added a solution of 1.2M HCl-ethanol (3.1 mL, 3.83 mmole) drop-wise. The resulting white suspension was stirred at ambient temperature for 2 h. The reaction mixture was poured into a mixture of brine (30 mL) and 2N aqueous NaOH solution (3 mL), and extracted with ethyl acetate (3×20 mL). The combined organic layer was washed with brine (20 mL), dried (Na$_2$SO$_4$), filtered, and concentrated and dried under high vacuum to give a light yellow oil. The liquid was purified by chromatography on silica (100 g), eluting first with 1% MeOH—CHCl$_3$ and gradually increasing the polarity to 2%, 3%, and finally to 5% MeOH—CHCl$_3$. Tubes containing the desired product were combined, concentrated, and dried under high vacuum to afford the product as colorless liquid. Yield: 0.3 g (47%); $^1$H NMR (300 MHz, CD$_3$OD) δ 7.35 (d, 1H, J=8.4 Hz, ArH), 7.28 (d, 1H, J=2.1 Hz, ArH), 7.06 (dd, 1H, J=8.1 Hz and 2.1 Hz, ArH), 3.42 (m, 1H, —CHCH$_3$), 3.16 (d, 1H, J=11.4 Hz, CH$_2$N), 3.00 (dd, 1H, J=11.1 Hz, 0.6 Hz, CH$_2$N), 1.73 (m, 1H, CHCH$_2$), 1.14 (d, 3H, J=6.3 Hz, CHCH$_3$), 1.01 (m, 1H, ArCCH$_2$), 0.76 (m, 1H, ArCCH$_2$); $^{13}$C NMR (300 MHz, CDCl$_3$) δ 144.94, 133.26, 131.54, 130.71, 130.05, 127.95, 56.35, 53.58, 33.74, 32.82, 17.36 13.02; LC-MS: (+) ESI: m/z=242 [M]$^+$ (100); UV ($\lambda_{max}$=218)=100%.

A solution of HCl-ether (2.0M, 6.6 mL, 1.32 mmole) was added to a stirred solution of amine (0.16 g, 0.66 mmole) in anhydrous diethyl ether (2 mL). The resulting white suspension was stirred at ambient temperature for 30 min. The reaction mixture was filtered and washed with cold anhydrous ether (5 mL) to give a bright white solid, and further dried to a constant mass under high vacuum. Yield: 0.172 g (94%); NMR (300 MHz, CD$_3$OD) δ 7.49 (m, 2H, ArH), 7.23 (dd, 1H, J=8.4 Hz, 2.1 Hz, ArH), 4.18 (m, 1H, CHCH$_3$), 3.71 (d, 1H, J=11.7 Hz, CH$_2$N), 3.62 (dd, 1H, J=11.7 Hz, 1.2 Hz CH$_2$N), 2.22 (m, 1H, CHCH$_2$), 1.44 (d, 3H, J=6.3 Hz, CHCH$_3$), 1.20 (m, 1H, ArCCH$_2$), 0.88 (m, 2H, ArCCH$_2$); LC-MS: (+) ESI: m/z=242 [M$^+$] (100); UV ($\lambda_{max}$=218)=100%.

D. Preparation of (±)-n-methyl-trans-4-methyl-1-(3',4'-dichlorophenyl)-3-azabicyclo[3.1.0]hexane

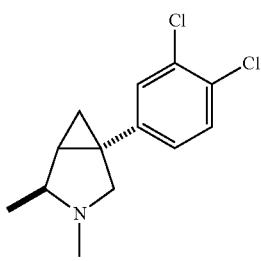

Amine (0.1 g, 0.41 mmole) and diisopropylethylamine (0.165 mL, 0.95 mmole) were dissolved in anhydrous DMF (1 mL) with stirring at ambient temperature for 30 min. Iodomethane (0.033 mL, 0.54 mmole) was added and stirring continued at ambient temperature for 20 h. The reaction mixture was concentrated and dried under high vacuum for 1 h to give a semi-solid that was purified via chromatography on silica eluting with 1% MeOH-EtOAc to afford the product as a colorless glass. Yield: 0.061 g (58%); $^1$H NMR (300 MHz, CDCl$_3$) δ 7.40 (d, 1H, J=8.1 Hz, ArH), 7.31 (d, 1H, J=2.1 Hz, ArH), 7.08 (dd, 1H, J=8.4 Hz, 2.1 Hz, ArH), 3.36 (d, 1H, J=9 Hz, CH$_2$N), 2.74 (m, 1H, CHCH$_3$), 2.71 (d, 1H, J=9 Hz, CH$_2$N), 2.32 (s, 3H, CH$_3$N), 1.86 (b, 1H, ArCCH$_2$CH), 1.35 (m, 1H, ArCCH$_2$), 1.16 (d, 3H, J=6.3 Hz, CHCH$_3$), 0.73 (m, 1H-1, ArCCH$_2$); $^{13}$C NMR (300 MHz, CDCl$_3$) δ 144.9, 133.3, 131.5, 130.7, 129.6, 127.5, 63.3, 62.9, 40.2, 32.8, 30.9, 29.3, 16.3, 15.6; LC-MS: (+) ESI: m/z=256 [M]$^+$ (100).

A solution of HCl-ether (2.0M, 2.2 mL, 1.32 mmole) was added to a solution of amine (0.06 g, 0.23 mmole) in anhydrous methanol (2 mL) and stirred at ambient temperature for 30 min. The reaction mixture was concentrated and dried under high vacuum to give an off-white solid that was triturated with anhydrous diethyl ether and filtered, washing with cold anhydrous ether (5 mL), and dried under high vacuum to give an off white solid. Yield: 0.030 g (44%); $^1$H NMR (300 MHz, CD$_3$OD) δ 7.49 (m, 2H, ArH), 7.21 (dd, 1H, ArH, J=8.1 Hz, 2.1 Hz, CHCH$_3$), 3.98 (m, 2H, CH$_2$N, CHCH$_3$), 3.65 (m, 1H, CH$_2$N), 2.93 (s, 1H, NCH$_3$), 2.28 (m, 1H, CHCH$_2$), 1.46 (d, 3H, CHCH$_3$, J=6.3 Hz), 1.23 (m, 1H, ArCCH$_2$), 0.89 (m, 1H, ArCCH$_2$); LC-MS: (+) ESI: m/z=256 [M]$^+$ (100); UV (λ$_{max}$=218)=100%.

Example XVII

Preparation of 1-Aryl-2-methyl-3-aza-bicyclo[3.1.0]hexane and 1-Aryl-2,3-dimethyl-3-aza-bicyclo[3.1.0]hexane Using Reaction Scheme 23

A. Preparation of (±)-1-(3,4-dichloro-phenyl)-3-azabicyclo[3.1.0]hexan-2-one

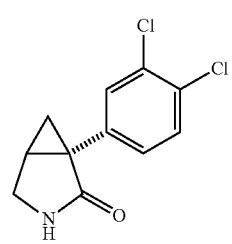

1-(3,4-dichlorophenyl)-3-aza-bicyclo[3.1.0]hexane-2,4-dione and toluene were combined in a 500 mL round-bottomed flask and stirred under Ar (g) for 10 min while cooling in an ice bath. Red-Al® was added via addition funnel dropwise over several minutes. Upon complete addition, the ice bath was removed and the reaction stirred at ambient temperature overnight. The reaction mixture was cooled in an ice bath and 150 mL of 5N NaOH was carefully added. The phases were separated and the aqueous phase was extracted with toluene (2×100 mL), DCM (3×100 mL), and the organic layers combined. The organic layer was washed with brine (200 mL) and dried over sodium sulfate for 8 h. The mixture was filtered, concentrated in vacuo, and dried to afford 5 g of a dark brown semi-solid. The semi-solid was purified on a silica gel column eluting with 20% EtOAc in hexanes increasing the polarity to 30% EtOAc and finally 50% EtOAc. The desired fractions containing the product were combined, concentrated, and dried to afford a light yellow solid. Yield: 2.0 g 30%; LCMS (+) ESI: m/z=242 [M]$^+$; m/z=264 [M+Na]$^+$; $^1$H NMR (300 MHz, CDCl$_3$) δ☐ 7.52 (d, 1H, ArH), 7.39 (d, 1H, ArH), 7.28 (dd, 1H, ArH), 6.02 (bs, 1H, NH), 3.64 (dd, 1H, NHCH$_2$), 3.40 (d, 1H, NHCH$_2$), 2.28 (m, 1H, NHCH$_2$CH), 1.50 (dd, 1H, ArCCH$_2$), 1.26 (m, 1H, ArCCH$_2$).

B. Preparation of (±)-1-(3,4-dichloro-phenyl)-2-oxo-3-aza-bicyclo[3.1.0]hexane-3-carboxylic acid tert-butyl ester

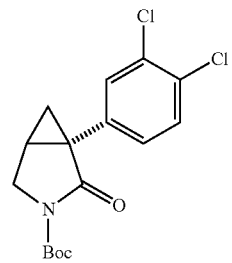

To a 50 mL, round-bottomed flask was added 1-(3,4-dichlorophenyl)-3-aza-bicyclo[3.1.0]hexan-2-one, a stir bar, triethylamine, DMAP, and DCM. The resulting brown suspension was stirred under Ar (g), and to this was added dropwise, a solution of di-tert-butyl dicarbonate in 4.1 mL of DCM over 10-15 min. The suspension became a solution within 1 hour and stirring continued overnight. The solution was quenched with isopropyl amine and stirred at room temperature for 1 hour. The organic solution was washed with 0.5N HCl (25 mL), water (25 mL), and brine (20 mL). The organic layer was dried over magnesium sulfate for 1 hour, filtered, concentrated, and dried. The brown tar was treated with 20 mL hexanes and placed in a freezer for 24 h. The resulting solid was warmed to ambient temperature and triturated with hexanes. The resulting powder was collected by vacuum filtration and dried under high vacuum for 24 h to afford a powder. A second crop could be collected by chromatography of the filtrate using 4/1 hex/EtOAc. Yield: 1.21 g 43%; $^1$H NMR (300 MHz, CDCl$_3$) δ: 7.50 (d, 1H, J=1.8 Hz, ArH), 7.39 (d, 1H, J=9.0 Hz, ArH), 7.24-28 (m, 1H, ArH), 3.91 (dd, 1H, J=5.4 Hz, CHCH$_2$), 3.79 (d, 2H, J=9.0 Hz, CH$_2$N), 1.45-1.58 (m, 10H, tert-Bu, ArCCH$_2$), 1.30 (t, 1H, J=4.8 Hz, ArCCH$_2$).

C. Preparation of (±)-[2-acetyl-2-(3,4-dichloro-phenyl)-cyclopropylmethyl]-carbamic acid tert-butyl ester

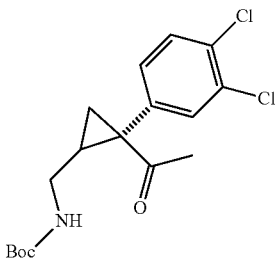

To a flame-dried, 10 mL round-bottomed flask was added a solution of 1-(3,4-dichlorophenyl)-2-oxo-3-azabicyclo[3.1.0]hexane-3-carboxylic acid tert-butyl ester in 2 mL of ether and 1.0 mL of THF under Ar (g). The solution was cooled in a dry ice/acetone bath with stirring. A solution of MeLi was added drop-wise and the resulting orange colored mixture was stirred at −78° C. for 3 hours. The solution was warmed to ambient temperature and quenched with 15 mL of 1N HCl. The organic layer was extracted with EtOAc (2×20 mL) and the combined layers washed with brine (20 mL). The organic layer was dried over sodium sulfate for 2 hours and filtered, concentrated under reduced pressure, and dried for 1 hour to afford 1.1 g of a brown oil. The oil was purified on a filter pad of silica eluting with 100/1 (v/v) CHCl$_3$/MeOH. The desired fractions were collected, concentrated under reduced pressure, and dried to afford a yellow oil. Yield: 0.659 g 52%; $^1$H NMR (300 MHz, CDCl$_3$) δ 7.46 (d, 1H, J=2.1 Hz, ArH), 7.39 (d, 1H, J=5.4 Hz, ArH), 7.20 (dd, 1H, J=5.4, 2.1 Hz, ArH), 4.73 (m, 1H, NH), 3.41 (m, 1H, CH$_2$N), 3.15 (m, 1H, CH$_2$N), 2.04 (s, 3H, CH$_3$), 1.80 (m, CHCH$_2$N), 1.45-1.58 (m, 9H, tert-Bu), 1.20 (dd, 2H, J=4.5 Hz, ArCCH$_2$).

D. Preparation of (±)-[2-(3,4-dichloro-phenyl)-(r/s)-2-(1-hydroxy-ethyl)-cyclopropylmethyl]-carbamic acid tert-butyl ester

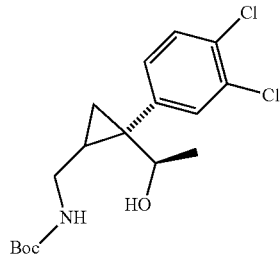

(±)-[2-Acetyl-2-(3,4-dichlorophenyl)-cyclopropylmethyl]-carbamic acid tert-butyl ester was added to methanol and stirred at ambient temperature under Ar (g) in a 50 mL round-bottomed flask. Potassium borohydride was added portion wise and the suspension stirred overnight. The resulting suspension partitioned between EtOAc (10 mL) and water (10 mL). The aqueous layer was extracted with EtOAc (2×10 mL), and the combined layers washed with brine (10 mL). The organic layer was dried over sodium sulfate for 2 hours and filtered, concentrated under reduced pressure, and dried for 1 hour to afford 0.523 g of a white sticky solid. The solid was purified on a filter pad of silica eluting with 4/1 hexanes/EtOAc (v/v), switching to 6/4 hexanes/EtOAc (v/v) upon collection of the major spot. The second (other)diastereomer was collected. The desired compound is pale oil; Yield: 0.328 g 49%; The undesired diastereomer is a white solid; Yield: 0.120 g 18%; $^1$H NMR: Desired diastereomer: (300 MHz, DMSO-d$_6$) δ 7.50-53 (m, 2H, J=2.1 Hz, ArH), 7.22-25 (dd, 1H, J=9.0 Hz, dr=1.8 Hz, ArH), 6.91 (bs, 1H, OH), 4.26 (m, 1H, NH), 3.50 (m, 1H, CH$_2$N), 3.32 (m, 1H, CH$_2$N), 3.26 (m, 3H, CH$_3$), 1.40 (s, 9H, tert-Bu), 1.02 (m, 2H, ArCCH$_2$), 0.55 (m, 1H, CHCH$_2$N); Undesired diastereomer (not shown): (300 MHz, CDCl$_3$) δ 7.57 (m, 1H, ArH), 7.50 (d, 1H, J=8.1 Hz, ArH), 7.31 (dd, 1H, J=8.4 Hz, J=1.8 Hz, ArH), 7.11 (bs, 1H, OH), 4.63 (d, 1H, J=3.3 Hz, NH), 3.46 (m, 1H), 3.33 (s, 3H), 3.12 (m, 2H), 1.38 (s, 9H, tert-Bu), 1.30 (m, 1H), 0.85 (d, 2H, J=6.0 Hz, ArCCH$_2$), 0.78 (m, 1H, CHCH$_2$N)

E. Preparation of (±)-1-(3,4-dichloro-phenyl)-(r/s)-2-methyl-3-aza-bicyclo[3.1.0]hexane hydrochloride

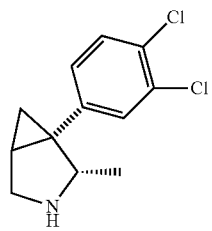

(±)-[2-(3,4-dichlorophenyl)-(R/S)-2-(1-hydroxyethyl)-cyclopropylmethyl]-carbamic acid tert-butyl ester was added to DCM and triethylamine and cooled in an ice bath under Ar (g) with stirring. Methanesulfonyl chloride was added dropwise with stirring over 10 min and the resulting suspension warmed to ambient temperature overnight. The resulting yellow solution was washed with water (2×10 mL) and the DCM layer dried over magnesium sulfate. The mixture was filtered and concentrated under reduced pressure to afford a yellow oil. This oil was dissolved in 0.8 mL of DCM and cooled in an ice bath under Ar (g). To this was added 0.8 mL of TFA and the resulting solution was stirred at ambient temperature for 1 hour. The solution was concentrated under reduced pressure, quenched with concentrated NaOH, and extracted with ether (2×10 mL). The organic extracts were combined and dried over magnesium sulfate, filtered, and concentrated under reduced pressure. The oil was purified on a filter pad of silica eluting with 10/1 CHCl$_3$/MeOH (v/v), to afford the desired free base. Yield: 0.065 g 30%; LCMS (+)ESI: m/z=242 [M+H]$^+$ (100); UV ($\lambda_{max}$=218)=95%; $^1$H NMR (300 MHz, CDCl$_3$) δ☐ 7.29-32 (m, 2H, ArH), 7.06 (dd, 1H, J=8.1 Hz, J=2.1 Hz, ArH), 4.36 (s, 1H, NH), 3.53 (q, 1H, J=6.6 Hz, CHNH), 3.28 (dd, 1H, J=1 Hz, J=3.0 Hz, CH$_2$NH), 3.00 (d, 1H, J=11 Hz, CH$_2$NH), 1.81 (q, 1H, J=4 Hz, CHCH$_2$), 1.01 (t, 1H, J=5 Hz, ArCCH$_2$), 0.91 (d, 3H, J=7 Hz, CH$_3$), 0.68 (dd, 1H, J=8 Hz, 5.4, ArCCH$_2$); $^{13}$C NMR (75 MHz, CDCl$_3$) δ☐ 140.9, 132.0, 121.2, 130.3, 130.0, 128.9, 57.6, 46.1, 37.0, 22.2, 18.9, 15.6.

To prepare the hydrochloride salt, 32 mg of free base, 1 mL diethyl ether, and 0.2 mL 2N HCl in diethyl ether were added to a vial. A white precipitate appeared in minutes and the suspension was stirred at ambient temperature for 1 hour. The suspension was filtered, collected, and dried to afford 27 mg of a pale yellow solid. LCMS (+) ESI: m/z=242 [M+H]$^+$ (100); UV (λ=218)=95%; $^1$H NMR (300 MHz, MeOH-d$_4$) δ☐: 7.60 (d, 1H, J=2 Hz, ArH), 7.52 (d, 1H, J=8 Hz, ArH), 7.33 (dd, 1H, J=8 Hz, J=2 Hz, ArH), 4.16 (q, 1H, J=7 Hz, NH), 3.74 (dd, 1H, J=11 Hz, J=4 Hz, CHNH$_2$), 3.46 (d, 1H, J=11 Hz, CH$_2$NH$_2$), 2.34 (q, 1H, J=5 Hz, CHCH$_2$), 1.21 (m, 1H, ArCCH$_2$), 1.14 (d, 3H, J=7 Hz, CH$_3$), 1.01 (m, 1H, ArCCH$_2$).

F. Preparation of (±)-1-(3,4-dichloro-phenyl)-(r/s)-2,3-dimethyl-3-aza-bicyclo[3.1.0]hexane

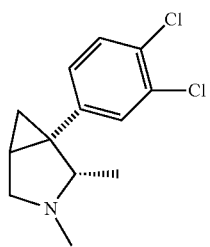

To a dried, 5 mL round-bottomed flask was added (±)-1-(3,4-dichlorophenyl)-(R/S)-2-methyl-3-aza-bicyclo[3.1.0]hexane, Hunig's Base, and DMF under Ar (g) with stirring. Methyl iodide was added drop wise with stirring over 5 min and the resulting solution stirred under ambient temperature overnight. The solution was concentrated under reduced pressure and purified after drying. The residue was purified by HPLC which failed to remove the impurities. This was further purified on a prep TLC plate eluting with 20/1 CHCl$_3$/MeOH (v/v). The desired band was collected, extracted with CHCl$_3$/MeOH, and concentrated after filtration to afford the desired free base. Yield: 0.005 g 15%; LCMS (+)ESI: m/z=256 [MH]$^+$ (100); 258 [MH+2]$^+$; (65); $^1$H NMR (300 MHz, CDCl$_3$) δ☐: 7.33 (d, H, J=12 Hz, ArH), 7.32 (d, 1H, J=2 Hz, ArH), 7.08 (dd, 1H, J=9 Hz, J=2 Hz, ArH), 3.31 (q, 1H, J=6 Hz, CHNH$_2$), 2.83 (s, 2H, CH$_2$N), 2.32 (s, 3H, NCH$_3$), 1.79 (m, 1H, CH$_2$CH), 1.40 (t(br), 1H, ArCCH$_2$), 0.73 (d, 3H, J=7 Hz, CHCH$_3$)., 0.60 (dd, 21-1, J=8 Hz, 4 Hz, ArCCH$_2$); $^{13}$C NMR (75 MHz, CDCl$_3$) δ☐: 131.2, 130.1, 128.9, 61.1, 53.8, 36.5, 21.9, 18.4, 11.6.

Example XVIII

Preparation of 1-Aryl-2-methyl-3-aza-bicyclo[3.1.0]hexane and 1-Aryl-2,3-dimethyl-3-aza-bicyclo[3.1.0]hexane Using Reaction Scheme 24

A. Preparation of (±)-1-(3,4-dichloro-phenyl)-2-methyl-3-aza-bicyclo[3.1.0]hex-2-ene

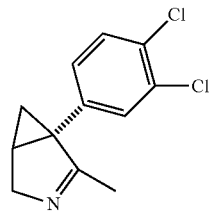

To an oven dried, 25 mL, three-necked round-bottomed flask was added (±)-1-(3,4-dichlorophenyl)-3-aza-bicyclo[3.1.0]hexan-2-one, triethylamine in 6.6 mL of toluene under Ar (g) with stirring. A solution of TMSCl in 1.1 mL of toluene was added drop wise over several minutes. The mixture was heated at 40° C. for 4 h, then cooled to 4° C. in an ice bath, and to it was added 6.6 mL of hexanes/ether (1/1, v/v). The mixture was filtered, and the filtrate concentrated under reduced pressure and dried under high vacuum for 2 h to afford 770 mg of the intermediate that was used in the next step. A flame-dried, 10 mL round-bottomed flask was equipped with a stir bar, purged with Ar (g) and cooled to −30° C. in a dry ice/MeCN bath. The flask was charged with methyl lithium, and to this was added a solution of the intermediate in 2.85 mL of diethyl ether over 10 minutes. The resulting yellow solution was stirred at −20 to −25° C. for 30 minutes, followed by ambient temperature for 1 hour. The mixture was poured into 4.9 mL of water containing 146 mg of ammonium chloride and stirred for 30 min. The layers were separated and the organic layer washed with brine (10 mL) and dried over sodium sulfate for 1 hour. The mixture was filtered, concentrated under reduced pressure, and dried under high vacuum to afford a yellow oil (488 mg). The oil was chromatographed on a filter pad of silica (12 g), eluting with 50/1 CHCl$_3$/MeOH (v/v). The desired fractions were collected, concentrated, and dried to afford the desired compound as yellow oil. Yield: 0.409 g 52%; LCMS (+)ESI: m/z=240 [MH]$^+$ (100), 242 [MH+2]$^+$ (60); UV (?=218)=95%; $^1$H NMR (300 MHz, CDCl$_3$) δ☐ 7.40 (d, 1H, J=8 Hz, ArH), 7.35 (d, 1H, J=2 Hz, ArH), 7.10 (dd, 1H, J=8 Hz, J=2 Hz, ArH), 4.09 (m, 1H, CH$_2$N), 3.80 (d, 1H, J=17 Hz, CH$_2$N), 2.09 (m, 1H, CH$_2$CH), 1.92 (m, 3H, CH$_3$), 1.44 (dd, 1H, J=12 Hz, 4 Hz, ArCCH$_2$), 0.60 (t, 1H, J=4 Hz, ArCCH$_2$).

B. Preparation of (±)-1-(3,4-dichloro-phenyl)-(r/s)-2-methyl-3-aza-bicyclo[3.1.0]hexane

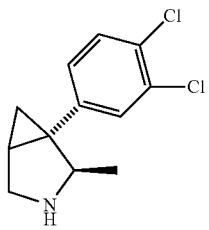

To a dried, 25 mL round-bottomed flask purged with Ar (g) was added product from Example XVIII A and EtOH. The mixture was stirred at ambient temperature for 5 min. To this was added sodium cyanoborohydride, followed by drop wise addition of 1.25 N HCl in ethanol over 10 min. The resulting mixture was stirred at ambient temperature for 2 hours. The solution was added to a mixture of brine/2N NaOH (20 mL/1.5 mL) and extracted with EtOAc (3×20 mL). The organic layers were combined and washed with brine (10 mL) and dried over magnesium sulfate for 1 hour. The mixture was filtered and the filtrate concentrated under reduced pressure, and dried under high-vacuum to afford 435 mg of an off-white wax. The wax was purified on 20 g of silica (230-400 mesh), eluting with 50/1 and gradient to 10/1 CHCl$_3$/MeOH (v/v). Two desired sets of fractions was collected; each was concentrated under reduced pressure and dried under high vacuum. Top set: yellow oil, yield: 0.154 g 37%; LCMS (+)ESI: m/z=242 [MH]$^+$ (100), 244 [MH+2]$^+$ (65); UV ($\lambda_{max}$=218)=99%; $^1$H NMR (300 MHz, CDCl$_3$) δ☐: 7.36 (d, H, J=5 Hz, ArH), 7.34 (d, 1H. J=1 Hz, ArH), 7.11 (dd, 1H, J=9 Hz, J=2 Hz., ArH), 3.41 (q, 1H, J=6 Hz, CH$_2$N), 3.17 (dd, 1H, J=12 Hz, 3 Hz, CH$_2$N), 2.99 (d, 1H, J=12 Hz, CHCH$_3$), 1.55 (m, 1H, CH$_2$CH), 1.08 (d, 3H, J=6 Hz, CH$_3$), 0.77-0.87 (m, 2H, ArCCH$_2$); $^{13}$C NMR (75 MHz, CDCl$_3$) δ☐: 131.2, 130.1, 128.9, 61.1, 53.8, 36.5, 21.9, 18.4, 11.6; Bottom set: white solid, yield: 0.141 g 35%; LCMS (+)ESI: m/z=242 [MH]$^+$ (100), 244 [MH+2]$^+$ (65); UV ($\lambda_{max}$=218)=99%; $^1$H NMR (300 MHz, CDCl$_3$) δ☐: 7.41 (d, H, J=8 Hz, ArH), 7.36 (d, 1H, J=2 Hz, ArH), 7.12 (dd, 1H, J=9 Hz, J=2 Hz, ArH), 3.75 (q, 1H, J=6 Hz, CH$_2$N), 3.44 (m, 1H, J=6 Hz, CH$_2$N), 3.33 (d, 1H, J=8 Hz, CHCH$_3$), 1.75 (q, 1H, J=4 Hz, CH$_2$CH), 1.30 (d, 3H, J=3H, CH$_3$), 1.10 (m, 2H, ArCCH$_2$); $^{13}$C NMR (75 MHz, CDCl$_3$) δ☐: 139.0, 132.6, 131.3, 130.7, 130.6, 128.3, 60.5, 47.6, 36.0, 24.9, 14.4, 9.8.

Preparation of the Hydrochloride Salts

Top set: To a vial was added 50 mg of the yellow oil obtained from the top set fractions as described above, 0.5 mL diethyl ether, and 0.12 mL 2N HCl in diethyl ether. A white precipitate appeared in minutes and the suspension was stirred at ambient temperature for one-half hour. The suspension was filtered, collected, and dried to afford 55 mg of a white solid.

Bottom set: To a vial was added 52 mg of the white solid obtained from the bottom set fractions as described above, 1.0 mL diethyl ether, and 0.12 mL 2N HCl in diethyl ether. EtOH (0.5 mL) was added to obtain a uniform solution. A white precipitate appeared in minutes and the suspension was stirred at ambient temperature for one-half hour. The suspension was filtered, collected, and dried to afford 40 mg of a white solid.

LCMS Top set: (+)ESI: m/z=242 [MH]$^+$ (100); 244 [MH+2]$^+$ (65); UV ($\lambda_{max}$=254)=95%; Bottom set: (+)ESI: m/z=242 [MH]$^+$ (100); 244 [MH+2]$^+$ (65); UV ($\lambda_{max}$=254)=95%

$^1$H NMR Top set: (300 MHz, DMSO-d$_6$) δ☐: 7.69 (d, 1H, J=2 Hz, ArH), 7.61 (d, 1H, J=8 Hz, ArH), 7.33 (dd, 1H, J=8 Hz, J=2 Hz, ArH), 4.00 (m, 1H, CHCH$_3$), 3.56 (m, 1H, CH$_2$N), 3.26 (m, 1H, CH$_2$N), 1.90 (m, 1H, CH$_2$CH), 1.15-22 (m, 4H, CH$_3$, ArCCH$_2$), 1.01 (m, 1H, ArCCH$_2$); Bottom set: (300 MHz, DMSO-d$_6$) δ☐: 7.69 (d, 1H, J=2 Hz, ArH), 7.61 (d, 1H, J=8 Hz, ArH), 7.33 (dd, 1H, J=8 Hz, J=2 Hz, ArH), 4.00 (m, 1H, CHCH$_3$), 3.56 (m, 1H, CH$_2$N), 3.26 (m, 1H. CH$_2$N), 1.90 (m, 1H, CH$_2$CH), 1.15-22 (m, 4H, CH$_3$, ArCCH$_2$), 1.01 (m, 1H, ArCCH$_2$)

C. Preparation of (±)-1-(3,4-dichloro-phenyl)-r/s-2,3-dimethyl-3-aza-bicyclo[3.1.0]hexane

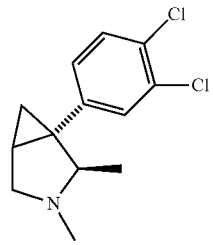

To an oven-dried, round-bottomed flask purged with Ar (g) was added either the yellow oil obtained from the top set fractions or the white solid obtained from the bottom set fractions as described in Example XVIII B above in DMF and Hunig's base. The mixture was stirred at ambient temperature for 5 min. To this was added MeI, drop wise, with stirring. The resulting yellow mixture was stirred at ambient temperature overnight. The solvent was removed via rotary-evaporation and the residue treated with 1.0 mL of 95% EtOH. The flaky white crystals/precipitate were collected by vacuum filtration and dried under high vacuum. Nature of the compound (from top set fractions): crystals, yield: 0.080 g 79%; Nature of the compound (from bottom setfractions): amorphous solid, yield: 0.042 g 40%.

LCMS

Top set: (+)ESI: m/z=256 [MH]$^+$ (100), 258 [MH+2]$^+$ (65); UV ($\lambda_{max}$=218)=99%; Bottom set: (+)ESI: m/z=256 NM$^+$ (100), 258 [MH+2]$^+$ (65); UV ($\lambda_{max}$=218)=99%.

$^1$H NMR

Top set: (300 MHz, CDCl$_3$) δ☐: 7.45 (d, 1H, J=9 Hz, ArH), 7.40 (m, 1H, ArH), 7.14 (dd, 1H, J==9 Hz, J=1 Hz, ArH), 4.07 (dd, 1H, J=25 Hz, J=6 Hz, CH$_2$N), 3.77 (q, 2H, CH$_2$N, CHCH$_3$), 2.88 (d, 3H, J=5 Hz, NCH$_3$), 2.29 (m, 1H, CHCH$_2$), 1.89 (q, 1H, J=5 Hz, ArCCH$_2$), 1.56-65 (m, 3H, CHCH$_3$), 1.24 (t, 1H, J=8 Hz, ArCCH$_2$); Bottom set: (300 MHz, CDCl$_3$) δ☐: 7.43 (d, 1H, J=9 Hz, ArH), 7.4 (d, 1H, J=2 Hz, ArH), 7.14 (dd, 1H, 0.1=9 Hz, J=2 Hz, ArH), 4.06 (d, 1H, J=11 Hz, CH$_2$N), 3.77 (m, 1H, CHCH$_3$), 3.30 (m, 1H, CHCH$_3$), 2.88 (s, 3H, NCH$_3$), 2.30 (m, 1H, CHCH$_2$), 1.88 (q, 1H, J=4 Hz, ArCCH$_2$), 1.63 (d, 3H, J=7 Hz, CHCH$_3$), 1.23 (t, 1H, J=8, ArCCH$_2$).

$^{13}$C NMR

Top set: (75 MHz, MeOH-d$_4$) δ☐: 139.6, 132.4, 132.1, 130.3, 70.2, 58.8, 39.6, 37.1, 23.4, 12.3, 11.3

Preparation of the Hydrochloride Salt

Bottom set: To a vial was added 47 mg of the white solid obtained from the bottom set fractions as described in Example XVIII B above, 1.0 mL diethyl ether, and 0.12 mL 2N HCl in diethyl ether. EtOH (0.5 mL) was added to obtain a uniform solution. A yellow precipitate appeared in minutes and the suspension was stirred at ambient temperature for one-half hour. The suspension was filtered, collected, and dried to afford 40 mg of a yellow solid. LCMS Bottom set: (+)ESI: m/z=256 [MH]$^+$ (100), 258 [MH+2]$^+$ (65); UV ($\lambda_{max}$=218)=99%; $^1$H NMR Bottom set: (300 MHz, MeOH-d$_4$) $\delta\square$: 7.68 (m, 1H, ArH), 7.54 (d, 1H, J=8 Hz, ArH), 7.40 (m, 1H, ArH), 3.97 (q, 1H, J=6 Hz, CH$_2$N), 3.76 (m, 1H, CH$_2$N), 2.99 (m, 3H, NCH$_3$), 2.0 (m, 1H, CHCH$_3$), 1.37 (d, 3H, J=9 Hz, CHCH$_3$), 1.30 (t, 1H, J=5 Hz, ArCCH$_2$), 1.21 (m, 1H, ArCCH$_2$).

Example XIX

Efficacy of Exemplary Compounds of the Invention for Inhibiting Monoamine Neurotransmitter Uptake The effects of exemplary compounds of the invention on the cellular uptake of norepinephrine (NE), dopamine (DA) and serotonin (5-HT) were tested in preparations of synaptosomes from different rat brain regions using the previously-reported techniques referenced below.

| Assay | Origin | Reference Compound | Bibliography |
|---|---|---|---|
| Norepinephrine (NE) Uptake | Rat hypothalamus synaptosomes | Protriptyline | Perovic and Muller (1995) |
| Dopamine (DA) uptake | Rat striatum synaptosomes | GBR 12909 | Janowsky et al. (1986) |
| 5-HT uptake | Rat brain synaptosomes | Imipramine | Perovic and Muller (1995) |

Whole brains were obtained from normal rats. Synaptosomal preparations were made from either whole brain (5-HT), striatum (DA) or hypothalamus (NE) by gentle disruption in 10 volumes (w/v) of 0.32 M sucrose (0-4° C.) using a Teflon-glass homogenizer. The homogenate was then centrifuged at 1000×g for 10 min. The supernatant was retained and centrifuged at 23000 g for 20 min. The resulting pellet was gently resuspended in 200 volumes of 0.32 M sucrose (0-4° C.) using the Teflon-glass homogenizer. Aliquots (250 µL) of this preparation were added to tubes, along with 0.2 µCi/mL of [$^3$H]5-HT, [$^3$H]DA, or [$^3$H]NE, 200 µL of the test compounds (to yield final concentrations of 100 nM, 300 nM, 1 µM, 3 µM, 10 µM, 30 µM or 100 µM) and 1 mL of Krebs-Ringer bicarbonate buffer (pH 7.4). The mixtures were incubated for either 15 (DA and 5-HT uptake) or 20 (NE uptake) minutes at 37° C. At the end of this period, the assay was terminated by rapid filtration over Whatman GF/C glass fiber filters. The filters were rinsed 3 times with 4 ml of Krebs-Ringer bicarbonate buffer (0-4° C.), and the radioactivity retained on the filters measured by liquid scintillation spectrometry.

Each assay was run according to the description of the respective publications cited above, and according to the following parameters/reagents/conditions.

| Assay | Substrate/ Stimulus/Tracer | Incubation | Reaction Product | Detection Method |
|---|---|---|---|---|
| NE uptake | [$^3$H]NE (0.2 µCi/ml) | 20 min. at 37° C. | [$^3$H]NE incorporation into synaptosomes | Scintillation counting |
| DA uptake | [$^3$H]DA (0.2 µCi/ml) | 15 min. at 37° C. | [$^3$H]DA incorporation into synaptosomes | Scintillation counting |
| 5-HT uptake | [$^3$H]5-HT (0.2 µCi/ml) | 15 min. at 37° C. | [$^3$H]5-HT incorporation into synaptosomes | Scintillation counting |

In each experiment, the respective reference compound was tested concurrently with the test compounds in order to assess the assay suitability. It was tested at several concentrations (for IC$_{50}$ value determination). The assay was considered valid if the suitability criteria were met, in accordance with the corresponding Standard Operating Procedure.

The results of these uptake inhibition assays are expressed below as a percent of control values obtained in the presence of the test compounds. Individual and mean values are presented with the results. The IC$_{50}$ values (concentration causing a half-maximal inhibition of control values) were determined by non-linear regression analysis of the inhibition curves using Hill equation curve fitting.

TABLE 3

Neurotransmitter Uptake Inhibition by 1-Aryl-3-Aza-Bicyclo[3.1.0]Hexanes of the Invention Having Multiple Substitutions on the Aryl Ring

| Structure | Uptake IC$_{50}$ (nM) NE | Uptake IC50 (nM) 5-HT | Uptake IC50 (nM) DA | Binding NET K$_i$ (nM) | Binding DAT K$_i$ (nM) | Binding SERT K$_i$ (nM) |
|---|---|---|---|---|---|---|
| 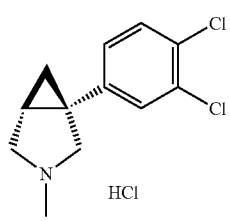 | 19 | 23 | 120 | 81 | 105 | 16 |

TABLE 3-continued

Neurotransmitter Uptake Inhibition by 1-Aryl-3-Aza-Bicyclo[3.1.0]Hexanes of the
Invention Having Multiple Substitutions on the Aryl Ring

| Structure | Uptake IC$_{50}$ (nM) NE | Uptake IC50 (nM) 5-HT | Uptake IC50 (nM) DA | Binding NET K$_i$ (nM) | Binding DAT K$_i$ (nM) | Binding SERT K$_i$ (nM) |
|---|---|---|---|---|---|---|
| (3,4-diCl-phenyl, N-methyl bicyclic)·HCl | 82 | 87 | 130 | 490 | 62 | 125 |
| (3,4-diCl-phenyl, N-ethyl bicyclic)·HCl | 15 | 56 | 80 | 32 | 13 | 88 |
| (3,4-diCl-phenyl, N-ethyl bicyclic alt)·HCl | 140 | 45 | 190 | 585 | 46 | 113 |
| (3,4-diCl-phenyl, N-propyl bicyclic)·HCl | 380 | 470 | 1000 | 1833 | 250 | 1667 |
| (3,4-diCl-phenyl, N-propyl bicyclic alt)·HCl | 550 | 590 | 1800 | 4000 | 220 | 2000 |

TABLE 3-continued

Neurotransmitter Uptake Inhibition by 1-Aryl-3-Aza-Bicyclo[3.1.0]Hexanes of the
Invention Having Multiple Substitutions on the Aryl Ring

| Structure | Uptake IC$_{50}$ (nM) NE | Uptake IC50 (nM) 5-HT | Uptake IC50 (nM) DA | Binding NET K$_i$ (nM) | Binding DAT K$_i$ (nM) | Binding SERT K$_i$ (nM) |
|---|---|---|---|---|---|---|
| 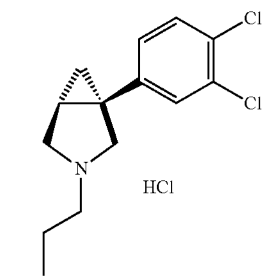 | 220 | 390 | 770 | 1073 | 170 | 2400 |
| 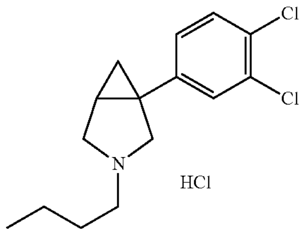 [SMILES: CCCCN1CC2CC2(c2ccc(Cl)c(Cl)c2)C1 ; Cl] | 1500 | 1200 | 78 | 2200 | 240 | 6100 |
| 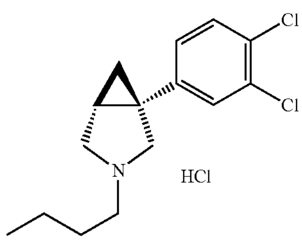 | 1700 | 3000 | 2200 | 1900 | 395 | 7600 |
| 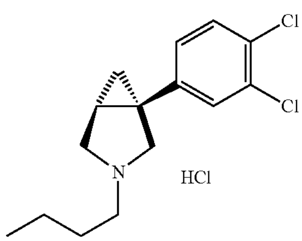 | 400 | 2600 | 1200 | 1100 | 215 | 8900 |
| 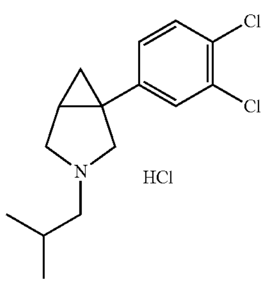 [SMILES: CC(C)CN1CC2CC2(c2ccc(Cl)c(Cl)c2)C1 ; Cl] | 3500 | 5100 | 8100 | >10000 | 1100 | 16000 |

TABLE 3-continued

Neurotransmitter Uptake Inhibition by 1-Aryl-3-Aza-Bicyclo[3.1.0]Hexanes of the
Invention Having Multiple Substitutions on the Aryl Ring

| Structure | Uptake IC$_{50}$ (nM) NE | Uptake IC50 (nM) 5-HT | Uptake IC50 (nM) DA | Binding NET K$_i$ (nM) | Binding DAT K$_i$ (nM) | Binding SERT K$_i$ (nM) |
|---|---|---|---|---|---|---|
| (3,4-diCl-phenyl, N-isopropyl, HCl) | 110 | 30 | 260 | 827 | 39 | 124 |
| (3,4-diCl-phenyl, stereo, N-isopropyl, HCl) | 64 | 170 | 330 | 510 | 25 | 330 |
| (3,4-diCl-phenyl, stereo, N-isopropyl, HCl) | 530 | 100 | 430 | 5150 | 72 | 132 |
| (3,4-diCl-phenyl, N-cyclopropyl, HCl) | 3800 | 2600 | 1500 | 9500 | 1700 | 3700 |
| (3,4-diCl-phenyl, N-tert-butyl, maleate) | 650 | 240 | 1500 | 9300 | 420 | 800 |
| (2,4-diF-phenyl, N-methyl, HCl) | 430 | 1100 | 7400 | 6600 | | |

TABLE 3-continued

Neurotransmitter Uptake Inhibition by 1-Aryl-3-Aza-Bicyclo[3.1.0]Hexanes of the
Invention Having Multiple Substitutions on the Aryl Ring

| Structure | Uptake IC$_{50}$ (nM) NE | Uptake IC50 (nM) 5-HT | Uptake IC50 (nM) DA | Binding NET K$_i$ (nM) | Binding DAT K$_i$ (nM) | Binding SERT K$_i$ (nM) |
|---|---|---|---|---|---|---|
| 3,4-diF, N-Me, HCl | 87 | 400 | 1800 | 990 | 1900 | 1600 |
| 3-Cl,4-F, NH, HCl | 210 | 310 | 1400 | 1700 | 680 | 230 |
| 3-Cl,4-F, NH, HCl (stereo) | 107 | 186 | 572 | | | |
| 3-Cl,4-F, N-Me, HCl | 86 | 79 | 770 | 350 | 640 | 190 |
| 3-Cl,4-F, N-Me, HCl (stereo) | 41 | 362 | 494 | | | |
| 3-Cl,4-F, N-Me, HCl (stereo) | 375 | 835 | | | | |
| 3-F,4-Cl, NH, HCl | 31 | 252 | 420 | | | |

TABLE 3-continued

Neurotransmitter Uptake Inhibition by 1-Aryl-3-Aza-Bicyclo[3.1.0]Hexanes of the Invention Having Multiple Substitutions on the Aryl Ring

| Structure | Uptake IC$_{50}$ (nM) NE | Uptake IC50 (nM) 5-HT | Uptake IC50 (nM) DA | Binding NET K$_i$ (nM) | Binding DAT K$_i$ (nM) | Binding SERT K$_i$ (nM) |
|---|---|---|---|---|---|---|
| 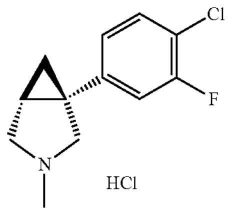 | 25 | 413 | 437 | | | |
| 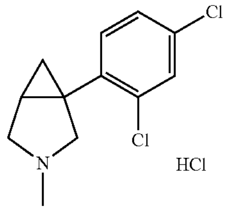 | 870 | 520 | 10000 | 6200 | NC | 500 |
| 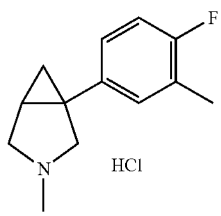 | 180 | 200 | 370 | 920 | 2200 | 540 |
| 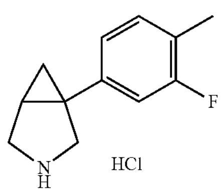 | 138 | 266 | 457 | | | |
| 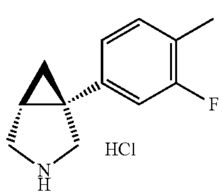 | 91 | 133 | 401 | | | |
| 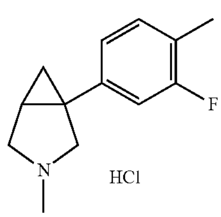 | 30 | 110 | 700 | 260 | 270 | 830 |
| 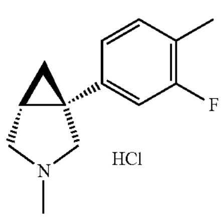 | 20 | 836 | 383 | | | |

TABLE 3-continued
Neurotransmitter Uptake Inhibition by 1-Aryl-3-Aza-Bicyclo[3.1.0]Hexanes of the
Invention Having Multiple Substitutions on the Aryl Ring
| Structure | Uptake IC$_{50}$ (nM) NE | Uptake IC50 (nM) 5-HT | Uptake IC50 (nM) DA | Binding NET K$_i$ (nM) | Binding DAT K$_i$ (nM) | Binding SERT K$_i$ (nM) |
|---|---|---|---|---|---|---|
| 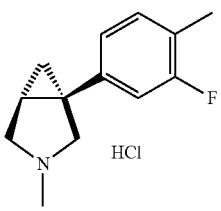 | 54 | 702 | 917 | | | |
| 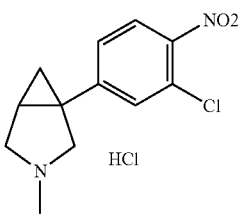 [SMILES: CN1CC2CC2(c2ccc([N+](=O)[O-])c(Cl)c2)C1 ; Cl] | 4500 | 790 | | | | 710 |
| 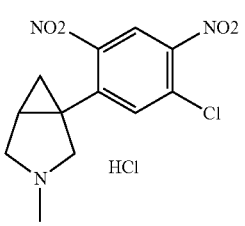 [SMILES: CN1CC2CC2(c2cc(Cl)c([N+](=O)[O-])cc2[N+](=O)[O-])C1 ; Cl] | | 8400 | | | | 4300 |
| 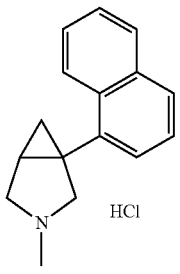 [SMILES: CN1CC2CC2(c2cccc3ccccc23)C1 ; Cl] | 68 | 119 | 512 | | | |
| 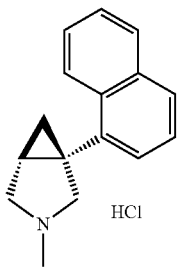 | 101 | | 903 | | | |
| 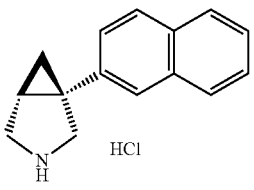 | <10 | 65 | 49 | | | |

TABLE 3-continued

Neurotransmitter Uptake Inhibition by 1-Aryl-3-Aza-Bicyclo[3.1.0]Hexanes of the Invention Having Multiple Substitutions on the Aryl Ring

| Structure | Uptake IC$_{50}$ (nM) NE | Uptake IC50 (nM) 5-HT | Uptake IC50 (nM) DA | Binding NET K$_i$ (nM) | Binding DAT K$_i$ (nM) | Binding SERT K$_i$ (nM) |
|---|---|---|---|---|---|---|
| 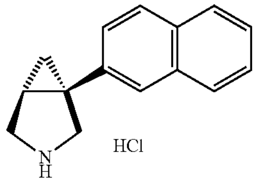 | 56 | 170 | 98 | | | |
| 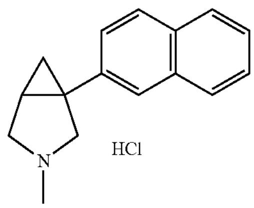 [SMILES: CN1CC2CC2(c2ccc3ccccc3c2)C1 ; Cl] | 98 | 31 | 350 | 520 | 68 | 6 |
| 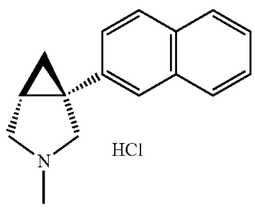 | 57 | <10 | 82 | | | |
| 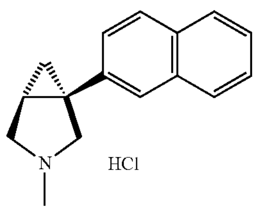 | 169 | 117 | 147 | | | |
| 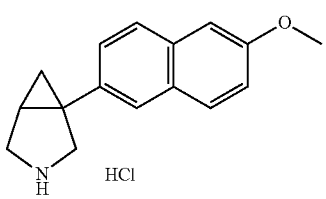 [SMILES: COc1ccc2cc(C34CNCC3C4)ccc2c1 ; Cl] | 82 | 82 | 208 | | | |
| 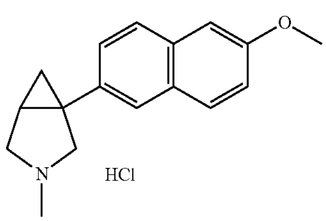 [SMILES: COc1ccc2cc(C34CC3CN(C)C4)ccc2c1 ; Cl] | 18 | 14 | 91 | | | |
| 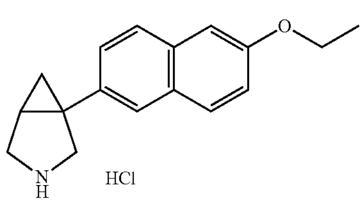 [SMILES: CCOc1ccc2cc(C34CNCC3C4)ccc2c1 ; Cl] | 202 | 700 | 563 | | | |

TABLE 3-continued

Neurotransmitter Uptake Inhibition by 1-Aryl-3-Aza-Bicyclo[3.1.0]Hexanes of the Invention Having Multiple Substitutions on the Aryl Ring

| Structure | Uptake IC$_{50}$ (nM) NE | Uptake IC50 (nM) 5-HT | Uptake IC50 (nM) DA | Binding NET K$_i$ (nM) | Binding DAT K$_i$ (nM) | Binding SERT K$_i$ (nM) |
|---|---|---|---|---|---|---|
| [structure: 1-(6-ethoxynaphthalen-2-yl)-3-azabicyclo[3.1.0]hexane · HCl] | 39 | 210 | 360 | | | |

Readily discernable from the foregoing results is the high degree of diversity with respect to the biological activity changes that were achieved by differentially altering aryl and aza substituents to yield novel 1-aryl-3-azabicyclo[3.1.0]hexanes according to the invention—whereby the absolute potency at any one transporter may be altered dramatically, and in distinct patterns among the exemplified compounds. Radical changes in the potency ratio were evinced among the exemplary, multiple aryl-substituted, and combined multiple aryl- and aza-substituted, compounds. The differential potency ratios for inhibition of neurotransmitter uptake affecting dopamine, serotonin, and norepinephrine transport yield profound and distinct therapeutic potentials among the different, novel compounds of the invention. Both the absolute changes in potency and the changes in potency "ratio" demonstrated herein for exemplary compounds of the invention would not have been expected or predictable with a reasonable expectation of success by persons of ordinary skill in the art The data provided in Table 3 demonstrate that several of the multiple aryl-substituted, and combined multiple aryl- and aza-substituted, compounds are potent (nM) inhibitors of norepinephrine and/or serotonin and/or dopamine uptake. As such, the compounds and related formulations and methods of the invention provide neurobiologically active tools for modulating biogenic amine transport in mammalian subjects. These subjects may include in vitro or ex vivo mammalian cell, cell culture, tissue culture, or organ explants, as well as human and other mammalian individuals presenting with, or at heightened risk for developing, a central nervous system (CNS) disorder, including neuropsychiatric disorders such as anxiety, or depression.

In certain embodiments, neurobiologically active compositions comprising a multiple aryl-substituted, or combined multiple aryl- and aza-substituted, 1-aryl-3-azabicyclo[3.1.0]hexane of the invention are effective to inhibit cellular uptake of norepinephrine in a mammalian subject. In other embodiments, these compositions will effectively inhibit cellular uptake of serotonin in mammals. Other compositions of the invention will be effective to inhibit cellular uptake of dopamine in mammalian subjects.

As illustrated by the foregoing examples, additional neurobiologically active compositions of the invention will be effective to inhibit cellular uptake of multiple biogenic amine neurotransmitters in mammalian subjects, for example, norepinephrine and serotonin, norepinephrine and dopamine, or serotonin and dopamine. In additional embodiments, the compositions of the invention are effective to inhibit cellular uptake of norepinephrine, serotonin and dopamine in mammalian subjects.

In further-detailed embodiments, as exemplified by the results presented in Table 3, neurobiologically active compositions of the invention surprisingly inhibit cellular reuptake of two, or three, biogenic amines selected from norepinephrine, serotonin and dopamine in a mammalian subject "non-uniformly" across an affected range of multiple biogenic amine targets. The distinct double and triple reuptake inhibition activity profiles demonstrated herein for exemplary compounds of the invention illustrate the powerful and unpredictable nature of the subject, multiple aryl-substituted, and combined multiple aryl- and aza-substituted, compounds, and further evince the ability to follow the teachings of the present disclosure to produce, select, and employ other substituted 1-aryl-3-azabicyclo[3.1.0]hexanes according to the invention having distinct activity profiles to fulfill additional therapeutic uses within the invention for treating diverse CNS disorders.

In exemplary embodiments, differential reuptake inhibition mediated by the compounds of the invention may yield a profile/ratio of reuptake inhibition activities for all three neurotransmitters, norepinephrine, dopamine, and serotonin, respectively, in reuptake inhibition profiles/ratios as exemplified in Table 3, selected from the following approximate inhibition profiles/ratios: (2:1:1); (3:10:1); (2:5:1); (12:1:5); (15:1:12); (3:8:5); (2:4:1); (3:1:2); and (2:4:1). Although these values are approximate, they will correlate in a measurable way with novel in vivo reuptake inhibition profiles/ratios as will be readily determined by those skilled in the art.

In related embodiments, neurobiologically active compositions of the invention inhibit cellular uptake of two, or three, biogenic amine neurotransmitters non-uniformly, for example by inhibiting uptake of at least one member of a group of transmitters including norepinephrine, serotonin, and dopamine by a factor of two- to ten-fold greater than a potency of the same composition to inhibit uptake of one or more different neurotransmitter(s). In exemplary embodiments, compositions of the invention comprising a multiple aryl-substituted, or combined multiple aryl- and aza-substituted, 1-aryl-3-azabicyclo[3.1.0]hexane, inhibit cellular uptake of serotonin by a factor of at least approximately two-fold, three-fold, five-fold, ten-fold or greater compared to a potency of the same composition to inhibit uptake of norepinephrine, dopamine, or both norepinephrine and dopamine. In other exemplary embodiments, different 1-aryl-3-azabicyclo[3.1.0]hexanes of the invention inhibit cellular uptake of dopamine by a factor of at least approximately two-fold, three-fold, five-fold, ten-fold or greater compared to a potency of the composition for inhibiting uptake of norepinephrine, serotonin, or both norepinephrine and serotonin.

In additional exemplary embodiments, the compositions described herein inhibit cellular uptake of norepinephrine by a factor of at least approximately two-fold, three-fold, five-fold, ten-fold or greater compared to a potency of the same composition for inhibiting uptake of serotonin. In different exemplary embodiments, compositions are provided that inhibit cellular uptake of dopamine by a factor of at least approximately two-fold, three-fold, five-fold, ten-fold or greater compared to a potency of the composition for inhibiting uptake of serotonin. In yet additional embodiments, neurobiologically active compositions are provided that exhibit approximately equivalent potency for inhibiting cellular uptake of norepinephrine and serotonin, while at the same time inhibiting dopamine uptake by a factor of at least approximately two-fold, three-fold, five-fold, ten-fold or greater compared to a potency of the composition for inhibiting uptake of norepinephrine and serotonin. In still other exemplary embodiments, compositions of the invention exhibit approximately equivalent potency for inhibiting cellular uptake of serotonin and dopamine, while at the same time inhibiting norepinephrine by a factor of no greater than approximately half the potency for inhibiting uptake of serotonin and dopamine. In certain embodiments, compositions of the invention exhibit approximately equivalent potency for inhibiting cellular uptake of norepinephrine, serotonin, and dopamine.

Compounds of the invention that inhibit uptake of norepinephrine and/or, serotonin, and/or dopamine have a wide range of therapeutic uses, principally to treat CNS disorders, including various neuropsychiatric disorders, as described above. Certain CNS disorders contemplated herein will be more responsive to a compound of the invention that preferentially inhibits, for example, dopamine uptake relative to norepinephrine and/or serotonin uptake, as in the case of some forms of depression. Other disorders will be determined to be more responsive to compounds of the invention that more potently inhibit norepinenephrine reuptake relative to serotonin reuptake and dopamine reuptake. Other CNS disorders, for example, attention deficit hyperactivity disorder (ADHD), may respond better to compounds of the invention that preferentially inhibit dopamine and norepinephrine reuptake relative to serotonin reuptake. Thus, the host of exemplary compounds described herein, which pro vide a range of reuptake inhibition profiles/ratios, will provide useful drug candidates for a diverse range of CNS disorders, and will effectively treat specific disorders with lower side effect profiles than currently available drugs.

It will be understood that the instant invention is not limited to the particular formulations, process steps, and materials disclosed herein as such formulations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

All publications and patents mentioned herein are incorporated herein by reference for the purpose of describing and disclosing, for example, the constructs and methodologies that are described in the publications, which might be used in connection with the presently described invention. The publications discussed above and throughout the text are provided solely for their disclosure prior to the filing date of the present application. Nothing herein is to be construed as an admission that the inventors are not entitled to antedate such disclosure by virtue of prior invention.

REFERENCES

Skolnick, P. et al Eur. J. Pharmacol. 461:99 (2003)
Skolnick, P. et al., Life Sci. 73: 3175-3179 (2003)
Armarego, W. L. F. et, al., J. Chem. Soc. [Section C: Organic] 19: 3222-3229 (1971)
Szalecki et al., patent publication PL 120095 B2, CAN 99:158251
Marrazzo, A. et al. Arkivoc 5: 156-159 (2004)
Cabadio, S. et al., Fr. Bollettino Chimico Farmaceutico 117: 331-42 (1971)
Mouzin, G. et al., Synthesis 4: 304-305 (1978)
Synthetic Communications 29: 4315-4319 (1999)
Tetrahedron 45: 3683 (1989)
"Nitrogen Protecting Groups in Organic Synthesis", John Wiley and Sons, New York, N.Y., 1981, Chapter 7
"Nitrogen Protecting Groups in Organic Chemistry", Plenum Press, New York, N.Y., 1973, Chapter 2
Green, T. W. and Wuts, P. G. M. in "Protective Groups in Organic Chemistry", 3rd edition, John Wiley & Sons, New York, N.Y., 1999
Quick Reference to the Diagnostic Criteria From DSM-IV (Diagnostic and Statistical. Manual of Mental Disorders, Fourth Edition), The American Psychiatric Association, Washington, D.C., 1994
Perovic, S. and Muller, W. E., Arzneimittelforschung 45: 1145-1148 (1995)
Janowsky, A. et al., J. Neurochem. 46: 1272-1276 (1986)
U.S. Pat. No. 6,132,724; Blum; Oct. 17, 2000
U.S. Pat. No. 4,122,193; Scherm et al.; Oct. 24, 1978

What is claimed is:

1. A method for treating a central nervous system (CNS) disorder in a mammalian subject in need thereof comprising administering to the mammalian subject in need thereof an effective amount of 1-(naphthalen-2-yl)-3-aza-bicyclo[3.1.0] hexane or a pharmaceutically acceptable salt thereof.

2. The method according to claim 1 wherein the mammalian subject is human.

3. The method according to claim 2 wherein the CNS disorder is depression.

4. The method according to claim 1 wherein the CNS disorder is an anxiety disorder.

5. The method according to claim 2 wherein the CNS disorder is an anxiety disorder.

6. The method according to claim 1 wherein the effective amount of 1-(naphthalen-2-yl)-3-aza-bicyclo[3.1.0]hexane or pharmaceutically acceptable salt thereof is an effective amount of (1R,5S)-1-(naphthalen-2-yl)-3-aza-bicyclo[3.1.0] hexane or a pharmaceutically acceptable salt thereof.

7. The method according to claim 2 wherein the effective amount of 1-(naphthalen-2-yl)-3-aza-bicyclo[3.1.0]hexane or pharmaceutically acceptable salt thereof is an effective amount of (1R,5S)-1-(naphthalen-2-yl)-3-aza-bicyclo[3.1.0] hexane or a pharmaceutically acceptable salt thereof.

8. The method according to claim 3 wherein the effective amount of 1-(naphthalen-2-yl)-3-aza-bicyclo[3.1.0]hexane or pharmaceutically acceptable salt thereof is an effective amount of (1R,5S)-1-(naphthalen-2-yl)-3-aza-bicyclo[3.1.0] hexane or a pharmaceutically acceptable salt thereof.

9. The method according to claim 4 wherein the effective amount of 1-(naphthalen-2-yl)-3-aza-bicyclo[3.1.0]hexane or pharmaceutically acceptable salt thereof is an effective amount of (1R,5S)-1-(naphthalen-2-yl)-3-aza-bicyclo[3.1.0] hexane or a pharmaceutically acceptable salt thereof.

10. The method according to claim 5 wherein the effective amount of 1-(naphthalen-2-yl)-3-aza-bicyclo[3.1.0]hexane or pharmaceutically acceptable salt thereof is an effective amount of (1R,5S)-1-(naphthalen-2-yl)-3-aza-bicyclo[3.1.0] hexane or a pharmaceutically acceptable salt thereof.

11. The method according to claim 2 wherein the CNS disorder is attention deficit hyperactivity disorder (ADHD).

12. The method according to claim 11 wherein the effective amount of 1-(naphthalen-2-yl)-3-aza-bicyclo[3.1.0]hexane or pharmaceutically acceptable salt thereof is an effective amount of (1R,5S)-1-(naphthalen-2-yl)-3-aza-bicyclo[3.1.0]hexane or a pharmaceutically acceptable salt thereof.

13. A method for treating a central nervous system (CNS) disorder in a mammalian subject in need thereof comprising administering to the mammalian subject in need thereof an effective amount of a pharmaceutical composition comprising 1-(naphthalen-2-yl)-3-aza-bicyclo[3.1.0]hexane or a pharmaceutically acceptable salt thereof and a pharmaceutically acceptable carrier or vehicle therefor.

14. The method according to claim 13 wherein the mammalian subject is human.

15. The method according to claim 14 wherein the CNS disorder is depression.

16. The method according to claim 13 wherein the CNS disorder is an anxiety disorder.

17. The method according to claim 14 wherein the CNS disorder is an anxiety disorder.

18. The method according to claim 13 wherein the 1-(naphthalen-2-yl)-3-aza-bicyclo[3.1.0]hexane or pharmaceutically acceptable salt thereof is (1R,5S)-1-(naphthalen-2-yl)-3-aza-bicyclo[3.1.0]hexane or a pharmaceutically acceptable salt thereof.

19. The method according to claim 14 wherein the 1-(naphthalen-2-yl)-3-aza-bicyclo[3.1.0]hexane or pharmaceutically acceptable salt thereof is (1R,5S)-1-(naphthalen-2-yl)-3-aza-bicyclo[3.1.0]hexane or a pharmaceutically acceptable salt thereof.

20. The method according to claim 15 wherein the 1-(naphthalen-2-yl)-3-aza-bicyclo[3.1.0]hexane or pharmaceutically acceptable salt thereof is (1R,5S)-1-(naphthalen-2-yl)-3-aza-bicyclo[3.1.0]hexane or a pharmaceutically acceptable salt thereof.

21. The method according to claim 16 wherein the 1-(naphthalen-2-yl)-3-aza-bicyclo[3.1.0]hexane or pharmaceutically acceptable salt thereof is (1R,5S)-1-(naphthalen-2-yl)-3-aza-bicyclo[3.1.0]hexane or a pharmaceutically acceptable salt thereof.

22. The method according to claim 17 wherein the 1-(naphthalen-2-yl)-3-aza-bicyclo[3.1.0]hexane or pharmaceutically acceptable salt thereof is (1R,5S)-1-(naphthalen-2-yl)-3-aza-bicyclo[3.1.0]hexane or a pharmaceutically acceptable salt thereof.

23. The method according to claim 13 wherein the CNS disorder is attention deficit hyperactivity disorder (ADHD).

24. The method according to claim 23 wherein the 1-(naphthalen-2-yl)-3-aza-bicyclo[3.1.0]hexane or pharmaceutically acceptable salt thereof is (1R,5S)-1-(naphthalen-2-yl)-3-aza-bicyclo[3.1.0]hexane or a pharmaceutically acceptable salt thereof.

\* \* \* \* \*